US012195744B2

(12) United States Patent
Rogers et al.

(10) Patent No.: US 12,195,744 B2
(45) Date of Patent: Jan. 14, 2025

(54) IDENTIFICATION OF T-CELL TRAFFICKING GENES AND USES THEREOF FOR INCREASING INFILTRATION OF T-CELLS INTO SOLID TUMORS

(71) Applicant: UNIVERSITY OF IOWA RESEARCH FOUNDATION, Iowa City, IA (US)

(72) Inventors: Laura M. Rogers, Iowa City, IA (US); George J. Weiner, Iowa City, IA (US); Adam J. Dupuy, Coralville, IA (US)

(73) Assignee: UNIVERSITY OF IOWA RESEARCH FOUNDATION, Iowa City, IA (US)

( * ) Notice: Subject to any disclaimer, the term of this patent is extended or adjusted under 35 U.S.C. 154(b) by 472 days.

(21) Appl. No.: 16/606,567

(22) PCT Filed: Apr. 18, 2018

(86) PCT No.: PCT/US2018/028071
§ 371 (c)(1),
(2) Date: Oct. 18, 2019

(87) PCT Pub. No.: WO2018/195145
PCT Pub. Date: Oct. 25, 2018

(65) Prior Publication Data
US 2020/0181574 A1 Jun. 11, 2020

Related U.S. Application Data

(60) Provisional application No. 62/545,758, filed on Aug. 15, 2017, provisional application No. 62/486,677, filed on Apr. 18, 2017.

(51) Int. Cl.
| | |
|---|---|
| *C12N 15/63* | (2006.01) |
| *A61K 39/00* | (2006.01) |
| *A61P 35/00* | (2006.01) |
| *C12N 5/00* | (2006.01) |
| *C12N 5/0783* | (2010.01) |
| *C12N 15/86* | (2006.01) |
| *C12N 15/90* | (2006.01) |

(52) U.S. Cl.
CPC .......... *C12N 15/86* (2013.01); *A61K 39/4611* (2023.05); *A61K 39/4631* (2023.05); *A61K 39/4632* (2023.05); *A61K 39/4644* (2023.05); *A61K 39/464492* (2023.05); *A61P 35/00* (2018.01); *C12N 5/0636* (2013.01); *C12N 5/0638* (2013.01); *C12N 15/90* (2013.01); *A61K 2239/31* (2023.05); *A61K 2239/38* (2023.05); *A61K 2239/57* (2023.05); *C12N 2510/00* (2013.01); *C12N 2740/10043* (2013.01); *C12N 2800/90* (2013.01)

(58) Field of Classification Search
CPC .............................. C12N 15/63; C12N 5/0636
See application file for complete search history.

(56) References Cited

U.S. PATENT DOCUMENTS

| | | |
|---|---|---|
| 2001/0001310 A1 | 5/2001 | Weiner |
| 2004/0087538 A1 | 5/2004 | Krieg |
| 2005/0197314 A1 | 9/2005 | Krieg |
| 2006/0115834 A1 | 6/2006 | Racila |
| 2007/0071717 A1 | 3/2007 | Weiner |
| 2007/0128626 A1 | 6/2007 | Racila |
| 2007/0191262 A1 | 8/2007 | Racila |
| 2009/0202565 A1* | 8/2009 | Labow et al. ....... A61K 39/395 424/172.1 |
| 2014/0127253 A1 | 5/2014 | Salem |
| 2018/0147224 A1 | 5/2018 | Salem |
| 2019/0136240 A1 | 5/2019 | Weiner |

FOREIGN PATENT DOCUMENTS

| | | | | |
|---|---|---|---|---|
| WO | WO2014134351 A2 * | 9/2014 | ............... | C12Q 1/68 |
| WO | 2017015427 A1 | 1/2017 | | |
| WO | WO2017191274 A2 * | 11/2017 | ............. | A61K 48/00 |

OTHER PUBLICATIONS

Yu et al. (Mar. 29, 2017) "Chimeric antigen receptor T cells: a novel therapy for solid tumors" Journal of Hematology & Oncology, 10(1), 1-13. (Year: 2017).*
Rogers, L. "Identification of Novel Cancer Immunotherapy Targets Using Sleeping Beauty Mutagenesis," poster presented at the 2015 University of Iowa Immunology Student Seminar, provided as NPL citation #16 of IDS filed Dec. 6, 2019. (Year: 2015).*
Rogers, L. "Identification of Novel Cancer Immunotherapy Targets Using Sleeping Beauty Mutagenesis," slides presented at the Autumn Immunology Conference, Nov. 21, 2015, provided as NPL citation #18 of IDS filed Dec. 6, 2019. (Year: 2015).*
Nguyen et al. (Jun. 2016) "Naïve CD8+ T cell derived tumor-specific cytotoxic effectors as a potential remedy for overcoming TGF-β immunosuppression in the tumor microenvironment" Scientific reports, 6(1), 1-10. (Year: 2016).*
Kasper et al. (2014) "Immunomodulatory activity of interferon-beta" Annals of Clinical and Translational Neurology, 1(8): 622-631. (Year: 2014).*

(Continued)

*Primary Examiner* — Teresa E Knight
*Assistant Examiner* — James Joseph Graber
(74) *Attorney, Agent, or Firm* — Quarles & Brady LLP

(57) ABSTRACT

Disclosed are compositions, kits, and methods for identifying genes that are involved in T-cell trafficking. In particular, the compositions, kits, and methods may be used to identify genes involved in T-cell trafficking and/or infiltration into tumors such as genes that encode immune checkpoint regulators and/or stimulatory agents. The disclosed compositions, kits, and methods utilize the Sleeping Beauty® transposon system in a mouse tumor model to identify genes that are involved in T-cell trafficking and infiltration into tumors. The genes identified in the disclosed methods may provide immunotherapy targets in the tumor microenvironment. The identified genes may be utilized in order to develop therapies that enhance T-cell trafficking and infiltration into tumors and/or T-cell killing of tumors such as in chimeric antigen receptor (CAR) T cell therapies.

14 Claims, 15 Drawing Sheets
Specification includes a Sequence Listing.

(56) References Cited

OTHER PUBLICATIONS

Gupta-Rossi et al. (2011) "The Adaptor-associated Kinase 1, AAK1, Is a Positive Regulator of the Notch Pathway" The Journal of Biological Chemistry, vol. 286, No. 21, pp. 18720-18730. (Year: 2011).*
Cribbs et al. (2013) "Simplified production and concentration of lentiviral vectors to achieve high transduction in primary human T cells" BMC biotechnology, 13, 1-8. (Year: 2013).*
Clark, K. et al. Phosphorylation of CRTC3 by the salt-inducible kinases controls the interconversion of classically activated and regulatory macrophages. Proceedings of the National Academy of Sciences of the United States of America 109, 16986-16991, doi:10.1073/pnas.1215450109 (2012).
Conner, S. D. et al. Identification of an adaptor-associated kinase, AAK1, as a regulator of clathrin-mediated endocytosis. The Journal of cell biology 156, 921-929, doi:10.1083/jcb.200108123 (2002).
Copeland, N.G., et al. "Harnessing transposons for cancer gene discovery." Nature Reviews Cancer 10.10 (2010): 696.
Gupta-Rossi, N. et al. The adaptor-associated kinase 1, AAK1, is a positive regulator of the Notch pathway. The Journal of biological chemistry 286, 18720-18730, doi:10.1074/jbc.M110.190769 (2011).
Henderson, D. M., et al. "A novel AAK1 splice variant functions at multiple steps of the endocytic pathway." Molecular biology of the cell 18.7 (2007): 2698-2706.
Hishiki, Takayuki, et al. "BCL3 acts as a negative regulator of transcription from the human T-cell leukemia virus type 1 long terminal repeat through interactions with TORC3." Journal of Biological Chemistry 282.39 (2007): 28335-28343.
International Searching Authority, International Search Report and Written Opinion for application PCT/US2018/028071, mailed on Aug. 2, 2018.
Kostich, W. et al. Inhibition of AAK1 Kinase as a Novel Therapeutic Approach to Treat Neuropathic Pain. The Journal of pharmacology and experimental therapeutics 358, 371-386, doi:10.1124/jpet.116.235333 (2016).
Mann, M. B., et al. Sleeping Beauty mutagenesis: exploiting forward genetic screens for cancer gene discovery. Current opinion in genetics & development 24, 16-22, doi:10.1016/j.gde.2013.11.004 (2014).
Nagato, T., et al. Combinatorial immunotherapy of polyinosinic-polycytidylic acid and blockade of programmed death-ligand 1 induce effective CD8+ T-cell responses against established tumors. Clinical cancer research : an official journal of the American Association for Cancer Research 20, 1223-1234, doi:10.1158/1078-0432.CCR-13-2781 (2014).
NCBI, Entry for Gene ID: 23131, updated Apr. 3, 2016. Accessed online at https://www.ncbi.nlm.nih.gov/gene/23131 on Oct. 25, 2019.
NCBI, Entry for Gene ID: 64784, updated Apr. 3, 2016. Accessed online at https://www.ncbi.nlm.nih.gov/gene/64784 on Oct. 25, 2019.
Riordan, J. D. et al. Sequencing methods and datasets to improve functional interpretation of sleeping beauty mutagenesis screens. BMC genomics 15, 1150, doi:10.1186/1471-2164-15-1150 (2014).
Rogers, L. "Identification of Novel Cancer Immunotherapy Targets Using Sleeping Beauty Mutagenesis," presented at the 2015 University of Iowa Immunology Student Seminar.
Rogers, L. "Immunotherapy Target Discovery In Vivo," presented at the 2015 University of Iowa Melanoma Symposium.
Rogers, L. et al. Identification of Novel Cancer Immunotherapy Targets Using Sleeping Beauty Mutagenesis, presented at the Autumn Immunology Conference, Nov. 21, 2015.
Tang, H. et al. Facilitating T Cell Infiltration in Tumor Microenvironment Overcomes Resistance to PD-L1 Blockade. Cancer cell 29, 285-296, doi:10.1016/j.ccell.2016.02.004 (2016).
Zhou et al., "In vivo discovery of immunotherapy targets in the tumour microenvironment." Nature Feb. 6, 2014;506 (7466):52-7.
Hudecek et al. Going Non-Viral: The Sleeping Beauty Transposon System Breaks on Through to the Clinical Side, Critical Reviews in Biochemistry and Molecular Biology 52(4):355-380, Published Online: Apr. 12, 2017.
Iwai et al., Cancer Immunotherapies Targeting the PD-1 Signaling Pathway, Journal of Biomedical Science 24(26), doi:10.1186/s12929-017-0329-9, Published: Apr. 4, 2017.
Rogers, L. et al. Use of Sleeping Beauty Mutagenesis to Identify Genes that Influence Intratumoral T Cell Infiltration, which was accepted for poster presentation at the American Association for Cancer Research (AACR) 2016 Meeting, Apr. 17, 2016, 4 pages.
Rogers et al., Using Sleeping Beauty Mutagenesis to Identify Novel Immunotherapy Targets in a Syngeneic Mouse Model of Melanoma, Abstract from the University of Iowa 2016 Melanoma Symposium, Apr. 2, 2016, 2 pages.

* cited by examiner

*Aak1 (AP2-associated kinase 1)*

Insertions clustered in intron 2: predicted disruption of kinase domain

Ab173329 + Ab59740 kDa
250 —
150 —
100 —
75 —
50 —
37 —

Lanes:
1. Ladder
2. EL4
3. EG7
4. ms brain (positive control)
5. ms spleen
6. ms CD8+ T cells
7. ms CD4+ T cells
8. hu CD8+ T cells
9. hu CD4+ T cells

IDENTIFICATION OF T-CELL TRAFFICKING GENES AND USES THEREOF FOR INCREASING INFILTRATION OF T-CELLS INTO SOLID TUMORS

CROSS-REFERENCE TO RELATED APPLICATIONS

The present application is the U.S. National Stage under 35 U.S.C. § 371 of International Application No. PCT/US2018/028071, filed on Apr. 18, 2018, which claims the benefit of priority under 35 U.S.C. § 119 (e) to U.S. Provisional Application No. 62/545,758, filed on Aug. 15, 2017 and to U.S. Provisional Application No. 62/486,677, filed on Apr. 18, 2017, the contents of which are incorporated herein by reference in their entireties.

STATEMENT REGARDING FEDERALLY SPONSORED RESEARCH OR DEVELOPMENT

This invention was made with government support under CA097274 awarded by the National Institutes of Health. The government has certain rights in the invention.

BACKGROUND

The field of the invention relates to compositions, kits, and methods for identifying and utilizing genes that are involved in T-cell trafficking into solid tumors. In particular, the field of the invention relates to the genes Aak1 and Crtc3 and modifying the expression of Aak1 and Crtc3 of gene products encoded by Aak1 and Crtc3 in T-cells in order to increase infiltration of the T-cells into solid tumors T cells in particular and the immune system in general have amazing potential to eliminate tumor cells throughout the body. This therapeutic potential is evidenced by the clinical success of immunotherapies designed to enhance T cell function, such as immune checkpoint blockade and chimeric antigen receptor T cell (CAR-T) therapies. Despite the remarkable progress to date, expanding success to a broader number of patients is a top priority in the field. T cell infiltration into tumors appears to be an important prerequisite for the success of both immune checkpoint blockade and CAR-T therapies. For example, patients with inflamed tumors have a better response rate to anti-PD-1 than patients whose tumors are immune excluded (T cells present at tumor border, but blocked from entry) or immune desserts (very few, or no, intratumoral T cells). Preclinical models have also demonstrated that increasing intratumoral T cell number enhances immune checkpoint blockade efficacy. Thus, increasing T cell infiltration into the tumor could have beneficial therapeutic impact.

To this end, we developed an innovative, systematic method to screen for novel therapeutic targets in T cells that impact T cell infiltration into tumors. We have identified 386 T cell genes using various cancer models, most of which have no previously described role in T cells or immunotherapy. Uses for the disclosed technology include, but are not limited to: 1) Using these genes to develop a diagnostic platform to predict immunotherapy success in patients, 2) Using these genes as the basis for developing novel co-therapies to existing immunotherapies including immune checkpoint blockade and CAR-T technologies, and 3) Using these genes as targets for novel single-agent immunotherapies—all of which would aim to improve our ability to treat human disease.

SUMMARY

Disclosed are compositions, kits, and methods for identifying genes that are involved in T-cell trafficking into tumors and activation. In particular, the compositions, kits, and methods may be used to identify genes involved in T-cell trafficking and activation in tumors such as genes that encode immune checkpoint regulators and/or stimulatory agents. The disclosed compositions, kits, and methods may utilize the Sleeping Beauty® transposon system in a tumor model system to identify genes that are involved in T-cell trafficking into tumors and activation, which may provide immunotherapy targets in the tumor microenvironment. The identified genes may be utilized in order to develop therapies that enhance T-cell trafficking into tumors and activation. Particularly disclosed are the genes Aak1 and Crtc3 which are shown to be involved in T-cell trafficking and whose expression may be modified in T-cells in order to increase infiltration and/or activation of the T-cells in solid tumors.

Also disclosed herein are genetically modified T-cells and therapeutic compositions comprising the genetically modified T-cells. As disclosed herein, T-cells may be genetically modified in order to modulate the expression of a gene that is involved in T-cell trafficking into tumors and/or activation, including, but not limited to, the genes Aak1 and Crtc3. The genetically modified T-cells disclosed herein may include T-cells that that have been genetically modified to express a chimeric antigen receptor (CAR), and in addition have been further genetically modified to modulate the expression of a gene that is involved in T-cell trafficking into tumors and/or activation, including, but not limited to, the genes Aak1 and Crtc3. As such, disclosed herein are CAR T-cells that have been generically modified further to increase in infiltration and/or activation of the CAR T-cells in solid tumors. The further generically modified CAR T-cells and therapeutic compositions comprising the further generically modified CAR T-cells may be administered to treat cancers characterized by solid tumors in a subject in need thereof.

DETAILED DESCRIPTION

Figure 1:
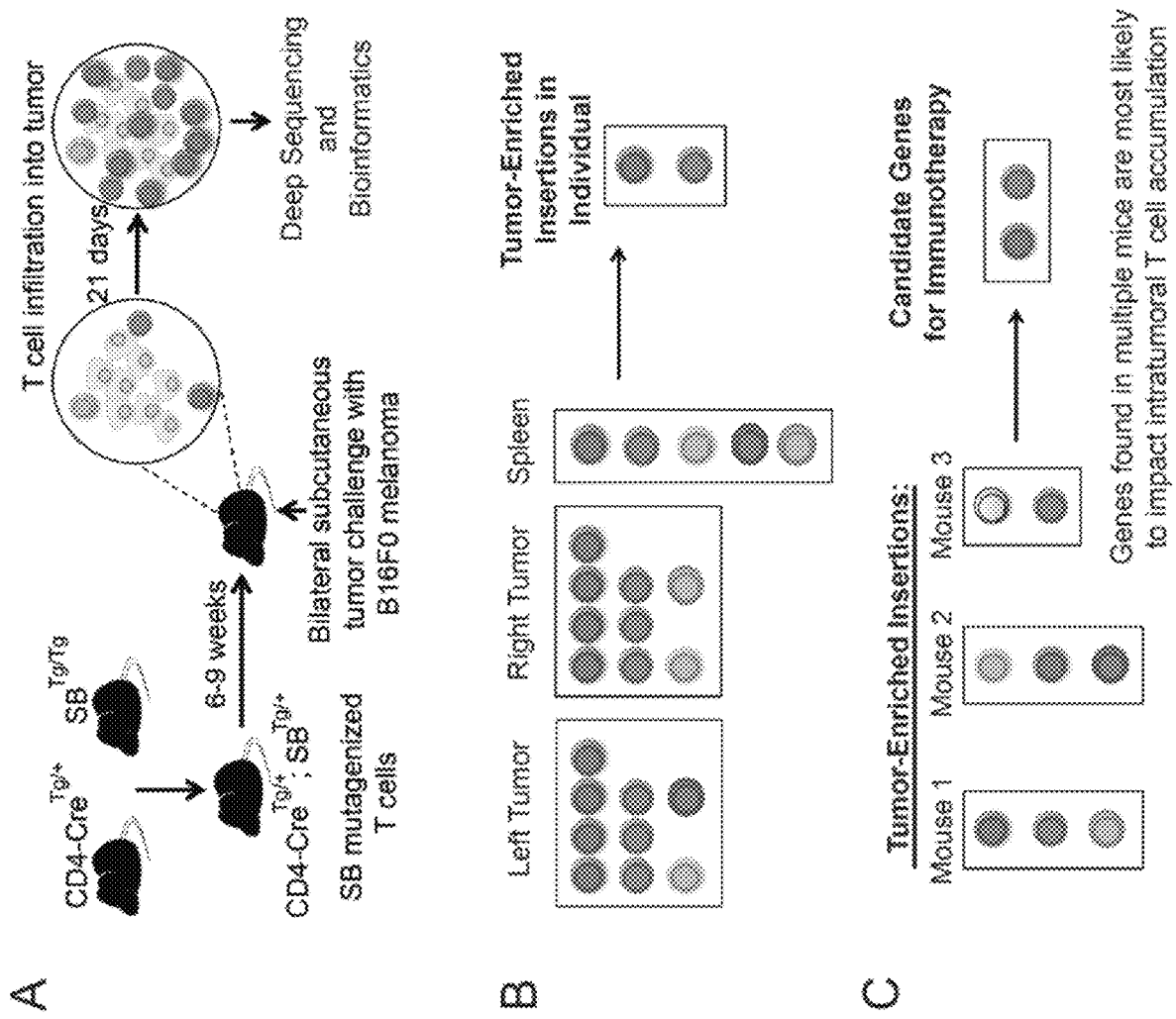
FIG. 1. Immunotherapy target discovery screen design A. Mice with T cell-specific SB transposition were injected on both flanks with 8,000 B16F0 cells in growth factor-reduced Matrigel® and tumors were allowed to grow for 21 days, at which point bilateral tumors and spleens were harvested. Genetic analysis was performed on either whole tissue or single cells suspensions of sorted CD4+ and CD8+ T cell populations. B and C. Overview of bioinformatics approach to identify candidate T cell genes involved in intratumoral T cell accumulation. Transposon insertion sites are sequenced in spleens and both tumors using Illumina Sequencing of SB amplicon libraries. Within each mouse, insertion sites identified in the spleen are used to represent background, or insertions that do not contribute to intratumoral accumulation. Insertions that are present in both tumors, but absent from spleen, within a single mouse are considered candidate genes (B). Furthermore, candidate genes are compared across animals to identify genes with greater confidence (C).

Disclosed are compositions, kits, and methods for identifying genes associated with T-cell trafficking in solid tumors and methods for treating cancer in a subject in need thereof, in particular in a subject having a solid tumor. The compositions, kits, and methods may be further described as follows.

Unless otherwise specified or indicated by context, the terms "a", "an", and "the" mean "one or more." In addition, singular nouns such as "gene," "T-cell," and "CAR T-cell" should be interpreted to mean "genes," "one or more T-cells," and "one or more CAR T-cells," respectively, unless otherwise specified or indicated by context. Similarly, the phrase "at least one", when employed herein to refer to an entity, refers to, for example, 1, 2, 3, 4, 5, 6, 7, 8, 9, 10, 15, 20, 25, 30, 35, 40, 45, 50, 75, 100, or more of that entity, including but not limited to whole number values between 1 and 100 and greater than 100.

As used herein, the term "and/or" when used in the context of a list of entities, refers to the entities being present singly or in combination. Thus, for example, the phrase "A, B, C, and/or D" includes A, B, C, and D individually, but also includes any and all combinations and subcombinations of A, B, C, and D.

As used herein, "about", "approximately", "substantially," and "significantly" will be understood by persons of ordinary skill in the art and will vary to some extent on the context in which they are used. If there are uses of the term which are not clear to persons of ordinary skill in the art given the context in which it is used, "about" and "approximately" will mean plus or minus ≤10% of the particular term and "substantially" and "significantly" will mean plus or minus >10% of the particular term.

As used herein, the terms "include" and "including" have the same meaning as the terms "comprise" and "comprising." The terms "comprise" and "comprising" should be interpreted as being "open" transitional terms that permit the inclusion of additional components further to those components recited in the claims. The terms "consist" and "consisting of" should be interpreted as being "closed" transitional terms that do not permit the inclusion of additional components other than the components recited in the claims. The term "consisting essentially of" should be interpreted to be partially closed and allowing the inclusion only of additional components that do not fundamentally alter the nature of the claimed subject matter.

The terms "subject," "patient," or "host" may be used interchangeably herein and may refer to human or non-human animals. Non-human animals may include, but are not limited to non-human primates, dogs, and cats.

The terms "subject," "patient," or "individual" may be used to a human or non-human animal having or at risk for acquiring a cell proliferative disease or disorder. Individuals who are treated with the compositions disclosed herein may be at risk for cancer or may have already acquired cancer including cancers characterized by solid tumors.

As used herein, the terms "condition", "disease condition", "disease", "disease state", and "disorder" refer to physiological states in which diseased cells can be targeted with the genetically modified cells disclosed herein. Any solid tumor cell that expresses a tumor-associated epitope can be targeted with the genetically modified cells disclosed herein, and any disease, disorder, or condition associated with solid tumors can be treated, and/or a symptom thereof can be ameliorated, using the genetically modified cells disclosed herein.

As used herein, the phrase "disease targeted by genetically modified cells" encompasses the targeting of any cell involved in any manner in any disease by the genetically modified cells of the presently disclosed subject matter, irrespective of whether the genetically modified cells target diseased cells or healthy cells to effectuate a therapeutically beneficial result. In some embodiments, the genetically modified cells target diseased cells only in order to effectuate a therapeutically beneficial result. The genetically modified cells include but are not limited to genetically modified T-cells, NK cells, hematopoietic stem cells, pluripotent embryonic stem cells, and embryonic stem cells. The genetically modified cells may express CARs, which CARs can target any of the antigens and/or epitopes expressed on the surface of target cells, including epitopes expressed on the surface of various cancer and tumor cells.

As used herein, the term "tumor" refers to any neoplastic cell growth and/or proliferation, whether malignant or benign, and all pre-cancerous and cancerous cells and tissues. The terms "cancer" and "tumor" are used interchangeably herein and can refer to both primary and metastasized solid tumors and carcinomas of any tissue in a subject, including but not limited to breast; colon; rectum; lung; oropharynx; hypopharynx; esophagus; stomach; pancreas; liver; gallbladder; bile ducts; small intestine; urinary tract including kidney, bladder, and urothelium; female genital tract including cervix, uterus, ovaries (e.g., choriocarcinoma and gestational trophoblastic disease); male genital tract including prostate, seminal vesicles, testes and germ cell tumors; endocrine glands including thyroid, adrenal, and pituitary; skin (e.g., hemangiomas and melanomas), bone or soft tissues; blood vessels (e.g., Kaposi's sarcoma); brain, nerves, eyes, and meninges (e.g., astrocytomas, gliomas, glioblastomas, retinoblastomas, neuromas, neuroblastomas, Schwannomas, and meningiomas). As used herein, the terms "cancer and "tumor" are also intended to refer to multicellular tumors as well as individual neoplastic or pre-neoplastic cells. In some embodiments, a cancer or a tumor comprises a cancer or tumor of an epithelial tissue such as, but not limited to a carcinoma. In some embodiments, a tumor is an adenocarcinoma, which in some embodiments is an adenocarcinoma of the pancreas, breast, ovary, colon, or rectum, and/or a metastatic cell derived therefrom.

As used herein, the phrase "tumor-associated" refers to a disease, disorder, condition, status, antigen, epitope, or glycosylation state that is primarily or secondarily the result of the presence of a tumor or cancer or a cell's status as being a tumor cell or a cancer cell. As such, in some embodiments a tumor-associated antigen or epitope is an antigen or epitope that is present on a tumor cell or a cancer cell or a cell that results from the presence of a tumor or cancer (e.g., an endothelial cell that results from tumor-associated angiogenesis).

As used herein, the phrases "tumor-specific" and "tumor-exclusive" refer to an antigen or an epitope thereof that is expressed by a tumor cell but that is substantially or completely absent from a normal cell from which the tumor cell was derived. In some embodiments, a tumor-specific or tumor-exclusive antigen or epitope is one that is overexpressed in tumor cells relative to normal cells. In some embodiments, a tumor-specific or tumor-exclusive antigen or epitope can be targeted by genetically modified cells as disclosed herein.

As used herein, the phrases "genetically modified cells", "redirected cells", "genetically engineered cells", and "modified cells" refer to cells that have been genetically altered in order to modulate the expression of one or more genes identified as being involved in T-cell infiltration and/or activation in a solid tumor as disclosed herein.

Immune Cells and Responses

As used herein, the phrase "immune cell" refers to the cells of a mammalian immune system including but not limited to antigen presenting cells, B-cells, basophils, cytotoxic T-cells, dendritic cells, eosinophils, granulocytes, helper T-cells, leukocytes, lymphocytes, macrophages, mast cells, memory cells, monocytes, natural killer cells, neutrophils, phagocytes, plasma cells and T-cells. Immune cells include immune cells that have been explanted from a subject, genetically modified (e.g., CAR T cells) and reintroduced into the subject (i.e., where the T cells are allogeneic).

As used herein, the phrase "immune response" refers to immunities including but not limited to innate immunity, humoral immunity, cellular immunity, immunity, inflammatory response, acquired (adaptive) immunity, autoimmunity, and/or overactive immunity.

As used herein, the phrase "target cell" refers to any cell that is associated with a disease, disease state, or disorder that can be targeted by the genetically modified cells disclosed herein (including but not limited to genetically modified T-cells, NK cells, hematopoietic stem cells, pluripotent stem cells, and embryonic stem cells). In some embodiments, a target cell is a tumor cell, a cancer cell, or a cancer stem cell that expresses an epitope associated with a solid tumor.

As used herein, the terms "T-cell" and "T-lymphocyte" are interchangeable and used synonymously. Examples include, but are not limited to, naive T cells, central memory T cells, effector memory T cells, and combinations thereof.

Polypeptides

Reference is made herein to peptides, polypeptides, proteins and compositions comprising peptides, polypeptides, and proteins. As used herein, a polypeptide and/or protein is defined as a polymer of amino acids, typically of length ≥100 amino acids (Garrett & Grisham, Biochemistry, $2^{nd}$ edition, 1999, Brooks/Cole, 110). A peptide is defined as a short polymer of amino acids, of a length typically of 20 or less amino acids, and more typically of a length of 12 or less amino acids (Garrett & Grisham, Biochemistry, $2^{nd}$ edition, 1999, Brooks/Cole, 110).

As disclosed herein, exemplary peptides, polypeptides, proteins may comprise, consist essentially of, or consist of any reference amino acid sequence disclosed herein, or variants of the peptides, polypeptides, and proteins may comprise, consist essentially of, or consist of an amino acid sequence having at least about 80%, 90%, 95%, 96%, 97%, 98%, or 99% sequence identity to any amino acid sequence disclosed or contemplated herein. Variant peptides, polypeptides, and proteins may include peptides, polypeptides, and proteins having one or more amino acid substitutions, deletions, additions and/or amino acid insertions relative to a reference peptide, polypeptide, or protein. Also disclosed are nucleic acid molecules that encode the disclosed peptides, polypeptides, and proteins (e.g., polynucleotides that encode any of the peptides, polypeptides, and proteins disclosed herein and variants thereof).

The term "amino acid," includes but is not limited to amino acids contained in the group consisting of alanine (Ala or A), cysteine (Cys or C), aspartic acid (Asp or D), glutamic acid (Glu or E), phenylalanine (Phe or F), glycine (Gly or G), histidine (His or H), isoleucine (Ile or I), lysine (Lys or K), leucine (Leu or L), methionine (Met or M), asparagine (Asn or N), proline (Pro or P), glutamine (Gln or Q), arginine (Arg or R), serine (Ser or S), threonine (Thr or T), valine (Val or V), tryptophan (Trp or W), and tyrosine (Tyr or Y) residues. The term "amino acid residue" also may include amino acid residues contained in the group consisting of homocysteine, 2-Aminoadipic acid, N-Ethylasparagine, 3-Aminoadipic acid, Hydroxylysine, β-alanine, β-Amino-propionic acid, allo-Hydroxylysine acid, 2-Aminobutyric acid, 3-Hydroxyproline, 4-Aminobutyric acid, 4-Hydroxyproline, piperidinic acid, 6-Aminocaproic acid, Isodesmosine, 2-Aminoheptanoic acid, allo-Isoleucine, 2-Aminoisobutyric acid, N-Methylglycine, sarcosine, 3-Aminoisobutyric acid, N-Methylisoleucine, 2-Aminopimelic acid, 6-N-Methyllysine, 2,4-Diaminobutyric acid, N-Methylvaline, Desmosine, Norvaline, 2,2'-Diaminopimelic acid, Norleucine, 2,3-Diaminopropionic acid, Ornithine, and N-Ethylglycine. Typically, the amide linkages of the peptides are formed from an amino group of the backbone of one amino acid and a carboxyl group of the backbone of another amino acid.

The amino acid sequences contemplated herein may include conservative amino acid substitutions relative to a reference amino acid sequence. For example, a variant peptides, polypeptides, and proteins as contemplated herein may include conservative amino acid substitutions relative to an amino acid sequence of a reference peptide, polypeptide, or protein. "Conservative amino acid substitutions" are those substitutions that are predicted to interfere least with the properties of the reference peptide, polypeptide, or protein. In other words, conservative amino acid substitutions substantially conserve the structure and the function of the reference peptide, polypeptide, or protein. The following table provides a list of exemplary conservative amino acid substitutions.

Table of Conservative Amino Acid Substitutions

| Original Residue | Conservative Substitution |
| --- | --- |
| Ala | Gly, Ser |
| Arg | His, Lys |
| Asn | Asp, Gln, His |
| Asp | Asn, Glu |
| Cys | Ala, Ser |
| Gln | Asn, Glu, His |
| Glu | Asp, Gln, His |
| Gly | Ala |
| His | Asn, Arg, Gln, Glu |
| Ile | Leu, Val |
| Leu | Ile, Val |
| Lys | Arg, Gln, Glu |
| Met | Leu, Ile |
| Phe | His, Met, Leu, Trp, Tyr |
| Ser | Cys, Thr |
| Thr | Ser, Val |
| Trp | Phe, Tyr |
| Tyr | His, Phe, Trp |
| Val | Ile, Leu, Thr |

"Non-conservative amino acid substitutions" are those substitutions that are predicted to interfere most with the properties of the reference peptide, polypeptide, or protein. For example, a non-conservative amino acid substitution might replace a basic amino acid at physiological pH such as Arg, His, or Lys, with a non-basic or acidic amino acid at physiological pH such as Asp or Glu. A non-conservative amino acid substitution might replace a non-polar amino acid at physiological pH such as Ala, Gly, Ile, Leu, Phe, or Val, with a polar amino acid at physiological pH such as Arg, Asp, Glu, His, or Lys.

Variants comprising deletions relative to a reference amino acid sequence or nucleotide sequence are contemplated herein. A "deletion" refers to a change in a reference amino acid sequence that results in the absence of one or more amino acid residues. A deletion removes at least 1, 2, 3, 4, 5, 10, 20, 50, 100, or 200 amino acids residues or a range of amino acid residues bounded by any of these values (e.g., a deletion of 5-10 amino acids). A deletion may include an internal deletion or a terminal deletion (e.g., an N-terminal truncation or a C-terminal truncation of a reference polypeptide). A "variant" of a reference polypeptide sequence may include a deletion relative to the reference polypeptide sequence (e.g., relative to any of SEQ ID NOs:2-5 and 7-9).

The words "insertion" and "addition" refer to changes in an amino acid sequence resulting in the addition of one or more amino acid residues. An insertion or addition may refer to 1, 2, 3, 4, 5, 10, 20, 30, 40, 50, 60, 70, 80, 90, 100, 150, or 200 amino acid residues or a range of amino acid residues bounded by any of these values (e.g., an insertion or addition of 5-10 amino acids). A "variant" of a reference polypeptide sequence may include an insertion or addition relative to the reference polypeptide sequence (e.g., relative to any of SEQ ID NOs:2-5 and 7-9).

A "fusion polypeptide" refers to a polypeptide comprising at the N-terminus, the C-terminus, or at both termini of its amino acid sequence a heterologous amino acid sequence, for example, a heterologous amino acid sequence that extends the half-life of the fusion polypeptide in serum. A "variant" of a reference polypeptide sequence may include a fusion polypeptide comprising the reference polypeptide.

A "fragment" is a portion of an amino acid sequence which is identical in sequence to but shorter in length than a reference sequence (e.g., a fragment of any of SEQ ID NOs:2-5 and 7-9). A fragment may comprise up to the entire length of the reference sequence, minus at least one amino acid residue. For example, a fragment may comprise from 5 to 1000 contiguous amino acid residues of a reference polypeptide. In some embodiments, a fragment may comprise at least 5, 10, 15, 20, 25, 30, 40, 50, 60, 70, 80, 90, 100, 150, 250, or 500 contiguous amino acid residues of a reference polypeptide; or a fragment may comprise no more than 5, 10, 15, 20, 25, 30, 40, 50, 60, 70, 80, 90, 100, 150, 250, or 500 contiguous amino acid residues of a reference polypeptide; or a fragment may comprise a range of contiguous amino acid residues of a reference polypeptide bounded by any of these values (e.g., 40-80 contiguous amino acid residues). Fragments may be preferentially selected from certain regions of a molecule. The term "at least a fragment" encompasses the full length polypeptide. A "variant" of a reference polypeptide sequence may include a fragment of the reference polypeptide sequence.

"Homology" refers to sequence similarity or, interchangeably, sequence identity, between two or more polypeptide sequences. Homology, sequence similarity, and percentage sequence identity may be determined using methods in the art and described herein.

The phrases "percent identity" and "% identity," as applied to polypeptide sequences, refer to the percentage of residue matches between at least two polypeptide sequences aligned using a standardized algorithm. Methods of polypeptide sequence alignment are well-known. Some alignment methods take into account conservative amino acid substitutions. Such conservative substitutions, explained in more detail above, generally preserve the charge and hydrophobicity at the site of substitution, thus preserving the structure (and therefore function) of the polypeptide. Percent identity for amino acid sequences may be determined as understood in the art. (See, e.g., U.S. Pat. No. 7,396,664, which is incorporated herein by reference in its entirety). A suite of commonly used and freely available sequence comparison algorithms is provided by the National Center for Biotechnology Information (NCBI) Basic Local Alignment Search Tool (BLAST) (Altschul, S. F. et al. (1990) J. Mol. Biol. 215:403 410), which is available from several sources, including the NCBI, Bethesda, Md., at its website. The BLAST software suite includes various sequence analysis programs including "blastp," that is used to align a known amino acid sequence with other amino acids sequences from a variety of databases.

Percent identity may be measured over the length of an entire defined polypeptide sequence, for example, as defined by a particular SEQ ID number, or may be measured over a shorter length, for example, over the length of a fragment taken from a larger, defined polypeptide sequence, for instance, a fragment of at least 15, at least 20, at least 30, at least 40, at least 50, at least 100, at least 150, at least 200, at least 250, at least 300, at least 350, at least 400, at least 450, at least 500, at least 550, at least 600, at least 650, or at least 700 contiguous amino acid residues; or a fragment of no more than 15, 20, 30, 40, 50, 100, 150, 200, 250, 300, 350, 400, 450, 500, 550, 600, 650, or 700 amino acid residues; or over a range bounded by any of these values (e.g., a range of 500-600 amino acid residues) Such lengths are exemplary only, and it is understood that any fragment length supported by the sequences shown herein, in the tables, figures or Sequence Listing, may be used to describe a length over which percentage identity may be measured.

In some embodiments, a "variant" of a particular polypeptide sequence may be defined as a polypeptide sequence having at least 20% sequence identity to the particular polypeptide sequence over a certain length of one of the polypeptide sequences using blastp with the "BLAST 2 Sequences" tool available at the National Center for Biotechnology Information's website. (See Tatiana A. Tatusova, Thomas L. Madden (1999), "Blast 2 sequences—a new tool for comparing protein and nucleotide sequences", FEMS Microbiol Lett. 174:247-250). Such a pair of polypeptides may show, for example, at least 20%, at least 30%, at least 40%, at least 50%, at least 60%, at least 70%, at least 80%, at least 90%, at least 91%, at least 92%, at least 93%, at least 94%, at least 95%, at least 96%, at least 97%, at least 98%, or at least 99% or greater sequence identity over a certain defined length of one of the polypeptides, or range of percentage identity bounded by any of these values (e.g., range of percentage identity of 80-99%).

The disclosed fusion polypeptides may comprise an amino acid sequence fused directly to a heterologous amino acid sequence or fused indirectly via a linker sequence. Suitable linker sequences may include amino acid sequences of 5, 6, 7, 8, 9, 10, 11, 12, 13, 14, or 15 amino acids or more, or a range bounded by any of these values (e.g., a linker of 5-25 amino acids). In some embodiments, the linker sequence comprises only glycine and serine residues.

Fusion polypeptide disclosed herein may include an amino acid tag sequence, for example, which may be utilized for purifying and or identifying the fusion polypeptide. Suitable amino acid tag sequences may include, but are not limited to, histidine tag sequences comprising 5-10 histidine residues.

A variant polypeptide may have substantially the same functional activity as a reference polypeptide. For example, a variant polypeptide may exhibit or more biological activities associated with binding a ligand, exhibiting fluorescence, and/or enzymatic activity.

Polynucleotides

Reference also is made herein to nucleic acid and nucleic acid sequences. The terms "nucleic acid" and "nucleic acid sequence" refer to a nucleotide, oligonucleotide, polynucleotide (which terms may be used interchangeably), or any fragment thereof. These phrases also refer to DNA or RNA of genomic or synthetic origin (which may be single-stranded or double-stranded and may represent the sense or the antisense strand).

The term "polynucleotide" as used herein includes but is not limited to DNA, RNA, complementary DNA (cDNA), messenger RNA (mRNA), ribosomal RNA (rRNA), small hairpin RNA (shRNA), small nuclear RNA (snRNA), short nucleolar RNA (snoRNA), microRNA (miRNA), genomic DNA, synthetic DNA, synthetic RNA, and/or tRNA.

The terms "percent identity" and "% identity," as applied to polynucleotide sequences, refer to the percentage of residue matches between at least two polynucleotide sequences aligned using a standardized algorithm (e.g., aligned with a reference sequence such as SEQ ID NO:1 or SEQ ID NO:6). Such an algorithm may insert, in a standardized and reproducible way, gaps in the sequences being compared in order to optimize alignment between two sequences, and therefore achieve a more meaningful comparison of the two sequences. Percent identity for a nucleic acid sequence may be determined as understood in the art. (See, e.g., U.S. Pat. No. 7,396,664, which is incorporated herein by reference in its entirety). A suite of commonly used and freely available sequence comparison algorithms is provided by the National Center for Biotechnology Information (NCBI) Basic Local Alignment Search Tool (BLAST) (Altschul, S. F. et al. (1990) J. Mol. Biol. 215:403 410), which is available from several sources, including the NCBI, Bethesda, Md., at its website. The BLAST software suite includes various sequence analysis programs including "blastn," that is used to align a known polynucleotide sequence with other polynucleotide sequences from a variety of databases. Also available is a tool called "BLAST 2 Sequences" that is used for direct pairwise comparison of two nucleotide sequences. "BLAST 2 Sequences" can be accessed and used interactively at the NCBI website. The "BLAST 2 Sequences" tool can be used for both blastn and blastp (discussed above).

Percent identity may be measured over the length of an entire defined polynucleotide sequence or may be measured over a shorter length, for example, over the length of a fragment taken from a larger, defined sequence (e.g. SEQ ID NO:1 or SEQ ID NO:6), for instance, a fragment of at least 20, at least 30, at least 40, at least 50, at least 70, at least 100, or at least 200 contiguous nucleotides. Such lengths are exemplary only, and it is understood that any fragment length may be used to describe a length over which percentage identity may be measured.

A "full length" polynucleotide sequence of a gene is one containing at least a translation initiation codon (e.g., methionine) followed by an open reading frame and a translation termination codon. A "full length" polynucleotide sequence encodes a "full length" polypeptide sequence (e.g. SEQ ID NO:1 or SEQ ID NO:6).

A "variant," "mutant," or "derivative" of a particular nucleic acid sequence may be defined as a nucleic acid sequence having at least 50% sequence identity to the particular nucleic acid sequence over a certain length of one of the nucleic acid sequences using blastn with the "BLAST 2 Sequences" tool available at the National Center for Biotechnology Information's website. (See Tatiana A. Tatusova, Thomas L. Madden (1999), "Blast 2 sequences—a new tool for comparing protein and nucleotide sequences", FEMS Microbiol Lett. 174:247-250). In some embodiments a variant polynucleotide may show, for example, at least 60%, at least 70%, at least 80%, at least 90%, at least 91%, at least 92%, at least 93%, at least 94%, at least 95%, at least 96%, at least 97%, at least 98%, or at least 99% or greater sequence identity over a certain defined length relative to a reference polynucleotide (e.g. relative to SEQ ID NO:1 or SEQ ID NO:6).

Nucleic acid sequences that do not show a high degree of identity may nevertheless encode similar amino acid sequences due to the degeneracy of the genetic code. It is understood that changes in a nucleic acid sequence can be made using this degeneracy to produce multiple nucleic acid sequences that all encode substantially the same protein.

A "recombinant nucleic acid" is a sequence that is not naturally occurring or has a sequence that is made by an artificial combination of two or more otherwise separated segments of sequence. This artificial combination is often accomplished by chemical synthesis or, more commonly, by the artificial manipulation of isolated segments of nucleic acids, e.g., by genetic engineering techniques such as those described in Sambrook, J. et al. (1989) Molecular Cloning: A Laboratory Manual, $2^{nd}$ ed., vol. 1 3, Cold Spring Harbor Press, Plainview N.Y. The term recombinant includes nucleic acids that have been altered solely by addition, substitution, or deletion of a portion of the nucleic acid. Frequently, a recombinant nucleic acid may include a nucleic acid sequence operably linked to a promoter sequence. Such a recombinant nucleic acid may be part of a vector that is used, for example, to transform a cell.

Transgene Expression

The genes disclosed herein that are involved in cell trafficking and/or activation in solid tumors may be overexpressed in cells, for example via transfection and/or transformation with an expression cassette. "Transfection" and "transformation" describe a process by which exogenous DNA is introduced into a recipient cell. Transfection and transformation may occur under natural or artificial conditions according to various methods well known in the art, and may rely on any known method for the insertion of foreign nucleic acid sequences into a prokaryotic or eukaryotic host cell. The method for transfection or transformation is selected based on the type of host cell being transformed and may include, but is not limited to, bacteriophage or viral infection, electroporation, heat shock, lipofection, and particle bombardment. The terms "transfected cells" and "transformed cells" include stably transfected cells or transformed cells in which the inserted DNA is capable of replication either as an autonomously replicating plasmid or as part of the host chromosome, as well as transiently transfected cells or transformed cells which express the inserted DNA or RNA for limited periods of time. The introduced gene or sequence can also be called a "cloned", "foreign", or "heterologous" gene or sequence or a "transgene", and can include regulatory and/or control sequences, such as start, stop, promoter, signal, secretion, or other sequences used by a cell's genetic machinery. The gene or sequence can include nonfunctional sequences or sequences with no known function. A host cell that receives and expresses introduced DNA or RNA has been "transformed" and is a "transformant" or a "clone", and is "transgenic". The DNA or RNA introduced to a host cell can come from any source, including cells of the same genus or species as the host cell, or cells of a different genus or species The polynucleotide sequences contemplated herein may be present in expression cassettes and/or expression vectors (e.g., an expression vector comprising an expression cassette). For example, the vectors may comprise a polynucleotide encoding an ORF of a recombinant protein (e.g., an exogenous sensor as disclosed herein). The polynucleotide present in the vector may be operably linked to a promoter (e.g., a eukaryotic promoter or prokaryotic promoter). "Operably linked" refers to the situation in which a first nucleic acid sequence is placed in a functional relationship with a second nucleic acid sequence. For instance, a promoter is operably linked to a coding sequence if the promoter affects the transcription or expression of the coding sequence. Operably linked DNA sequences may be in close proximity or contiguous and, where necessary to join two protein coding regions, in the same reading frame. Vectors contemplated herein may comprise a heterologous promoter (e.g., a eukaryotic or prokaryotic promoter) operably linked to a polynucleotide that encodes a protein. A "heterologous promoter" refers to a promoter that is not the native or endogenous promoter for the protein or RNA that is being expressed. For example, a heterologous promoter for a LAMP may include a eukaryotic promoter or a prokaryotic promoter that is not the native, endogenous promoter for the LAMP.

As used herein, "expression" refers to the process by which a polynucleotide is transcribed from a DNA template (such as into and mRNA or other RNA transcript) and/or the process by which a transcribed mRNA is subsequently translated into peptides, polypeptides, or proteins. Transcripts and encoded polypeptides may be collectively referred to as "gene product." If the polynucleotide is derived from genomic DNA, expression may include splicing of the mRNA in a eukaryotic cell.

As used herein, an "expression cassette" minimally refers to a recombinant polynucleotide comprising a promoter operably linked to a recombinant coding sequence. An expression cassette may be present in a vector (e.g., an episomal vector which is transfected into a cell and remains episomal and/or which recombines into the genome of the cell). A vector may include one or more expression cassettes which express one or more coding sequences (e.g., one or more coding sequences for sensors as disclosed herein).

Compositions

A "composition comprising a given polypeptide" and a "composition comprising a given polynucleotide" refer broadly to any composition containing the given polynucleotide or amino acid sequence. The composition may comprise a dry formulation or an aqueous solution. The compositions may be stored in any suitable form including, but not limited to, freeze-dried form and may be associated with a stabilizing agent such as a carbohydrate. The compositions may be aqueous solution containing salts (e.g., NaCl), detergents (e.g., sodium dodecyl sulfate; SDS), and other components.

"Substantially isolated or purified" nucleic acid or amino acid sequences are contemplated herein. The term "substantially isolated or purified" refers to nucleic acid or amino acid sequences that are removed from their natural environment, and are at least 60% free, preferably at least 75% free, and more preferably at least 90% free, even more preferably at least 95% free from other components with which they are naturally associated.

Vectors

The term "vector" refers to some means by which DNA fragments can be introduced into a host organism or host tissue. There are various types of vectors including plasmid, bacteriophages, cosmids, viruses, and bacteria. As used herein, a "viral vector" (e.g., an adenovirus, Sendai virus, or measles virus vector) refers to recombinant viral nucleic acid that has been engineered to express a heterologous polypeptide. The recombinant viral nucleic acid typically includes cis-acting elements for expression of the heterologous polypeptide. The recombinant viral nucleic acid typically is capable of being packaged into a helper virus that is capable of infecting a host cell. For example, the recombinant viral nucleic acid may include cis-acting elements for packaging. Typically, the viral vector is not replication competent or is attenuated. An "attenuated recombinant virus" refers to a virus that has been genetically altered by modern molecular biological methods (e.g., restriction endonuclease and ligase treatment, and rendered less virulent than wild type), typically by deletion of specific genes. For example, the recombinant viral nucleic acid may lack a gene essential for the efficient production or essential for the production of infectious virus.

Any of the conventional vectors used for expression in eukaryotic cells may be used for directly introducing DNA into a cell. Expression vectors containing regulatory elements from eukaryotic viruses may be used in eukaryotic expression vectors (e.g., vectors containing SV40, CMV, or retroviral promoters or enhancers). Exemplary vectors include those that express proteins under the direction of such promoters as the SV40 early promoter, SV40 later promoter, metallothionein promoter, human cytomegalovirus promoter, murine mammary tumor virus promoter, and Rous sarcoma virus promoter. Therapeutic quantities of plasmid DNA can be produced for example, by fermentation in *E. coli*, followed by purification. Aliquots from the working cell bank are used to inoculate growth medium, and grown to saturation in shaker flasks or a bioreactor according to well known techniques. Plasmid DNA can be purified using standard bioseparation technologies such as solid phase anion-exchange resins. If required, supercoiled DNA can be isolated from the open circular and linear forms using gel electrophoresis or other methods. Purified plasmid DNA can be prepared for injection using a variety of formulations (e.g., lyophilized DNA which may be reconstituted in sterile phosphate-buffered saline (PBS)). The purified DNA may be introduced to a subject by any suitable method (e.g., intramuscular (IM) or intradermal (ID) administration).

The term "vector" refers to some means by which nucleic acid (e.g., DNA) can be introduced into a host organism or host tissue. There are various types of vectors including plasmid vector, bacteriophage vectors, cosmid vectors, bacterial vectors, and viral vectors. As used herein, a "vector" may refer to a recombinant nucleic acid that has been engineered to express a heterologous polypeptide (e.g., the fusion proteins disclosed herein). The recombinant nucleic acid typically includes cis-acting elements for expression of the heterologous polypeptide.

Any of the conventional vectors used for expression in eukaryotic cells may be used for directly introducing DNA into a subject. Expression vectors containing regulatory elements from eukaryotic viruses may be used in eukaryotic expression vectors (e.g., vectors containing SV40, CMV, or retroviral promoters or enhancers). Exemplary vectors include those that express proteins under the direction of such promoters as the SV40 early promoter, SV40 later promoter, metallothionein promoter, human cytomegalovirus promoter, murine mammary tumor virus promoter, and Rous sarcoma virus promoter. Expression vectors as contemplated herein may include eukaryotic or prokaryotic control sequences that modulate expression of a heterologous protein (e.g. the fusion protein disclosed herein). Prokaryotic expression control sequences may include constitutive or inducible promoters (e.g., T3, T7, Lac, trp, or phoA), ribosome binding sites, or transcription terminators.

The vectors contemplated herein may be introduced and propagated in a prokaryote, which may be used to amplify copies of a vector to be introduced into a eukaryotic cell or as an intermediate vector in the production of a vector to be introduced into a eukaryotic cell (e.g. amplifying a plasmid as part of a viral vector packaging system). A prokaryote may be used to amplify copies of a vector.

The presently disclosed methods may include delivering one or more polynucleotides, such as or one or more vectors as described herein, one or more transcripts thereof, and/or one or proteins transcribed therefrom, to a host cell. Further contemplated are host cells produced by such methods, and organisms (such as animals, plants, or fungi) comprising or produced from such cells. The disclosed extracellular vesicles may be prepared by introducing vectors that express mRNA encoding a fusion protein as contemplated herein. Conventional viral and non-viral based gene transfer methods can be used to introduce nucleic acids in mammalian cells or target tissues. Non-viral vector delivery systems include DNA plasmids, RNA (e.g. a transcript of a vector described herein), naked nucleic acid, and nucleic acid complexed with a delivery vehicle, such as a liposome. Viral vector delivery systems include DNA and RNA viruses, which have either episomal or integrated genomes after delivery to the cell.

In the methods contemplated herein, a host cell may be transiently or non-transiently transfected (i.e., stably transfected) with one or more vectors described herein. In some embodiments, a cell is transfected as it naturally occurs in a subject (i.e., in situ). In some embodiments, a cell that is transfected is taken from a subject (i.e., explanted). In some embodiments, the cell is derived from cells taken from a subject, such as a cell line. Suitable cells may include stem cells (e.g., embryonic stem cells and pluripotent stem cells). A cell transfected with one or more vectors described herein may be used to establish a new cell line comprising one or more vector-derived sequences. In the methods contemplated herein, a cell may be transiently transfected with the components of a system as described herein (such as by transient transfection of one or more vectors, or transfection with RNA), and modified through the activity of a complex, in order to establish a new cell line comprising cells containing the modification but lacking any other exogenous sequence.

Genetic Modification Using CRISPR/Cas9 Systems

Cells comprising genes identified herein that are involved in T cell trafficking and/or activation in solid tumors may be genetically modified in order to delete or otherwise inactivate the genes. The cells may be modified in particular using CRISPR/Cas9 systems as known in the art, e.g., to delete or otherwise inactivate one or more genes identified herein that are involved in T cell trafficking and/or activation in solid tumors. (See, e.g., Wang et al., CRISP/Cas9 in Genome Editing and Beyond," Ann Rev Biochem. Vol. 85:227-264 (June 2016); the content of which is incorporated herein by reference in its entirety.

Identification of Genes Involved in T Cell Trafficking and Activation in Solid Tumors Via the Sleeping Beauty® (SB) Transposon System The disclosed compositions, kits, and methods may include or utilize systems for identify genes associated with T-cell trafficking and activation in solid tumors. In some embodiments, the disclosed compositions, kits, and methods may include or utilize Sleeping Beauty® transposon system in order to identify genes that are involved in T-cell trafficking and/or T-cell infiltration into tumors. The Sleeping Beauty® (SB) transposon system comprises the Sleeping Beauty® (SB) transposase, which is a Tc1/mariner-type transposase, and a transposon that is designed to insert specific sequences of DNA into genomic DNA at a target sequence. (See Plasterk R H (September 1993). "Molecular mechanisms of transposition and its control." Cell 74 (5): 781-786. doi: 10.1016/0092-8674 (93) 90458-3). In the SB transposon system, the transposon is translocated from one DNA site to another in a simple, cut-and-paste manner (in which a defined DNA segment is excised from one DNA molecule and moved to another site in the same or different DNA molecule or genome. Like all Tc1/mariner-type transposases, the SB transposase inserts a transposon into a "TA" dinucleotide base pair in a recipient DNA sequence. (See Plasterk RH, Izsvák Z, Ivics Z (August 1999). "Resident aliens: the Tc1/mariner superfamily of transposable elements." Trends Genet. 15 (8): 326-332. doi: 10.1016/S0168-9525 (99) 01777-1). The insertion site can be elsewhere in the same DNA molecule, or in another DNA molecule or chromosome. In mammalian genomes, including humans, there are approximately 200 million TA dinucleotide sites which provide targets for SB transposition. The TA dinucleotide insertion site is duplicated in the process of transposon integration, which is the hallmark of SB transposition. The transposase can be encoded either within the transposon or the transposase can be provided in trans, in which case the transposon becomes a non-autonomous element. Non-autonomous SB transposons are useful as genetic tools because after insertion they cannot independently continue to excise and re-insert. As such, non-autonomous SB transposons can be used to create gain-of-function mutations or loss-of-function mutations in order to identify genes associated with a desired biological activity. For example, in the present application, non-autonomous SB transposons were used to identify genes that are involved in Tcell trafficking and/or T-cell infiltration into tumors.

Others have used shRNA libraries targeting portions of the genome to successfully identify a gene in vivo that increased T cell proliferation in a different murine tumor model. (See Zhou et al., "In vivo discovery of immunotherapy targets in the tumour microenvironment." Nature 2014 Feb. 6; 506(7466):52-7). Key improvements in the screening strategy disclosed herein include, but are not limited to, whole genome coverage and gain- and loss-of-function mutation capabilities. Additionally, we have successfully identified three genes in our preliminary studies, and have potential to identify more upon experimental expansion. Additional research plans include expanding our current studies to identify additional gene candidates, validation experiments of gene candidates we discover, and determining whether these candidates augment current therapeutic strategies in vivo.

The disclosed methods may be utilized to identify genes associated with T cell trafficking and/or infiltration into a variety of tumors and/or T cell activation against tumors, which may include but are not limited to melanomas, adenocarcinoma, sarcomas, and teratocarcinomas. In particular, the disclosed methods may be utilized to identify genes associated with T cell trafficking and/or infiltration into a variety of tumors and/or T cell activation against tumors such as tumors of the skin, adrenal gland, bladder, bone, bone marrow, brain, breast, cervix, colon, gall bladder, ganglia, gastrointestinal tract, heart, kidney, liver, lung, muscle, ovary, pancreas, parathyroid, prostate, testis, thymus, and uterus.

Genes involved in T-cell trafficking and activation in solid tumors may include, but are not limited to: Aak1, 1300002E11Rik, Ehhadh, Map7d1, Ptprd, Smr3a, Susd4, Wdr59, Astn2, Gpatch8, Cpa6, Cpne4, Crtc3, Dab1, Grid2, Itga2b, Kdm4c, Lingo2, Nfu1, Opcml, Pappa2, Skint6, Stau2, Thsd7b, 2310015D24Rik, 2610307P16Rik, 2810055G20Rik, 4732456N10Rik, 4930444G20Rik, 4930521E06Rik, 4930544M13Rik, 6330409D20Rik, 9330175M20Rik, A330023F24Rik, Abca12, Abcg2, Actn2, Adam19, Adk, Agbl4, Ago3, Agtr1a, Aldoart1, Alg6, Ammecr1, Ankrd13c, Ankrd44, Ankrd6, Antxr2, Apaf1, Arhgap15, Arhgap25, Armc9, Atl3, Atp1b1, Atp2c1, Bag1, Bai3, Bc1, Bckdhb, Bcl2, Birc2, Bnc2, Bre, Brinp3, Brwd1, C430002N11Rik, Cachd1, Cadps, Camk1g, Ccdc19, Ccdc23, Cd46, Cdc51, Cdk5rap2, Cdyl2, Cep162, Cga, Chd1, Chm, Chmp5, Clvs1, Cntn5, Cntnap5b, Col5a2, Csmd2, Ctnna3, D030040B21Rik, Dag1, Dennd1a, Dip2c, Dis3l2, Disp1, Dlx5, Dnajc6, Dnm3, Dock1, Dopey1, Dpp10, Dpy1914, Dsp, E030011O05Rik, E130309D14Rik, E130309F12Rik, Edem3, Eif4g3, Elavl1, Elavl4, Emr4, Eomes, Epha4, Epha6, Erc2, Ermap, Esp34, Etohd2, Exoc6b, Faf1, Faim, Fam172a, Fbxl17, Fhit, Fipl11, Foxj3, Frmd3, Fyb, Gad2, Gli3, Glycam1, Gm11487, Gm4847, Gm9054, Gnb1, Gpatch2, Gpatch21, Gpc5, Gpr63, Grhl3, Gtdc1, Gulp1, Hcn1, Hdac4, Hecw2, Hmgcll1, Hoxc4, Htr1d, Htr5b, Hykk, Ibtk, Igfbpl1, Il23r, Iqcf5, Isca1, Jam3, Kcnd2, Kcnd3, Kcnh1, Kcnk5, Krt75, Lama2, Lnp, Lrch1, Lrrfip2, Lsamp, Lypd6b, March1, Mdga2, Mir297c, Mir29b-2, Mir29c, Mir669a-1, Mir669a-10, Mir669a-11, Mir669a-12, Mir669a-4, Mir669a-5, Mir669a-6, Mir669a-7, Mir669a-8, Mir669a-9, Mir669e, Mir669p-1, Mir669p-2, Mmp16, Mogat1, Msh3, Mtfr1, Mtr, Mycbp2, Naa15, Naalad2, Nay1, Ncam2, Nckap5, Ndst4, Nfx1, Nkain3, Npas2, Ntm, Olfr1259, Olfr1367, Olfr250, Olfr846, Olfr887, Olfr899, Ormdl1, Osgin2, Pappa, Pard3b, Pax3, Pax5, Pbx1, Pcca, Pcdh11x, Pcdh15, Pde6c, Pde8a, Pde8b, Pdpn, Pdzrn4, Peak1, Pik3r3, Pitpnm2, Pkhd1, Pknox2, Pla2g7, Plcl1, Pms1, Ppapdc1b, Ppp1r9b, Prex2, Prg4, Primpol, Prkag2, Prkdc, Ptprc, Ptprt, Pum1, Pvr, Rab3b, Ralgps2, Rasa3, Rasal2, Rassf3, Rb1cc1, Rbm6, Reep1, Rfx7, Rgs7, Ric3, Rims1, Rims2, Riok2, Rngtt, Rora, Rpgripl1, Rtn1, Rtn3, Sall1, Serpinb3d, Sf3a1, Sgca, Sgpp2, Skint1, Skint3, Skint5, Slc25a21, Slc41a2, Slitrk6, Smap1, Smarcal1, Sores1, Spata17, Srgap2, Ssbp3, Stat1, Tab2, Tacc2, Tanc1, Tbc1d10a, Tbx20, Tcaim, Tceb1, Tek, Tenm2, Tll1, Tmem163, Tmem65, Top2b, Tor2a, Tox, Tox3, Tppp, Tpst2, Trpm3, Ttc39b, Txlng, Ubtd2, Uggt1, Ulk4, Unc13c, Unc80, Utp20, Vcp, Vti1b, Vwc2, Wdfy3, Whscl11, Zbtb7a, Zcchc2, Zfp292, Zfp62, Zfp692, Zfp827, Zmym4, Zswim6, Syndig1, Ak1, Cntnap5a, Cpa5, Dhdds, Eng, Fbxl5, Filip1, Gm10439, Gm13490, Goltlb, Lin28a, Magi2, Me2, Mtus2, Nfia, Orc3, Recql, St8sia6, Ube2cbp, 1700019G24Rik, 4930527F14Rik, Aff2, Aff3, Arhgef101, Astn1, Cd2ap, Cd9912, Chl1, Cyp2b10, Dync1i1, Esr1, Fam19a5, Fermt2, Fmn2, Foxn2, Frmpd4, Il1rap11, Itga6, Klf13, Lepr, Mir1933, Myo3a, Nacc2, Olfr850, Olfr851, Pgam2, Phf21a, Raf1, Rictor, Ugp2, and Wbscr27.

Modulating Expression of T-Cell Genes to Enhance Immunotherapy

The methods disclosed herein may be utilized to identify genes that are involved in T-cell trafficking and activation in solid tumors. The expression of the identified genes may be modulated in T-cells to enhance immunotherapy, for example, CAR T-cell immunotherapy for treating a cell proliferative disorder in a subject in need thereof. In some embodiments, the disclosed methods may include genetically modifying a T-cell to modulate the expression of a gene involved in T-cell trafficking and activation in solid tumors and/or administering a therapeutic agent to the subject that modulates the expression and/or the biological activity of a gene involved in T-cell trafficking and activation in solid tumors.

The disclosed therapeutic methods may include administering chimeric antigen receptor (CAR) T-cell therapy to a subject wherein the CAR T-cells administering in the therapy target an antigen expressed on a solid tumor. In some embodiments, the CAR T-cells may be further genetically modified in a manner that results in increased or decreased expression of a gene that is involved in T-cell trafficking or activation, which may include, but is not limited to Aak1, Crtc3, or both of Aak1 and Crtc3 (and/or gene products encoded by Aak1 of Crtc3). In further embodiments, the CAR T-cells may be administered with a therapeutic agent that results in increased or decreased expression or biological activity of a gene involved in T-cell trafficking or activation, which may include, but is not limited to Aak1, Crtc3, or both of Aak1 and Crtc3 (and/or gene products encoded by Aak1 of Crtc3). As such, the therapeutic agent administered in the disclosed methods, which modulates the expression and/or biological activity of the gene productions of the identified genes, may include a therapeutic agent that is utilized for administering chimeric antigen receptor (CAR) T-cell therapy to the subject.

In particular, the disclosed therapeutic methods may include methods for treating cancer such as melanoma, adenocarcinoma, sarcoma, teratocarcinoma, and lymphoma. In some embodiments, the disclosed therapeutic methods may be utilized for treating tumors of tissues selected from adrenal gland, bladder, bone, bone marrow, brain, breast, cervix, colon, gall bladder, ganglia, gastrointestinal tract, heart, kidney, liver, lung, muscle, ovary, pancreas, parathyroid, prostate, skin, testis, thymus, and uterus.

The disclosed therapeutic methods may include administering a therapeutic agent that modulates the activity of T cells. In some embodiments, the therapeutic agent modulates T cell trafficking and/or infiltration in to a tumor and/or the therapeutic agent modulates T cell stimulation and/or activation (e.g., against a tumor).

The disclosed compositions, kits, and methods may be utilized to identify genes that are involved in T-cell trafficking and/or T-cell infiltration into tumors. For example, the disclosed compositions, kits, and methods may be utilized to identify immune checkpoint regulators in order to develop new immunotherapies such as immune checkpoint inhibitor therapies. Immune checkpoint inhibitors are known in the art and include anti CTLA-4 antibodies (e.g., Ipilimumab or Tremelimumab), anti PD-1 antibodies (MDX-1106, BMS-936558, MK3475, CT-011, AMP-224), anti PD-L1 antibodies (e.g., MDX-1105), anti IDO-1 antibodies, anti IDO-2 antibodies, anti KIR antibodies, anti CD70 antibodies, anti LAG-3 antibodies (e.g., IMP321), anti B7-H3 antibodies (e.g., MGA271), anti B7-H4 antibodies, anti TIM3 antibodies, and combinations thereof.

The disclosed therapeutic methods may include administering immunotherapy to a subject. As such, the therapeutic agent administered in the disclosed methods, which modulates the expression and/or biological activity of the gene productions of the identified genes, may include a therapeutic agent that is utilized for administering immunotherapy to the subject. Optionally, the disclosed methods may include administering another therapeutic agent that is utilized for administering immunotherapy to the subject (e.g., an immune checkpoint blockade modulator such as an anti-PD-1 therapeutic agent to the subject (e.g., an anti-PD-1 therapeutic agent comprising an anti-PD-1 antibody or an antigen binding fragment thereof)).

The disclosed therapeutic methods typically include administering a therapeutic agent that modulates the expression and/or biological activity of the gene productions of the identified genes. In some embodiments, the therapeutic agent is an antibody or an antigen binding fragment thereof (e.g., a single chain variable fragment (scFv)) that binds to the gene product and modulates (e.g., inhibits) the biological activity of the gene product. A suitable antibody or an antigen binding fragment thereof may include a monoclonal antibody or an antigen binding fragment thereof (e.g., a humanized monoclonal antibody or an antigen binding fragment thereof).

In some embodiments, the therapeutic agent that is administered in the therapeutic methods is a therapeutic agent that is a small molecule that inhibits the biological activity of the gene products of the identified genes. In some embodiments, a gene product of an identified gene has an enzymatic activity (e.g., kinase activity), and the small molecule inhibits the enzymatic activity of the gene product.

In some embodiments, the therapeutic agent that is administered in the therapeutic methods is a therapeutic agent that inhibits expression of the gene product. For example, the disclosed therapeutic methods may utilize RNA interference to inhibit expression of a gene product of an identified gene. Methods of utilizing RNA interference are known in the art and may include, but are not limited to, the use of small interfering RNA (siRNA) and/or small hairpin RNA (shRNA).

Experimental Mice and Screening Methods

Also disclosed herein are methods for identifying T cell genes that may be associated with T cell biological activities such as trafficking and/or infiltration into a tumor and/or T cell stimulation and/or activation against a tumor. In some embodiments, the methods include: (a) isolating T cells from a syngeneic tumor in mice comprising endogenous T cells that have been mutagenized using a Sleeping Beauty® transposon system; and (b) identifying in genomic DNA of the isolated T cells genes that have been mutagenized by the Sleeping Beauty® transposon system (e.g., by sequencing the genomic DNA). The T cells isolated in the method may include, for example, CD4+ cells and/or CD48+ cells. In some embodiments, the mice will be treated with an immunotherapeutic agent prior to isolating T cells from the tumors of the mice. For example, the mice may be treated with an anti-PD-1 therapeutic agent prior to isolating T cells from the tumors of the mice. The identified genes further may be tested to determine whether the identified genes are associated with T cell biological activities such as trafficking and/or infiltration into a tumor and/or T cell stimulation and/or activation against a tumor. Suitable tumors for use in the disclosed methods may include, but are not limited to, tumors of melanoma cells, adenocarcinoma cells, sarcoma cells, or teratocarcinoma cells. Suitable tumors for use in the disclosed methods may include tumors comprising cancer cells of a tissue selected from, but not limited to, adrenal gland, bladder, bone, bone marrow, brain, cervix, gall bladder, ganglia, gastrointestinal tract, heart, kidney, liver, lung, muscle, ovary, pancreas, parathyroid, prostate, skin, testis, thymus, and uterus.

Also contemplated herein are experimental mice, optionally cohorts of mice, comprising endogenous T cells that have been mutagenized using a Sleeping Beauty® transposon system. The contemplated experimental mice may be utilized in the disclosed methods by inserting a syngeneic tumor in the mice, optionally treating the mice with a immunotherapeutic agent (e.g., an anti-PD-1 therapeutic agent), isolating T cells from the syngeneic tumor, and identifying in genomic DNA of the T cells genes which have been mutagenized using a Sleeping Beauty® transposon system.

Aak1 Gene

Herein the Aak1 has been shown to be involved in T cell trafficking and/or activation in solid tumors. As such, expression of the Aak1 gene including any polypeptide encoded therein may be modified in T cells in order to modulate trafficking and/or activation in solid tumors.

The nucleic acid sequence of the Aak1 gene and the amino acid sequence of the Aak1 protein and variants are known in the art. The Aak1 gene is present on chromosome 2 of the human genome and it nucleic acid sequence is reported in the Genome Reference Consortium Human Build 38 patch release 12 (GRCh38.p12). (See NC_00002.12 (69457995 . . . 69643845, complement). SEQ ID NO:1 provides the sequence of the Aak1 gene. Transcription variants are expressed from the Aak1 gene and encode a long form Aak1 polypeptide having 961 amino acids (SEQ ID NO:2) and a short form Aak1 polypeptide having 823 amino acids (SEQ ID NO:3), wherein the short form Aak1 polypeptide lacks the 138 C-terminal amino acids present in the long form Aak1 polypeptide.

Using the methods disclosed herein, the present inventors have identified a variant of the Aak1 long form polypeptide (SEQ ID NO:4). The variant is translated from a variant mRNA having a start codon positioned at amino acid position 126 of the Aak1 long form polypeptide precursor and amino acid position 80 of the processed Aak1 long form polypeptide precursor having the signal peptide removed. As such, the variant includes an 80 N-terminal amino acid truncation relative to the Aak1 full-length processed polypeptide and may be referred to herein as dN80, signifying the 80 amino acid N-terminal truncation relative to the Aak1 full-length processed polypeptide. The dN80 variant also has a C-terminal truncation relative to the Aak1 full-length processed polypeptide and lacks the 139 C-terminal amino acids that are present in the Aak1 full-length processed polypeptide and terminates with a GGS amino acid sequence. The dN80 variant, therapeutic compositions comprising the dN80 variant, and uses thereof for modulating T cell trafficking and/or activation in solid tumors are specifically contemplated herein.

The Aak1 gene is hypothesized to encode a further polypeptide having 302 amino acids. (See SEQ ID NO:5).

Crtc3 Gene

Herein the Crtc3 has been shown to be involved in T cell trafficking and/or activation in solid tumors. As such, expression of the Crtc3 gene including any polypeptide encoded therein may be modified in T cells in order to modulate trafficking and/or activation in solid tumors.

The nucleic acid sequence of the CREB Regulated Transcription Coactivator 3 (Crtc3) Aak1 gene and the amino acid sequence of the Crtc3 protein and variants are known in the art. The Crtc3 gene is present on chromosome 15 of the human genome and it nucleic acid sequence is reported in the Genome Reference Consortium Human Build 38 patch release 12 (GRCh38.p12). (See NC_000015.10 (90529886 . . . 90645345)). SEQ ID NO:6 provides the sequence of the Crtc3 gene. Transcription variants are expressed from the Crtc3 gene and encode a long form Crtc3 polypeptide having 619 amino acids (SEQ ID NO:7), a medium form Crtc3 polypeptide having 586 amino acids (SEQ ID NO:8), and a short form Crtc3 polypeptide having 428 amino acids (SEQ ID NO:9).

Chimeric Antigen Receptor (CAR) T-Cells

Chimeric Antigen Receptor (CAR) T-cells and their use in immunotherapy for diseases such as cancer are known in the art. (See, e.g., June et al., "CAR T cell immunotherapy for human cancer," Science 2018 Mar. 23; 359(6382):1361-1365; Xu et al., "The development of CAR design for tumor CAR-T cell therapy," Oncotarget. 2018 Jan. 12; 9(17): 13991-14004; Chen et al., "Driving CARs on the uneven road of antigen heterogeneity in solid tumors," Curr Opin Immunol. 2018 Mar. 16; 51:103-110; Vormittag et al., "A guide to manufacturing CAR T cell therapies," Curr Opin Biotechnol. 2018 Feb. 17; 53:164-181; D'Aloia et al., "CAR-T cells: the long and winding road to solid tumors," Cell Death Dis. 2018 Feb. 15; 9(3):282; Ye et al., "Engineering chimeric antigen receptor-T cells for cancer treatment," Mol Cancer. 2018 Feb. 15; 17(1):32; Li et al., "Chimeric antigen receptor T cell (CAR-T) immunotherapy for solid tumors: lessons learned and strategies for moving forward," J Hematol Oncol. 2018 Feb. 13; 11(1):22; Yoon et al., "Incorporation of Immune Checkpoint Blockade into Chimeric Antigen Receptor T cells (CAR-Ts): Combination or Built-In CAR-T," Int J Mol Sci. 2018 Jan. 24; 19(2); Wang et al., "New Chimeric Antigen Receptor Design for Solid Tumors," Frontiers in Immunol. 2017 December; 3:1934; the contents of which are incorporated herein by reference in their entireties).

Methods for preparing CAR-T cells and their use in treating cancer have been described in patent documents. (See, e.g., U.S. Pat. Nos. 9,932,572; 9,932,406; 9,932,405; 9,931,347; 9,920,132; 9,914,909; 9,913,882; 9,907,842; 9,889,161; 9,889,160; 9,868,774; 9,856,322; 9,855,298; 9,855,297; 9,845,362; 9,834,545; 9,828,435; 9,822,340; 9,821,012; 9,821,011; 9,815,901; 9,809,581; 9,803,022; 9,790,282; 9,790,278; 9,783,591; 9,777,064; 9,777,061; 9,765,342; 9,765,142; 9,745,368; 9,725,519; 9,714,278; 9,701,758; 9,688,760; 9,688,740; 9,670,281; 9,663,763; 9,662,405; 9,657,105; 9,650,428; 9,636,388; 9,629,877; 9,624,306; 9,624,276; 9,598,489; 9,597,357; 9,587,237; 9,587,020; 9,580,685; 9,573,988; 9,572,837; 9,572,836; 9,562,087; 9,540,445; 9,522,955; 9,518,123; 9,499,855; 9,492,499; 9,487,800; 9,481,728; 9,464,140; 9,453,075; 9,447,194; 9,446,105; 9,422,351; 9,416,190; 9,409,994; 9,409,992; 9,402,865; 9,394,368; 9,393,268; 9,365,641; 9,359,447; 9,328,156; 9,315,585; 9,273,283; 9,272,002; 9,266,960; 9,220,728; 9,181,527; 9,175,308; 9,169,328; 9,163,258; 9,156,915; 9,102,761; 9,102,760; 9,101,584; 9,040,669; 8,975,071; 8,956,828; 8,916,381; 8,911,993; 8,906,682; 8,822,647; 8,822,196; 8,802,374; 8,486,911; and 8,465,743; the contents of which are incorporated herein by reference in their entireties.

CAR-T cells having receptors that are targeted to antigens present on solid tumors have been designed and are being tested in clinical trials. (See Wang et al., "New Chimeric Antigen Receptor Design for Solid Tumors," Frontiers in Immunol. 2017 December; 3:1934). Antigenic targets of these CAR-T cells for solid tumors include epidermal growth factor receptor (EGFR) (e.g., for targeting glioblastoma and non-small cell lung cancer), mesothelin (e.g., for targeting pancreatic cancer, mesotheliomas, ovarian cancers, and lung cancers), glypican-3 (e.g., for targeting hepatocellular carcinoma (HCC), malignant rhabdoid tumors (MRTs), embryonal sarcoma, and lung cancers), receptor tyrosine-protein kinase erbB-2 (e.g., for targeting lung cancer ovarian cancer, and breast cancer), prostate specific membrane antigen (PMSA) (e.g., for targeting prostate cancer), human epidermal growth factor receptor 2 (HER2) (e.g., for targeting breast cancer and sarcoma), mucin 1 (MUC1) (e.g., for targeting hepatocellular carcinoma (HCC), non-small cell lung cancer, and triple-negative breast cancer), carcinoembryonic antigen (CEA) (e.g., for targeting liver metastases), and IL-13 receptor alpha (e.g., for targeting glioblastoma). As such, suitable antigenic targets for the modified CAR-T cells as contemplated herein may include, but are not limited to epidermal growth factor receptor (EGFR), mesothelin, receptor tyrosine-protein kinase erbB-2, prostate specific membrane antigen (PMSA), human epidermal growth factor receptor 2 (HER2), mucin 1 (MUC1), carcinoembryonic antigen (CEA), and IL-13 receptor alpha.

CAR-T cells as contemplated herein may include, but are not limited to so-called first generation, second generation, and third generation CAR-T cells. (See, e.g., Hartmann et al., "Clinical development of CAR T-cells—challenges and opportunities in translating innovative treatment concepts," EMBO Molec Medic. (2017) e201607485; the contents of which is incorporated herein by reference in its entirety).

CAR-T cells as contemplated herein express a chimeric antigen receptor that typically comprises a "single chain variable fragment." As used herein, the phrases "single chain variable fragment", "single-chain antibody variable fragments", and "scFv" antibodies refer to forms of antibodies comprising the variable regions of only the heavy and light chains, connected by a linker peptide.

Single-chain antibody fragments can overcome some of the problems associated with the use of antibodies containing a part or all of a constant domain. For example, single-chain antibody fragments tend to be free of undesired interactions between biological molecules and the heavy-chain constant region, and/or other unwanted biological activities. Additionally, single-chain antibody fragments are considerably smaller than whole antibodies and can therefore be characterized by greater capillary permeability than whole antibodies, allowing single-chain antibody fragments to localize and bind to target antigen-binding sites more efficiently. Also, antibody fragments can be produced on a relatively large scale in prokaryotic cells, thus facilitating their production. Furthermore, the relatively small size of single-chain antibody fragments makes them less likely than whole antibodies to provoke an immune response in a recipient. The single-chain antibody fragments of the presently disclosed subject matter include, but are not limited to single chain fragment variable (scFv) antibodies and derivatives thereof such as, but not limited to tandem di-scFv, tandem tri-scFv, diabodies, triabodies, tetrabodies, miniantibodies, and minibodies.

EXAMPLES

The following examples are illustrative and are not intended to limit the disclosed and claimed subject matter.

Example 1—T-Cell Trafficking Genes Identification Using the Sleeping Beauty® Transposon Reference is made to the Invention Disclosure Form submitted in 2016 and entitled "T-Cell Trafficking Genes Identification Using the Sleeping Beauty Transposon," by George Weiner, Laura Rogers, and Adam Dupuy.

Immune checkpoint blockade therapies, including anti-PD1 and anti-PDL1, have been hugely beneficial in treating late-stage malignant melanoma. However, therapeutic success is only achieved in about 30% of patients. One important determinant of immune checkpoint blockade success is intratumoral T cell infiltration. Thus, increasing T cell infiltration is a viable approach to enhance immunotherapy response. We developed an in vivo screen-based approach to identify novel candidate genes involved in T cell trafficking. Our genetic screen approach uses the Sleeping Beauty® (SB) transposon system to randomly mutagenize the genome of endogenous T cells, followed by subcutaneous injection of B16F0 melanoma cells. We hypothesize that mutations in T cells that are over-represented in intratumoral T cells compared to splenic T cells will reveal candidate genes biologically responsible for T cell trafficking and expansion within tumors. In initial studies, we identified three candidate genes (Crtc3, Astn2, Gpatch8) that, when disrupted, could increase intratumoral T cell trafficking. These three genes have not been well characterized in the literature, but what is known about them suggests they could impact on intratumoral trafficking or growth. Additional clonal insertion sites were identified in genes with known functions involved in T cell activity, but these were not statistically significant due to the cohort size of these preliminary experiments. We expect to be able to identify additional candidate genes as the studies progress. These genes could be used as therapeutic targets to enhance the efficacy of checkpoint blockade therapy. For example, the genes identified in the disclosed methods could have therapeutic and diagnostic applications in the fields of immunology, oncology, and cancer research, and be used to overcome a drawback to current immunotherapies, specifically that current therapies have limited efficacy in poorly-infiltrated tumors. The genes we have identified have the potential to augment intratumoral T cell infiltration, and extensive literature searches have not produced any publications that previously implicated these as functionally contributing to tumor infiltrating lymphocyte behavior.

Example 2—Using Sleeping Beauty® Mutagenesis to Identify Novel Immunotherapy Targets in a Syngeneic Mouse Model of Melanoma Reference is made to the Abstract entitled "Using Sleeping Beauty mutagenesis to identify novel immunotherapy targets in a syngeneic mouse model of melanoma," which refers to a presentation given at the 2016 University of Iowa Melanoma Symposium.

Background and Rationale: Immune checkpoint blockade therapies, including anti-PD1 and anti-PDL1, have been hugely beneficial in treating late-stage malignant melanoma. However, therapeutic success is only achieved in about 30% of patients, and understanding response determinants has become a major area of research. It is becoming clear that at least one important determinant of immune checkpoint blockade success is intratumoral T cell infiltration. A recent publication demonstrated that treating tumors with an agent that increased T cell numbers in the tumor enhanced the efficacy of anti-PDL1 in their mouse model (Tang et al., 2016). Thus, increasing T cell infiltration is a viable approach to enhance immunotherapy response. We have designed an in vivo screen-based approach to identify novel candidate genes involved in T cell trafficking using the B16F0 syngeneic mouse model of melanoma. Our rationale for using the B16F0 melanoma model is that subcutaneous tumors are poorly infiltrated by T cells and, perhaps as a result, respond poorly to immune checkpoint blockade. Our genetic screen approach uses the Sleeping Beauty® (SB) transposon system to randomly mutagenize the genome of endogenous T cells, followed by subcutaneous injection of B16F0 melanoma cells. We hypothesize that mutations in T cells that are over-represented in intratumoral T cells compared to splenic T cells will reveal candidate genes biologically responsible for T cell trafficking and expansion within tumors. These candidate genes can then be validated in subsequent experiments to determine whether they impact on T cell function, increase T cell infiltration and enhance the efficacy of checkpoint blockade therapy.

Methods:

We performed a forward genetic screen to identify genes that impact on infiltration of T cells into melanoma using SB transposon insertional mutagenesis in T cells. By carrying out this screen in vivo, the complexity of the tumor microenvironment is preserved. Other advantages of using the SB system include the ability to cause both gain- and loss-of-function mutations, as well as unbiased mutagenesis of the entire genome followed by easy identification of insertion sites using an Illumina sequencing-based method. Adult mice with mutagenized T cells were injected subcutaneously with B16F0 melanoma cells bilaterally, and tumors were allowed to grow for three weeks (n=70). At that time, left and right tumors, as well as the spleen, from each animal were harvested and submitted for high throughput sequencing. Bioinformatic analyses were performed to determine which insertions were present in both tumors but absent from the spleen within an individual mouse.

Results:

In initial studies, we identified three candidate genes that, when disrupted, could increase intratumoral T cell trafficking. These three genes have not been well characterized in the literature, but what is known about them suggests they could impact on intratumoral trafficking or growth. Additional clonal insertion sites were identified in genes with known functions involved in T cell activity, but these were not statistically significant due to the cohort size of these preliminary experiments. We conclude that Sleeping Beauty® mutagenesis can be used to identify novel immunotherapy targets using the B16 model.

Future Studies:

We plan to use our approach to identify additional candidate genes by repeating our protocol in additional mice. We will simultaneously begin validation experiments using various knockdown or knockout approaches to investigate the impact of the identified candidate genes on relevant T cell phenotypes both in vitro and in vivo. We hypothesize that modulation of our candidate genes will result in enhanced intratumoral T cell trafficking. Finally, we aim to determine whether modulating these targets enhances checkpoint blockade efficacy in mice. Any that are found to enhance T cell infiltration and/or checkpoint blockade efficacy will be considered promising novel therapeutic targets for melanoma treatment. Submission of this research for NIH and other peer-reviewed funding is planned.

Relevance to Melanoma:

Our preliminary data have identified three candidate genes that may be involved in intratumoral T cell trafficking, which is a prerequisite for optimal immune checkpoint blockade therapeutic success. Further identification and characterization of our gene candidates may provide novel immunotherapeutic drug targets that could be used to enhance the efficacy of current immunotherapies. This has the potential to be highly beneficial for melanoma patients that experience suboptimal response to anti-CTLA4, anti-PD1, or anti-PDL1.

Example 3—Use of Sleeping Beauty R Mutagenesis to Identify Genes that Influence Intratumoral T Cell Infiltration Reference is made to the Abstract entitled "Use of Sleeping Beauty Mutagenesis to Identify Genes that Influence Intratumoral T Cell Infiltration," which was accepted for poster presentation at the American Association for Cancer Research (AACR) 2016 Meeting, Apr. 16-20, 2016.

Immune checkpoint blockade antibodies (e.g. anti-CTLA-4 and anti-PD-1) enhance T cell anti-tumor activity and have produced exciting and durable results in treatment of a number of cancers including melanoma. Unfortunately, response to first generation checkpoint blockade therapy is limited to a subset of patients. A more comprehensive understanding of the genes and molecules involved in T cell checkpoint control and other aspects of anti-tumor T cell activity may allow a wider patient population to benefit from this exciting and new approach to cancer therapy.

To this end, we performed a forward genetic screen to identify gene pathways that influence intratumoral T cell infiltration using Sleeping Beauty® (SB) mutagenesis. More specifically, this genetic T cell screen was designed to identify additional genes and molecules responsible for selection and expansion of intratumoral T cells via a variety of T cell processes including T cell receptor (TCR)-mediated activation, clonal expansion of tumor-specific T cells, T cell trafficking into the tumor, and maintenance of prolonged viability once there. Advantages of using SB in a genetic screen include the ability to cause both gain- and loss-of-function mutations, as well as mutagenesis of the entire genome followed by easy identification of insertion sites. In addition, SB screens are performed in vivo, and thus preserve the complexity of the tumor microenvironment.

We generated a pilot cohort of mice (n=12) with SB-mutagenized endogenous T cells. These mice were challenged with syngeneic B16F0 melanoma cells subcutaneously. After tumor development (21 days after tumor challenge), tumor-infiltrating CD4+ and CD8+ T cells were harvested. Splenic T cells representing unselected CD4+ and CD8+ populations were also isolated from the same animals at time of tumor harvest. Harvested T cells were evaluated by high throughput sequencing to identify SB insertion sites. T cells harvested from tumors demonstrated a decrease in clonal insertion sites compared to splenic T cells suggesting intratumoral clonal selection. Moreover, clonal insertions in intratumoral T cells were significantly enriched in or near genes, signifying likely selection for insertions impacting gene function ($p<0.000003$, Fisher's exact test). Clonal insertion sites in T cells from tumors that were absent from spleens, representing potential immunotherapy targets and including insertion sites in genes known to be associated with the T cell response, were identified. We are currently in the process of expanding this experimental cohort using a larger number of mice.

We conclude T cell specific SB mutagenesis has the potential to identify novel molecules that influence intratumoral T cell infiltration and can be used to identify additional genes that may contribute to the anti-tumor T cell response.

Example 4—Modulating T Cell Genes to Enhance Immunotherapy

Reference is made to the Invention Disclosure Form submitted in 2017 and entitled "Modulating T Cell Genes to Enhance Immunotherapy," by George Weiner, Laura Rogers, and Adam Dupuy.

T cells in particular, and the immune system in general, have amazing potential to eliminate tumor cells throughout the body. This therapeutic potential is evidenced by the clinical success of immunotherapies designed to enhance T cell function, such as immune checkpoint blockade and chimeric antigen receptor T cell (CAR-T) therapies. Despite the remarkable progress to date, expanding success to a broader number of patients is a top priority in the field. T cell infiltration into tumors appears to be an important prerequisite for the success of both immune checkpoint blockade and CAR-T therapies. For example, patients with inflamed tumors have a better response rate to anti-PD-1 than patients whose tumors are immune excluded (T cells present at tumor border, but blocked from entry) or immune desserts (very few, or no, intratumoral T cells). Preclinical models have also demonstrated that increasing intratumoral T cell number enhances immune checkpoint blockade efficacy. Thus, increasing T cell infiltration into the tumor could have beneficial therapeutic impact.

To this end, we developed an innovative, systematic method to screen for novel therapeutic targets in T cells that impact T cell infiltration into tumors. We have identified 386 T cell genes using various cancer models, most of which have no previously described role in T cells or immunotherapy. The disclosed T cell genes include the following genes: Aak1, 1300002E11Rik, Ehhadh, Map7d1, Ptprd, Smr3a, Susd4, Wdr59, Astn2, Gpatch8, Cpa6, Cpne4, Crtc3, Dab1, Grid2, Itga2b, Kdm4c, Lingo2, Nful, Opcml, Pappa2, Skint6, Stau2, Thsd7b, 2310015D24Rik, 2610307P16Rik, 2810055G20Rik, 4732456N10Rik, 4930444G20Rik, 4930521E06Rik, 4930544M13Rik, 6330409D20Rik, 9330175M20Rik, A330023F24Rik, Abca12, Abcg2, Actn2, Adam19, Adk, Agbl4, Ago3, Agtr1a, Aldoart1, Alg6, Ammecr1, Ankrd13c, Ankrd44, Ankrd6, Antxr2, Apaf1, Arhgap15, Arhgap25, Armc9, Atl3, Atp1b1, Atp2c1, Bag1, Bai3, Bcl, Bckdhb, Bcl2, Birc2, Bnc2, Bre, Brinp3, Brwd1, C430002N11Rik, Cachd1, Cadps, Camk1g, Ccdc19, Ccdc23, Cd46, Cdc51, Cdk5rap2, Cdyl2, Cep162, Cga, Chd1, Chm, Chmp5, Clvs1, Cntn5, Cntnap5b, Col5a2, Csmd2, Ctnna3, D030040B21Rik, Dag1, Dennd1a, Dip2c, Dis3l2, Disp1, Dlx5, Dnajc6, Dnm3, Dock1, Dopey1, Dpp10, Dpy1914, Dsp, E030011O05Rik, E130309D14Rik, E130309F12Rik, Edem3, Eif4g3, Elavl1, Elavl4, Emr4, Eomes, Epha4, Epha6, Erc2, Ermap, Esp34, Etohd2, Exoc6b, Faf1, Faim, Fam172a, Fbxl17, Fhit, Fip1l1, Foxj3, Frmd3, Fyb, Gad2, Gli3, Glycam1, Gm11487, Gm4847, Gm9054, Gnb1, Gpatch2, Gpatch21, Gpc5, Gpr63, Grhl3, Gtdc1, Gulp1, Hcn1, Hdac4, Hecw2, Hmgcll1, Hoxc4, Htr1d, Htr5b, Hykk, Ibtk, Igfbpl1, Il23r, Iqcf5, Isca1, Jam3, Kcnd2, Kcnd3, Kcnh1, Kcnk5, Krt75, Lama2, Lnp, Lrch1, Lrrfip2, Lsamp, Lypd6b, March1, Mdga2, Mir297c, Mir29b-2, Mir29c, Mir669a-1, Mir669a-10, Mir669a-11, Mir669a-12, Mir669a-4, Mir669a-5, Mir669a-6, Mir669a-7, Mir669a-8, Mir669a-9, Mir669e, Mir669p-1, Mir669p-2, Mmp16, Mogat1, Msh3, Mtfr1, Mtr, Mycbp2, Naa15, Naalad2, Nav1, Ncam2, Nckap5, Ndst4, Nfx1, Nkain3, Npas2, Ntm, Olfr1259, Olfr1367, Olfr250, Olfr846, Olfr887, Olfr899, Ormdl1, Osgin2, Pappa, Pard3b, Pax3, Pax5, Pbx1, Pcca, Pcdh11x, Pcdh15, Pde6c, Pde8a, Pde8b, Pdpn, Pdzrn4, Peak1, Pik3r3, Pitpnm2, Pkhd1, Pknox2, Pla2g7, Plcl1, Pms1, Ppapdc1b, Ppp1r9b, Prex2, Prg4, Primpol, Prkag2, Prkdc, Ptprc, Ptprt, Pum1, Pvr, Rab3b, Ralgps2, Rasa3, Rasal2, Rassf3, Rb1cc1, Rbm6, Reep1, Rfx7, Rgs7, Ric3, Rims1, Rims2, Riok2, Rngtt, Rora, Rpgrip1l, Rtn1, Rtn3, Sall1, Serpinb3d, Sf3a1, Sgca, Sgpp2, Skint1, Skint3, Skint5, Slc25a21, Slc41a2, Slitrk6, Smap1, Smarcal1, Sorcs1, Spata17, Srgap2, Ssbp3, Stat1, Tab2, Tacc2, Tanc1, Tbc1d10a, Tbx20, Tcaim, Tceb1, Tek, Tenm2, Tll1, Tmem163, Tmem65, Top2b, Tor2a, Tox, Tox3, Tppp, Tpst2, Trpm3, Ttc39b, Txlng, Ubtd2, Uggt1, Ulk4, Unc13c, Unc80, Utp20, Vcp, Vti1b, Vwc2, Wdfy3, Whsc1l1, Zbtb7a, Zcchc2, Zfp292, Zfp62, Zfp692, Zfp827, Zmym4, Zswim6, Syndig1, Ak1, Cntnap5a, Cpa5, Dhdds, Eng, Fbxl5, Filip1, Gm10439, Gm13490, Golt1b, Lin28a, Magi2, Me2, Mtus2, Nfia, Orc3, Recql, St8sia6, Ube2cbp, 1700019G24Rik, 4930527F14Rik, Aff2, Aff3, Arhgef101, Astn1, Cd2ap, Cd9912, Chl1, Cyp2b10, Dync1i1, Esr1, Fam19a5, Fermt2, Fmn2, Foxn2, Frmpd4, Il1rapl1, Itga6, Klf13, Lepr, Mir1933, Myo3a, Nacc2, Olfr850, Olfr851, Pgam2, Phf21a, Raf1, Rictor, Ugp2, and Wbscr27.

Uses for this disclosed technology include, but are not limited to: 1) Using these genes to develop a diagnostic platform to predict immunotherapy success in patients, 2) Using these genes as the basis for developing novel co-therapies to existing immunotherapies including immune checkpoint blockade and CAR-T technologies, and 3) Using these genes as targets for novel single-agent immunotherapies—all of which would aim to improve our ability to treat human disease.

We have verified that at least one of the identified genes (Crtc3) impacts T cell production of cytokines in vitro, which are important signaling molecules within the tumor microenvironment that influence T cell anti-tumor activity. Further, these genes were identified in tumors that displayed an increased % T cells inside the tumor, suggesting they may positively impact this process in vivo. Further testing is needed to determine whether manipulating the activities of these genes directly enhances existing immunotherapies, or alone as a therapeutic agent, in preclinical models. Further testing is also required using human expression data to assess the predictive value of these genes as biomarkers for immunotherapy clinical success.

Example 5—Rationally Improving T Cell-Mediated Cancer Immunotherapy Using Sleeping Beauty® Mutagenesis Reference is made to the Abstract and Poster entitled "Rationally improving T cell-mediated cancer immunotherapy using Sleeping Beauty mutagenesis," which will be presented at the University of Iowa Immunology Retreat on Aug. 17, 2017.

Background:

T cells have amazing potential to eliminate tumor cells throughout the body, evidenced by the clinical success of immunotherapies designed to enhance T cell function like immune checkpoint blockade and chimeric antigen receptor T cell (CAR-T) therapies. Expanding success to a broader number of patients is a top priority in the field. T cell infiltration into tumors is an important prerequisite for the success of both immune checkpoint blockade and CAR-T therapies, thus, increasing T cell infiltration into tumors could have beneficial therapeutic impact.

Methods: We designed a forward genetic screen to identify genes that contribute to intratumoral T cell accumulation using Sleeping Beauty® (SB) transposon mutagenesis in T cells. The genes we identified have the potential to modify important T cell functions including trafficking to the tumor, clonal expansion, and sustained viability once inside the tumor.

Results:

We identified 312 tumor-enriched genes that were mutated in tumors, but not the spleen, of individual mice. Twenty of these were detected in more than one mouse, representing strong gene candidates for validation. We demonstrated that one gene candidate is functionally associated with T cell response to activation signals. Specifically, CRISPR-mediated knockout of this gene in a murine T cell line resulted in cytokine production defects after T cell receptor stimulation. Additional screening has begun using other tumor models and anti-PD-1 therapy. Preliminary data from these indicate that few genes are conserved across tumor models and treatment groups.

Conclusions:

We are currently investigating the role of candidate genes in intratumoral T cell accumulation and immunotherapy enhancement using an in vivo approach. Together, these experiments have the potential to expand our understanding of T cell infiltration into tumors and may provide previously unexplored strategies to rationally enhance immunotherapy efficacy.

Example 6—Rationally Improving T Cell-Mediated Immunotherapy Using Sleeping Beauty® Mutagenesis Reference is made to the Application for Federal Assistance dated Jun. 8, 2017, and entitled "Rationally Improving T Cell-Mediated Immunotherapy Using Sleeping Beauty Mutagenesis," principal investigator Laura M. Rogers.

Research Strategy

Significance.

T cell-mediated immunotherapies, including CAR-T and anti-PD-1, have clear clinical activity in many tumor types, but there is considerable room for improvement[3,4]. The determinants of success are only now being defined, but they likely require a pre-existing anti-tumor T cell response[5-7]. Tumors that have minimal T cells infiltrating into tumors, called "immune deserts", have poor response to immunotherapy in general. At least one group has demonstrated that enhancing T cell infiltration can increase checkpoint blockade efficacy[1]. Our unbiased screen approach is designed to identify genes that can be modified in T cells to enhance the efficacy of T-cell cancer immunotherapy. Our work is well suited to address one of the most pressing issues of cancer immunotherapy: rationally identifying promising combinatorial approaches to provide therapeutic success to a broader patient population. This could lead directly to practical approaches to enhancing T cell therapeutics including CAR-T and immune checkpoint blockade therapies such as anti-PD-1.

Innovation.

We have designed an innovative, systematic method to screen for novel therapeutic targets in T cells that impact T cell infiltration into tumors. This screen allows us to evaluate both loss-of-function and gain-of-function mutations in genes across the entire genome. In studies of intratumoral T cell infiltration in melanoma and lymphoma, we have identified genes that were not previously known to be involved in tumor-associated T cell biology. Thus, both our genetic screening method and the immunotherapeutic potential of the novel genes we have identified are highly innovative.

Approach

Introduction.

T cells in particular, and the immune system in general, have amazing potential to eliminate tumor cells throughout the body. This therapeutic potential is evidenced by the clinical success of immunotherapies designed to enhance T cell function, such as immune checkpoint blockade[4] and chimeric antigen receptor T cell (CAR-T) therapies[3]. Despite the remarkable progress to date, expanding success to a broader number of patients is a top priority in the field.

T cell infiltration into tumors appears to be an important prerequisite for the success of both immune checkpoint blockade and CAR-T therapies[7-10]. For example, patients with inflamed tumors have a better response rate to anti-PD-1 than patients whose tumors are immune excluded (T cells present at tumor border, but blocked from entry) or immune desserts (very few, or no, intratumoral T cells)[7]. Thus, increasing T cell infiltration into the tumor could have beneficial therapeutic impact.

We have designed a forward genetic screen to identify T cell genes that contribute to intratumoral T cell accumulation using Sleeping Beauty® (SB) transposon insertional mutagenesis in T cells (FIG. 1). The SB transposon mutagenesis system has traditionally been used as a cancer gene discovery tool and model of a variety of malignancies[11]. SB insertional mutagenesis is accomplished in mice by engineering strains that carry both the DNA transposon and the SB transposase. The SB system was further refined by the design of a Cre-inducible transposase allele. This allows for tissue-specific expression of transposase, thus limiting mutagenesis to a desired cell type. With respect to this proposal, the application of the SB technology to immunotherapy target discovery is entirely unique.

Preliminary Data

SB Screen to Identify Novel Candidate Immunotherapy Targets.

While SB screens have been used as cancer gene discovery tools in the past, we have begun using the system instead to identify T cell genes involved in the intratumoral accumulation of T cells. The genes we identified have the potential to modify important T cell functions including trafficking to the tumor, clonal expansion, and sustained viability once inside the tumor. We generated a large screen cohort of mice with SB-mutagenized T cells by crossing SB transgenic mice with the CD4-Cre strain (FIG. 1A). In this way, we induced mutation of both CD4+ and CD8+ T cell subsets, as CD8+ T cells also express CD4 during the double positive stage of T cell development. Adult offspring with mutagenized T cells were then injected bilaterally with syngeneic melanoma cells (B16F0). This was done using young mice that harbor up to hundreds of mutations in each T cell, but which have not had adequate time to develop T cell malignancies (that emerge at 49 months on average[12]). B16F0 melanomas developed untreated for three weeks to allow for spontaneous T cell infiltration before tissues were collected. High throughput sequencing was performed on the tumors (two tumors per mouse) and spleens from each mouse to identify genes in the T cells mutated by transposon insertions. Sequencing was performed on amplicon libraries generated using primers specific for transposon sequences, enabling rapid identification of the insertion sites. Note that SB insertions arise only in the T cells from these tissue samples due to CD4-Cremediated tissue specificity. Thus, the malignant cells themselves do not contribute to the genetic signature.

Significance of candidate genes was determined through subsequent bioinformatics analysis, carried out in two steps (FIG. 1B,C). The first step identified insertion sites that were present in T cells in both tumors, but absent from the spleen, of an individual mouse. By subtracting out background splenic T cell mutation signatures, we are able to focus specifically on tumor T cell-enriched genetic signatures. Moreover, we expect bona-fide, tumor-specific T cells to be present systemically in both tumors from an individual animal, and so we filtered out mutations that occurred in only T cells from one of the two tumors. These analyses resulted in a list of tumor T cell-enriched insertions: genes that were significantly mutated in intratumoral, but not splenic, T cells from an individual mouse. The second bioinformatics step identified recurring, significantly mutated genes across all mice in the experimental cohort. We hypothesize that tumor-associated T cell genes significantly mutated in more than one mouse are most likely to functionally contribute to intratumoral T cell accumulation and are strong candidates for therapeutic intervention to enhance intratumoral T cell infiltration.

The Gene Candidates Identified Impact T Cell Function.

We observed that clonal insertions in T cells from tumor samples were significantly enriched in or near genes, signifying likely selection for insertions impacting gene function ($P<0.000003$, Fisher's exact test). Importantly, the mice in which we identified strong genetic signatures also had the highest percentage of T cells inside the tumors (FIG. 2A), supporting their role in enhancing intratumoral T cell accumulation.

Figure 2:
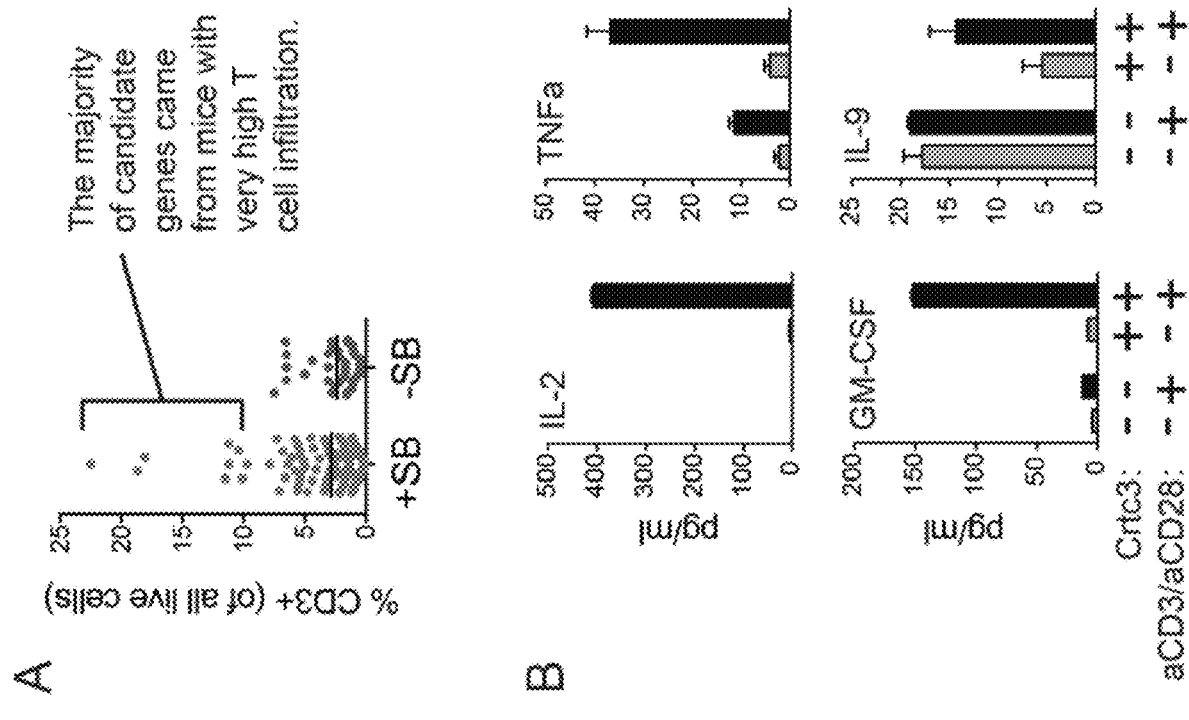
FIG. 2. Identified genes impact T cell function. A. Flow cytometry analysis of tumors included in the B16F0 melanoma cohort revealed that a minority of tumors displayed very high T cell percentages compared to the nonmutagenized (-SB) control cohort. Yet, the identifiable gene signatures come mostly from these highly infiltrated tumors, suggesting SB insertions are functionally contributing to increased T cell accumulation in tumors. B. One immunotherapy gene candidate, Crtc3, was specifically shown to be involved in regulating the expression of cytokines by activated T cells. Briefly, murine T cell lymphoma cells (EL4) were transduced with either a lentiviral CRISPR vector targeting Crtc3 or a non-targeting control. After selecting an EGFP positive clones and verifying complete knock out of Crtc3, T cells were activated for 24 hours with anti-CD3/anti-CD28 beads and Luminex was performed. Loss of Crtc3 resulted in altered (though largely impaired) cytokine production, which could impact an anti-tumor response. (Additional cytokine data not shown.)

As designed, we expect our screen to identify T cell genes that increase trafficking into the tumor, enhance clonal expansion after activation, and sustain viability within the tumor microenvironment. In fact, a number of gene candidates that we identified do have known functions impacting various T cell processes including metabolic programming of T cells, and T cell receptor (TCR) signaling. In total, we identified 312 tumor-enriched T cell genes that were mutated in both tumors, but not in the spleen of individual mice. Twenty of these were detected in more than one mouse, representing strong gene candidates for validation. Further, we demonstrated that one gene candidate, Crtc3 ($P=1.40\times 10-32$), is functionally associated with T cell response to activation signals. Specifically, CRISPR-mediated knockout of Crtc3 in a murine T cell line resulted in cytokine production defects after T cell receptor stimulation (FIG. 2B, manuscript in preparation). Together, these data highlight the power and legitimacy of our screen approach.

Additional Screens and Identification of Aak1 as a Promising Immunotherapy Target Candidate.

Given that different tumor types can have different immune microenvironments, we felt it important to perform a second SB screen using a different tumor model. We selected the EL4 lymphoma model. The lymphoma screen was performed as depicted in FIG. 1, with the exception that EL4 cells were injected instead of B16F0 cells. While this cohort was smaller (n=22 mice versus 98 in the melanoma cohort), we identified 65 tumor-enriched T cell genes and 23 of these were observed in more than one mouse. This experiment is ongoing, with the goal of generating a similar size cohort to that of the melanoma screen.

We reasoned that genes identified in both tumor models would represent the best candidates to pursue, as they might contribute to T cell accumulation despite differences in the tumor microenvironments. However, genes that passed both bioinformatics steps 1 and 2 (enriched in the tumor versus spleen AND observed in more than one individual) were not shared between tumor models. We did, however, identify 11 genes shared between tumor models that were present in only one mouse in each cohort (FIG. 3A). It is possible that with additional mice in the EL4 cohort, that this list could strengthen.

In addition to assessing multiple tumor types, we reasoned that perhaps a better approach to identify T cell genes that specifically synergize with immune checkpoint blockade would be to do a sensitized screen with anti-PD-1 treatment. Thus, we generated a small pilot cohort of mice (n=13) injected with B16F0 melanoma and treated twice weekly (10 mg/kg doses, injected intraperitoneally) with anti-PD-1 (clone RMP1-14) until tumors were harvested 3 weeks later. Despite having only a small cohort to analyze, we identified 8 tumor-enriched insertions, with 3 in two or more individuals. The top gene candidate, Aak1 (AP2-associated kinase 1), is particularly notable. It was overwhelmingly identified in the anti-PD-1 treated cohort, observed in 9 of the 13 mice (69%). Aak1 was also the top gene candidate in the untreated melanoma cohort mutated in 6 of 98 mice (6%), and it was the only gene identified in all 3 screen cohorts, appearing in 1 of 22 mice (5%) in the lymphoma cohort. The selection for Aak1 mutation in 3 screens using 2 distinct tumor models strengthens its potential as a candidate to broadly augment immunotherapy efficacy. Thus, Aak1 (described in more detail in Aim 1) is a major focus of this research proposal.

As briefly mentioned, SB mutagenesis can cause both gain- and loss-of-function mutations due to promoter and stop/poly-A signals carried within the transposon itself. Thus, when inserted in the forward orientation, it can promote expression of downstream exons. If inserted in the reverse orientation, it can introduce a premature stop. All insertions within Aak1 are located in intron 2, with the majority in the reverse orientation (FIG. 3B). As the coding sequence for the functional kinase domain of Aak1 spans exons 2-3, we would predict that the SB insertions in intron 2 introduce a loss-of-function mutation. Because of this, we propose studying Aak1 knock out T cells in our initial experiments.

Summary and Hypothesis.

In order to identify T cell genes that could enhance existing immunotherapies by increasing intratumoral T cell infiltration, we designed an unbiased forward genetic screen approach using SB. We have completed a screen using an immunocompetent model of melanoma and are well into generating a complementary screen cohort in a model of lymphoma. We have successfully identified a number of promising gene candidates, one of which (Crtc3) we have demonstrated impacts cytokine production by activated T cells. Finally, we completed a small pilot study, introducing anti-PD-1 treatment to our screen design to identify mechanisms that synergize specifically with checkpoint blockade. One notable gene candidate, Aak1, was identified in mice from all 3 screen cohorts, and Aak1 mutations were extremely frequent in the anti-PD-1 treated group. Thus, we hypothesize that the genes we identify, including Aak1, will enhance intratumoral T cell accumulation and augment anti-PD-1 therapeutic efficacy.

In Aim 1, we will investigate the role of Aak1 in T cell trafficking into tumors (Aim 1A) and the anti-tumor activity of modified T cells (Aim 1B) using an in vivo adoptive transfer experimental approach. Positive results would be of interest to the CAR-T field. In Aim 2, we propose continuation of our screening approach using additional tumor models and anti-PD-1 treatment. Based on the success of our initial screens, we are confident we will identify additional T cell intrinsic mechanisms that represent rational combinatorial pathways. We will begin by testing Aak1, with Crtc3 as a second candidate, but any newly identified gene candidates from Aim 2 can undergo testing similar to that proposed in Aim 1. We will focus on those candidates that are relevant to more than one tumor model. Together, these experiments have the potential to expand our understanding of T cell infiltration into tumors and may provide previously unexplored strategies to rationally enhance immunotherapy efficacy.

Experimental Design

Aim 1. Assess Whether Modulating Gene Candidate Aak1 Impacts T Cell Infiltration or Anti-Tumor Activity.

The top candidate we identified in our screens was Aak1, which is an AP2-associated kinase expressed in T cells and involved in clathrin-mediated endocytosis[13]. This process impacts a number of T cell signaling proteins, including Notch and CTLA4[14,15]. Gene expression data from the Immunological Genome Project shows Aak1 expression correlates with PD-1 (Pdcd1) expression (ImmGen.org Data Browser)[16]. Together, these data support the functional relevance of Aak1 in modulating T cell anti-tumor activity and its promise as a candidate for additional validation.

Figure 3:
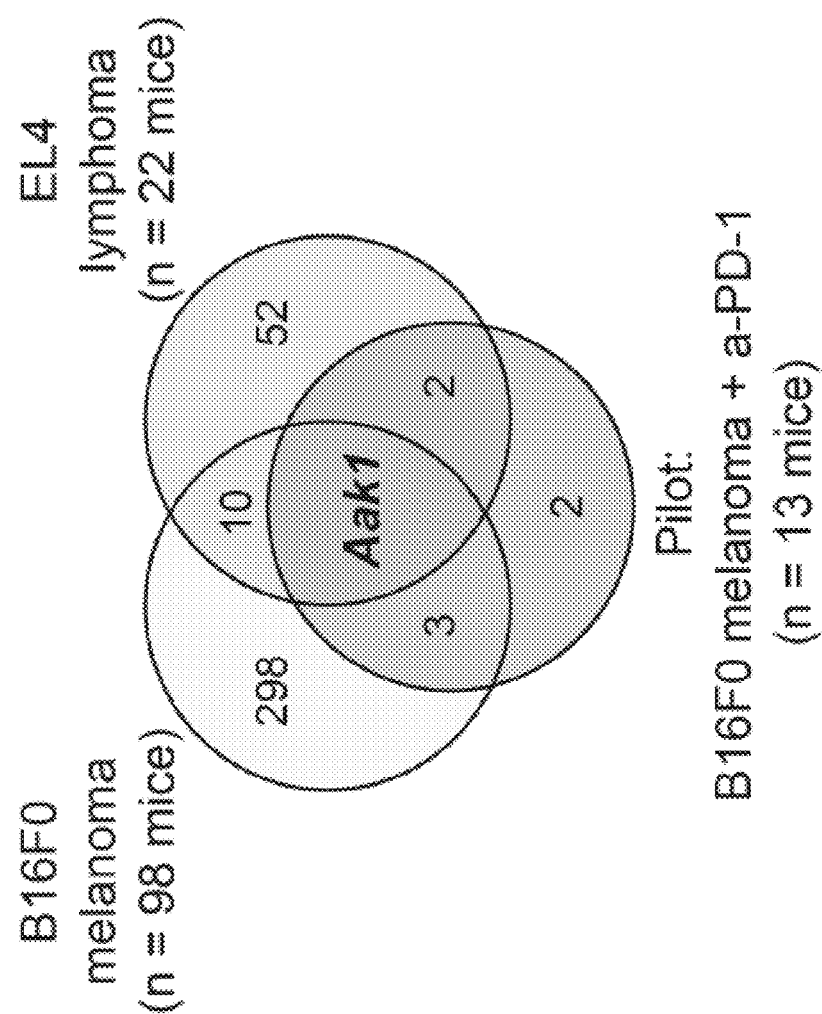
FIG. 3. Aak1 is a promising immunotherapy target candidate. A. Three SB screens have been performed using two different tumor models. Numbers represent the tumor-enriched genes discovered in each cohort (mutated in tumors, but not spleens, of at least one mouse). As indicated, some genes are shared between two of the three cohort screens. The only gene shared between all three is Aak1, which we hypothesize would enhance intratumoral T cell infiltration. B. The Aak1 gene (to scale). Red triangle indicates where transposon insertions are clustered. Because the protein coding sequence for the kinase domain spans exons 2-3, we hypothesize insertions are introducing a loss-of-function mutation.
Figure 3:
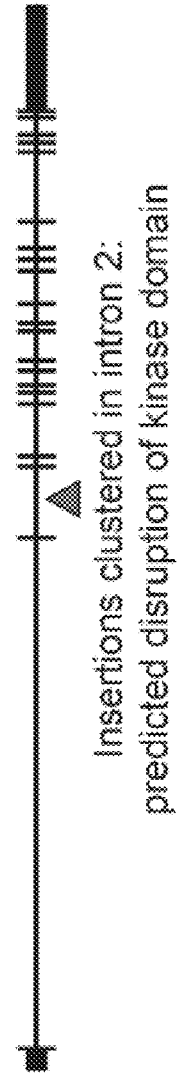

Importantly, Aak1 was mutated in tumors, but not spleens, from SB mice in two independent tumor models (FIG. 3). It was prevalent in the B16 melanoma cohort (mutated in 6 of 98 mice), and the EL4 lymphoma cohort (mutated in 1 of 22 mice). Importantly, Aak1 was mutated in tumor infiltrating T cells in 9 of 13 mice treated with anti-PD-1. All SB insertions were located in Aak1 intron 2, disrupting the kinase domain and likely causing loss-of-function of Aak1. Thus, we hypothesize that disrupting Aak1 expression will result in enhanced T cell accumulation into tumors.

Our experimental setup for both Aim 1A and Aim 1B will make use of the same lentiviral CRISPR-Cas9 vector previously used to knock out Crtc3 in T cells (FIG. 2B). We have engineered this vector to include a fluorescent reporter (EGFP or mCherry) that allows us to select transduced cells using FACS live sorting and will also allow us to quantify modified T cells in tumors. For this experiment, we have generated two CRISPRCas9 lentiviral constructs: an Aak1 KO vector with both an mCherry or EGFP reporter, and a control non-targeting CRISPR vector with an EGFP reporter.

We have successfully transduced and adoptively transferred primary CD8+ T cells using the following approach: primary murine CD8+ T cells are isolated from pooled spleens of donor mice (1 donor mouse per recipient mouse) using a negative selection kit (Miltenyi). CD8+ T cells are then activated in vitro for one day prior to transduction using anti-CD3/anti-CD28 beads (Dynabeads®, Invitrogen) and cultured for 2-4 days posttransduction in media containing 50U/ml rIL-2 (Peprotech). EGFP or mCherry positive cells are collected using live FACS sorting (FACS Aria, BD), resuspended in saline. A portion of modified T cells will be withheld to confirm Aak1 knock out by Western blot (anti-AAK1, Abcam). The remaining modified T cells will be injected intravenously into recipient mice as indicated in Sub Sims 1A and 1B.

Aim 1A: Assessing Intratumoral T Cell Infiltration.

To test whether Aak1 KO enhances intratumoral T cell accumulation, tumor-bearing recipient mice will be generated by injecting wild type C57BL/6J mice (Jackson) with B16F0, or B16F10-Ova, tumor cells subcutaneously on each rear flank. The B16F0 melanoma cell line was used in the original screen, so it is our first choice for initial validation experiments. We will also use the ovalbumin expressing B16F10 (B16F10-Ova) in these studies. Ovalbumin is a model antigen specifically recognized by T cells from OT-1 T cell receptor transgenic mice[17]. Thus, by adoptively transferring OT-1 T cells, we not only ensure all donor cells are antigen-specific, but we also mimic the CAR-T approach that has been successful in human clinical trials. Limitations of this approach are discussed below.

Figure 4:
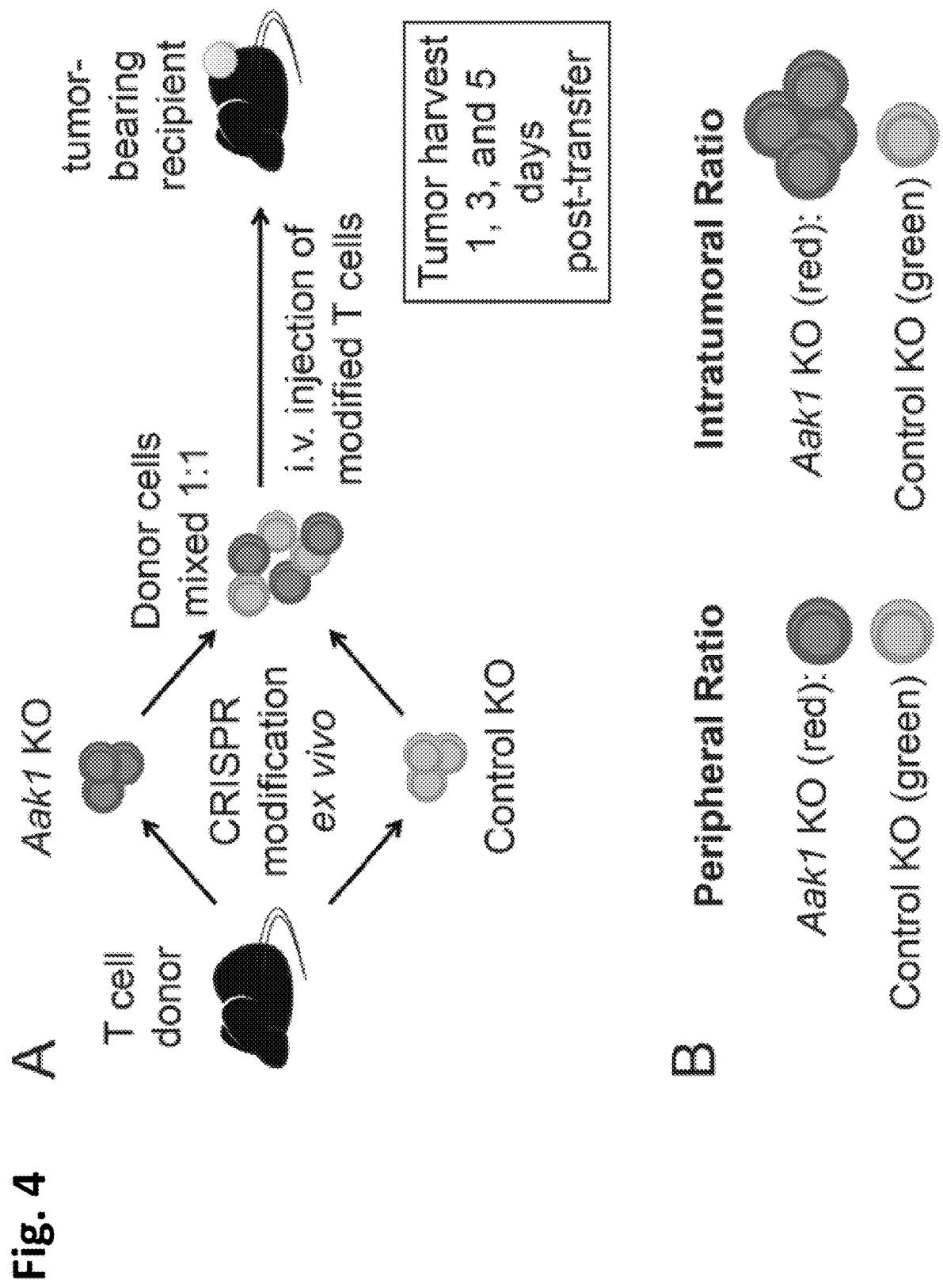
FIG. 4. Experimental design for Aim 1A measuring the effect of Aak1 loss on intratumoral T cell infiltration. A. Donor T cells will be harvested and transduced ex vivo with a lentiviral vector containing CRISPR-Cas9 machinery targeting Aak1 for knock out and containing an mCherry reporter. Control knock out cells are transduced with a nontargeting CRISPR-Cas9 vector containing an EGFP reporter. Fluorophore positive KO cells will be purified using FACS live sorting (Aria, BD), mixed 1:1, and adoptively transferred into tumor-bearing recipient mice. Intratumoral T cell accumulation will be measured as percent mCherry or EGFP positive cells of all live cells 1, 3, and 5 days later by flow cytometry. B. Anticipated results if our hypothesis that Aak1 KO will result in enhance intratumoral T cell infiltration, where the ratio of Aak1 KO (mCherry) to control KO (EGFP) cells is larger in tumors than in spleen.

Tumors will be allowed to grow for 7-10 days, and then tumor-bearing mice (n=10 per experimental replicate) will receive $1 \times 10^6$ transduced C57BL/6J or OT-1 T cells intravenously. We will mix FACS-sorted Aak1 KO (mCherry) and control cells (EGFP) 1:1 and adoptively transfer this mixture into tumor-bearing mice, such that each tumor-bearing mouse receives both experimental and control cells (FIG. 4a). Tumor-bearing mice will be euthanized 1, 3, and 5 days posttransfer, and flow cytometry will be performed to assess the percentage of CD8+, Aak1 KO (mCherry+), and control KO (EGFP+) T cells inside each tumor and spleen from each mouse.

Data will be analyzed as ratios of percent Aak1 KO (mCherry+) to percent control (EGFP+) in tumors and spleen (FIG. 4B) using a 2-way ANOVA with multiple comparisons and Sidak correction to determine if there is a significant difference in infiltration between Aak1 KO and control KO cells at each time point. Splenic data will help us determine what effects are tumor microenvironment-specific and what are universal (such as engraftment differences). Based on our hypothesis that disruption of Aak1 in T cells will increase their intratumoral accumulation, we expect to see an increased ratio of Aak1 (mCherry) to control (EGFP) cells in the tumor compared to the same ratio in the spleen, indicating enhanced T cell infiltration with Aak1 KO. In subsequent experiments, we will inject mice with wild type B16F0 tumor on one flank and B16F10-Ova tumor cells on the other to assess the relative tumor infiltration of Aak1 modified OT-1 cells into antigen positive and antigen negative tumors.

Mouse numbers for Aim 1A were calculated such that candidate genes may be tested in at least 2 technical replicates of each experiment, with 10 mice per experimental group per replicate, and using a 1:1 donor to recipient ratio. Experimental group sample size was determined using a 2-sample 2-tailed power calculation to detect a ~2-fold difference in T cell infiltration with 80% power. The use of dual fluorescent reporters allows us to assess relative numbers during flow cytometric analysis of tissues after euthanization and will minimize technical variation.

Our screen results indicate that different tumor models impact which genes are identified as important for T cell infiltration. In fact, we chose to validate Aak1 specifically because it was identified in more than one tumor model. Thus, it is important to assess the effect of Aak1 on T cell infiltration using a second tumor model. Our lab also possesses an ovalbumin-expressing EL4 lymphoma cell line (EG7), and we plan an analogous set of experiments using EG7 tumor-bearing mice as modified-OT-1 recipients.

The SB system was developed on the C57BL/6 strain background, and all our screens were performed on this background. However, it is widely appreciated that strain background strongly influences the anti-tumor immune response. It will therefore be valuable to assess the impact of modifying Aak1 in other genetic backgrounds as well. Our laboratory has extensive experience studying immunotherapy, including anti-PD-1 therapy, in the A20 B cell lymphoma model that originated on the BALB/c background. We will therefore assess the effect of knocking out Aak1 on infiltration of adoptively transferred BALB/c T cells into A20 tumors.

Aim 1B: Assessing T Cell Anti-Tumor Activity.

Figure 5:
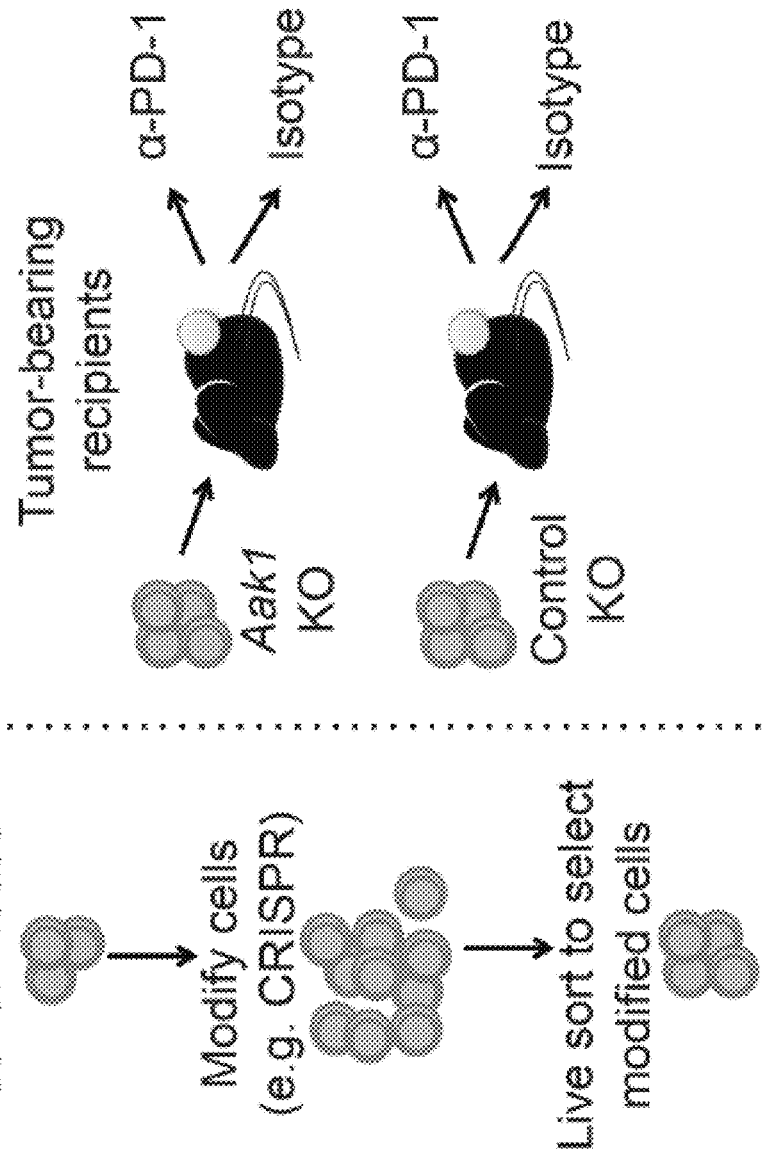
FIG. 5. Experimental design for Aim 1B: measuring effect of Aak1 loss on tumor regression with and without anti-PD-1 treatment. We hypothesize that knocking out Aak1 in adoptively transferred T cells will enhance anti-PD-1 therapy. We propose initial assessment of therapeutic response by measuring tumor regression, but other markers of enhanced T cell response may also be assessed, including expression of CD137 and other anti-tumor activation markers.

We will also test whether knockout of Aak1 in CD8+ T cells has therapeutic anti-tumor effects, alone or in combination with anti-PD-1. We hypothesize that loss of Aak1 will enhance CD8+ T cell anti-tumor activity, particularly if Aak1 impacts intratumoral infiltration. To directly test this, we plan to adoptively transfer Aak1 KO cells or control cells into tumor-bearing recipients, along with anti-PD-1 therapy or isotype control, and measure tumor growth (FIG. 5). The specific tumor model to used (melanoma or lymphoma) for these therapy studies will be selected based on which model demonstrated the greatest increase in intratumoral T cell infiltration after Aak1 knockout.

Given the robust immune response by OT-1 cells to ovalbumin antigen, it is likely that B16F10-Ova or EG7 tumor-bearing mice receiving Aak1 KO OT-1 cells will exhibit tumor enhanced regression when combined with anti-PD-1 treatment. However, it should be noted that a recent shRNA screen successfully identified at least one novel therapeutic gene that, when knocked down in adoptively transferred T cells, had a therapeutic anti-tumor effect in the absence of other treatments. Therefore, it is important to include treated and untreated subgroups in both the Aak1 KO and control KO groups, so that we will be able to measure the anti-tumor effect Aak1 KO alone has, and whether additional therapeutic effect is achieved in combination with anti-PD-1.

Thus, our experimental design is as follows: recipient mice will receive subcutaneous tumor 7-10 days before adoptive T cell transfer in order to establish tumors before treatment. Tumor-bearing recipient mice (n=15 per treatment group) will then receive Aak1 KO (EGFP positive, live sorted) CD8+ cells or control KO (also EGFP positive, live sorted) CD8+ cells and treated with anti-PD-1 or isotype control antibody. Tumor growth will be measured twice weekly once tumors become palpable and monitored for signs of tumor regression. Survival will also be followed, graphed as a Kaplan-Meier plot and evaluated for significant differences using a log-rank test. Mouse numbers for Aim 1B were calculated such that candidate genes will be tested in at least 2 technical replicates of each experiment using a 1:1 donor to recipient ratio. The experimental group sample size (n=15 mice per experimental group per replicate) was determined using a Cox proportional hazards 2-sided model to assess survival with a hazard ratio of ~3 with 80% power.

Expected Results and Alternative Approaches

Aim 1A. Gene Modification Effect on Intratumoral T Cell Accumulation.

We hypothesize that knocking out Aak1 in T cells will enhance their accumulation in the tumor. Therefore, we expect that Aak1 KO cells will be present at higher percentages than control KO cells in tumors (FIG. 4B), such that the mCherry:EGFP ratio will be above 1, and higher than the ratio in the spleen. It is possible that knocking out Aak1 in T cells will not enhance their intratumoral accumulation. Results indicating a marked reduction in intratumoral T cells (opposite to our hypothesis) might suggest that testing Aak1 overexpression (or gain-of-function) is more appropriate. Results indicating no change in intratumoral accumulation would suggest that we should choose one of our many other gene candidates, such as Crtc3, to focus our efforts on instead.

While widely used to study antigen-specific immunological responses, the OT-1/Ova system does not fully recapitulate the tumor antigen specific immune response. We chose to begin our experimentation using this system because it is so well studied, induces a robust antigen-specific T cell response, and is likely to achieve measureable T cell infiltration even by control "knock out" cells, thus allowing us to provide proof-of-concept data for further study of Aak1 as a therapeutic target. Additional studies could make use of a second, more physiologically relevant, TCR transgenic/tumor antigen combination such as the Pmel-1/gp100 model[18] or murine CAR-T cells.

Finally, we have chosen to focus on CD8+ T cells, rather than CD4+ T cells, due to preliminary sequence data on sorted cell populations suggesting that the SB insertions were primarily derived from the CD8+ subpopulation (data not shown). Moreover, many adoptive transfer therapies have focused on using CD8+ T cells due to their cytotoxic potential. However, the role of Aak1 in CD4+ T cell function may also be important to study.

Aim 1B. Gene Modification Effect on Anti-Tumor Activity.

The proposed experimental design will allow us to determine whether Aak1 KO in adoptively transferred T cells enhances the therapeutic effect of the T cells. If Aak1 KO enhances the anti-tumor efficacy of T cells, with or without anti-PD-1, we would have strong evidence supporting the validity of our hypothesis. Either finding will be useful in enhancing T cell mediated immunotherapies. If tumor regression is not enhanced with adoptive transfer alone or in combination with anti-PD-1, we have other candidate genes produced by our screens, including Crtc3, which we have already shown impacts cytokine production upon T cell activation in vitro. Finally, we expect to generate additional gene candidates in Aim 2 that could be validated in vivo using the same experimental approaches outlined in Aim 1.

Aim 2. Identify Additional Genes that Influence Intratumoral T Cell Infiltration and Anti-Tumor Effects in Combination with Anti-PD-1 Across Tumor Types.

Preliminary studies suggest the combination of CAR-T therapy with anti-PD-1 may improve CAR-T efficacy[19]. There are likely many as yet undefined molecular mechanisms that may act synergistically with these immunotherapeutic approaches. Aim 2 focuses on identifying additional gene candidates with a focus on those that might be effective in combination with anti-PD-1 and can eventually be tested with retargeted T cells. We hypothesize that SB mutagenesis of T cells in additional tumor models and with anti-PD-1 treatment will identify additional genes that act synergistically with anti-PD-1.

As described in the preliminary data section, we performed a pilot screen (n=13) similar to that in FIG. 1 to assess how anti-PD-1 treatment impacts genetic selection of SB insertions in intratumoral T cells in the B16F0 model. Aak1 was the top gene candidate, mutated at a significantly higher rate with anti-PD-1 treatment (9 of 13 mice) than without treatment (Fisher's Exact, P<0.0001). This suggests that anti-PD-1 has a large impact on the selection of T cell genes that are important for intratumoral T cell accumulation, even if it does not have a large therapeutic effect as a single-agent therapy in the B16F0 melanoma model. These results are encouraging, and provide rationale for expanding our pilot screen to include a larger number of mice in order to identify additional T cell genes that may specifically synergize with anti-PD-1 therapy.

Further, few gene candidates were shared between the melanoma and lymphoma screen cohorts, suggesting that additional tumors models are needed to identify conserved mechanisms that could be broadly applicable to more than one tumor type. Therefore, we propose applying our screen approach to two additional immunocompetent mouse models: MC38 colon carcinoma and LLC lung carcinoma, both of which respond poorly to immune checkpoint blockade alone[20,21]. As described in our preliminary data, we will generate mice with SB-mutagenized T cells by breeding CD4-Cre transgenic mice with SB strains, with and without anti-PD-1 treatment (n=70 each model, calculated to allow us to determine significance of a 4-fold difference in prevalence between cohorts with 80% power).

Candidate genes identified in more than one (and ideally, all) tumor models will be considered the strongest candidates for development as potential immunotherapeutic targets. Further, genes identified in the presence of anti-PD-1 will be compared to the candidate genes from the untreated cohort (n=98) using a Fisher's Exact approach to strengthen the specificity for anti-PD-1 action. For example, clonally expanded insertion sites present in a higher proportion of the anti-PD-1 treated cohort (like Aak1) represent gene candidates that could functionally impact anti-PD-1 therapy. We anticipate that this approach will allow us to identify key signaling pathways mediating anti-PD-1 blockade, perhaps including molecules that participate in other immune checkpoint pathways. Promising gene candidates will be targeted in T cells as outlined in Aim 1 to assess their impact on T cell infiltration into tumors (Aim 1A) and therapeutic effect (Aim 1B).

Expected Results and Alternative Approaches

Based on our pilot data, we anticipate that expanding our screen to include other tumor models treated with anti-PD-1 will allow us to successfully identify additional gene candidates that are either unique to, or overrepresented in, the anti-PD-1 treatment cohort. These genes will be tested similarly to Aak1 in for roles in T cell infiltration and therapeutic synergy with immune checkpoint blockade. Given the differences observed between the tumor models, it may be informative to compare the gene candidate lists from untreated counterparts as well.

Strain background also strongly influences the anti-tumor immune response. Currently, our tumor model choices are limited to the C57BL/6 strain background, since the SB transgenic mice are not available on other strain backgrounds. Thus, it will be important to validate promising candidates using diverse strain background as described in Aim 1.

Future Studies and Long-Range Objectives

Our studies are designed to identify T cell genes that can be modified to enhance T cell-mediated immunotherapies such as CAR-T and immune checkpoint blockade. Preliminary studies have confirmed the SB model can be used to identify candidate genes that impact T cell function, and we have already identified Aak1 as the most promising to test in preclinical models. Successful completion of the proposed studies could lead to three different avenues of investigation:

1. Modifying AAK1 (and alternative genes identified in our SB screen) in human T cells could be explored as a way to enhance the efficacy of CAR-T cells or other adoptive T cell therapies.

2. AAK1 and CRTC3—another candidate identified in the melanoma screen—are kinases for which small molecule inhibitors have been developed[22,23]. While their protein expression is not limited to T cells, further studies could be done to assess whether such small molecules impact on T cell infiltration into tumors.

3. Further studies could be done to understand the biology of how modification of the genes identified in our SB screens impact on T cell infiltration into tumors. Understanding whether modification enhances T cell trafficking, expansion or sustained viability within the tumor could be particularly important. This would include both laboratory studies and correlative science exploring expression of the identified gene (such as Aak1) in tumor infiltrating lymphocytes using immunohistochemistry on human tumor biopsies.

REFERENCES

1. Tang, H. et al. Facilitating T Cell Infiltration in Tumor Microenvironment Overcomes Resistance to PDL1 Blockade. *Cancer cell* 29, 285-296, doi:10.1016/j.ccell.2016.02.004 (2016).
2. Zhou, P. et al. In vivo discovery of immunotherapy targets in the tumour microenvironment. *Nature* 506, 52-57, doi:10.1038/nature12988 (2014).
3. Wang, Z., Guo, Y. & Han, W. Current status and perspectives of chimeric antigen receptor modified T cells for cancer treatment. *Protein & cell*, doi:10.1007/s13238-017-0400-z (2017).
4. Iwai, Y., Hamanishi, J., Chamoto, K. & Honjo, T. Cancer immunotherapies targeting the PD-1 signaling pathway. *Journal of biomedical science* 24, 26, doi:10.1186/s12929-017-0329-9 (2017).
5. Gajewski, T. F., Louahed, J. & Brichard, V. G. Gene signature in melanoma associated with clinical activity: a potential clue to unlock cancer immunotherapy. *Cancer journal* 16, 399-403, doi:10.1097/PPO.0b013e3181eacbd8 (2010).
6. Ji, R. R. et al. An immune-active tumor microenvironment favors clinical response to ipilimumab. *Cancer immunology, immunotherapy: CII* 61, 1019-1031, doi:10.1007/s00262-011-1172-6 (2012).
7. Chen, D. S. & Mellman, I. Elements of cancer immunity and the cancer-immune set point. *Nature* 541, 321-330, doi:10.1038/nature21349 (2017).
8. Kershaw, M. H. et al. A phase I study on adoptive immunotherapy using gene-modified T cells for ovarian cancer. *Clinical cancer research: an official journal of the American Association for Cancer Research* 12, 6106-6115, doi:10.1158/1078-0432.CCR-06-1183 (2006).
9. Papa, S., van Schalkwyk, M. & Maher, J. Clinical Evaluation of ErbB-Targeted CAR T-Cells, Following Intracavity Delivery in Patients with ErbB-Expressing Solid Tumors. *Methods in molecular biology* 1317, 365-382, doi:10.1007/978-1-4939-2727-2_21 (2015).
10. Enblad, G., Karlsson, H. & Loskog, A. S. CAR T-Cell Therapy: The Role of Physical Barriers and Immunosuppression in Lymphoma. *Human gene therapy* 26, 498-505, doi:10.1089/hum.2015.054 (2015).
11. Mann, M. B., Jenkins, N. A., Copeland, N. G. & Mann, K. M. Sleeping Beauty mutagenesis: exploiting forward genetic screens for cancer gene discovery. *Current opinion in genetics & development* 24, 16-22, doi:10.1016/j.gde.2013.11.004 (2014).
12. Berquam-Vrieze, K. E. et al. Cell of origin strongly influences genetic selection in a mouse model of TALL. *Blood* 118, 4646-4656, doi:10.1182/blood-2011-03-343947 (2011).
13. Conner, S. D. & Schmid, S. L. Identification of an adaptor-associated kinase, AAK1, as a regulator of clathrin-mediated endocytosis. *The Journal of cell biology* 156, 921-929, doi:10.1083/jcb.200108123 (2002).
14. Gupta-Rossi, N. et al. The adaptor-associated kinase 1, AAK1, is a positive regulator of the Notch pathway. *The Journal of biological chemistry* 286, 18720-18730, doi: 10.1074/jbc.M110.190769 (2011).
15. Shiratori, T. et al. Tyrosine phosphorylation controls internalization of CTLA-4 by regulating its interaction with clathrin-associated adaptor complex AP-2. *Immunity* 6, 583-589 (1997).
16. Heng, T. S., Painter, M. W. & Immunological Genome Project, C. The Immunological Genome Project: networks of gene expression in immune cells. *Nature immunology* 9, 1091-1094, doi:10.1038/ni1008-1091 (2008).
17. Clarke, S. R. et al. Characterization of the ovalbumin-specific TCR transgenic line OT-I: MHC elements for positive and negative selection. *Immunology and cell biology* 78, 110-117, doi:10.1046/j.1440-1711.2000.00889.x (2000).
18. Overwijk, W. W. et al. Tumor regression and autoimmunity after reversal of a functionally tolerant state of self-reactive CD8+ T cells. *The Journal of experimental medicine* 198, 569-580, doi:10.1084/jem.20030590 (2003).
19. John, L. B. et al. Anti-PD-1 antibody therapy potently enhances the eradication of established tumors by gene-modified T cells. *Clinical cancer research: an official journal of the American Association for Cancer Research* 19, 5636-5646, doi:10.1158/1078-0432.CCR-13-0458 (2013).
20. Nagato, T., Lee, Y. R., Harabuchi, Y. & Celis, E. Combinatorial immunotherapy of polyinosinicpolycytidylic acid and blockade of programmed death-ligand 1 induce effective CD8+ T-cell responses against established tumors. *Clinical cancer research: an official journal of the American Association for Cancer Research* 20, 1223-1234, doi: 10.1158/1078-0432.CCR-13-2781 (2014).
21. Kodumudi, K. N. et al. Immune Checkpoint Blockade to Improve Tumor Infiltrating Lymphocytes for Adoptive Cell Therapy. *PloS one* 11, e0153053, doi:10.1371/journal.pone.0153053 (2016). Contact PD/PI: Rogers, Laura M. References Cited Page 8
22. Clark, K. et al. Phosphorylation of CRTC3 by the salt-inducible kinases controls the interconversion of classically activated and regulatory macrophages. *Proceedings of the National Academy of Sciences of the United States of America* 109, 16986-16991, doi:10.1073/pnas.1215450109 (2012).
23. Kostich, W. et al. Inhibition of AAK1 Kinase as a Novel Therapeutic Approach to Treat Neuropathic Pain. *The Journal of pharmacology and experimental therapeutics* 358, 371-386, doi:10.1124/jpet.116.235333 (2016).

Example 7—Aak1 as a Modulator of T Cell Infiltration in Solid Tumors

Figure 6:
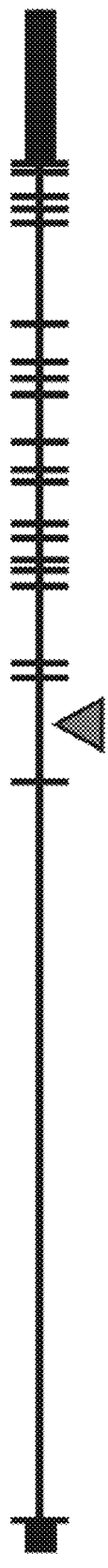
FIG. 6. Schematic representation of Aak1 gene illustrated cluster of insertions in intron 2.
Figure 6:

The role of Aak1 in T cell infiltration and activation was further studied in vitro and in vivo. FIG. 6 provides a schematic representation of Aak1 gene. In the SB assay, we observed that transposon insertion were clustered in intron 2.

Aak1 or is a protein kinase shown to interact with AP2, from which interaction its name is derived, i.e., "AP2-associated protein kinase." Aak1 is known to positively regulate Notch signaling, which can have pro-proliferation activity. Aak1 also is involved generally in clathrin-mediated endocytosis and endosomal recycling. Specifically, Aak1 is involved in major histocompatibility complex I (MHCI) and epithelial growth factor receptor (EGFR) internalization. AP-2 interacts with the T cell receptor (TCR), so Aak1 may modulate the TCR through its interaction with AP-2. A small molecule inhibitor of Aak1's kinase activity called LP-935509 has been described and is under preclinical models to prevent neuropathic pain.

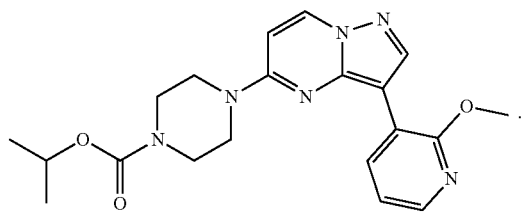

LP-935509

Aak1 has a predicted molecular weight of 103,885 Da. The Aak1 polypeptide includes an N-terminal serine/threonine kinase domain, followed by a QPA rich domain, following by a C-terminal α-interacting domain (see FIG. 6), through which Aak1 interacts with AP-2 and clathrin. Aak1 autophosphorylates as well as phosphorylates AP-1, AP-2 and Numb, that latter of which is required for IL-2R recycling. Aak1 is localized at the membrane in early endosomes and regulates endocytosis of the transferrin receptor, EGFR, and Notch.

The human and mouse forms of Aak1 exhibit 91% sequence identity. As such, mouse models of Aak1 activity are expected to correlate well with human AAK1 activity.

Figure 7:
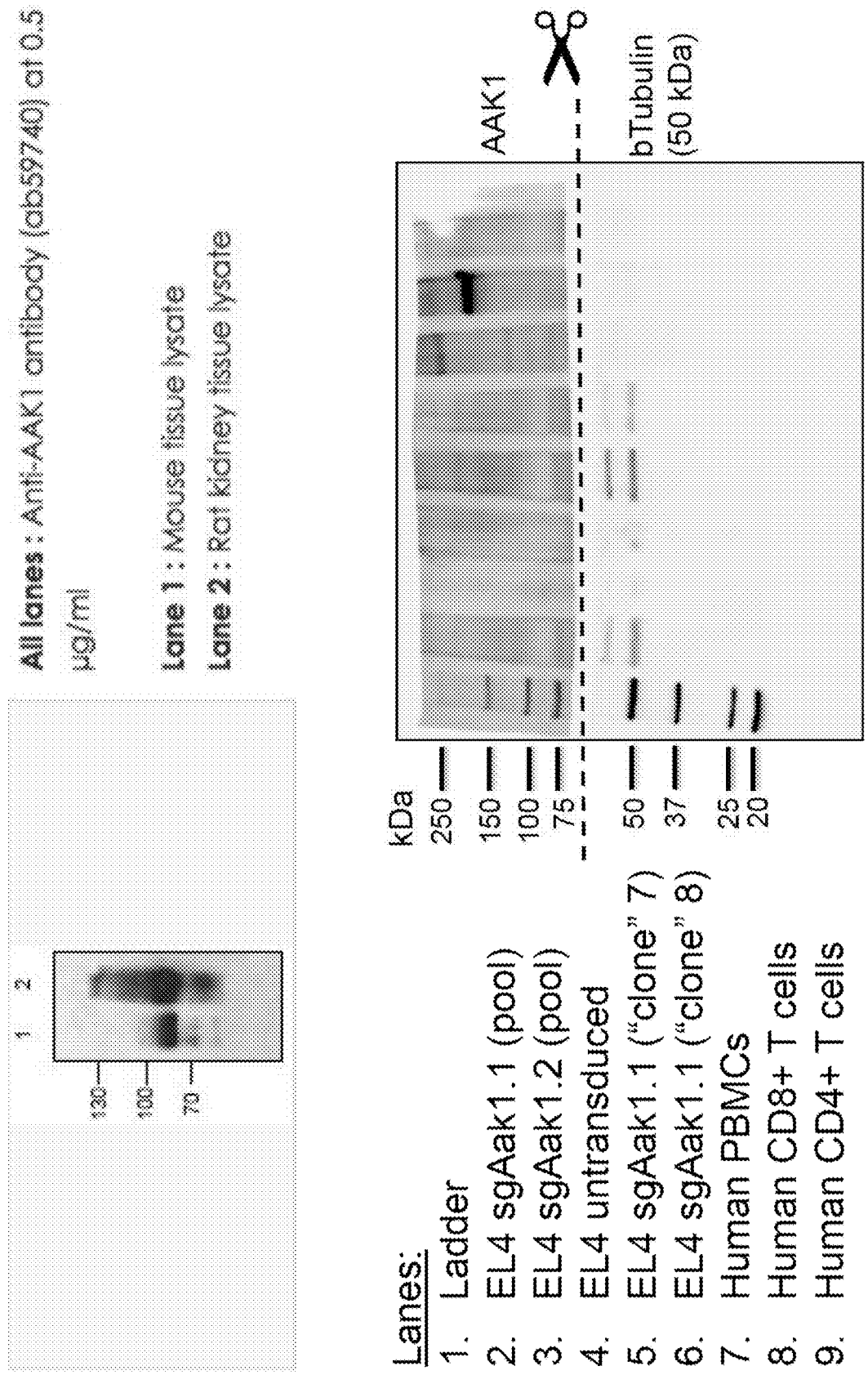
FIG. 7. Western blot of cell lysates using Aak1 monoclonal antibody specific for the long form of Aak1.
Figure 8:
FIG. 8. Western blot of cell lysates using Aak1 monoclonal antibody specific for the long form of Aak1 and Aak1 monoclonal antibody for both of the long form of Aak1 and the short form of Aak1.

Aak1 has a long form having 961 amino acids (SEQ ID NO:2) and a short form having 823 amino acids (SEQ ID NO:3), which is truncated at the C-terminus relative to the long form. The long and short forms have equivalent kinase activity. However, the extended C-terminus of the long form may facilitate additional clathrin binding. A monoclonal antibody that binds both of the long and short form via binding an epitope nearer the N-terminus have been described (Abcam #173329). As well, a monoclonal antibody that is specific for the long form via binding to a C-terminal epitope not present in the short form also has been described (Abcam #59740). FIG. 7 illustrates a Western blot of cell lysates using Aak1 monoclonal antibody specific for the long form of Aak1 (Abcam #59740). Expression of the long form of Aak1 was detected in mouse tissue lysate, rat kidney lysate, and human CD8+ T cells. FIG. 8 illustrates a Western blot of cell lysates using Aak1 monoclonal antibody specific for the long form of Aak1 (Abcam #59740) and a monoclonal antibody for both of the long form of Aak1 and the short form of Aak1 (Abcam #173329). The long and short forms of Aak1 were detected in ms brain tissue lysate whereas the long form of Aak1 was detected in human CD8+ T cells.

Figure 9:
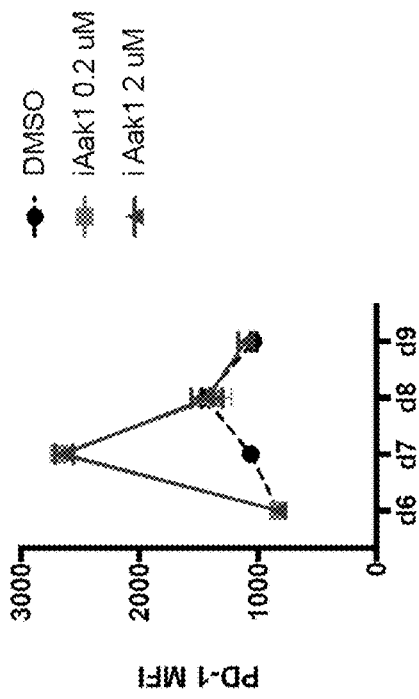
FIG. 9. In vitro treatment of primary mouse CD8+ T cells with Aak1 inhibitor (iAak1) results in a transient increase in PD-1 expression.
Figure 9:
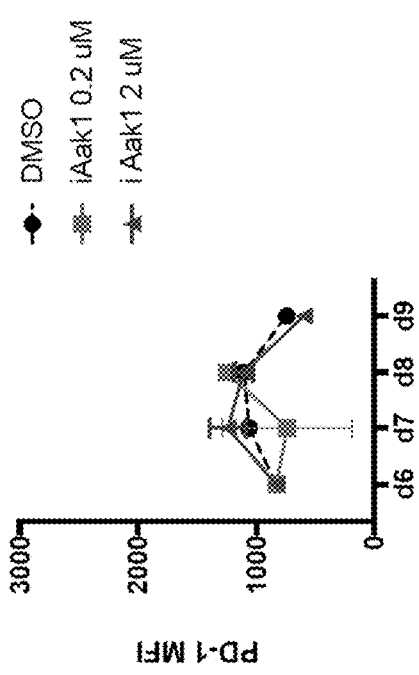

FIG. 9 illustrates the results of in vitro treatment of primary mouse CD8+ T cells with Aak1 inhibitor (iAak1 aka LP-935509) on PD-1 expression. Primary mouse CD8+ T cells were treated with the indicated concentration of LP-935509 and PD-1 expression was measured at days 6, 7, 8, and 9. A transient increase in PD-1 expression was observed when activated CD8+ T cells were treated with the Aak1 inhibitor.

Figure 10:
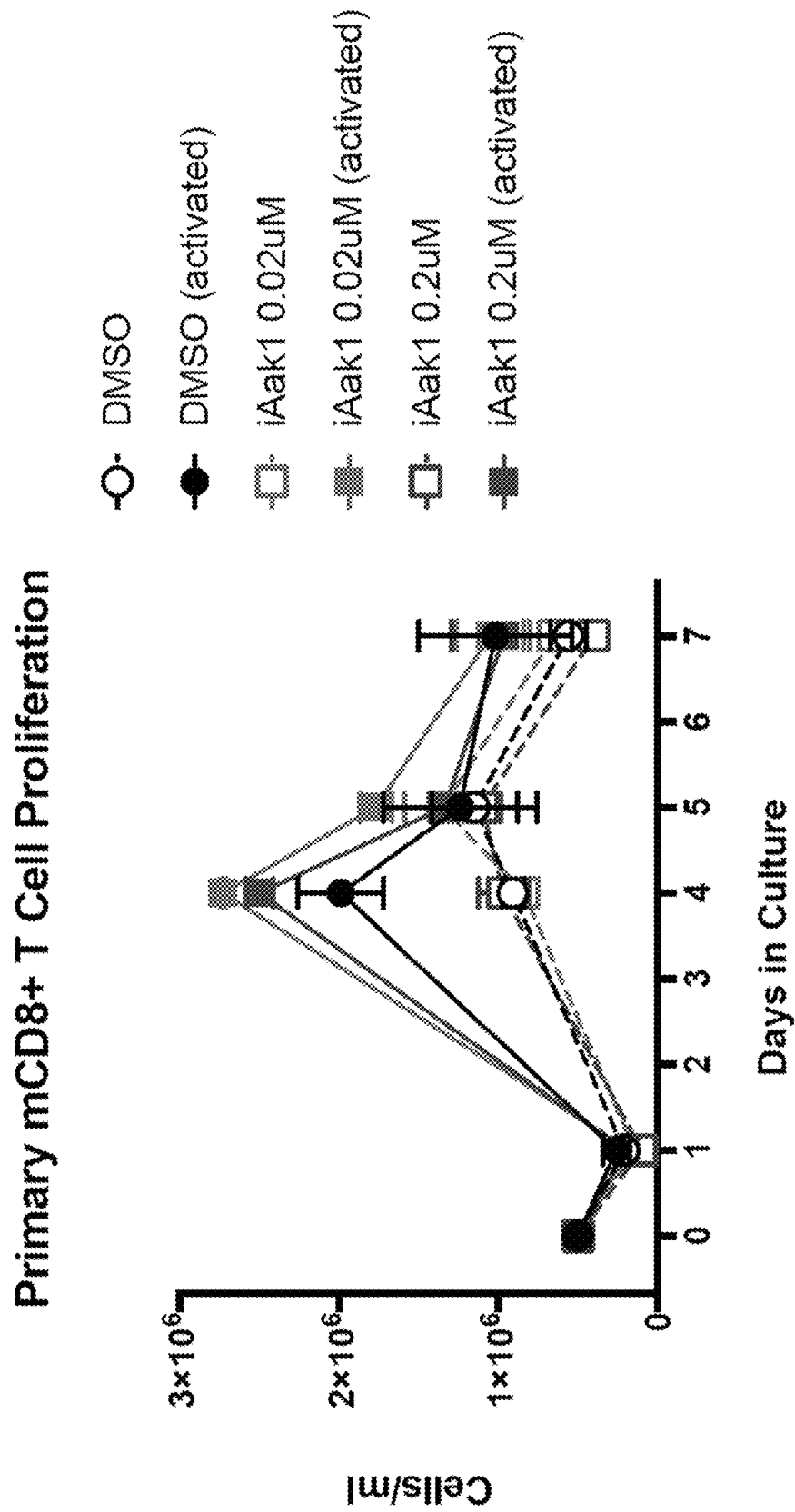
FIG. 10. In vitro treatment of primary mouse CD8+ T cells with Aak1 inhibitor (iAak1) modestly enhances proliferation.

FIG. 10 illustrates the results of in vitro treatment of primary mouse CD8+ T cells with Aak1 inhibitor (iAak1) on cell proliferation. Primary mouse CD8+ T cells were treated on day 0 with the indicated concentration of LP-935509 and optionally activated. Cell proliferation was assessed at days 1, 2, 3, 4, 5, 6, and 7. A modest enhancement in proliferation was observed when the CD8+ T cells were administered the Aak1 inhibitor.

Figure 11:
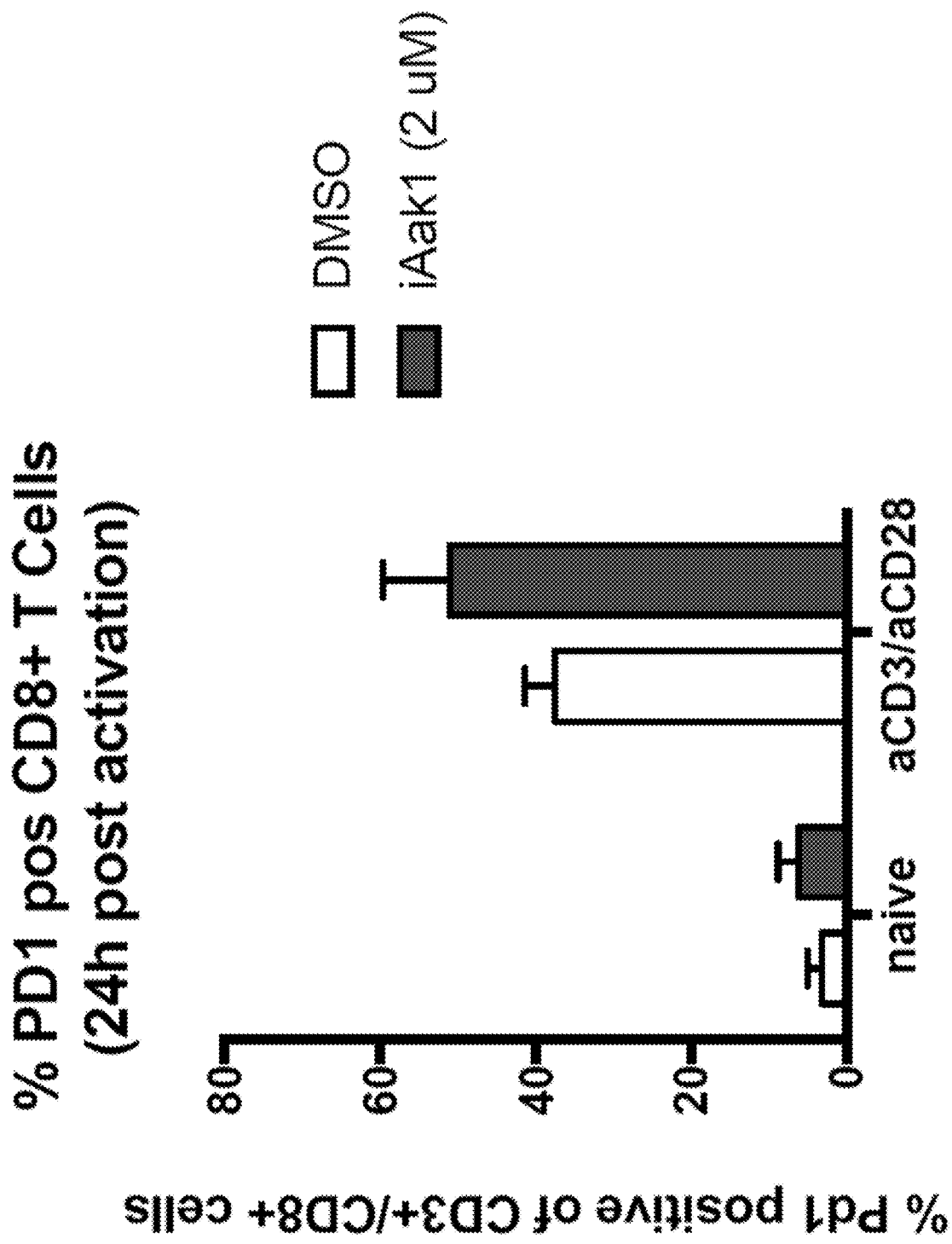
FIG. 11. In vitro treatment of primary mouse splenocytes with Aak1 inhibitor (iAak1) increases PD-1 expression on CD8+ T cells.

FIG. 11 illustrates the results of in vitro treatment of primary mouse splenocytes with Aak1 inhibitor (iAak1) on PD-1 expression. Mouse splenocytes were treated with 2 μM concentration of iAak1 and PD-1 expression was assayed in CD8+ T cells. A modest increase in PD-1 expression was observed in CD8+ T cells derived from splenocytes.

Figure 12:
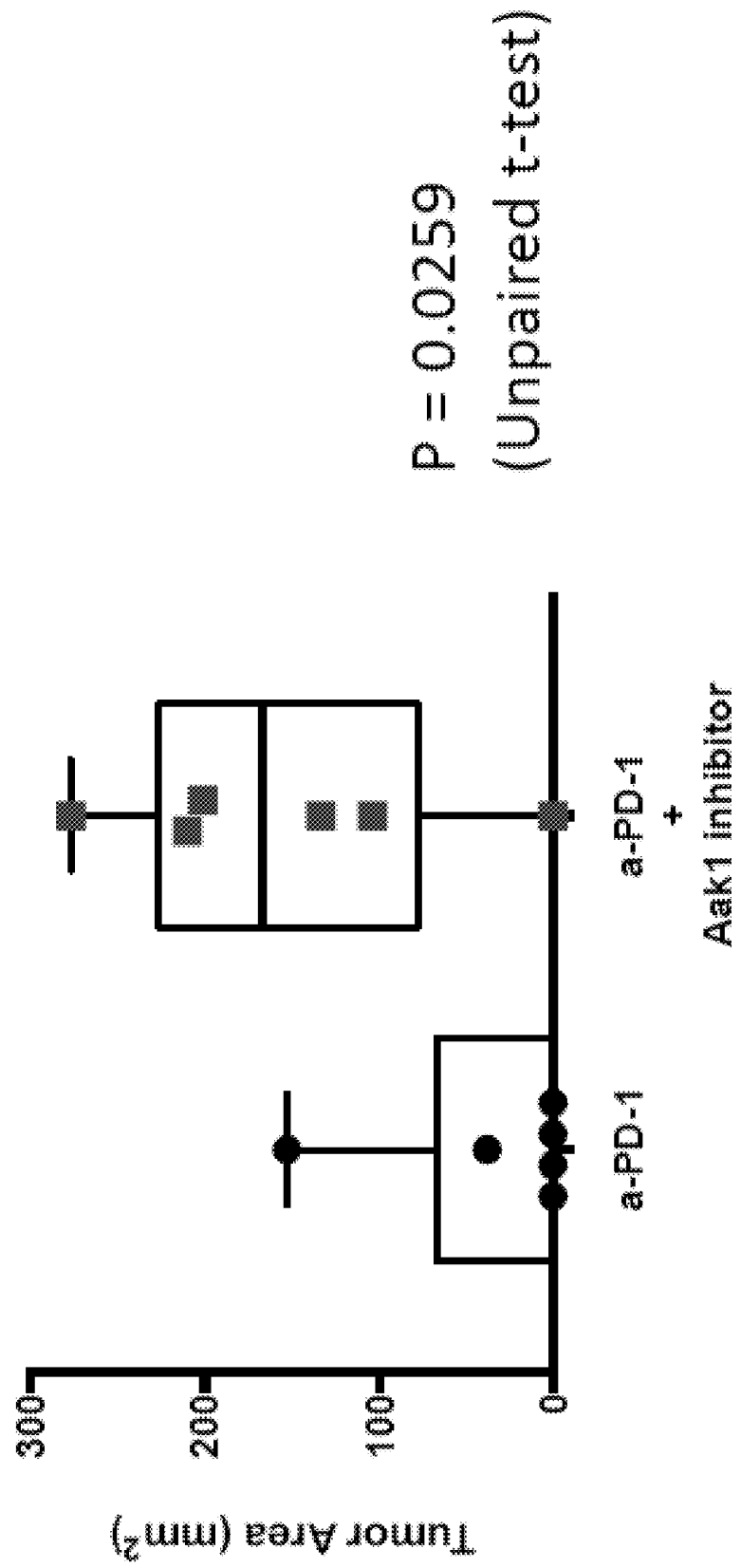
FIG. 12. Aak1 inhibitor (iAak1) results in increased EG7 tumor growth in vivo.

FIG. 12 illustrates the results of Aak1 inhibitor (iAak1) on the growth of EG7 tumors in mice. Mice were inoculated with EG7 tumor cells. Treatment began three (3) days post tumor inoculation. All mice received twice weekly IP injections of aPD1. Five (5) mice received DMSO, and five (5) mice received iAak1 via oral gavage on same days as aPD1 treatment. Treatment with iAak1 resulted in increased EG7 tumor growth in vivo.

Figure 13:
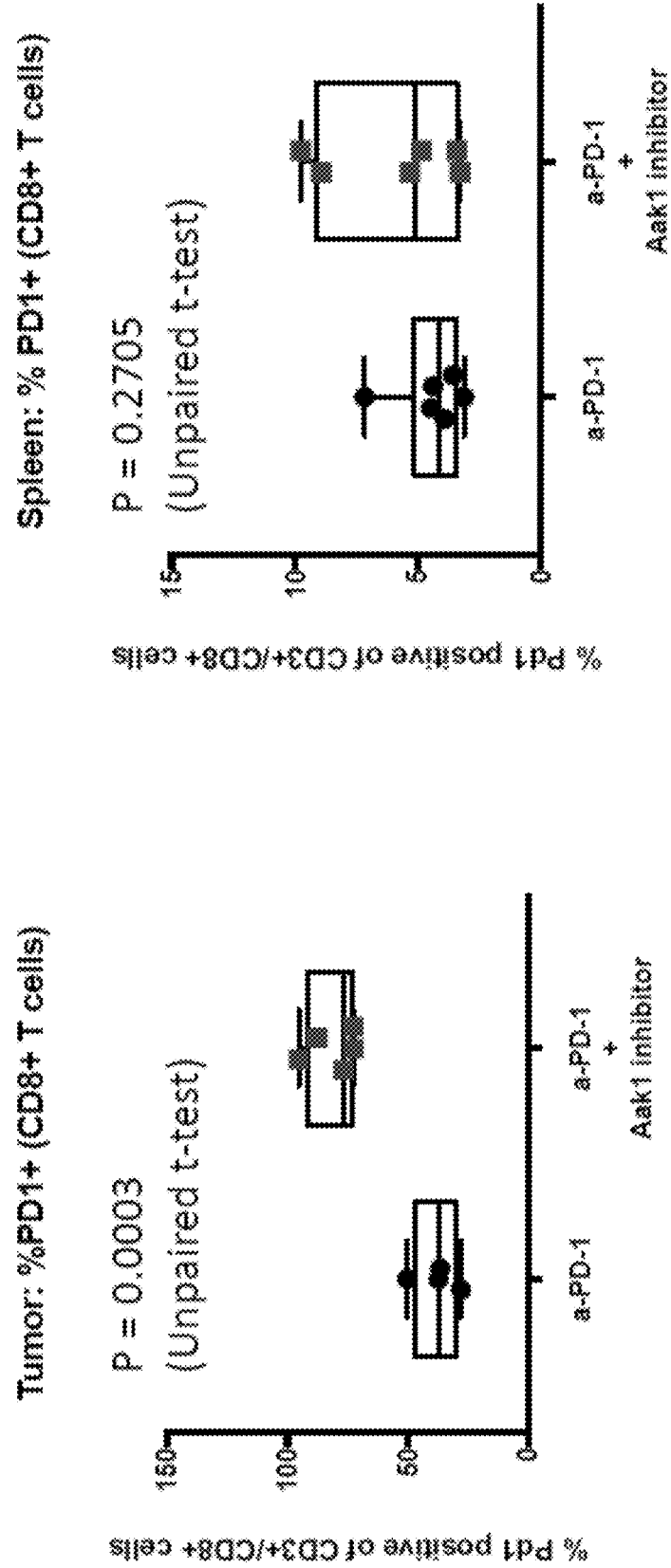
FIG. 13. Aak1 inhibitor (iAak1) increased PD-1 expression on tumor-infiltrating but not splenic CD8+ T cells in EG7 tumor model.

FIG. 13 illustrates the results of Aak1 inhibitor (iAak1) on PD-1 expression in tumor-infiltrating versus splenic CD8+ T cells in an EG7 tumor model. Mice were inoculated with EG7 tumor cells. Treatment began three (3) days post tumor inoculation. All mice received twice weekly IP injections of aPD1. Five (5) mice received DMSO, and five (5) mice received Aak1inh via oral gavage on same days as aPD1 treatment. The Aak1 inhibitor (iAak1) was observed to increase PD-1 expression in CD8+ T cells isolated from tumors but not in CD8+ cells that were isolated from the spleen.

Figure 14:
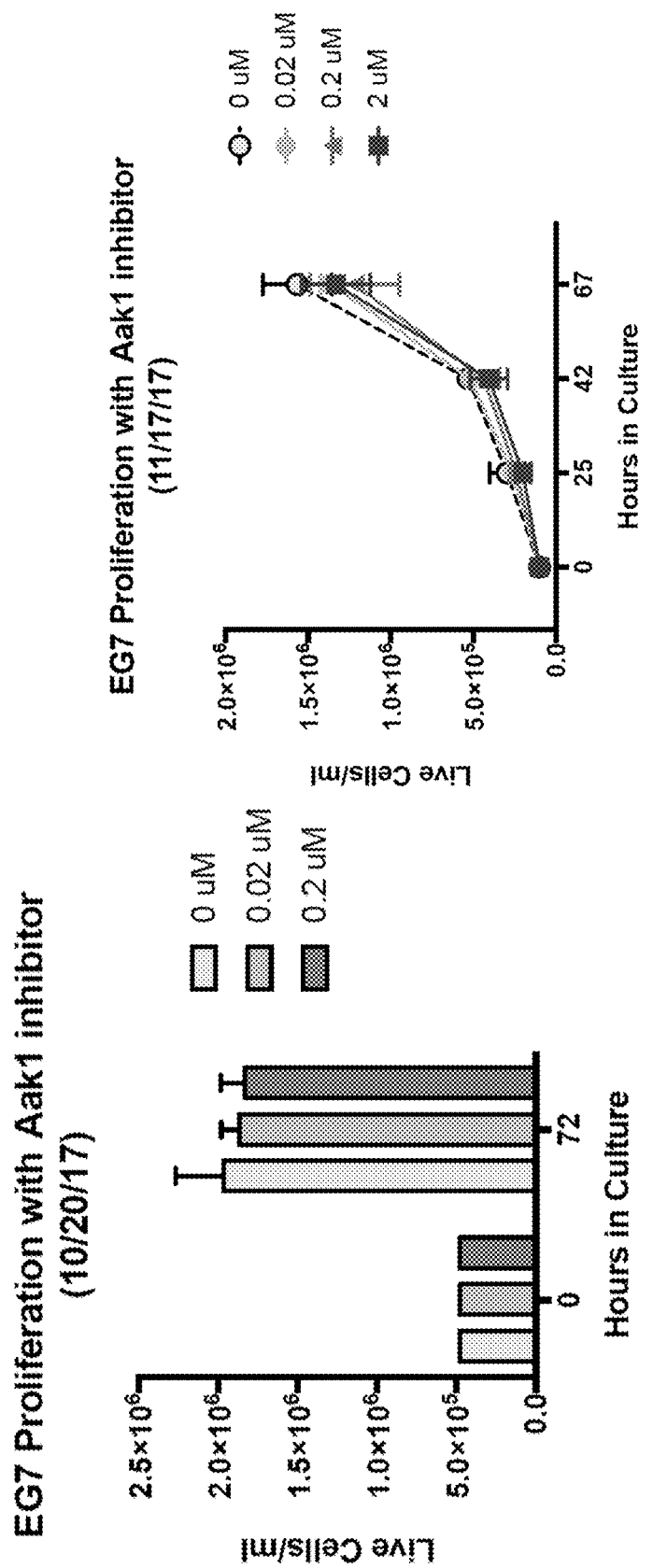
FIG. 14. Aak1 inhibitor (iAak1) did not directly increase EG7 cell proliferation in vitro.

FIG. 14 illustrates the results of Aak1 inhibitor (iAak1) on growth of EG7 cells in vitro. The Aak1 inhibitor (iAak1) was not observed to directly increase EG7 cell proliferation in vitro at concentrations as high as 2 μM.

Figure 15:
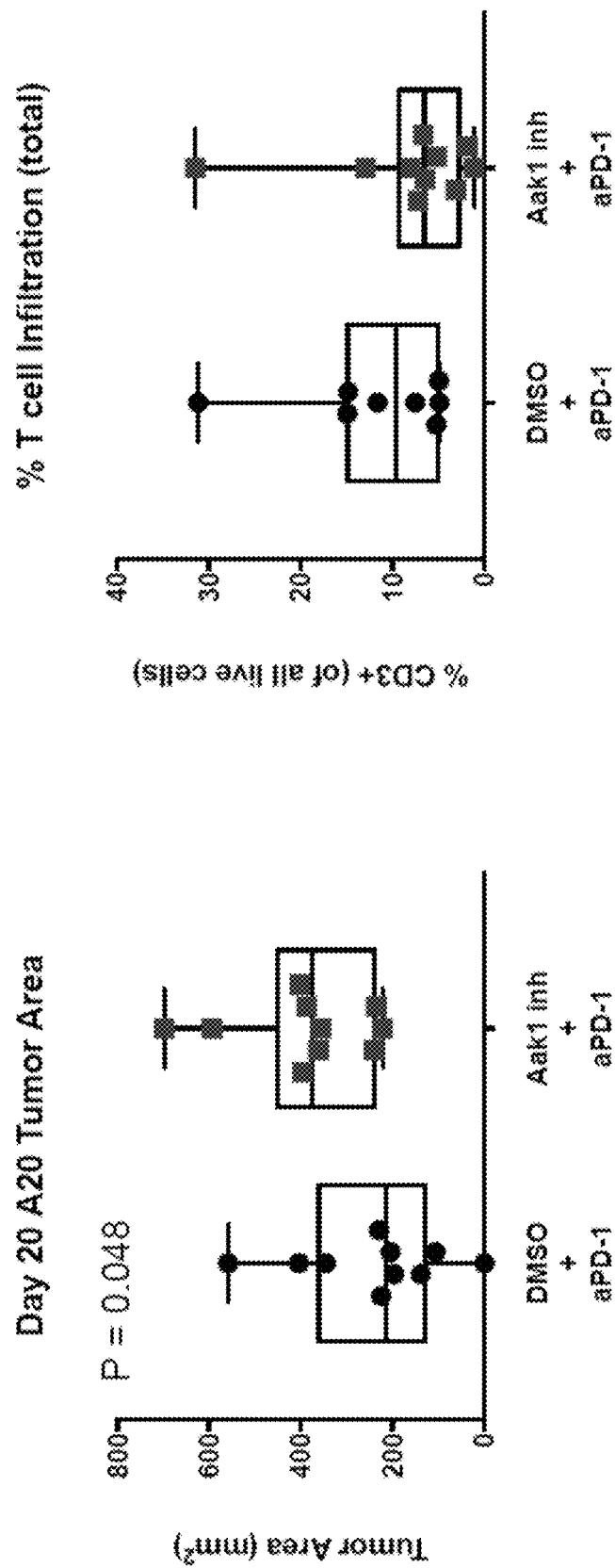
FIG. 15. Aak1 inhibitor (iAak1) enhanced A20 tumor growth in vivo.

FIG. 15 illustrates the results of Aak1 inhibitor (iAak1) on the growth of A20 tumors in mice. Mice were inoculated with A20 tumor cells. Treatment began ten (10) days post tumor inoculation. All mice received twice weekly IP injections of aPD1. Ten (10) mice received DMSO, and ten (10) mice received iAak1 via oral gavage daily. Treatment with iAak1 was observed to result in increased A20 tumor growth in vivo and to moderate inhibit CD3+ T cell infiltration of the tumor.

It will be readily apparent to one skilled in the art that varying substitutions and modifications may be made to the invention disclosed herein without departing from the scope and spirit of the invention. The invention illustratively described herein suitably may be practiced in the absence of any element or elements, limitation or limitations which is not specifically disclosed herein. The terms and expressions which have been employed are used as terms of description and not of limitation, and there is no intention in the use of such terms and expressions of excluding any equivalents of the features shown and described or portions thereof, but it is recognized that various modifications are possible within the scope of the invention. Thus, it should be understood that although the present invention has been illustrated by specific embodiments and optional features, modification and/or variation of the concepts herein disclosed may be resorted to by those skilled in the art, and that such modifications and variations are considered to be within the scope of this invention.

Citations to a number of patent and non-patent references are made herein. The cited references are incorporated by reference herein in their entireties. In the event that there is an inconsistency between a definition of a term in the specification as compared to a definition of the term in a cited reference, the term should be interpreted based on the definition in the specification.

We claim:

1. A genetically modified CD8⁺ T cell comprising a recombinant nucleic acid comprising an AP2-associated kinase 1 (Aak1) cDNA sequence encoding a gene product selected from the group consisting of SEQ ID NO: 3, SEQ ID NO: 4, a variant of SEQ ID NO: 3 having at least 95% identity to SEQ ID NO: 3, and a variant of SEQ ID NO: 4 having at least 95% identity to SEQ ID NO: 4;
   wherein the variant of SEQ ID NO: 3 lacks amino acids 824-961 of SEQ ID NO: 2;
   wherein the variant of SEQ ID NO: 4 terminates with a GGS amino acid sequence and lacks amino acids 1-125 and amino acids 823-961 of SEQ ID NO: 2.

2. The T cell of claim 1, wherein the T cell has been genetically modified by inserting into the genomic DNA of the T cell an expression cassette for overexpressing the gene product, wherein the expression cassette comprises the recombinant nucleic acid.

3. The T cell of claim 2, wherein the expression cassette is inserted by administering to the T cell a retroviral vector comprising the expression cassette for overexpressing gene product.

4. The T cell of claim 1, wherein the T cell further expresses a chimeric antigen receptor (CAR).

5. The T cell of claim 4, wherein the CAR is targeted to an antigen expressed on the surface of a solid tumor.

6. The T cell of claim 5, wherein the antigen is selected from the group consisting of epidermal growth factor receptor (EGFR), mesothelin, receptor tyrosine-protein kinase erbB-2, prostate specific membrane antigen (PMSA), human epidermal growth factor receptor 2 (HER2), mucin 1 (MUC1), carcinoembryonic antigen (CEA), and IL-13 receptor alpha.

7. A therapeutic composition comprising a population of the T cell of claim 1.

8. A method for treating a subject having cancer characterized by a solid tumor, the method comprising administering to the subject the composition of claim 7.

9. The method of claim 8, wherein the cancer is selected from brain cancer, pancreatic cancer, ovarian cancer, lung cancer, liver cancer, breast cancer, and prostate cancer.

10. The CD8+ T cell of claim 1, wherein the gene product consists of a sequence with at least 95% identity to SEQ ID NO: 3, wherein the gene product lacks amino acids 824-961 of SEQ ID NO: 2.

11. The CD8+ T cell of claim 1, wherein the gene product consists of a sequence with at least 95% identity to SEQ ID NO: 4, wherein the gene product terminates with a GGS amino acid sequence and lacks amino acids 1-125 and amino acids 823-961 of SEQ ID NO: 2.

12. A genetically modified T cell comprising a recombinant nucleic acid comprising an AP2-associated kinase 1 (Aak1) cDNA sequence encoding an amino acid sequence selected from the group consisting of SEQ ID NO: 3, SEQ ID NO: 4, a variant of SEQ ID NO: 3 having at least 95% identity to SEQ ID NO: 3, and a variant of SEQ ID NO: 4 having at least 95% identity to SEQ ID NO: 4;
   wherein the variant of SEQ ID NO: 3 lacks amino acids 824-961 of SEQ ID NO: 2;
   wherein the variant of SEQ ID NO: 4 terminates with a GGS amino acid sequence and lacks amino acids 1-125 and amino acids 823-961 of SEQ ID NO: 2.

13. The genetically modified T cell of claim 12, wherein the amino acid sequence consists of a sequence with at least 95% identity to SEQ ID NO: 3, wherein the amino acid sequence lacks amino acids 824-961 of SEQ ID NO: 2.

14. The genetically modified T cell of claim 12, wherein the amino acid sequence consists of a sequence with at least 95% identity to SEQ ID NO: 4, wherein the amino acid sequence terminates with a GGS amino acid sequence and lacks amino acids 1-125 and amino acids 823-961 of SEQ ID NO: 2.

* * * * *

SEQUENCE LISTING

```
<160> NUMBER OF SEQ ID NOS: 9

<210> SEQ ID NO 1
<211> LENGTH: 185851
<212> TYPE: DNA
<213> ORGANISM: Homo sapiens

<400> SEQUENCE: 1
cggtccctcg ccgcgccgcc ccgaggggca cttccggcgg cggttcactt cctggttggg      60
tggatggagc cgggcgggag cgcgcgcggg ggaggggcgg cgggtcagtc tccgcccggc     120
gctcccggga tcagctggcg ggcgggcggg agccgagcgc ggccccggct ctcgctgcag     180
cgccgcctct tctctgcgtc gcaggccggc ccggcggccg tgacaatgtc gcggggctgg     240
tagcagggcg ccggccgccg agccgtctca agtgggtgct gccaggatgc cgcctcgagg     300
ggcggcgggg agacccggga ggagcgggag gcagtgcccg ggagggtcgg cgctgccgga     360
gcagctcgga tccctccttt ctccgagctc ccggctcggg ggtcccgggt tctggggccg     420
gggtcgcgtt ttcagcccca cggttttttct cgccgggaaa atacatgaag cgtttcccca     480
ggatgatggc ttttgctccc cctaggactc agcggttgaa tttttaagcg tgttactgat     540
tcatcctctc tttcttcctc tgtcatcaca ggtttaaact tacacgaatc gctttctgga     600
ggaggagggg acccgctgcg cgattgacac gcatattcct ataggcatcc tccctcagcc     660
cccaccccca cggccggatt cgggtggctc ctctccgagg tgaaatctga gaagaaatcc     720
ttggatctct tttcttaaaa aaaaaaaaaa aaaaaaaaaa tctagaaacc atcggtattt     780
```

```
tgctttgctg ctccctattc gcaagatgaa gaagttttc gactcccggc gagagcaggg      840
cggctctggc ctgggctccg gctccagcgg aggaggggc agcacctcgg gcctgggcag      900
tggctacatc ggaagagtct tcggcatcgg gcgacagcag gtcacagtgg acgaggtgtt     960
ggcggaaggt acgtggggc tcaatgcgcc gtaaattaaa atcttgtgct gatgcggcaa      1020
tactgtggtt tctagttgtt gcatgtatga atgggctttg accagttgac cctcccttcc     1080
cccttcactt gccctgtgag tcattgtcct tgagagattt aaaattgaga tttgaaagtg     1140
actgggctta tggggtgtg gggaggttgc cgaaattgtt tacgttagtg gccttttatt      1200 tttattttt taatattgag aagccaaatt ttgaggatca cacaagaaaa cgtatgtgtg      1260
aaagtgtaaa gctttatgcc aaaggcaggg tgatgggctt gtcatcctcc taaaacttaa     1320
aatcttgatg tgaaggctga agggtggggg gacttttaag aagagagggg tttctccttc     1380
tcctacccaa ctttcccact tccatgagca ggcattggaa ggaagagagg attttcggag     1440
aacgtgaacg tgttttcca agggccaagg ctcttggtgg atttcactag tagatttgtt      1500
tcctgaccca actgtaatca ggtccccagg ttatagcaaa gataacagaa attacataaa     1560
acaaatgtgg ttattttgaa ctcagtctag taggcccctc ttccttctcg ctttaggttt     1620
tgttttttgt ttttttaatc aaaagaaaaa ttacttgaga gtggctctga ttttgttttt     1680
tcgctatcag agaggatgtt atttagatct gctgcataaa ttccctctgt gtttcatctg     1740
tgtgtctata ctcacgtaga tatacatctt gattccccca ggctttcggg aaatctttgc     1800
atgtctcttt tggtaacctt aacctcgacc ttcataatta tgccagactc atacttttca     1860
cagcccttcg cctgcctagt gtgctttat ttttaataaa agcagcaatt tccttggcat      1920
gaagcaattc agactgattg gatggggcca acctgctgta ggttgtgtta tagaccgaga     1980
ggggttggaa gaagggagag gtctctctta ctgcaacatg gtgatggtag ggaacagttt     2040
tattagcaag ggaagagaga aagctaagag gcctctttaa aaagggcct tttgcaagct      2100 aaagttgaag caagggtcct gacctgggcc tgggaaatgc ttaccatggt ggatgttgcg     2160
ggctggtggg tgggtttgga agaggaagaa gctgtgttg gctctcagct tgtgtaagca      2220
ctggattcag cagggcccag ttttctggga atagagttga agtctgtact ttaaaaacat     2280
gatttttaaa aaagatctct gacagttaat gtccatgtga aattattgct cttccaatct     2340
cagtactgtt ctagctgcgc tttatctggg gccagagtca ctgtcccctt ggatctttcc     2400
cgtggacttt ggtgcaggct aggagatgct tctgtgcccg ctgccagatc cgcacccttg     2460
agtctgatct gtctctttca tccctgtgcc aaagccctta actgcagtgg ggtggagaaa     2520
cagtgaaaag gagagtgtgt cagagagaaa tcaggagaaa cgaagggcca cagaacactt     2580
tcctcccctc tgaatggcct ctgctgacct tatagcccac gagcgttttg ttcagctagg     2640
atgttgtctc atcacggatg atgctgccct aagcggtgca tgttctccaa gtgtgagaga     2700
agtgataggg aaaagaaaag gcaaaattgg tctttgttac ctaggctgcc ttcctcttct     2760
ctgggattca tctttgagaa ctgcgcatca cgtattgtga tattttaca cagaatttag      2820 gacttgtagc tctgcattta ttcattcaac agtttatgga gttgcctgtg aagtgccagg     2880
tgctgtgcta ggctctgggg gtatactgtt aaactgatg ctagctttta ccaactgctt      2940
taagagatgg aaaatagcca gttatagtgg attggtaaat gccatcatag agataaactt     3000
agggtgcagt ggccccagt tttagggagc ccaggatttc tgaaggaagt gactgaagag      3060
tgagtaggag ttagtgtggt ggcaccatgg gcaaagacag agtagcgaga gagaatgtca    3120
```

```
cgtaaaactg ggtctggcta tgcgcccttt ttgtgttctt tggcttaagt tgagtttgaa    3180
tttgtggctc ttagaagtat gtagatatgt aggagccagt atacaaagta tttatgtagc    3240
acctaccaag tccaaagacc ctatgaagtt ctgagatgga tgagggaggt ctatagtgtg    3300
attgacatct gcctttaagg atctgccaat gaatttggga agatgaggca tacattcaca    3360
catacagtag catggttacc agcactgtct gtagagtcag acagatctag gttcaaattc    3420
tggatctgtt ctttactagc tgtggaactg taggcaagac attccaaacc actcttgaat    3480 ctctgttttcc ctgtggcagt ggttctcaaa gtggggcata cttatcacct gcgagcttgt    3540
tggaaatgga gattctcagg cctcactctg taggctgtgg gtgtggggct taataagttc    3600
ctggagagat tctgacgcaa ggtcaagttt gagaaccact gcttaatggg ctggtcatga    3660
agattaaatg aggcaatata tataattaac attttcaggt gttcaataaa tggtagccat    3720
tacttaccag caacgttata catcatatgt atatatgtgg gggggagag agagagagag    3780 agagagagag agtgtgtgtg tgtgtgtgtg tgtgtgtgtg tgtgtgtgtg ttaaagggga    3840
gtgggagcaa tgtgaaagct agttgagctg cagcaatctg aagcaattcc tttcccccat    3900
tgttagggga cagagccaga tgttcttttgc agagtcctca ccagctcctt aaaggcttaa    3960
cagacgtttt gggtagccat gctccttccc tggactctct tctctgtgag tccccgagtg    4020
ctgacttatc tacagttcta gccagagttg tttaaggacc acaggagttg taccctgtgt    4080
gcccagagcg gtggctaggc agtttaggga ggagtggtgt gagaggcttc aaaacacaga    4140
ccagattacc accacattcc gctgatgatc tcttttttctc tagcgtgggt attggtctgt    4200 gcttttttcat aaggaattgc aagaacccca aggagcaggt gctgggtaag acaaaaagat    4260
gtcgcactgc catacctccc ctggtagcat cagccttcct ggcctggttt cactaactag    4320
tccagcaggg gctgtttggg ggaagtgaag gctttaagtt atgagtttag aggaatatgg    4380
ctatttctag gctgggtgcc agggagaata ttttcttttct agctttctca gcaaagatgc    4440
catgatgaga agctaaatca tgtctaagtt aatgggcata tgatatcaag gaagatttg    4500 gtttaagctt ccagaatgag ctcaatggga aaattggagc aatgttcaaa gaaggattga    4560
gaagctgtgc ttttatcata cttccttagc tatacgagga cttatatcta agctttaaac    4620
aataaatgtt tatttattac tgtgttgaag acaacattct ggaactataa ggtggactag    4680
atggctcctc agaacagctt tctaatttat attcaaggaa tccaggtcca aggctgatga    4740
gaagtaccaa atgtccacat cagtaaactt tgataatttc tcctacctac agagcaaact    4800
agtaaggctt aaaaatgtgt gtgaaatcac caaaaattcc attaaaggca cataatatgt    4860
tggtggtatc aatatgatac acgtacgtgc ctctttgtgg caggcactgt attaggttcc    4920
agagatccta agatgaatgg gacacaggcc tgactcttaa cagagctcaa cacctgagat    4980
aagtgtccag cacttaagcg tggcctttga catacatacc ttagatggta aaagatgtta    5040
tgataaagag cctggggggtg agagttcata ggtgacatga agtttgaaca ggaatagaaa    5100
ttgcccagca gatgttccag atgggggtta ctcaggacct ctcaggctga gagaatagta    5160
taggcaaagt ggtgaaacag catgataaat tttgagaata ctgactagtt tagtgttacc    5220
attttcatca gtacacattt cctccccaga atcaaggaaa aaggacaga ggacacggag    5280 tggtagaatg aaattcttta agttgctccc tggaggtgct tgctactcac tttcttcagt    5340
ggccctgggc cttttgaaag actgatgaat aggtaccaag aatgcacggc tcccctcctg    5400
tgcctcagcc ccgtgccaat tgtggggaaa gggagcagcg agtgtctggg gaaagagtgg    5460
tcccagaagg tttgataaga ggctagaagc ttaagcaaaa gcaggcaggg aagggaaatg    5520
```

```
accagtgtta ccgaaaggta tgaacagggg agatattgaa ggtgtttgac cagagcagaa    5580
ggtacattgg agagaaaagg aaggactaat tttatgagaa atcttgagtg ccaggcagag    5640
agatttagtt ataagcacct gagaccttct cttgacgcaa acaccaattt gatccctccc    5700
acttcagatg tctttgcctg ctgggaagtc tggttttta gaggcaactg cagattttca     5760
gggggtggtt tgtgaatggt gtcttcttcc tggctttggg catgatgacg gttgtagctt    5820
tgctaaatat agccaaatct agaattcaga aatgaagtcc agaataagca attgccatgg    5880
tcaaactctt tctttcagtc tttctaacaa agtaaagctc atttaataac aaataatgat    5940
gaagagagag cagcagtttc acgtgacttt tgagtgggag ggtatgaggg agacataca    6000 cttgtaccct ggtagctaaa acgccatgta gagtacacaa gaaaggtttg ataaatatta    6060
acaaaacaca caaaaaatat tactgcatca gagccgtcat tttaacttgc aatatttgaa    6120
tgttgacgct tcggaaaggg gactagtacc accttcatct tgcaccettt caaggatgca    6180 tgccttctga gcctacttat gaggtaactg tgacatccgc atctgaaaga gaaaaaaatg    6240
ataataatag aaacgtattg tctattaaag tagcatctag cactgtgagc tagcagagac    6300
ttgcctccgg tctatttat ggagccatat tttggtgtgg tggaaagaac actgcattat     6360
gaattgggag atcaaggttt gtcagttcat tcactcccectt attcagtaaa tgttactgag   6420
cattcattat gtgccaggca tcatgcggag ataaatgaga catggctgtg ccttgaggac    6480
ctcacagtca taggatttca gatatgtgag caaatagctg cagatgctgc gctggagtca    6540
tgtaaaagag ctggggaaca gacccaaggc aacaattttg tgggttgggg agtagtcagg    6600
gaaagctaaa gaaaggtgac atttgaggtg tgtcttcaaa aatgagaact tattgctaga    6660
tggacaaggt agaagaacat tctaggcaga gagaataaca tggccaaaga cacaaaagca    6720
gaaaaataac tgcttactgg ggagctgtat gttttgagat agcgataatc tactagtggc    6780
ccagggctgt gctgttcaat aaagtagccc actagccaca tatggctatt taaattatct    6840
aaaataggcc gggtgcagtg gctcatgcct gtaatcccaa cactttggga ggctgaggca    6900
gatggatcac ctgaggtcag gagtttgaga ccagcctggc caacatggtg aaaccctcgtc   6960 tctagtaaac acacaaaaat tagccgggcg tggtggcggc tacctgtaat tccagctact    7020
tgggaggcta aggcagcaga tcgcttgaa tccgggaggc agaggttgca gtgagccaag     7080
atcctgccac tgtactccag cctgggtgac agagtgagtc tccgtctcaa aaaaaaaaa    7140 gaaaaagaaa aataaatta tctaaaatag cagttcatca gatgcactag ccacattttg    7200
attgcttaat agtcacatgt ggctagtgct tacagttttg gacagcacag gtgagatgta    7260
tttcatcatc acaagttctg gcagtgttgg tctagagcag tagtctctaa acttttgga    7320 tagaatagtg ctctagttaa aaaacatgcc atatcttcat gtatgtgtgc ttgtttattt    7380
gtaagttata ttcatgtcct gctatcatta gctaatatct gaagtcacat tatatactta    7440
ggatgaagtt catcataaat gatagtggat gcaaatctat atttaaata atctcaacaa     7500 gattttggtt aacttattca attgtgattg tgtctacatt gcagtgtgac tatgtatgaa    7560
gagtatgcca ggaatagata tgacagctct gccattctct tgttcatttt tgattgcatt    7620
atctttaatc caaggttttt ttttagtaga atctttta agcctctagt ttgttttgtg      7680
atgattaatt aatttaaaat aatgtaatca gtgaatccat ttaaccaagc acacatgaac    7740
tatagtatat ctcagtgtgc tataaagatg tcacccate agecctcaat agtggacatg     7800 tgactgaaca ttgactgaat gggagtgcta gtgttgggcc atatgttata tattaacaag   7860
```

```
gacaaaatct tattttttct aaatttttaa atgtaaaata cacataacct aaaatgtatt    7920
atcttaatca tttttaaatg tacgtctagg tgttaaatat attcataata tgcaaccatc    7980
accaccatcc attcccataa ctcttttcat cttgtaaaac tgaaattgta cctattaaat    8040
gacaactctc attcccacct ctctctagcc tctggcaacc agcgctccac ttactgtctc    8100
tatgatttttt actacgttga atacctcata taagtggaat attactgtat ttggccttttt   8160
gtcattggct tatttcactt agcataatgt cctcaaggtt catttgtttt gtaccatgtg    8220
tcagaatttc cttcctgttt aaggttcagg aatatgccat tgtatatata tgccacatgt    8280
atcattcatc agtggacact gggttgcttc cacctttag ctattgtgaa taatgttgct     8340
acagttatga acatggatgt acaaatatct cttcaagacc ctgcgttctt ttgggtatat    8400
actcagaaat gcaattgcta ggtcatatgg taatcctatt tttaattttt taaggaattg    8460
ccacattgtt ttccatagcg gctgtaccca tgtttcattc ccatcaacag tgcacaaagg    8520
ttccagttat tcctcattct caccgacact tgttttctgt tttgtgacag tggctatcct    8580
aatggatgtg aggtggtatc ttcttatact tttgatttgt atttccctag taatttgtga    8640
tgtcacgcat cttgttatgt gtttattagc tatttgtata tcttctttgg aaaatgtcta    8700
tttaagtcct ttgcccatttt ttgaattggg ttgttatttt aggagttctc tgtatattct    8760
gggtatcaat tccttatcag atacatgatt tgcagatatt ttctcacatt ctgtgggttg    8820
ccttttact tggaaaatct tactttttaa atgaaaata aataaaaata gaggatcttt      8880
tattttcttt gtctaccca gtgcattgtc atcttgtaca ctactgtttt gagaccattg     8940
tagtctagag cagtggttct gtaccatttt ttgttcctca aaaaaagacc aaaaatattg    9000
caatacttac tttaacttta ctaagagaaa actagaacat aggtaaagat ggtgaactag    9060
atgcagcaag gttccatgaa ggtgaggtta cagagaaaag actcagttaa gaatagtctg    9120
tcttcatgaa atctttcata accattgcag tcctctctga tctccttcct tcaaacccat    9180
agcttagaga ctacaccaca gaccccatca ctgcaagaga tatgtaattg ccttttgggg   9240
ttcagttgtt tcttgtgtgt tggtcatatc atgccaacta gcaggacagg agccgagtct   9300
tccattactt ctctgtttgc catagcatct cagacagaga acatatgaga tgcttagtaa   9360
aaccttgctg cctctttcac tggcaggaca agctgctctt atgcgaaata gccttatatc   9420
tacatactct cattttgtga ttgcgtcatc cctgcagagg tagaaagcat ggttattact   9480
ccagctgtac agatgaggaa gcagtggctg acattggttg aatgacttct tcaaagtcat   9540
attggcaaga agtagcagtg aatgaacttg aacccgaggc tcctagctac aagtatagga  9600
ttcttcctta aaattcttcc ttgtacaaag gatcatcagt atcttttctc ataacattct   9660
ttttatatat atatttttca gacagagtct tgctgtcgcc caggctagag tgcagtggca   9720
caatcttggc tcactgcaac ctctgcctct cagatttaag caattctcct gcctcagcct  9780
ctcgagtagc tggaactata ggcatgtgcc accacaccca gctaattttt gtattttag    9840
tagaggtagg gtttcaccat gttagccagg ctggtcttga actcctgacc tcaagtgatc   9900
cacctgcctc agcctcccaa agtggtggga ttacaggcgt gagccactgt gcccggccct  9960
ctcataacat tgttgacctt taataaccaa cccttcccag ctgaatctcc ctgtgagctt   10020
ttcaagtcag ataatgcttc catagcattt gaaggttgct tactggctta gttcctctgg  10080
gctgctgtaa caaaatatca gaaactaggt agcctataaa caatagaaat ttatttccca  10140
cagctctgga ggctatgaag tccaagatca gagtaccagg atggtcaggt tctagtcagg  10200
gccctcttct gggctacaga ctactgagtt tttttttttt tttttttgaga cagcgtctca  10260
```

```
ttctgtcgcc aggctggagt acagtggtgc gatcttggct cactgcaacc tctgcctccc    10320
gggttcaaga gattctcctg cctcagtctc ccaagtagct ggtactgcag gcgcgtacca    10380
ccatgcccag ctaattttg tgttttagt agagatgggg tttcaccatg ttgaccagga    10440
tggtctcgat ctcctgacct catgatccac ccaccttggc ctcccaaagt gctgggatta    10500
caggcgtgag ccaccgtgcc tggcactgct gacttcttga tgtcagcagt ggaagggact    10560
gctgctttct gggacctctt tttgcctgtt ttctttctct tttttcttgg ggccttttt    10620 ttttttttgaa acagagtctc actctgttgc ccaggctgga gtgcagtggc gcgatctcgg    10680
ctcactgcaa gctccacctc ccgggttcat gccattctcc tgcctgtcgg ctgagtagct    10740
gggactacag gtgcctgcca ccatgcctgg ctaatttttt ttaattttt tatttttatt    10800 tatttttttt attgagacgg agtcttgctc tgtcacccag gctgtagtgc agtggcctga    10860
tcttggctca ctgcgagctc tgcctcccgg gttcacacca ttctcctgcc tcagcctccc    10920
gagtagctgg gactacaggt gcccaccacc atgcccggct aattttttgc attttagta    10980 gagacggggt ttcaccgtga tagccaggac ggtctcgatc tcccgacctc gtgatccact    11040
cgcctcggcc tcccaaagtg ctgggattac aggcgtaagc caccgtgccc ggcttttttt    11100
tttgtatttt tagtagagac ggggtttcac catgttagcc aggatggtct cgatctcctg    11160
acctcgtgat ctgcctgcct ggtctcccca aagtgttggg attacaggcg tgagccatcg    11220
cgcctggcgc tagttcattg attctaagaa acaaatttg aaaattaggt gatttgccta    11280
aagtcacacc gccaattagg cccttctgag caactcccaa ctactgtctc ttcccacatt    11340
ggtcaacagt catttgtgct accttggcac tactaacatt ttggtctggg taactctttg    11400
ttgtggaggg ctgtcttgtg cactatggga tctttagcag tatccatggc ctctacccac    11460
tagttgccag aattatataa tacatacaca gcctactgtg gcaatgaaaa atgtctcaac    11520
attgctaaat gtcacctgtg gggcaaaatt gcctgtttta gagaacatgt ctagttcagc    11580
atgtttgtat atgttctggt cttctgttgg taaagttgaa gtaagtattg caatattttt    11640
ggtctttttt gaggaagaaa atggtctaca taaataattc agatgttctg tgtttatacc    11700
caaagcaaaa aagccttta tttgctgtga atttaatcac tcaggaatga taaactatta    11760
gcttgtaagg tgatactggc tgtagcattt tatacctcct ttctcccttt tttgttttta    11820
ttattattga tctattattt ttattattta gcctattatg tatactttat ttattttga    11880 gacagggtct cactttgtca cccagtgggg tgatctcagc tccctgcaac ctccgcctcc    11940
cgggctcaag cgatccttcc acctcagcct cctgaatatc tgggaccaca ggtgcgcacc    12000
accacacctg gctaatcttt gtatttttg tagaggtgga gttttgccat gttgcccagg    12060
ctggtcttga accctgggc ccaagcaatc cacctgcctc agcctcccaa agtgctggaa    12120
ttacaggtgt gagccactgc acccttaaaa caatcccact tctgttgagt cacaagtaat    12180
tgttaggaaa gaggattcct tttggaggag acttccacct tggcagagga caagttcctg    12240
aaatttgaag tttcatttga ggtctgctgt gggtgaatca gtttgagctg tcagttttc    12300 tccttgggct ctgtgttaac cttggcagac aaggaatggc agtgccaact gaagctttgt    12360 tattttgtc aaaaaacaga gattattgga ccaaagagct catggtatct attattatta    12420
tagaaggcta agcatagcat tgatgctaga ttatcttttg tcgttataat gagcttaaat    12480
aatgatgcct gtcatctagg acttgaatcc tgtagaaagc aacataatgc cacataattt    12540
gtttgctgca tgttttcaag gacacttaca gctattgtac tgggaccttt agggtaagag    12600
```

```
aaagattatt gtcctttggg tactgagcat gaatttgaga acaaaatgat gactttatta    12660
cctatgggga caggaagaag gaatggaact aaggcatcgt aggttgggtc cttcctggag    12720
gactggggcc tgagcagcat ttactgagat ggcaggtctc ctgctagtac cttggttcat    12780
tttctctggt cagtgaatct gattgattca ggaagtgctg attattttac aggttttgtta   12840 gacttgttta atctcccctg ggatagccca ccctgttcc acaggccttt gttctctgct     12900
gtttttagaa gccttggaat cttggtattg gaggggaagg gggcagcact ggaagaaata    12960
atttcattgg gcttttggc tgtagagaaa aatcttggct tgaccaggtg taactcagta     13020
atgattatgg aaaacctgat atccaatact gtctttcctc cccttccccc ctggaataaa    13080
gggagtgcta tgatgttctc cttaggagaa gactttcaag gttagtactg tgtgtgatgg    13140
tttaaaagca tgagaattga aggtaaatag cccttggctg gaatcctgga catgtccctg    13200
tgatgttagg aaaagttaac taagatctag tcttctcatc tataaaatgt agatttgtaa    13260
aatgcaaaag catgggttgt tgtaagaatt aaatgatgta tgcaaagcac ttcacacagt    13320
gactggtgta tgttagttag cagtttgtaa atggtaactc ttagtattga ggtgcatgaa    13380
ttttgttttt atcaggccat atttgtatca ctatgtatat aacctggtgg agttagagtt    13440
ttggaaatac acacaggagg tctctctctc tccctccccc tccctctccc tcccctccc    13500 cccccacccc ccgccccact cagagtattc acaaaccccc agatgaggaa tagggagaag    13560
agaaagagaa atattgtagt ttgatttttg ttttttaaac tctcacctct tgaaagctac    13620
ctgtgtgtca gggagttttt cttaacctat caagttttta taagtatgat gggcctctct    13680
acctgccagg aatgcctggc acctgctgcc tatccaattt aaatgcttgt gtgctaatgc    13740
cgcaggtctg ctgcttccac caggcctgcg ccctcctcac catctttgta ccgtggattt    13800 agttcttttcc agttctttac tcatggtgtt ccccgcagct gggatatttc ctccttcccc   13860
acccgcctac cttagtccta cctaagattt attttaccta gcctaggtat tcaccacagc    13920
tgcctctgga tgcctgtctt tttttgctgg ctatcttaac ttttttgggc cataaccctc    13980
aaagttttat tttactgttt attttgtttg tatctacttt ctagtgttag ataattagtt    14040
attgccttag gctatttttg tatccaattg agtactcgta aatttgaaca tggcaacagt    14100
gggtactgga gaatgaatta actggatgaa tattacagta aatcagtact aattaaaact    14160
tgctgggcag gcaggagaga ctagacggat ttgagatata caaacctccc ttatttatcc    14220
ctattccaat cgtataatag atctgtgttt gaggacttca cctcgcttat tacaataaga    14280
actattgaat cttatagagt ttcagtaaag ttgagaaata acaaaatcca aagcaaagta    14340
gaacatcttt cagaaagcca tgtgaatctc tattgattgg attaaattat tggcgtctgg    14400
taccattgat ctcaaaagta gagatatagg gtgtatctta gctatataaa ggaactctaa    14460
accatttaaa tgctatactg taaagatgga gacaattagc tcatgtgtca aaaactcaga    14520
tattactgaa attcatcttt aagcaaagca tacattcatt ttctagttga tgattggcat    14580
tggcctgcag taaattagga cagtgatttt taacttgtat ttggggtagt gagcatgcag    14640
acaggtcaca aataggaagg gaatatataa tttgaaaatg catagattgg ctccaggtcc    14700
agccagaaaa ggagagaacc tcaaagaaga tggggattgg ctgtataccc tctaaagagg    14760
cacattatag acttaagagg tcggagtgtg gagaagacgt gagattttca tatttatcaa    14820
agaagatatg gttttaaaa gactgataaa tatggcatta agcagctgag ttataaaatg    14880
agtctagaga ggtggtacct gtagttgagt actgtatgta cctctgggaa caaacatatt    14940
tcttcctgtt cttgctagtt tcagagagga ggagtgaaaa gagcaatcaa cagcaaattc    15000
```

```
tgcgtggtgg tttgctgtga gctccacagc attttttgaaa ggtcagctct aggtggctcg   15060
ctcaccaatg atgagaattt ccttgaaaaa agttaatttt agatcataga gacttcctca   15120
gaagatgaag tattcctttc tcttttaaaa tcatagtgtt agaatcagta taacatcaaa   15180
tgggttattt aagtggctgt ctactcaccc agcaattatg tggtgatttt taaggtggta   15240
tgacagagtg ttgttcaagt ctaccatcaa atcctgcttc tagggttagc tcacagaaca   15300
caaatgaaca actgtatgag atagggaagt aggttatctg gtctcttcag tgatcttgga   15360
tatatcactt cccctctctg agcttgtctt atgtgaataa ggagatcacc gggtgatctt   15420
gaaggtctct tctagtgcaa acatggtttt taagttctgt ggttttttgtt gacactattt   15480 gggagggaga atgagattgg gttgatgaga cggaaatgtt agacctatgt agctgggata   15540
agaaaacatt aaaaaaaaaa agaaaagaaa cagggttttg ctatgttgcc caggctggtc   15600
tcaaacttct ggttttaagc agtcctccca cctcggcctc ccaaagtgcc aggattacag   15660
gcgtgagcca ccacgcccag ccaagacaat agttttgagg tggattgtta accttggcct   15720
acgtatggtc ctcacaggga ggtatcattc ttactggagg tgaaagattc cattcctttt   15780
tttctgcttt ccttctttct atatctttac cttaaactta gaaaaatcag tgttaataat   15840
tagatgttgc agatgacaga aagctagatt ggatcttggg ctactggctt aagtgactgg   15900
gtagataatg gtgtcaataa aaagaagaaa gaatagtgtt tgaggaaaag agacgggctt   15960
cagttaggga cttttttaatg agccatcagt ggaaatccaa gtatggatgt agttcaggat   16020
gctgttgcat aggactggcc tgcattgtag agaaaagttg gagtgggagt tgtcataaaa   16080
ccacaagata ggaatgaaaa ctgaaatgga gtgagatctc ataaggagac tgtgtggagg   16140
aagaggagtc cacctggaat aaaatccaaa ctcctcacac tgacctgcaa acccctacaa   16200
tagcttgtgt ctctcttccc ctcaaccact tgctttttag tcacagtgat tcttgttcat   16260
cttttttgag catagaacat agtttcttct ttagtgtcta aggcttggct ggtgcctttt   16320
cctggaatgt tcttccttct tgtcttccct tggttggctt tttgtcattc agagctcact   16380
taaatcccac ttcatagagg ctgtcccttta ccgcccagtg taaggaacca atcctgtttt   16440
atttcaccgt gtagcatgta tcagcagatt ttcttgctta ttatttattt atcactccca   16500 ctcccccccac tagaatttca gctccatgag aatctttttt ttttttttttc tcttttttgag   16560 acagagtctc actctgtcac ccaggctgga gtgtaatggt gcagtctcgg ctcactgcaa   16620
cctccgtctc ctgggttcaa gcgattctcc tgcctcagcc ttcctagtag ctgggactac   16680
aggcgcccgc caccacgcct agctaatttt tgtatttttta gtagagacgg gggtttcacc   16740
atattggcca ggctggtctc gaactcctga cctcaggaga tccacccgcc tcggcctccc   16800
aaagtgctgg gattataatt gtgagccacc atgcctggcc tccatgagaa tcttgtctga   16860
cttgttcatg gctggatccc cagtgtctag aatagtgagt gcctggcaca tctgcagagc   16920
tcagtagaaa ccagttgaat gaaagagtag gcacatgaag gaggcagaaa gaatgattga   16980
cggtagaatc aggaggatgt gaagtgacga aaataaatcc taagtaaaat taaaagaaga   17040 agggccgag tgcctggtg gcccatgcct ataatcccag cactttgaga ggccaaggca   17100 ggggattgc ttgagcccag gagttcaaga ccagtctggg caacatggca aaccctgtc   17160 tctacaaaaa aaaaaaaaaa aagccaggca tggtggaatg cacctatagt cccacctact   17220
taggaggctg aggtgggaag atcgcttgag cctgggaggt tgaagctaca gtgagctgtg   17280
atcgcgccac ctcactccag gctgggagac agagtgagac cctgtctcaa aaaaaaataa   17340
```

```
taataataat aattaattaa tttaatttta aaatggaagg aatggacact tcagagtgtt    17400
aactcattac agacgtcaag ataagtgtta attggatttg gaaatatgga ggtaatttgt    17460
gagcttcgtt agcagtttct gtggagcagt gactgaagtc caggtggcag tgaaatgatg    17520
actgactggg aagggaggtg gatgctgaat cagggcagaa tttattatta tttcttaata    17580
ataattgtat tatttttaat aataatataa tttttgtaat gatggacaag tcttgagtat    17640
attaggcaga gaagaagcaa tcaaagagag gaagaggttg aaaatacagt actgggtat     17700 cattgatgga gtaacccaaa gaagggatgg gaggtcatgg gtgaggtcgt gaactcaagt    17760
aacagagata accttggaca ggagaaaggg tacttcattc actgacctgg aaggaaggag    17820
agaaggaata gatacagagg aagagaaatt gggtgaggtt tggtaagttg agggagttct    17880
tgcttctgtt ttctattgaa tgctgtgaat ggagttgaat tggatttaag aagagtaggg    17940
aaaggatatg gaggagttcc ttagatgtgt ggagagaaga aatgacaaag gataggtaga    18000
agaatggcct ggtcttatga agagcccatt tgagacaact cattgttgga aaagagatgt    18060
tcctggccca tgaaagtgta tcaatttttta agtttttact atttttgaaat attttataca    18120 tatatttcct gtcttccagt tttgaaatat gttatacata tatttcctgt cttctggagt    18180
gtataccaca gaggcagcgt gacataagtg gaaagtactc ctgaactgaa cctgtttagt    18240
gacctcacca catactgtac tctgacacat tgcttcccag ttccgtccac caggctccct    18300
atgtgtaaaa tgaggactag atggtaaatt tactttccaa ctctaacatc ttatggttcg    18360 ttaatttta tatatgcatt ttattagagt gttactgttt tgttatagat ctgttagggt    18420
gtttgcttga tacggatgag acagacagct tgctcttcaa tgaaatggcc ctggattgct    18480
gtcttttttg aatttcatgt ttgtgcttta tggtggtttc cgcttcctta tgagactgtt    18540
agctgtcctt cttgctgcta tccatgtgcc ttcctgaatt aacactactc ctctaatttg    18600
ctgcttttaa tctgctgtgg actggacact ggatgactaa gcttgttaga actgtgtgtg    18660
acaataaaga ggctcttagt gagagttcga aggtcttgtc tgagatcaag atacgtgggt    18720
tttatatctc ttgttggcac agaaaccatt tttttatgtc tcacattcta taaaggttga    18780
gtttggaaga gataacggct taccatttga cacttactgt taatgaaatg tgtttataac    18840 cattttctg aagagttgag tagcaatgct cagggactta acttatttct gttttctttt    18900
ttgcttgcaa tcccttccct tactcttcca accctccctt ctcagtctct gcccacaca    18960 ttcaatgtaa ggcattgttc taggcactgt tataatattg tttcggttat tccatttcta    19020
tttatggaag ccacagagag ggttccagga ttgtaactca ctgttcagtg ctggatgtgc    19080
ttatatctca gtagggctct gctggagact ctcagatgag gtttagtgtt ggggactagg    19140
aaacttgaag caatgaaatg aatactggtt ccatatactg tataatcttt ggttgatatg    19200
gaagaaagca atcaagaagt cttaaaatta ttttggacat gcaaattaat ctattatgat    19260
agtggaatga ttagaagata aagccagaca aaaatagaaa gtgttaccca tagtcccata    19320
gattgtcatt gttaatattt tgatattata ttcttcttca agactttgca aaaataagaa    19380
tatattccac atcatcccct gtaatctgct ttctcactta gcaatagatt gcagctctct    19440
ttctgtgtta aaggtctgca tcatcaattt tagtccattg tttggagatg ttgcaattta    19500
cttaaccaat ttcctatttt tagacattta tgttatttta tagatattac aaaacagctg    19560
caacgaattt ttttttaagcc tttgagtact tgttctatta cttctttaga attaatttct    19620
ggacacaaaa tggctggatc aaaagatatg cttatttttac cttttgatgc aaattacaag    19680
ctggcctcca taaaaattaa acctgtatat acttccatct tgtgtatgtg gttggacgtg    19740
```

```
ttccctccct ctctcccttt ctcctctagc tccctccctt ccttctcttt tcttttcctc    19800
cctgccttct tccttccctc cctctctgtt ttttatattt attttatggt gaattttgt     19860 ttatgttcct ttacttatat tccggttagg gcacttgttt cttaatgact taataggagt    19920
tctttacata tttaagacat taatcctttg ttatatacat tgcgggtttt ttttctattt    19980
tgtcatttac cttaatagtg ggcttttgc agatatttta aattttgtg ctatcaagta      20040 tgttagtctt ttcctttatg attttgttg gcagccatcc ttggaaaggc ctgagaagaa     20100
aggcaggtcc ttgatcacag agagtctgaa gtttatcttt gagtagtatc agagccattc    20160
agagttgtgg ggtttaaaaa atacatttt ttcttgtaga gacagggttt tgctatattg     20220
cccatgctgg tctcaaactc ctgacctcaa gcggtcctcc cacctgggcc tcccaaagtg    20280
cttacagtca tgagccacag cacccagccc tccattcaga gttttcaga ggggctggca     20340 tgatcagaaa agcacttgag ttagatttct ggagggtgac cagagggagc tgagtctgga    20400
ggaagggcat ctacgaggct gttgacatga tccaggttca agactgccag gtctgagtgg    20460
cagagtggtg acaggaacag agagaagtgc agactaggaa tattttggca gtcgtaatgt    20520
gtccagaatt ggtgggttct tggtcttact gacttcaaga atgaagccgc ggaccctcgc    20580
agtgagtgtc acagttctta aaggcggtgt gtttggagtt tgttccttct gatgttcgga    20640
tgtgttcaga gtttcttcct tctggtgggt tcgtggtctc gctagctcag gagtgaagct    20700
gcagaccttt gcggtgagtg ttacagctca taaaggcagt gtggacccaa agagtgagca    20760
gcagcaagat ttattgcaaa gagcgaaaga acaaagcttc cacggtgtgg aagggaccct   20820
gagtgggttg ccactgatgt ctctggcagc ctgctttat tcttatttgg ccccacccac    20880
attctgctga ttggtccatt ttacagagag ccgattggtc tgtttacag agagctgatt    20940 ggtccatttt gacagggtgc tgattggtgc gtttataatc cctgagctag acacaaaagt   21000
tctccacgtc cccactagat tagctagatg cggagtgtcg attggtgtat ttacaaaccc   21060
tgagctagac acagggtgct gattggtgtg tttacaaacc ttgagctaga tacagagtgc    21120
caattggtgt atttacaatc cctcagctag acataaaggt tctccaagtc cccaccagat    21180
taactagata cagagtgcca ttgatgcatt cacaaaccct gagctagaca caaggtgctg    21240
attggtgtgt ttataagcct tgagctagat acagagtgtc gattggtgta cttacagtcc    21300
ctcagctaga cataaaggtt ctccaagtct ccactagact cgggagccca gctggcttca    21360
cccagtggat cttgcaccag ggccgcaggt ggagctgctt gccggtcccg tgccgtgcac    21420
ctgcactcct cagcccttgg gcagttgatg ggaccgggcg ctgtggagca gggggtggcg    21480
ctcgtcgggg aggctccggc tgcgcaggag cccaccgccg ggcggggag ggggaaggc    21540 tcaggcatgg cgggctgcag gtcccaagcc ctgccccgcg gggaggcagc taaggcccgg    21600
ccagaaatcg agggcagcag ctgctggctc aggtggtaag cccctcactg cctggggccc    21660
gctgtctgct ctgagtgcgg ggcccaccaa gcccacgccc acctgaaact ggcgctggcc    21720
cacaggcgcc ctgcgcagcc ccggttcccg cccgcacctc tccctccaca cctccctgca    21780
agctgaggga gccagctctg gccttggcca gcccagaaag gggctcccac agtgcagcgg    21840
cgggctgaag ggctcctcaa gcacggccag agtgggcgcc aaggccgagg aggcgtcgaa    21900
agcgagtgag ggctaggagg gctgccagca cgctgtcacc tctcagtaac atcaggcctt    21960 ggtgccggt tggattcgga gttggagggg aggtgtggaa tcaagagtga ttccaggctt     22020
tcagtttgag tgcctaacta agggtgagat ggaagtggca cccactgagc agtgttacac    22080
```

```
agcagagagg gaaggttgaa agagggaaga tacaggttta atgagaggag gcagcgtgtt    22140
cgtagttggc catgatcagt ttgcagtgtg cttgggttgt gttttagtca tctattgctg    22200
tataacaaac caccccaaaa ccttgtggcc taaaccaaca acagcttata attgctcatg    22260
attctgtggg ttgactgagg gttcagctgg acttctacta gggcttctgt tcatctcatt    22320
tgaggtctgt caaaattaca aattgccttt actcctttttt ttttttggtg gagttttgct   22380
ctgtcgccca ggctggagtg gtgcagtggc acaatctcag ctcactgcaa cctctgtcgc    22440
ctttttttcaa gcgattcttc tgcctcggcc tcccgagtag ctgggactac aggtgcacac    22500
caccaagccc ggctaatctt ttttgtattt tgttagaga cagagtttca ccatgttggc     22560
gaagctggtc tcgaactccc gacctcaggt gatgccttag tttcccaaag tgctgggatt    22620
acaggcgcaa gccaccacgc gcaaccaaaa ttgcctttac tcctaccact cgactctact    22680
atatacttga attcagaaca tcccagcatg gaccagtata tcacctaaca ccgtgcttcc    22740
tccttaaaag aaatacacat gtcagtgaaa gacaggaagt actatgagtg tatatacaag    22800
gctctggtgt tctttacacc ctggtggacg caccacagtg agagttgggc aaagggtatg    22860
cttttaaaa atttattc attaaagttg gctaatggct ttgagaaact tgggcaaatc        22920
attttaagga aagatatcta gggaagttaa gtatcatggc attgatttgt ttgaagctgt    22980
ccatacaggg atacttgtat tcaagtttgc aaatcactag tcaagagtca aagagtagt     23040
gggctgagga tggaatttag gcttagcaac atttaagggg tagcttagta aggagagccc    23100
ttaaaggtga cagagaagga atgtccagcg aggtgggagg agaatcagta gaatgcagtg    23160
tctcgcagac atgggatcca acaaaattaa aaagttggaa gtaaagaggg tcaaatatcc    23220
cagagaggtc aagtaggata aagactggaa agtgtcctct ggattggcca gtggagtggc    23280
attgacctct gcaagagcat tcagaagagt gatggaaacg gaattataga ttacagtgag    23340
ttggtgagtg ggagcaccaa gtctaaacta tttctttgag aaatgttcat aagaaaagaa    23400
agggagagat catagcttgg gagatgcttg agcatatcag taggctgatg ggaagaggca    23460
ccaggctaga gagaggaggt caggggagag attgaggtta aaacagaaga gagggcagtt    23520
cctcatggag caaggtccca gaggagacag gagggaatgg agtagtcttc attttttaaaa  23580
attgcaattc cattctttta gatactcagg ccaaaaacct cttgtcattc agtttatcag    23640
aaaatcctgt ttgctctata ttcacaatac agccaaggtc caaccacttc ttactgcctt    23700
cgttgctgtc tctctgggcc agcctgtcat tggcctggat gatggcagct gtttcttcac    23760
tggtctctcc actgctgcct gagcctcctc agtctactca gcacagtagc cagagtgagc    23820
ctttaaagtg ccaatcattt catgttagtt actcctctgc tcagaagcgt ccagtgattc    23880
cccatctcag agtaaaactg taaatcctgc tgtggcctag aaagtgctat gctctgcccc    23940
accgtttcct ctctgcattc ttattttact cttctcctct ggttattgct ctctatccat    24000
actggcttcc ttcctgtggt ttcttaaagc agggcagatt cgcacctccc tgctcaggcc    24060
tcttgtactt gctgttcccc ttgcctgtgg aatgtgtcct ctaggtagcc ccaaagcttg    24120
ctctccctca cctatttgc ttaaatgtca cttcctgaga gagtccttcc ctgaccattc      24180
cattaaaatt tgcaacccct ccctcccggc agcactccct ccctcttccc tgctttggct    24240
ctgctatata acgtgcttgt ttgtgtattg tctctcctct ttggaactta agctttatga    24300
gcttttctgt tttattccaca ggcctagaac catggctctc atagagtagg gacacagtaa   24360
atatttgttg attaaatggg tggatggatg aataagatca aggctgaacc ttgggaaaga    24420
agagggaaat ttcacactct gagacaggag gagatgagtg aatctgtatg gatatagata    24480
```

```
agtttgtagt gggaagcct  tgggggtagg gtgggaattg aaggcaatca taacagatac  24540
cctcaatttt ctggagtaag gaggcaaggt tgtctgccga ggatagtggt aagtatgggg  24600
ctgaggatac tcctgagagt tgggttagtc atcgagggga atgagagagg gagctaacca  24660
aggacaagga aaggacccaa gccaggatgg acaccatgag gcagtcttgt aaggctgtgt  24720
gatttgaggt taggaacaga gcaggtggat ttagcattga ttcaaggttg gggaggtgtg  24780
aggggaggct aggagtgcac agaaatcaaa ggagcagtgt agatggtcaa ccatggggcc  24840
agaatgggga gacaagcctg tctaagcagg gggttgattg gttgattgaa agaaaatgga  24900
agagtcagag catggaggac tggatggtca ggccagaatg aaagcctaag ggaatggaag  24960
tcttggaggg tgtgtcagaa tgggggagac tgatgtttaa gatttgtgtt gacaaggtct  25020
agagggtggc catggatgtg taggtcattg agaggaccaa aggtcagtgt cgtgaagaaa  25080
tctggaggct gcagtttagg aataagtgga ttttgagacc acccagaaag atggtaggag  25140
ttgcagtgga gggaagccaa gatgctacag gcatccgtga atgttagaga ctgagccaga  25200
gggggaagta caaaggcaag gcagggtgga agccagtgta gccacgtggc atgagctcaa  25260
aggagcagga atttttacat gagggtggag gagtgatggt ttggagtcaa ctcaggagag  25320
caaggaaagt tctgacctcc tgcgctaagc tactgaggcg taggaaaata tggcatcaga  25380
gggctagtga tgcaagtgat attggctggt gcaggagcag gaccgagcaa gttggatgat  25440
ttatcctttg gcttgattgt ggagctaagt tgttttttatt gttaggtatt tataatttat  25500
ggcatttatt tggcagctta acttcctctt attaaaagga acccattttt attttgcatg  25560
tattttactt atatattagt atattgaata ttatatattt atttatatct ctacttatat  25620
ttaattttat gtgtacatga attcttttt ctcctttggg tcttggcttt gtgacaaaaa  25680
agaccttgca tggtcgctgt agaggcatct tcaggacctg gttttgaatt tgcttttgt   25740
attttattgc tgggagctcc tgcttacctt tcacttttat gccctcctgg tcaggttggt  25800
tgcctcatgg ttctttttta tcactagact aatgattaat tcttagtgaa gcccttcacc  25860
tcagaggttg ctgaatgatg aaggaccact tccctgaatc tttgctcagc agcctcgaga  25920
taaaggagga ggtatgactc tgtcagccaa aaagcctaat ctttgagttg gaaatggttt  25980
attccttgta tattctttct aggtgttaac aaaccaaaat agtagaggca tctccattaa  26040
atgtggcctc ttctatactc ctaatgcttc cagctcttca ctttatccct tcacaggagc  26100
aggcacagcg tgctgctggg aatgtctgtt cacttctttt acatgtgatt agttgttcct  26160
gatgtttgca ctctcataca ctcaagcatg tggcacatac ctctttagga tttgctgcat  26220
cttacaataa cgatttattt atcagtcttc taagctgttc tcccttcatc cctgacccaa  26280
cttggactcc ttgagggtat ggttaggttc tcactcatct ttttgtatgc ttttaataag  26340
taggtattta ggaagtaggt attaaattaa tgcattaaac ttagaattca aacagcctaa  26400
ctcacagatc ttgcaaagga gaaactatgc ccagaggatt aaatggcctg tccgaaacta  26460
cacagctagg ttcaattggg attagaatcc atttctcctc tcaagcttgt ggggtcttct  26520
gaaagattaa tgtcaaagca actcgatgtg aattgattgt gttccttaaa gttagagata  26580
attgaattcc ttgaaaattc acttatatct tctagggata ggggctttca accttttcatt 26640
tcacctgtta ccctgtttgg gggtggtgtg atggtttgga attttgttgt tcttgactga  26700
gattagagaa tgagggccta ggcacaggga ggctctgttc tgcttgtcaa accagtaggt  26760
ttgcttttc cttgacctat accttaagga catccttcta tcttgtaggt gctagtggag   26820
```

```
ctatgttacc atacactggg gataggatga gggcccctgg ataatctgtg gcctggcaag    26880
tgacacaggc agaaagcagc atgtccaggt ccctcgtggg tggcttgggg gaacttgggg    26940
ttagaaaaag ggcattataa ccaggtgcta gaagttcaca gataggtcat ttgtggctgg    27000
taggattggc aggaaacaat gagtcacact ggtaggtata caagggatag aaaaagaaga    27060 aattttgat aattgctaga gagcccttt tccatttaga ccagtaggtc tcaattgtgg     27120
ctgttttgcc ccccaggaga cacttggcaa tatctagaga cattttgat tgtcacacct    27180 aggaaagggc tattacaggc atcaaacgaa tggaggtcag ggatgctggt gaatatcctg    27240
tagtgcatgg gatggggatg gcccccataa cagggaatta tacagtccaa agtcatgagc    27300
gtccaggttg agaatccctg atttacaccc tgggccccaa catcagtact ctggtggtta    27360
cttaagtcat aaaaaaaata gttttttata tatactttac tttgaactct attgttaaat    27420
ggcaaaatca ggtttatttc accttttct tttcgttctt tttttaaaat ggaggcaaaa     27480
ttcacataac ataattaacc attttaaagt gaacagttca gtggcattta gtacattaac    27540
aatgttgtgc agctgggcat ggtggctggt ggctgtgatt cctgctactc aagcggctga    27600
ggtgagagga tcacttgagc ccagaagctc agcctggaca acagcaaact tcatctctaa    27660
aagaaaacca gaaaccaaaa ctaaacataa tgttgtgcaa ccactacctc tatctagttc    27720
caaaacattt tcatcgcccg aaaaggaaag tggtacccac taatcagttt ttagtacaga    27780
cagggttttg ccgtgttgcc caggctggtc ttgaactcct gagctcacat gatttgtctg    27840
ccttgacctc ccaaagtgct gtgattacag gcatgagcca ccatgcccag tcactatgtt    27900
tagctttaac ataaaattta ccattttagt atttaaccct tgatatagac ttgtcattcc    27960
acaaacacat tttaagcccc atgtcatgag ggcactgttg aaagcactgc ataaattatg    28020
atgaacaaaa cagttatagg tgttttctc ctagagctta cagtctagtg gggaaggcag    28080
acattgaact cccaccagta agttttcaag tccgggaagt gaatttagct gtaaaagtat    28140
aggagttgaa gccagtgcag taggattgac tgtcacagtt tcttgctttc cactttcttt    28200
ctgtgtgagt acagtttctt tcatataaga gcaaattcat agccaaaaag aaacagggaa    28260
ggaagaaatg aagaaaataa atgagagaaa gcaagaccca ggagcgagga ggagggagga    28320
ttggggaggt cctcccagga aatcccgtgt ttcaggttct tctagaaact cctcaggcca    28380
gttcttaaaa catcttccac tgtggtctgt ctttatcttt tgagtcatat agatgggaat    28440
ggtatttcca tttggttaaa tggtactggg ttaaaaagca aaataacata ccctgcctcc    28500
catcctctgt gtctctcata aggatcagag cccaagtgac atgaggtcag ctgagtgccc    28560
agcaggactg aactattctg gcctgcgggg cttctctgcg aagtcccgag aagtggctaa    28620
gctgaggtcg aagtccacat ggaaaggaca gcaccaatgg gcatgcagtt tccttggtag    28680
actatgtaag tgaaaaccct agaaggaagg tttttgatgg tgcccatgag gaaagaggac    28740
agcaacatgt tttgttttt tcctcgtggt tggggtcata ttaattcttt agggccacag    28800
taacaaatga ccacaaactg ggtggcttac accagtagag attaattaac cttctcacag    28860
ttctggaggc cagaagtgag aaatcaatgt gttgacaggg ccgtgctccc tcaaaagctc    28920 cagggagaa tcatttcttg cctattctgg cttctcgtgg ctccaggcat tccttggttt     28980
gtggctccat cactccagtc cctgtctcag tttttgcatg accttctcct cttctgtgtg    29040
tctctcctct gagtgtctct tctaaggaca cttatcatta gatttagggt ctgccagcat    29100
aatccaggat gaccccatc ttgagatctt tcaattaatt acacctacaa agactctttt    29160
tctatataag gtcacatttta caggtttctg ggcttaggac atggaccttt cttttgggg    29220
```

```
aaccattatt caacctacca gagtggtgaa ggagacaggg tgttgggagc aaaggttttt    29280 gttttttgttt ttgttttcct ggttgggaga aaggaagca aaatgccgtg gagagtgcca    29340
tgactaaatc cctcacctgg gaccctgcac tgttgctgcc actctcggga aactttcagc    29400
ttgaaatgcc agctccacgg ggcaggactg gaatggcctg accaggtctg gcttcatgag    29460
agagagttta ctagactcct ccttccagct gttacacctg tccctgtgtg actccatgtc    29520
tgccttcctt caatgagcct ttcctcttcc ctttctcctt ccttgccttt gttttcagcc    29580
tgttttctca ccagtatttt gtgtttcttt ggtatttctc tctagtcatg gacagtaaat    29640
gaaacagaag taggcatttt actaatttta acctttatta atgaattctt tgttgcttgt    29700
cttctgagct gactcacctg atagtggtgc tcaaaaggaa aaccatttcc tctactcaca    29760
tttctgacac caaatctaag ttttttccac actaacaatc agttatttga cttcctagac    29820
accgtttggg tgtcctacta ttcaaattaa ttctgacact atctatttgg agttagcttc    29880
agattttaca gattaagggc tcaagactgc ccccatttca gatgccagtt gcaagcttct    29940
ggtaccaggt tagctacaaa ttaggggttc tcattacccc ttcctcctgt ttgatcattt    30000
gcaacagtgg ctcacaccac tcagggaaat actttatgtt tatcagttta ttgtaaagga    30060
tacaaatgaa caaccaggta agagctacct aggacaaggg atggggaagg ggcatggagc    30120
ttgcatgccc tctctgggca tgccaccctc caggtacctc cacatacgga gctatctaga    30180
agctctttaa acccctttat ttagggtttt tatggaggct ttattacata ggtatgattg    30240
attaaatcac tggcccttgt tgattagctc tatctctagc tcttgccctc ctcagaggct    30300
aggggtaaga cttaaggttc taaccttcta atcacatggt tgagttccct gccaaccagc    30360
ccccatccgg aagctaccta ggaagcccag ccactagcca tttcattcac ttacaaaaag    30420
acactctgca ttctggagat ttcaagggtt ttagacgctt ttgtgttagg aaacaggggc    30480
taagaccaaa tattaacaaa agatgctcct atcacccta ccactcagga aattactaca    30540
agggttttag gtgctctgtg tcaggaatca ggggcaacga ccaaatatat atttcttatt    30600
gcatcatggt gctgtagctt ggaagtgatt tcccctcttc ctgggtcttt gatcattggc    30660
cccatgattt ggggtgtgat tctaggagct gttgggattg cacaaagcct gtgccttcag    30720
atgcttgcat ctcatcttcc ttgacaagat gcctgtctta aagtgggcca ttggactgag    30780
ggaggtgatg ggcctcatga gacctcaaat tacccactta cactgaattt tcctggtctc    30840
cagatctaga gcttaggcca tttcacatgg ctaaactgct ttgttaaaat gctgctttcc    30900
cctaaggaca ctgatatgtc taaaggtcca gaagcctagt cagcacttct ccaggtaata    30960
ctttaacttt gaccaaaaca taaagttgac atcatagtag agtggaagac acagagcctt    31020
tgaaggcttt gactaactgg gagattgtca ttgacttgct ttctgtaaac tggctcatgt    31080
cttccatctt ggtatgaatg taccagtttt tcatttttcca aggattggct tgcctcctta    31140
gacaacactg agacttcctt ggtaaaactt atacagcaca tggtttagag ttgaatggtg    31200
aaggaggcaa ggaccataga gaagatgcta gaaagaacct ttatcataaa atatcaaaca    31260
atgtgaaaac attcttccct agataatgac tccaaaatac aactgttgtc gttttctggt    31320
gaaacgtcta gagccagctg tgccattctc atagcatctt cataataata agagctgact    31380
tttagtgctt atgtagcaag tgcctgttgg aattatctta tttatctcca cagccctact    31440
gttacctcat tttacttccg agaaagttta agcaacttgc cacaaagttg tctgctaata    31500
ggtagaagga ctgctgactc taaacccaag cccttttttta aagttgtgg ttacatacat    31560
```

```
aatataacat ttaccatttt aatccttttt tagtatacag ttctatggca ttaagtacat    31620
tcacattatt ttttttctct ctaacagatg aaatacttta atccatatat taataaatcc    31680
ccagttggat aactttttt attatacttt aagttctagg gtacatgtgc acaacgtgca     31740
gtacattcac attattgtgt actcatgacc accatccatc tccagaactt tttcatcgtc    31800
ccaactgaaa gtctatgccc attaaacact aactccctat tcccttctc ccccaagccc     31860 ctggcagcca ccattctact ttctgtccct atgaatttgc ctactctaga tacctcatct    31920
aaaatggaat catagagtgt tttgcttttt gtgagtggct tatttcactt agtataatgt    31980
cttcagagtt catccatgtt atagtatatg tcaaaatgtt cttccctttt aaggctaaat    32040
aatattccat tgcatgtcta taccacagtt tccttatcca ttcatctgtt gatggatggc    32100
tggattgctt ctaccttctg gctgttgtga gaaatgttgc tgtgaacatg ggtatacgta    32160
tctctcttca agaccctgca ttctgttctt ttgggtgttg tatttgggtt ctccagaggg    32220
acagaaccaa taaggtatat gtatatataa agggagttta ttaggagaa ttggctcata     32280 aaattacaag gcaaagtccc atgataggcc atctgcaagc tcggggagag agaagccatt    32340
agtggctcag tccaagcccg aaagcctcaa aaccaactct aaaccatgtg ctgtataagt    32400
tttaccaagg aagtctcaat gttgtctgac agtgcagccc ccagtctgag gccgaaggcc    32460
caaaagcccc caggaagcca ctggtccgag tcccaaagtc caaaagcaga agaatctgga    32520
agtctgatgc ccaagggcag gaggagagga agcaaagagt cctgcatgtg aagagagaga    32580
gagcgagaag actctgcagg ctatttatcc cccttctgcc tactttgttc tagccgcgtt    32640
ggcagccagt tggatggtgc ccacccacat tgagggtggg tctcccccctc gtagtccacc    32700 aactcaaatg tcagtctcct ctggcaacac cctcatagac acacccagaa actgcctcac    32760
cagccatcta ggcatccctc aatccagtca aattgacacc taatattagc cataacaggt    32820
atatacccag aaatggaatt gctggatcat aaggtagttc agtgctcagc ttttttagga    32880
attggcatac cattttccac agcagctgca ccatattaca ttcccatcag caatccataa    32940
gagttccaat tattccacat cctcaccaaa acttgttatt ttctgctgtt ttttcttagt    33000
aatagctatc ctagtgggtg tgaaatgata atcacgttgt tgtttgattt acatttccct    33060
aatgactaat aatgttgagc atcttctcct gtgcttatta ttagctgttt gtatatctca    33120
tttgtatatc ttcttggag aaatgtctat taatagtcca ttgttcattt ttctaatagg     33180
gctgttattg aattttagga attttaata ttttctggat gttaacttct tatcagatgt     33240
atgatttata aatacagtat ttccttccat tccatggatt gcctttctac tcttttgcta    33300
gttgtccttt gatactcaaa agtgtttaat ttttgctatg gttccatttg catattttg     33360 catttgttgc ctgtgccttt ggtatcatat ccaagaagtc atcgctaaat tcaatgtcat    33420
gaagattttc ccatatgttt tcttctgagg aatttgtagt tttagctttt tagatgtttg    33480
atccaatttg agttaatttt tgtgtagtca tgaggtaaga aggggtcctc cttttttgc     33540 atgtgggtat ccagttttcc cagttccatt tgttgaagag gttatccttt ccccctttgaa   33600 tggtcttggc acgcttgctg aaaaatcatt tgaccatata tgtgagggtt tatttctggg    33660
atctctattt tattctatta gtctctatat ctgtctttat gccagtacca cactgttttg    33720
atgactgtag ttttgtagta agtttttaaa tcagaaggta tgtgacctcc aatttttttt    33780
tttttttttt ttttttgagac agagtctcac tctgtcgccc aggctggagt gcagtggtgt    33840
gatctcggct cactgcaaag ctccgcctcc cgggttcacg ccattctctt gcctcagcct    33900
cccgagtagc tgggactaca ggtgcccgcc accatgctcg gctaattttt tgtattttt     33960
```

```
agtagagatg gggtttcacc atgttagtca ggatggtctc gatctcctga cctcgtgatc    34020
cacccacctc ggcctcctaa agtgctggga ttacaggcgt gagccaccgc acctggccca    34080
attttgttat ttttctaatt tgttttggtt attcagagtc ccttgagatt tcgtgtgggt    34140
ttaggttgga ttttcttatt ttttatttt attattattt tttagatgga gtctcactgt    34200
gtcacccagg ctggggtgca atggcacaat ctcggctcac tgcaacctct gccttctggg    34260
ttcaaatgat tctcctgcct cagcctcagg cacccaccac cgtgcctgac taattttgt    34320 attttagta gaaacggagt tttgccatgt tggccaggct ggtctcaaac tcctgacctc    34380
aggtgatccg cctgcctctg ccttccaaaa tgctgggatt acaggcctga gccaccgtgc    34440
ctggcctgga ttttaattt tattggtatt ctcttttgt tttgagatag gtctcactc     34500 tgtcacccag gatggagtgt agtggcacaa tcttggctca ctgcaacctc ccctcctgg    34560 gtttaggtga ttctcccacc tcagcctccc gaatagctgg gactacaggc acccgccacc    34620
aagcccggct aatttttgtg tgttttggta gagatggggt tccactatgt tggccaggct    34680
ggccttgaac tcctgacctc aagtgatccg cctgccttgg cctcccaaag tgctgggatt    34740
acaggtatga gccactgtgc ccagcctatt ttattgggat ggcattgaac ctgtagattg    34800
ctttggatag tattgacatc ctaacaacaa gtcttccaat ccacatacac aagatgtctc    34860
cttttatgtg tgtcttctcc aatttctttc agcattgttt tatcattttc ggtgtacaag    34920
tctttcatct ccttagttga gtttattctt gattatttta ttgtttttga tgcattgtaa    34980
atgaaatgga tttatttccc tttcatatta ttcgctgtta gtgtatagaa atgtaactga    35040
ttttgtatcc ttcaactttg ctgaatttat tatttctaag aagttttttt gttaagctta    35100
agcttttaat atgccatgtt cttctctgt cctgtgttaa aattaatctc tacctcattt    35160
ttgtcttctg acatttctga gttcttgggg aatttgtttc gcttttccaa tttgattgta    35220
tagtcttcaa tttgctgttc cttccctccg ttactattta aaccagtatt caaagtttta    35280
atttccattc agtctttcct atttcagaaa tccctttta aaaccactt acttaagtat     35340 catagttaca ctgactcctt aaatcttatt ctgaacatag ttttacagcc atcaccataa    35400
tctcatggga gatgaattct tagagagata attgtgagtc tctgtcttct tcatattcaa    35460
atgaaggagc aagggaaat tttaggttga ctgaatttac actggctgcc cgtgccagac     35520
ccagcccttc agtgccactc cctctgccaa gctgttggcc tgggcaggga gctgggtggg    35580
tgaatgtctg ctcaaggctc tgaggaaagc tgttggttgc gccttggctt gtgttgtagg    35640
agttctgtgc ctgctgccct agccttcttt tgtgtcctgc aggtgctgcc tgcatttatt    35700
gctgcctgca tttattgcca ggacacattg cttcttagaa agctagctgg gccttctttg    35760
gtcctgctcc atcttgacta aatctagcag atattcctca aagttctagg caggttggat    35820
ggcatccttc ctggtttcca actcaaatgc atgttttgt ctattttgt gtgcctttag      35880 tttatttaa aaggacctgg gggcaggaga catgtgttcc cctgttgcca ttgtactcag     35940
atgtcctata agacaattct tttgaccaac tccacctgat gagattatca ggctcttccc    36000
cttccctgct gtagcacata tgtctgttca cagcaagctg agtggtcatg gctaatctct    36060
agtctgccca caccctggat gatccaacca ctggcctgat tgattgggtt ggagaagaga    36120
gagtttctct tgtatcatta ctcttatgat tcagggaaaa atcaatttaa aaaattactg    36180
agttagaaat aggttggctt attataagta taatctagaa ggttttcatg atactgtccc    36240
acctctcgat ggccatgttt aatagatttt gtatcctggt agctagcagt agtcgttacc    36300
```

```
cgtgtttgat aaattatttt attcctgagt accatttggg gggcttgtgg gagtcagaga    36360
gagtaaccaa atactcatgg gaaagaaaag tagaagagat aaagtgttaa cgcatcatca    36420
gaaatcaagg caaagtcttt cctgtttctt acaaggccat acgatgaccc ctcctcttac    36480
ctctgcctta ctgagcccat tttctgatat tcacctgctc cactcttctt tttagtcctt    36540
gagtatgcca ggtgtgctcc tgcccgtcct tccctctccc tggggttctc ttcctccaaa    36600
tagccccatg ctctgcccac tcacctcctt cacagttttg ttcatatgtc accttcttgg    36660
ggaacccttc tctgacccct taatttgaaat tcttcaccct cttcccccac ataacactct    36720
ctgtcaaacc ttcttgcttt attttctcc acagcgttta tcacaatcta acgcactttt    36780 ttttttttt tttttttttg aggcaagact ggagtgcaat gtgtgatct cggctcactg    36840 caacctctgc ctcttgggct caagccatcc tcccacctca gcctgccaag tagctgggac    36900
tacaggcatg caccaccacg cccggctaat ttctgtattt tttgtagaga tggggtttta    36960
cctggttgcc caggctggtc ttgaacttgt gagctcaagc agtcctcccg cttaggtctc    37020
ccaaagtgtt gggattatag gcgtgggcta ccacacctag cctctaacct acttttaat    37080 gtatgtattt attttatggc ctgtctccct ggttgagtgc aagctccatg agggcagata    37140
tttgtgtcag ttttgtttac tgctgtatct ccaataccta gagaggtgct tgtcatgcag    37200
tagtcacttt gtaagcattt attgagtgat caatgattgg tggcttctag tgtcattcag    37260
cggcagcagg acgatgtatg tctgttctag atcactgagt cttaaaatgt tttcaagtga    37320
cctacagatt tttatcattc attcattcat tcattcaaga agttgctgtg tgtatcctca    37380
gtgaatcaga cattgaggta ctagcctgga agtctcatca ggggatattt atctttgtat    37440
ctccagcact aagtgcagca agtgccaggt agtacaagag aaggatttgt gaaagtctgt    37500
gggatcaaac tgctgaggtc ttgtgaagac aaaagtgaat aatacacatc cttgtgttca    37560
attggatcgt ggtcaagtgg ggaagacatg gacacccaat aatcctgtga cttgagtgct    37620
ataagagagg gattacagag atgagaaaaa acagttgctt ggggatggta gaaatcagga    37680
agcagctttt tgtaaatatg atatttatgc tgaaccttaa agatggttct tctgagtgaa    37740
caagcaggga gagaaggtta gacataggaa caacatgagc aaagatacaa aggcaggaaa    37800
gtgcaaagca tgttcctagg acagtgaatt gtcctgtgta gctggaatag tgagttcatg    37860
ggggtggagg ggaggaatgg gctgaacagt agctctggat cacatcctga aggccttgaa    37920
tgccacagat gaggtctgtg aaccttctgt aggcagtggg acactgttaa aagtgtccat    37980 agaagagat gaaaacacat tagtggttac caggaattag gggcagtgtg ggggcagggg    38040
gaaggtagga gcggaggatg actataaaga ggcagcataa gggatctttt tggtgatgga    38100
acagttctgt atcctgactg tggttgtggt tacacacatc tacacattat aaatttacat    38160
acaactacac atacatatga gtgcatgtaa aactggtgta aaacatcctc agcatgtttt    38220
ttaagtctct gcctcagcct ggagtgaata aggtctgtgg attgtgccaa tgtcagtttc    38280
ctggttttga cgttgtacca tagttatgtc agatgtcacc attgggggaa actggatgaa    38340
gggtacgtgg atctcctctg cactatttc gcaacttcct gtgaatctat acttaattca    38400
aaataaaaag ttagaaaaaa tgcataagaa ggaaaaggca gagcaaggag aatggttagg    38460
gtttccacta gtttaccatg atttcattgt gaaatgctat gttcggatac catgtaagat    38520
gcttgggaag catcttttc agaagttaca aaacacagtg tctacccttg agaaatttgt    38580
tgttgaatgg aggaaacaag ttttaagtag tgatcattct gtgtgctggc ttttagtagt    38640
aaaggtaggt acacagcaag gtgagagcaa ggaaaaaggg gacaaactgc tggggtaggg    38700
```

```
agggcttcat agtgacacaa ggactgggct gactccaggg aagagtggga gtttgtgtgg   38760
cacatgctgg ggctctgtaa aagcccgggt gagacataag gctgaaatta gtgctaggag   38820
gaattgagag tagggaatgg attcaagagc attttggaga agcattgatg caaattgttg   38880
aagtactgtg tgttgagaca gagagggaag agtctgaggt gacttaagtt ttcagcttga   38940
ctgaaagcat ggtggctcca ttagccaaaa tttagagtct agaaggagaa aggttttggc   39000
tagggtatgt ttagtgtgag gtatctgagg gactccatgc agagaggctg gggtgcagtt   39060
ggggtgtggc acccgggaga agcagtgcca gagctagaga cgtattggac cctaaggtgc   39120
agccccactg gaccgcttgc cacttcccca gtcatcctca gcatgttttt aaagtctctg   39180
cctcagcctg gagtgtccct ctgttccttc tccatcctgt gaaatcccac ccctgtgtca   39240
gctcgtatgt tccttcagtg tctgcttcag aatagaggtg atgactttaa accttgcgag   39300
cttgtggatt ttgtccactg atactatggt ggggcaagaa ggtaagaggg tgagttagca   39360
atgagcattt ggaggtgtcg tgccctagag gaggagagaa acagtggag aggagaagaa    39420 gcatgaaagc aatgaggcca catggaagct tggctgctca gcctctgcag agctgcccac   39480
ccagaattag acatgaccag gagaagaaat aggcagtgag ctaaatcaca gaagttcatg   39540
acaacacgaa agataagcat tcactctacg tcaccccaga gctccacctc ctgtgtaaag   39600
ctgcctgaca ttgaatggtg tctggccagc ctgattaatt tttaatattt gattctctgg   39660
tgaggtggct aggcattgag gtgcatcaaa ggcagctttt gtttctatga agttggtcaa   39720
aataacactg gagagtcagg ttactgcagc cttgagctct ggttgttctg aagggatgag   39780
atcagactct ctaactaacc gagtttcaga aggatctttg ccttttgcaa ggaaagttat   39840
ttggaactgg aagtgggtat gcttcctctt ggattctata tctcttatta tcggaaaata   39900
cctcattttt cagccacaga tagaaaacag catcagtgca tcaggtttcc aattctgtcc   39960
atgactcaaa tgatgtctga gttctgaaaa cctgctgcca actcctgaaa caccagagaa   40020
tttaaacaca aatgttctct aaataatatg ctccttacgc tgtgtagcct gcaaagcaga   40080
tgatgatgat gatgatgatg atgattttaa ttctgcacag tatctcctta attctctaat   40140
ttccccatct tttaaattgt atacctaaat gttctctctt aaaatttttt atttttttacc   40200 ctcttatctt tctacacaga gcccttcata gctgaggatg gatagtatct gagtggtgag   40260
aacctacatg tgaggagagc tgctctgaag tgactcacat gtggatttgc gaccttctgc   40320
agtgatggct ggttaggcag gagggggaag atcatggaaa gggaggcgat agtgtgactc   40380 catttttatca gtggtatgct ttgtgagagc ccacaagcta acagaggaat tgcctttat   40440 tctcagaata gggttctctc tctctctctc ctctgtttct tgcgtgctgg ctcgtgatct   40500
acctacttgt aaagatgctt tcacaagctt gaaagactcc acagtgtcat ggactgtgag   40560
gaaactctat tctacccact tttgccttac ttggaaattt ttacaataat catgattact   40620
tttataatca gaaaagttat aaacagtccc actggaaaaa taaacattta aaaatcagga   40680
aaagatgttc aaatgttgaa aatgcctctt tattgaattt ctaagtcttt atcttttttg   40740
acttccataa ctgataaatt atttaatga atttcttgat atttgtccat ccctccatcc    40800
attcatcctt acttttttga accaacttga ttttgccatg gtgtcttatt cttttaatgt   40860
actgcctgat tcaatttact agtaatttgt aaatgggata atacatagtt ttcttttcac   40920
ctgtactgaa tgccagagtt ttggtattag ggctgtactt aacttgctcc ataaaataaa   40980
tgaggaagcg tttcatattt ttctgttgct ttttaaaaat ttgaaataat aaataccatc   41040
```

```
tttttttagt gagcttagtt tatgtgaggc acaatgattg gaacccagat ctgcacagct   41100
ctgaagtctt tgctcatcct gtttgtcact gcagtatcaa aggaggaagg ccagccttgg   41160
aaccctgagt ctctgtggtc aggagcgcct caggggggctg gacttttcac tcatcttgtc   41220
cttttctttt cttaattaaa aatttcattt tgaaataatt tcagttacat aaacagtaga   41280
aaaatgatac acaagattca catatactct tcacccagat tcaccgatgg ttaatatttt   41340
gctacatttg ttttatcata tttttctgag ttatttgaaa gtcagccaca taatatataa   41400
tatcccttta taattatata cagtatataa tataaacatt ttagtgtata tttccttaaa   41460
aaaacaaact aaactaataa aaaacaaagt atagatgtca caatcaggat attaactttg   41520
atataaactg ttatctaatc tgtttattca gattttacta attgtcccag tcgtgcccgt   41580
tgtagcaaaa gaaaaacatt ttccttcggt tcaggattta atctgggatc aaacattgtg   41640
tttagttgtc atgtctttta aatctctttt aatctggaac agctccttaa tcttacattg   41700
tctttcatga ccttgacatt tttagtttac aggccagttc tactttatag gatgttcctt   41760
aatttgagtg attttgatgt tccctgtgct tagatttaag gtatgtgttt ttgactggga   41820
tactgcaatg gtgtgtcttt ctaggtgcat cataacaaga ggtcctgatg cctacttgtc   41880
ccatcactga taaccaacct aaatcatcta gttaactggt atctgccagg cttctccact   41940
gttaagttac tattttttcac tttgtaatta gtaagtattt tgtagggtga tactttgtat   42000
ataaatcctc ttccttatca aactttcatt tactaatgct agtgtccatc cttctgaagc   42060
aacaaagtga gacatgcaaa gtgaatagac tctaccccct ggagctaaaa tgaagccaag   42120
agaaagtgaa ccattcagtc cgtttaggca gataagccaa ttttttttttt ttttaactca   42180 ctacctatgg tctttgggtt ttgtctttgc aaaggttaat tgaaatctag tcatactctt   42240
gagaatagtg attggctgta gcttgtaacc tttgggttcc tattttggtc acccagggct   42300
caagatgggt ccacccagtt tattctggtc ataagtgccc cttggggctt tggccgatgg   42360
ctctgttcta tctttggctc tttgatcctt tgtctttgcc tctaagatgc tgtcaattgg   42420
agtcccaata aactgcctct gtgctgaatc acctataaac aagcatcgct tctggctaca   42480
gacttatctc atcagacaac tctctactga gcccagttac acagcctatg ctatctatgc   42540
taaggctgca gttgtatgag tcacacaagt agttttttagt atgtcagaga gtccagaact   42600
gtgtgtcata tgaagaaata ttaaaaacac ccagtggtat acttgggcac actttagcta   42660
ttgcaggttc tgttccagac cactgcaata aagcaaatat cacagtaaag ggagtcacac   42720 aactttttttg gtttcccagt gcatataaaa gttatgttta cactatacta tagtctacta   42780
agtgttttaa gcctactaag tgttaagtct aaaaaatgta catacctgaa tttaaacata   42840
ttttattgct aaataggcta acaatcatct gagccttcag tgagtcataa tcttttttgct   42900 ggtggagggt cttgccttga tgttgataac tgctgactga ccaggggggt ggttgctgaa   42960
agttggggtg actgtgacag tttcttaaaa taagacaaca atgaagtttt ccacatccat   43020
taactcttcc tttcatgaag aagaggaaga gttgtctgga gtatttgatc ctgtttgata   43080
gcattttacc cacagtagct tctttaaaat tggagtcatc cctcccaaac tctgctgctg   43140
ctttatcagc taagttgatg taattctaaa tcctttgttg tcatttcaac aatgttcaca   43200
gcatcttcac cgggaggaga ttcatctcaa gaaaccactt tttttgccca tccgtaagaa   43260
gccacttcca tccgttcaag tttgatcatg agattgcgac aattcagtca catcttcagg   43320
ctccacttct aattctagtt gtcttgctat tttcaccaca tctgtagttg ttgttacttt   43380
ctctgctgaa ggcttgaatc cccaaagtca tccatgagag ttggaatcag cttcttccaa   43440
```

```
actcctatta atgttggtat tttgacttct tctcatgaat cacgattttt ttttccttt   43500 tccttttttc ctctttattc acaaactgat tgttagtgca aaaaaaaaaa aaaaactgag   43560
acagattaag aatgcaactt ggatcttcag tcttctcttt tcaactcaat cctggaatat   43620
tcataatatt ctagccatcg ggttctctcc tttcttttt gtcttcaaag tccttttccaa   43680 aaggaaacat actgcttggc attctatatt attcctaatt tccaggtgga aaaatgagac   43740
agtgacatct aaaaacattg gagaggctgg acacagtggc tcatgcctgt aattctagca   43800
ctttgggagg ccaaggaagg aggatccctt gagcccagga gttcaagacc agcctggaca   43860
acatagtgag actctgtctc tacaaaaaaa aaaaaaaaaa attagctgga tatggtggca   43920
tacacttgta gttccaacta ttcaggaggc tgaggtgaga ggactgattg cacccgggag   43980
gtcaaggctg cagtgagccg tgatcatacc actgcactcc agcctcagtg acagagtgag   44040
accccgtttc aaaacaacaa caacaaacac acacacacat tgcagactgt attttttaaaa   44100 acaaggcaat aattcaggct tttcttgctt taattctctc tatattatca cagtaaaatg   44160
tttaacaaag tccaagagat tactgataca caataacaac ctaagacttt acattaatgg   44220
agctatcaat aataacctaa tcagtgaaat aactagaaaa gcatcaaatg taaagagtga   44280
tttgctattc tatttatata gtattgaaac tgtcataaca tttacagacc cagaaagtct   44340
gaggtaatat cgaataatac ttgataactg aaatactgca acatcgtgaa ggatcttcta   44400
aatgaccaaa aacagttgaa attttgtttg gtataatttc agtgaagttt ttttttttt   44460 ttttttacac agaactatat attttttaa attagtaatc cacataagtt atacacaaaa   44520
ttaagtgact agattgttca gtaaaactct acattgcttt cttattatgg actaatgagc   44580
ttataattca ctgtcacttt taagaaattc tagtctatag acatgttcga attgtttggt   44640
cttattagtt tcagtagcaa aaaccaccac ttcttttata tttaattctt ttgaatatca   44700
tctttaaaga gcctgacttg aatttttgtca aaataaatca caccttaacc ctccagtctc   44760
tagtctgtgt gttcttcatg agcttcagtt cagtgtaagc tagcacacgg acctccccat   44820
gaattttcta caactttaac actttccaca aagtgtcatg tccttctcta ggcttttggt   44880
agaatgtgaa gttaataatg gcatgtgatg ttccttagca taatctatca aaagtaatg   44940 atctccttgt aaaaaaagcc atgggctgca atcacacatc tgagttgaca gacatccaca   45000
tcaactcttc ataaaaagaa aaggggtggg acattagcgg ctcataccta taatcccagc   45060
actttgggag gctgaggcaa gtggatcgct tgagctcagg agtttgagac cagcctgggc   45120
aacatagcag gaccctggtc tttacaaaaa ataaaaaaat tatctgggtg tggtgttgtg   45180
cacctgtagt cccagctgct caggaggctg aggtgggagg atcacttgaa cccaggaggc   45240
aaacattgca gtgagctgaa atcacaccac tgcactccag cctgggcact agagtgagaa   45300
cctgtcttca aaaaaagaa aaaaaaag aaaagaaaa cgtttgtgtc ttctggagta   45360
taaatatcca cttttaagaa attcaaacag atcccaacat aaacgtcttc aaacttaatg   45420
ggttttacat gactcatcat ttatagatcc ttggcaccaa cctctggaca ttttataacc   45480
caacacactg cagtatggag ggaacaccat gaaaggatac ttctggtata aaatatgggg   45540
tttttggtga atcctctgt aggaataatt gttactcaga ggataacctg tgaaaaactt   45600
ctctggtttc agtttaaaag atactttact aaatttcaaa tatcgatgga aacatcagtg   45660
tctgtattca tgatgtactt ggcattgggg caaaactcag ttacccacct gaatgccata   45720
atggttttca aggtcatgtt attatatgta tccaaaacat gtggttgcat tatgtcacca   45780
```

```
taaagaaggt gttcaccctc taagcacagt gctaacattt tgtcttccct ttcagacata   45840
acgtaagaat ctcttatctc caccaacact ttttttttcat ctcaagtaac tccaatggcc   45900
tgtctggctt tcatatttga gggatgggaa gttactggga tgatgagaaa tggttggtta   45960
gttggttgat tttgagaccc gatcttactc tgtctccagg ctggagtaca gtgtggcatg   46020
atcatggctc actgcagcct tgaccttctg ggctcaagcg atcctcccag ctagtagctg   46080
ggactagtgg tgcatgccac catgcctggc tgttttaaaaa aaaaattttt ttttttttgg   46140
tagagatgga gtctccctct gttgcccaga ctggtctcga actcctgagc tcaagtgatc   46200
ctcctgcctt agcttcccaa agtgttggga ttacaggcat gagccattgc actgggtcca   46260
gaaatgggtt ttgatgagag cagtttgaat gctctcaaaa tgcaaagtga aggtattgtc   46320
tgtaaattgt ctcatactcc agaagcacat ccagtttaca tgttctgtca cattgtagtg   46380
gggaaggctg aggtaacaca tcacgaggaa actcaggagc gatagcaaca ggagacccca   46440
tgtgagggat cctagtgaca tcctacttgg aagggctgtc cagggagctg gggctgtcca   46500
gagagccgga gccatccgta gcagctcaga agcatgcgag ctgcaggttc ttcctcttga   46560
ttaatttctt gtcaatgaaa tactttcagt ttcaccagtt gaacatttag ctgtatgtag   46620
ttttcaaaaa taatgccacc aaaaaaaaag agaatctcag attggcttga aattctgcca   46680
taaatgcctt ataaaacaca cacctgtaga atttcagatg agattaaagc actagctaaa   46740
atttttttgtt gttttgtgtg ttccatgctt taagtaaaac actcagattt gctgtgaaca   46800
ctatgaacac agaaaaaaaa aaagacccaa tttggtaata cttcccttcg tagtagcttt   46860
tcccaacaaa acagccacct cctaaacaca ggcactggta acaccctcgc cttctactcc   46920
cccaccacca tggcaaaaac ccccagccac tcctgggggc gttagaaggc agagagtgca   46980
ccctgggaca aggcaaggtg gccaacatgc agcttcagcc tgggctcacc accacatacc   47040
ccagcattct tctgcatcgc ccacagctcc accaggctcc ttctccagca ctcacctgag   47100
cagggaactg ctagtcacag aggcccactg cctgaggttt ggtggctcag ctcctgccat   47160
gctccagaaa agcatgaatg gtcttagcaa tatctaagat ggtgagtcct ttccagaagg   47220
ttttaaattt actttgccca ggtccatcag aggagcctct atctgtggca gctattgcct   47280
tatgaaatgt atttcttaaa taataatact tgaaagtcaa aattccccgg gcatggtggc   47340
ccacacctgt aattccagca ctttgggagg tgaaggcagg tggatcacct aaggtcagga   47400
gttcaagacc agcctggcca acatggcaaa accctgtctc tagtaaaaat acaaaaatta   47460
gctgggcgtg gtggcaggtg cctgtaatcc tagctactgg ggaggctgag gtggggagaa   47520
ttgcttgaac ctgggaggcc aaggtctcag tgagccaaaa tggcgccact gcacttgagc   47580
ctgagcaaca gagtgagact ttgtctcaaa aaaaaaaaaa aaaagtcaaa attactcctt   47640
gatccatgag ctacagaatg tatgttgtgt tagcaggcat gaaaacatta atctccttgt   47700
gcatctccgt cagagctctt ggatgactag gtgcattgtc aaggagcagt aatattttgc   47760
aacgaatttt gttttttcctg agtagtaagt ctgcagtggg cttaaattat tcagttaacc   47820
attctgtaaa cagatgtgct gtcatccagg ccttgttgtt ccatttatag agcacaggca   47880
gaatagattt agcataactc ttaagtgccc taggatttc agtctggcca atgagcattg   47940
gctttaacct aaagtcacca ggtgcattag ttcctaacag gagcatcagc ctgaccttca   48000
caggtttgaa gccaggcact gacttctcct ctctagctat gaaagtctta gatggcatct   48060
tcttccaata taaggctttt catctccatt gagaatctgt tgtttagtga agccaccttc   48120
atcaatggtc ttatctagat cttatggata acttgctaca actacatcag cacttgctgc   48180
```

```
ctcaccttgc actttatgt aatagagatg acttcttgtc ttaaacctca tgaaccaacc    48240
tctgctggct tcaaacttct tctggagctt tcttacctcc ccagccttca tagaattgag    48300
gagagttagt ggtgcctagc tctagattag actttggcgt aagggaatgt tttggcaggt    48360
ttgttcttat atccagcaca ctaaaacttt atccatatca ttcatgtagc acttcaaatt    48420
tccttcaaga ggtttgggtgc agtggctcac gcctgtaatc ccaacacttt gggaggccga    48480
ggtggacgga tcacttgagg tcatgagttc gagaccagcc tagccaactt ggtgaaaccc    48540
cgtctctact aaaaatacaa aaacaactag ccaggtgtgg tggtgcgtgc ctgtaatccc    48600
agctactcag gaggctgagg caggagaatc gcttgaacct gggaagcaga ggttgcagtg    48660
agccaagatc acaccactgc actccagcct gggcaacaga gtgaaactcc atctcaaaaa    48720
caaacaaaac aaaacaaaaa agaaacaaaa tcctagcttt ttccatgctg atagtgctca    48780
cgcaaacatg gtgaacgttc ctaaaacccg ctggacttgt gtcagaagtg tggcaagcac    48840
caaccccaca aagtgacaca gtaaaaaggg caaggattct ctgtatgccc agggaaagtg    48900
gcgttatgac aggaagcaga gtggctgtag tgggcaaact aagccgattt tctggaaaaa    48960
ggctaaaact acaaagaaga ttgtgctaag gcttgagtgc gttgagccca actgcaggtc    49020
taagagaatg ctggctatta aaagaggcaa gcattctgaa ctgggaggag gtaagaagag    49080
aaagggctaa gtgatccagt tctaagtgtt accttttctt ttattatgaa gacaataaaa    49140
ccttgagttt atattcactt aaaaaaaatt ccttcaagaa cattttcttt gcattcacaa    49200
cctggctaac tgtttggtac aagaggcctc actttcggcc tgtggtaatt agacatagta    49260
gtgttctatt tcttcagtag ccacattcct ggcagtagta accatgaaaa catggctctc    49320
tgctatggta ttaccacaca cctctgtcat gtggttaagt ataaagcact gaattgtaaa    49380
tcatttattt tgaaattcat tcatataaac aaataagttc aaagttatcc tcacgataac    49440
atgactgtcc ttcaaatttt gatacgtttt cttgagtgca aagaatgatg tggaggtaca    49500
gctcttaccc taagggggcta cacacgatcc acaggatcct cctacttgaa ctagagccct    49560
tatgtgggtg ccagatgtcc atgggcatat gtcttatttt tgaatgtctt tggatatatg    49620
tgttatggtg gagagagttg aacaattgtg ctaaaaccta gctttgaatt tagagatata    49680
ccactacctc ccctccccctt cccaaagaaa aatctggggg cagtagaaat tgctcacaaa    49740
agcggattcc aacttgtacc ttaggagaga ccctgtcccc tccctcagtc ttttttattct    49800 ttcttgtttt tattaatgag ttcttatact tttgatttac tgttgaatta aaagcaatac    49860
attaaaatgg agaaggacgc caacctgaca gtagagaaca atggcaagag ccgctaaggt    49920
caaagacaga aatgttaaag ctggcagagg agttaaaagg attacagtct ggagctacct    49980
aatgagtgag ggaagtagca ttgtacactc tagtagcctc tgaggcatcc cagcattgag    50040
tgagaaacag gtaataaatg tttgtgatga tttctccagt taactagaaa aggtggaatt    50100
ttatccagta tacagtttgg agcactgaga tgtaaatagt agcttatctt gacaaatttt    50160
actgcaacta attcacatta attataaata tttagaaaca tgaaagaaaa gatatataaa    50220
acaactcata tcacccatag atttaattac ttttagcaca ttagtatggt atttagctct    50280
tcagcccttt tctatgtata aagatagtat ataataagat atatttgcat attatataaa    50340
atacatgtta tataatatat ataccaaatt tatgtgtgag aacatgaagc ctgcttttt    50400 atttaaaaaa aatttacttg tggtaaaaat acacaataaa aagtatacccc tcttaaccat    50460 tttgtaaagc ctgtttttttt aaactcaata atatgttgtg aacatttttc catatcactg    50520
```

```
agtatagatg tttattttaa ggctgcatgg atataccata atctagttag tcaatttcct   50580
agtgctaaat atttaggttt ccaactttgg ttattaacac tgcataaagc atcttttaaat  50640 atatatactt ctacatttca tcagagtccc aaaataattg ttggatcaat ggatgtctac   50700
tttctgaatg cttccaatgt atcttatcaa agcacacttc tgtttcacta tattcttgcc   50760
aatatttgat gttataattc ttttaaatta atgtttatgt aatttagtct ttaatactaa   50820
aaatgcaagc agcagtggaa actaaagtca atgagaaaat gcattttagg gaatgtgacg   50880
catgaagtta ttcaggctta taaactagca aaccactggt tctgtaagag aagaacttaa   50940
cacagcaact atttagaaca caggcatgat gagccttaag acactcactt gttcatggag   51000
tgtacaaaat tcatgtaagt cttcatgaat gtgaagaaat gcctcataat ttgaagaaga   51060
gatgttaaat gagtccaatt atcataagcc aaatctgtga atctcagggt agaactgtga   51120
atctcagggt agaactttat tgaattttgt gtaacatttt tgatgttgaa acttttttc    51180 acttgccact aactttgtgg gttttgtttt atttgccaca gagaagtttc acatttaat    51240 gaggaagaaa tgaatcaaat ttttggttac tcttttcatg ttatgtttat agaaaaccat   51300
ctctacctcc aaagttatag tacagttgta attttctttt agcagtttta cagttttatt   51360
tttgacactt aagtcagaag ttgcaaacat ttttattgaa tagaccgctg ttgtgggggg   51420
ctgtcctgtg cattattagg atgttggcat cccttgacct ctgcccactt gatgccagca   51480 gcacccttg tctccccagt tgtgacaact ggaaatgtct ccagatattg ccagttgccc    51540
tctttgggcc aaaactaccc tctcttgaga agcagtggta tgataaacct taaagtgagt   51600
tgaggcagta cccaataaga aacactggca ggacaagaga ccagtcattg gctgagtgga   51660
atactcaggt cgactatttc ttgaaaattg tattctagtc tagagattgg agatactggg   51720
aatttggagc ggtcttcctt ttgttgcagt tttggattcc aaactgcaat gaaagatctt   51780
ggttcttctg cttcacttcc tcatttgctc ttattgacct ctctgtggac taggagaacc   51840
aggagagggt aactgggagt tattaataaa agtgttagga aaattgtcag cagatgcctt   51900
ggtgacatct tgttccaact ttccaattta agctccatta aactggctgt ggtctttgtg   51960
gtttgaaata tagaacaggc caggcgcagt ggctcacgcc tgtaatccca gcactttggg   52020
aggctgaggc gggcggatca cgaggtcagg agtttgagac cagcctgacc aaaatgatga   52080
aaccccgtct ctgctaaaaa tacaaaaatt agccaggcgt ggcggtgggc acctgtaatc   52140
ccagctactc aggaggctga ggcaggagaa tcgcctgaac ctgggaggca gaggttgtag   52200
tgagccgaga ttgcgccact gcactccagc ctgggaggca gaggttgcag tgagccgaga   52260
tcacgccact gcactccagc ctgggagaca gagcgagact ccctctcaaa aaaaaaaaa    52320 aagaaaaaga aaaaagaaa aaaaaattat agaaccaact ttaaccccgt tggctctaga   52380
ataaagtgat ttatgagtct tttatgaaga catcatcctg caacatagtc ttatttctct   52440
ttccctggtt taccatggct tgtaggaatg atacttccat accttggtgg catatggtaa   52500
atctcttggg tacggtcaca gtggtgttgg tcagtagacc ttactggttt tgattgatca   52560
ccagttattt catgctcctg tagagcctgg gtgctgaact gggcttcatt ttcttctttg   52620
ctgttgtgac cttttgagtt gagttctttc tccactttgt gcctaaatct ccatatttct   52680
aaaagtcata gagagtgact gatgatattt ataatgttaa ctccttaact gtagatattc   52740
taactacagt ttaaataaat gctccataca atatggacat agaaaatgga tttgccgttt   52800
ccaatcttac cagtctttca gaattcatct gaaatctgtt cgcaaaaaac tttccctagc   52860
aatcgagctg acattcatct ttccatagta ggtgctcgat gtaggcttat attttttctc   52920
```

```
aatgtctcat gccttatcgc tccaataaag tttgtgtttt ggggaggtgg gaatggagat    52980
tggaagagac agtacatttt gttgccatat taaatctctc gtgatttatt tcatttgact    53040
tttctactaa ttttaagatt gataggatat acttattccc attttacaac tgtgaaaatg    53100
gagctttaga gaagttgagg cttttccagt tagtagatgg ttaagccaaa gatagtatgt    53160
attgatattg ggattcctaa ctagagaaat tgtgcaaatc taaaaatggt ttttgatttg    53220
ctcctgtatc tgcaatatgc agaatcttag cgttgccagt taaaaattga gacatctaag    53280
cctgctatat taagtaggct gtgtacaagg ttagtgggga tggcttatgc tgaatcactc    53340
ctgccctggc tctgtcctcc aggaaggaca ggcactgcgg aatggcagtc tgggggtggg    53400
tgtaccgact gatcaaaaca gtttctctgt atagctttct tggaatgtgt gctctcctct    53460 gttctcagge atctttgcta accaaagccc ccagtgtcct ctgctttaat ccttagcatt    53520
tctgctgcta cggaaagggc tttgtgataa ataccaacg aaaagtgggt ggtttagggg      53580
caggttccag tcggcctctt tttcacattt ctgatatgta ctgaagtgac taggaagtta    53640
atgcgccttg tctagtttgt ggagactgta gagaatgaca tgatgtgttc tgctggagga    53700
agaggatgat ggagtcttgt ttttacctga gctcatgcag tggtagtgaa gctcccagct    53760
tatcttcctg tctggcttcc attgctggtc gtccctagtg agcagagcca ttcagaggtt    53820
ttttgactta ttccctggcc tggcagagct agcttctatg aattttttt ttaatcagaa     53880 ccagttggac catgttctct ttttattatc ttgcttggct ttcttctgtg gagacaaaat    53940
ggagctacct taaacaaag taggagctgc tcacttccct gtgcctgact ctactccagg     54000
tactttgtta tctgtacctg aacgctcaag gcagatcatt cctagggatt gctctctgct    54060
ttcaggacac ttccatcagc ttttcggacc caatactcct ttactttctt tctttctttt    54120
tttttttttt tttttttgag acagagtttc tctttgttgc ccaggctgga gtacaatggc    54180
gcgatctcgg ctcactgcaa cctccgcctc ccgggttcaa gagattctcc tgcctcagcc    54240
tcccaagtag ctgggattac aggcatgcgc catcaagccc ggctaatttt tgtattttta    54300
atagagacag ggtttcatca tattggtcag gctggtctcg aactcctgac ctctggtgat    54360
ctgcctgcct cggcctccca agtgttggg attacaggca tgagccactg tgcctggccc      54420
caatactcct ttactttctt tgagttacaa tgttgcatct attctgttca cagcccctag    54480
gactcctttt cctgctgatc tttctaggtc ttgactctct gcctcgttgc ttgaccgcta    54540
cccggcttca gagtccaata attatatttt caactttgtc ctgtatatgc tccacttctt    54600
ggctggaact ctgttcagtt tatttcctga ctttgaacta tctccacgta gtgccacctt    54660
gtttcctgat ctaaggactg tgcaactcct ctccagtcgg ccacatctct gaccaaggga    54720
ttcagtgaaa actctggttt ctcacctgaa cttttgatctt taaccccagc tgacactagt    54780
aatggccttt gtgatcaggc tctgaaagaa gactgacttc atgtgaacca tgtgagcata    54840
ttgttcatat atccctcaag gtggattcct tcttttctaa aaggcatcta aaaagcaacg    54900
gaagttcttt tgaaaatcag aggctgcctt tttggtagca gttctttcat ttattctgta    54960
gaggatccag attgagctct ttataaaata ttctcctaca taatgtactg ggatagtcct    55020
aacaatagta aaccttgatc cacagatcac atgtgccatt ggataaaaat aaataatgca    55080
gaggaactca ataagaccag cctgtttaaa ggagacatca taaaaacctc cattaaaaaa    55140
agaaaaaaaa aatcatgtag ctgtggtagc aagtataaaa caaatgtaag aactgaggag    55200
taacaaaatg atgcaattag cttagcaccc acagatggtt tcagatacac tcagatgtca    55260
```

```
caggcatcca ggactaggcc tgctttgatc atttggaggg caggatttct ggatacctgc    55320
gtcacctgta gccatctact gctgaaacaa accgttataa cagagaggga gttcttagtt    55380
aagggaatgg gtttactctt ctttcttact ataagggatg gggaaactga tgtccgtgac    55440
aaatactgaa agtggagcat gtcctatatc agcaaaagtt cccataacta gagtttttct    55500
gaaggtgcag gtgatgtcag gtacccacct gatgggcctt acttaggaaa gaaggggtg    55560 gaggagacag ggatgaacat tgttaagag cttctgtgtt tagatgtgtg ccgggtgctt    55620
tatgatgctg tctcacataa tcttcacaat aacctctgtg gaacagggga tggttgctca    55680
tgttatatgt gaactcaggt cacgttacta tggagtgttg gctgtgggat ttgaacctt    55740 atctaactcc aaagtcttgc tccttagaaa tgaagcaggt ttggctgggc atggtagctc    55800
atgcctgtaa tcccagcact ttagggaggc tgaggtagga ggatcgcttg aggccagggg    55860
ttcaagacca gcctggacaa catagtgaga ccttgtctct acaaaaaatt taaaaaaaag    55920
aaaaaagaaa tgaggcctgg catggtggct tatgcttgta actcccaaca tttgggagg    55980 ccaaggtagg aagatcactt gagcccagga gttcaagacc agcctgagca acatagtaaa    56040
actctgtctc tacaaaaaaa tttaaaaata ttagctgggc aactgggtgc agtggcttac    56100
acctgtaatc tcagcacttt gggaggctga ggcaggtgga tcacctgagg tcaggagttc    56160
aagaccagtc tggctaacat ggcgaaaccc agtctctact aaaaatacaa aaattagctg    56220
ggcatggtgg catgccctg taataccagc tacttgggag ctgagacag gagaatcact    56280 tgaacccaag aggcggaggt tgcagtgagc cgagatcccg ccactgcact ccagcctgg    56340 caacaagagc gaaacgacat caaaaaaata tatatata tatacacaca catatataca    56400
tatacacata tgtatatata tgtgtatata tacacatgtg tatatatgta cacacgtgtg    56460
tgtatatatg tgtgtgtaca cgcatatgtg tatatatgtg tgtgtgcacg catatgtgta    56520
tatatgtgcg tatatataca tgcgtatata cgtgtgtata catgtgtgta tatatacaca    56580
tgtgtatata tatataagct gagcatggtg gcaagccct gtagtcctag ctattcgaga    56640
ggctgagatg gaaggattgc ttgagcccag gaggtcgagg ctgcagcgag ctgtcagcat    56700
gccatcgtac tccagcctgg gcaacagaac aagaccctgt cttaaaaaa aaaaagttt    56760 ttttttaaag aaaagaaatg aggcaggttt gctttagaaa atgaaagctg ctgatttggg    56820
cagaaaggca gaagatatgg aagaaggacc cagcctcaag tcccttgttc cttgaagatt    56880
agaagattac tgcatttgaa agcatggtgc attggttctc acagctaact gcctattagg    56940
ctcacctgtg cagattttac cctccgcccg acccaaaccc accaccctaa ggattttgaa    57000
tctcagtatg ttccagctgg gaaactggag aattatcttt ttaaaaactt ccaaggtgat    57060
tctgatgtgc tgttagaatt gagaaacttt tctgtgtcta aagaacaatg gaatgaatgt    57120
gagcccggga gtggccctag ggataatctt tccaactctt ttgtgatata gagagaaaa    57180 ctaaggccca gagatctcag aagccagaca ctccttcatt cagtagttac cgagcattga    57240
ctttgttatt ctaggtgatt cagacaatgc aaagaaaaat actttccttg tctttgaaga    57300
gtttttagcc taagatcaca tagctggtta atgcagagcc acaattggaa cccaggtttc    57360
ctgacgtctt ttgtgttttt aagcctttg aatattgtca ttgccaggcc tcctttgagc    57420
tcctgaagct ctgtaaatgg ttcctcaaca ctgtggtaag ttgcctccaa agcccatggt    57480
taccttgtgc caaagtccc ctgcctgcct ttctgcctca ttaccagcct ggtattcaac    57540
cacccacttt gccttaggtt cataggccca caggttttca gttgactgct ttgttctcag    57600 ttcatttta agcatctcac ctggaaaagg cctgaaaaag ctgcataatg attattttag    57660
```

```
aaatgcagtg cttagacaaa acctgcccca ctggtggtca ccctgatctc tttgctattc  57720 ttttaatga gttcataatc ctccggttca tctcacagtg ttcttgtaga ctgcatattt   57780
ttcggagttt ttcccagacc ccttgggca gtgacgtgcg gagggcaggg agcactccgc    57840
accaatcagg cagagggtgg tgccagaggg aaggtgagg gaaagttgt ttgcccagca    57900 ctgtgctagg ccaattttg tatatttttt tctttagtgc ttttcaatag ctttggggga   57960
gaaagtttcc acatctgtaa aatatggata ataactgagg cttaaagaag ttaagtaact  58020
ttctcaagtt tatgtaaaca agtttcattg ctagaaatca aaccctggaa actactgact  58080
gaaaggtcat cctcttttcc tagtaccata tgccacatca tatgtaaaac tttgatcta   58140 gtccaaacat actttttggg taagtgattc ttaaatttgg tttctggtat ttttcagtag  58200
gttttagaac tcaaggctgc ctttaacgat gcaggagaga tacaggactt tggacaggac  58260
tctggagagg agggtagcgt taggtattgg agtctgagaa ttgcagtgat gacaggcacc  58320
aagctcctag gccagcccat tggaaccagg ggccaacata actactgtcc cagtccaggg  58380
tcagaacttg gaaaactcag tgccgaagca taaatgttaa ccagaggtcc ttggggagtt  58440
ggggtggtgt ggggacatgg acctctagct taagaatatc tcctggctgg gcgcagtggc  58500
tcacacctgt agtcccaata ctttgggagg ccgggccagg aggattgctt gaagccaggg  58560
atttgaaacc agcctgggca acaaagtgag accccatctc tacaaaaaat taatttaaaa  58620
aagaatatct cttatatgtt atgccaattg gagattatag atctctcctt ttcatagaat  58680
agtctcttct tataatcctc gattaaagct tgaattttta tgtagttttt ttggataaca  58740
cttatctgga cctcagtttt tgaatctaca aaatgataat ttgggtttat tgtgatgagg  58800
aaatgggaac atgtatgtag atgacttttc ttcactgtag actattcata cagatatgag  58860
atgggtatga gacccaggat ccctaaaaac agattggtaa gaaaggcagt gtagttgttg  58920
ggcaaaggga acagtgattt ttagagtgtg gaaagctcta ggagaaggag ggagaccaga  58980
gtggggatgc tgcactggaa gtgaggtgga aggctttaga tttcctggtg agtaatcgag  59040
gtctctgagt gcctgggtt gaaggttgag ggagttcaaa gacttgatgc tgacctggga  59100
tcttactgag accagtcgct gcctgtgtgc gtgaggatac caccttgtgc aatctagttc  59160
aatggtgtgt caccaagagc ctgacctgac acctaaatgt gacgtagtgt cccttagaaa  59220
tcatgtcatg tgatgtaacg tttagcttga gtcctgtatt agaaccagtg caactgggga  59280
ttggcttgag gcaagttccc aacttgaaac aagttgggaa accaaggcac caagagaaaa  59340 agttaccct acaagtctgg actattcaaa actgaagctg aaagcaacct tctgactctg   59400
actttcttat actcttaccc catttctttt cttttatcaa aacatggtat taccaagttc  59460
ccaagagcga attataatta aagtaaccac agtgtaaagc tcatcaaccc agagtctcgg  59520
aatgaggtgg agagaagcta gttagagaag aggtattatg taatgaccta attatgaggc  59580
ctgccatctg cttaggagtc acgcctgcct ggttaggatt ccctgattgt gttttttaag  59640
gaagatgcta gattgttaaa gggggtaggg agagaaggta actataccag aatcattagg  59700
gcctttcttg aaggaggcgg gtgggttttg cggggaggga gatgaagcag ccatggaggg  59760
ctcctaagca gatgttcccc attagcttgg agagcagtgt agaaggttaa ttattctgta  59820
aaagaggttc cttattaggg aagggtggtc aggtgaagct ggctatcaga acatggctga  59880
taccccaggt ttacctggag agacaactaa gacatttttt ttccattcag gggaaagagt  59940
gagaaatcca ctttatttt ttaagtggac attttgtgct gtggatgaag atccgtagct  60000
```

```
tgaaaaaata tccagaaact tgaaaagtg gaacgaagtc aacttagaat agaaacacaa    60060
accacaatgc tcatggcacc tagtgagttg cctctaaagg gactcagggc caagaatcag    60120
atgaaaaaat tgtacacata tcaagaaagt ggcaggtgaa gagagtgagt ctttggaccc    60180
actaagggta tagctctaat gctgaacggg ctctttggac tttcagccat gaagccgaga    60240
cccaggagga tgtggacaca ctgcttgtac tgcttgtaca gtagacatac aaggagtgac    60300 ttcaaggaa attattaaac ttcctgaaca ctctttcaga gaatctttaa cagaaaatct    60360
cttttgcctt c aggtttcaaa aatgtgccta tattagggag atcagagtga ttggagcata    60420
aagagtgaat atccccaagg aagtaatgct tccctaattc ctgcctctac ttcccacctg    60480
tcagggagct tcttttaatt tacttccatc ctctgctcac caccacactc cagtgtgaaa    60540
gcaatgttgt cttttaaaga attagtaatt caaatccctg tatagaattt cggaggttat    60600
ttggtgtatt tcatatccct gaagaatcac caaaatgtgg caaatgtcca gctccaaagg    60660
tgagagatgt ttatgtccct cactttcact ttataaataa ggaaactgag ggccagtgaa    60720
gtatagtgac ttgctcaagg tcatagcttg ttatttgtgg aacttggacc acaactaggc    60780
ctcctgactc ctgatggttc tttctgttgc cttttggtat ctctcacgtg gagttttatt    60840
tgaattgctg ccaggagttc tgtggctgtg gcagttacat atgatcacgg tgggtgtaac    60900
tgcacagtca acagatataa ccctgtaggg gtaatatggg gctctcactg gtgtcttaac    60960
ttccagcaac agagtcctca gagctccagg gaagagtttt gagatgctag acatcagcat    61020
tctttctgta agtttgcaat gactttggaa cagaaaattt tatttccaca tctgagtctg    61080
tctcttctct tccttttgac caccacttct tgttggacac tgtttgtgga gtgtggacta    61140
accttgtgtc tttcacttga ttttttaac attcaaactt ttagcttgag cagacagctg    61200
gcaagaggtt tctctgtaga atattgaata gccatttaga atgtgggtta tgatgttccg    61260
ccctcacccc ccagtagcag gtcttttag gggacaggaa tttgcaaagt cattagcttc    61320
cttcccagga ccaaaagagc cagcgtgggc aaacttcctc accacctctc ccaccccgaa    61380
accactggta gggtttattt aatttagtct tgtgcatgtg tgcacgcaca cacgcgca    61440 cacacacgca cacacacacg tgcacacaca cgcacacacg gaggttttc atgtatagag    61500 atactctgat tctattctaa gtgttctcag tatactgcag tttctacttc ttatttcaaa    61560
gagatctgaa atatgtcctg atcctgggac agtggttccc caaactggca gatgatctgt    61620
gttgtctgtg aggcttttgt aaaaaataga tccagggccc cactcaggct tgctgaatca    61680
gactctatca gcatttagct atttatttac taagtacttt atcagtgatg taatacatat    61740
tttgtaaatt aggtacttaa taagtagctt atgaatttta caaaatgcaa aagccaaaat    61800
ttgtctttaa aaaatatttt ttcacacgac actgatttat cttcaaaaat gcactttttt    61860 tttttaaag acagggcact ctgtcaccca ggctggaatg cagtgacgca atcatggctc    61920
actgcagctt caaccacctg ggctcaagca attctcccac cacagcctct tgagtagcta    61980
ggaccacaga tgcgcaccac catgcctggc taagttttta aaaattatt ttgtagagac    62040 tgggtctcgc tgtgttgccc aggccggtct caaattcctg ggctcaagtg atcttcccac    62100
ttcagcctcc caaagtgctg ggattatagg catgaaccac catgcccagc ccaaaaaaga    62160
tctattttta acctaaagaa agtgttttgc gtcaattttc aacctgttat cataaatgta    62220 cattttaaa ttactccctt tttttgaagcc ctgaattaaa acgttgctct gcaattttagc    62280 aatctcattt gacactcggc aggtgggcca gtccattttc aaatgggcca ttttcaaacg    62340
tatttagaga atacttttca ctagtcatcc ttatattatt gcagaaaaaa atacattcac    62400
```

```
tctacaatgc cacactgatt gtagtgcact gtttttaaaa aaacaaaacc agctgggcgc   62460
agtggctcac tcctgtaatt ccagcacttt gggaggctga ggtgggtgga tcatgaggtc   62520
aggagccaac gtggtgaaac cccatctcta ctgaaaatac aaaaattagc tgggtgtggt   62580
ggcgtgtgcc tgtaatccca gctactcagg aggctgaggc aggagaattg cttgaacccg   62640
ggaggcggag gttgcagtga gccgagatcg tgccactgca ctccagcctg ggagacagag   62700
tgagattccg tctcaataaa taaataaata aaattaaaaa acaaaacctt ttgtcctctc   62760
agcaggctct agataaattc ataagctact tattaaatat ctaatatgta aagcatgtgt   62820
tacttacatg tacttctata aaaaaaaaaa gatcattttt attaatttgc ttgtaaactt   62880
gcatagttta aaaacttgta acaaaatgca accctaaata tgcatatgac tgtccttggg   62940
ctggtggtga ccatcatttt gcgcattaga ctgaatatag aaaaagcaca catactctgc   63000
tcaaagaatg tagtgcatta aagccttcat agagttcatg taattcagtc ttttggtttt   63060
atagatagga gagctgagat caagtgagaa gaagtgagtg gattcaaatg tattaaccaa   63120
gacactctgt gggcacatta acagttatct acttaaacga gctgaaataa aaagggaaat   63180
gtgaaaaaga caagttggtg ggtgtttcta acggaacctg gagcaaaagt gctactgacc   63240
ctcgccaaga gtctgaaatt agaagaaaaa ggccaccagg agtgtttctc tctctctcat   63300
ctctgctttt tttctgcttc tgctttggtc ttctttttta atgcagatag actttctctg   63360
tttaatattc ctatggcacc atatggtttc cgtgcagctc ccacttttca cttgctgtag   63420
tttaagttgt ctgcacatac ttataccaaa ttccacttttt ccaggaaaga atctgagttg   63480
cctggtgtgg atcagatgtc catgatggtc ccatgaagtc tggcaaggat ggggaaaggg   63540
tattctttag tacaaacata atgggtggag gagaggggat gtccagagaa aggtggatca   63600
ttgagttgca cagaccccca ccaaaggttt ctgttctgag agtacactaa gaaattctag   63660
tagtctagga gaaaaatgag gaggatctga aataagccag tggctgttag tatgggcaga   63720
agttagcaga cttgaaagag atggagacaa atcatcaaga tttggttgtt agttggatat   63780
tggggagagg gagtttctga agacaggaaa tggggtagat ggtggtcaca gcattgggga   63840
acacagaaag ggaggcttgg gaggtatgtg tggagggac acctgggggtt tgatttcagt   63900 tttaaacatg ttgagtttgg ggtgcctgtg aaaattacaa gtggaaatgt ttatcagctt   63960
aattgagaaa gtcaaatata tgggtctgga cctctggaga tagttgtcaa tattatgaat   64020
gtaattaaag gatgtttaaa tgcctaatgg gtgaaatcaa ccagggcgca tttatagggt   64080
gaacagagat gactcaggac tgaacgctga ggaaacactg gcaattaagg aacaggagga   64140
agacgaacaa ctctaaagga gatcaagaag tggacagaga tgtaggggaa atactgagca   64200
tgtcatgtcc ttttctttgg aagcccaaag gaaagagtag ttttttaaaat tctttatttt   64260 agacatggtc tggctctgtc attgaggctg gagtgcagtg gcacagtctc agcttctcag   64320
ctcacttcaa cctccacctc ccgggcccaa gcaatcctcc cacctcagtc tcctgagtag   64380
ttgggtctct aggcatgcac caccacaccc agttaatttt tgtattttt gtagagatgg   64440 ggtctctcca tgttgcccag tctagtctca acccctcggc tcaagcagtt ctcccacctc   64500
ggcctcccaa agtactggga ttacaggcat gagccaccag gcctggctgg aaagagtgat   64560
tcaagaatgt caccagtgaa aagtgctcag tagctgtcac acaaggtgcc atctgaaaac   64620
catccgcttg attgagccac agagaggtcc tgggccttgg agagggcaga atctacttca   64680
taagaggttt ctgaatgact gggaggtaga atgtggagag agtgagagaa tagacaggtt   64740
```

```
gaaatgtcta gttgtaaaag agaggaaagg ggtggtagct agttggatca agaaagaggt   64800
aaagacgagg tcaggagatc gagaccatcc tggctaacac agtgaagccc cgtctctaat   64860
aaaaacacaa aaaattagc cgggcatggt ggcacgcacc tgtagtccca gctacttggg    64920
aggctgaggc aggagaactg cgtgaacccg ggaggtggag cttgcagtga gccgagaccg   64980
cgccactgca ctccagcctg ggcgacagag cgagactccg tctgaaaaaa aaaaaaaaa    65040 agaggtgaag agattttgt ttctttttat gatcagagag acttggagct tgtttaaaca    65100
ctggtgggag aaaggcagta gagagggaac aatttcttca gggagtgaag tccctaaacg   65160
atgggctcta gagacaggag gggaagccag gctgggcttc agatagagga gagcagggaa   65220
tgtaaacgtt gagggattgg gacgttttag gacttcagag tgttggtaga ttggggtggt   65280
ggaaagggag gaatggtggc tcctctcagt gttcagagat ttttaaatgg catttttgac   65340
cctggaaata gcttcagata aaaagtagg tagctgtgct gtatagatca gtgggagttg    65400
gggaggaggt ggtgcacctg caagcaggat ctcattgcat ttgaactcta gtctgagcca   65460
ggttgttgat gtgctcagca ttggactctc aggtttcctt aggattgaat cactaattgc   65520
catgaagcag gctctgacca cagtcagcat ctcttactat tcagcattca gagaaaagcc   65580
taaaggcatc tttctattct atatttcact gaaaacattt tccgcactcc catcacgtct   65640
tcttactaat gtaaccctat cgggatgtgt gcaagatctg attttgtcta atgctaacca   65700
tttttcactt catctaaagc cctggactcg tagtaattaa ttactgcttg aaagctgaga   65760
ggtgaggtgg ccctgttccc tttaacagcc cgagggaggg aaggggggtgg agaatgcaat   65820 gaattcttcc tcttctccaa ctctggccct tccttccacc tcagatcatg ttgtcttggg   65880
agactgaatt tcttagggtg ccttagtgaa gatgaaggtg aaaggaatac ccaggaatgg   65940
tgaaaataaa tagaatttaa gataagtcc accatctcca ccatccctgc cccctcccca    66000
acctacagcg ctagccccca tgggaatgtg ctggctcttg gtctgagtcc ctcctgcctc   66060
ctgtggagac agttgtggtg agtggggatt aagagaagtc ttgccctggc ctcctgtttt   66120
ggcacagtgt agattgcacc ctgcttccag ctgttgaggc aagtacaaag gacaagagta   66180 gggggttaggg ccaggaagga aagaatgtaa ctcaatcttt gaagctgaaa tccctaccac   66240
agcctggtct gggaaatgat ctccactgtg taccagtagt tcttggcgct ctcccatatt   66300
gccactcagc tctgcctgtc atggaggta gaggggatgt ttcacctgga atgagtgtta    66360
gggcaccatt tcttcttcac agcaggggag taaattctac agagtagtct agttcctcag   66420
gatggcaccc tgccccctct taagtacgtg gggtcagaga tcagacagtg gaaagtcagg   66480
tgaatttctt accttgcggt gtctcatttt acttattggt aaactgggcc ttgagtctct   66540
gatgagtgat gggtaacttg gtgagaaaag cacagtagaa catgctggag atcctcttg    66600 taggtgggct ttaagaaatg agcctgctag gcacaggcca agagcactgg gcaaacaacc   66660
agattttggg cagaagacag gggttctgct gctcagagtg aacctgcagt tggttccccg   66720
tcggcaagac tggtgtaata gtactcgcct cacaggcttg tcatgaggat gcaattaggt   66780
aatgcatgtg aaagtgcttg gcgcagagct gaatctcaat agtgctgttt ttggatgtgt   66840
cctaaacaga tgtgctgtta agtagctgga agatgtgaag gtctggtagg gactaggcca   66900
tgtggtctta atgccgtgga gaatgatatt gcatgtatgt ttcttcccct ttatatttgg   66960
attatatttg tgttgttacc agagcagttt tcagaccgc tatctaaggt ggagacactt    67020
ccatggtcat ttatttgatc ttgtagaagc gaggctctag aggccatttt tttctaggca   67080
tatacggaaa tgccaccagg tggacctagg ctttgataaa cttctcataa gcatggttaa   67140
```

```
ttgagctaat cattttcatt cactctgatt cacttgtttt tggaatgctt atgtgtttat   67200
acctccattg aaactcaagc ataaaactaa tgcaggaaca gaaaatcaaa tactgcatgt   67260
tctcacttgt aagtgggagc taaatgatga ggacttagga acacaaagaa ggaaacagca   67320
gacactgggg tatacttgag ggtggagggt gggaggaggg agaggagcag aaaagataac   67380
tattgggtac tgggcttaat acctgggtga tgaaatgatc tgtacaacaa accccgtga    67440 cacgagttta cctacataat taataaacct tcacatgtac ccccaaacct aaaataaaag   67500
ttagaaaaaa aaaacctcaa gcataattgt taacatatat gtatcttaaa atagtattct   67560
gttaaagact aacactcccc ttgtggttag ggaggggttg tcaatcattg tatattgtat   67620
attttcttaa tggattttc tgttttaatc ccagaaagtc attggggaga gagcttgggc   67680
tagtggagag tgaggagggt tttgtaggag ttgtggtctg gcagggcctg agagagtgca   67740
tgggtttctt tagaccaggc tattccccgc tccagggtac tttcattctt cttttgttcc   67800
tgtttagggc tggcattaga gcagacaggc attggtgtgc cccactgccc tgaccatgat   67860
ggaagggtga aaacattttc taggaaatta gcccatcagg attacagtaa gcaagaaaca   67920
aattaatgca aaaagtcttc catgaacaaa gtatcagaat ttaaaataaa gacaggatca   67980
gtaactgtgc tgagcccagc catattggag cctgaggcaa aaagaaaaat caatactgaa   68040
atactgatcc tgtctttatt taaaaatttg aaatttgtgg ccgggcacgg tgtctcacgc   68100
ctgtaatcct agcactttgg gtggccaagg cgggtggatc acctgaggtt aagagttcga   68160
gaccagcctg gccagtgtag ccaaatcctg tctctactaa aattacaaaa attagccgac   68220
atgttggcgc gtgcctgtaa tcctggctac ttgggaggct gaggcaggag aatcgcctga   68280
accagtgggc ggaggttgca gtgagccgag attgcgccat tgcactccag cctgggcgac   68340
aagagtgaaa ctctgtctca aaaaaaaaa aaaaaaaaa atttgtttat cttggatttt    68400
atttgcccta atttcaattt taaaaaaata ttgcagtaaa atagtattta tctggactac   68460
tgagattttt tggcacccttt ctaaattttg tgccctagc aagtgcctca ttccccttac    68520
cctagtcctg gccctggttt tataccagag acaaaggaag ttttcccctc acataattca   68580
gttcattgat tggtgctagt gtgctcccgg tccttcttgg agggtcgcct tcttaacaag   68640
cctcaagttt ggaggacagg tttttctaaa aacaaacaac caaaaatgta ttttcataga   68700 aaaaagata atatatggtc attatagaac atagatcatc atccacaagt aaatcagtct   68760
tagaagttgt ttgttttgtt ttagtcacag catttgttg tgtgtgtggt tttttttttt    68820
tttttgtagt cttttttgcta tacgtatttt tatttgtaaa gacagaattt cgccctgtca   68880
cccaggctgg agtgcagtgg cacaatgata gttcaatgta tgaactatgt atgtatcata   68940
gtttaatgta tgatcactgg gctcaagtga tcctcctgtt tcagcctccc gagtagctag   69000
gaccacaagt gtgcaccacc agctattttg tttgtttttg tagagatgag gtcttgctat   69060
gttgcccagc tggtctttaa ctcctggcct caggaaatcc tctcgcctca gcctccagaa   69120
gtactgggat tatgggcatg agccaccatc cccgtcgtgt acatttaatg ttcaatattt   69180
tactagctat agaatgttct ttcgtataaa caaactattt tttttaagc caaatatctc    69240 tctctctctc ttatttttt aaggcaatgg gctcttgcta tgttgcccag gctggagtgc    69300
agtggctatt cacaggtggg atcattgtgc actgcagcct tgaactccct ggctccagcg   69360
atcctcctgc ctcagcctcc caagtagctg ggactacagg catacaccac catgcccagc   69420
cccaatctct ctctctttct cttctctttt ttttttttt ttttttttga gagggagtct     69480
```

| | |
|---|---|
| tactctgtca cctagtctga agtgcagtgg tgtgatctct gctcactgca gcttccgcct | 69540 |
| cccggattca agattcaagc aattctcctg ccccagcctc ccgagtagct gggattacag | 69600 |
| gtgtgcacca ctatacccag ctaattttg tattttagt agagatgggg tttcactgtt | 69660 |
| ggccaggctt gtctccaact cctactcctg acctcaagtg atccacctca gcctcccaaa | 69720 |
| gtgcttggga ttacaggctt gagctaccat gcctggctct aatctctttt cattgggcat | 69780 |
| ttaagtgact tctattttt atgtttatag tttttgtc ttgactttat ttttattt | 69840 |
| attttatt tgagatggag tcttgctctg tcacccaggc tggagtgcag tggcatgatc | 69900 |
| tcagctcact gctctaccct ccaagttcag gcgattctcc tgcctcagcc tcccaagcag | 69960 |
| ctgagattac aagcacccgc aaccacgccc agctaatttt tgtatttta gtagagacgg | 70020 |
| gtttcactat gttggccagg ctggtctcga actcctgacc tcaagtgatc tgcctgcctc | 70080 |
| ggcctcccaa agtgctggga ttacaggtgt gagccaccaa acctggcctg tcttaactat | 70140 |
| ttttgtacat actttgtgga tatttcaggt tatttcctta agatggattc ctagaagtgg | 70200 |
| aatttaggag ttgaaagatc tcttgggttt ttatgcatat tgccacattg ctttccaggc | 70260 |
| acacgccagc caacattcta ccagaggtct ttctgcctca ctgagactac ttgccgatgc | 70320 |
| agcttatgga ttactcagct cccattcctt tccctcttct caatatttt tgacatgtag | 70380 |
| ccttaccact agcattagat acttgggtgg aatgcttctc gtcttccttc caggtcaggt | 70440 |
| gggattccct gttcttcttc agagctactt ttcctccttg ttttagcata tatcttgtct | 70500 |
| aaaccgtgtg acaccttggt ttgtcctggt gccctgtcct ggcttctgaa tgaatgagca | 70560 |
| ctttcctaat taagcttcag atattttttc cttaggcttc tgactgctct gcactgacct | 70620 |
| cgtggcctct ctcttcaacc ctttgttgag gccccaaga ctctggttat ggaagaccca | 70680 |
| ccttcctccc cagcccacat tctgtctctg ttctgttttg cctggtaccc atttattatc | 70740 |
| aatctagttg atgagtttat actcatttgg tttttaggtt gttaatgcta ggtctctgct | 70800 |
| tcagggaagc tgggtttctt tatgttttat ttggagcctg agtcaagtct gatctcagct | 70860 |
| ttgtccaaga gggctgagtc ggccatccct ggagcttact gcatcgctgg agcttccact | 70920 |
| gagagccaga aactgactcc tcagttttgt ttctcttcct attacccagc tctcacttcc | 70980 |
| ttggagtcac taggtttctg tttacccgga ggaatgtctt gacctctcag gtcttttgga | 71040 |
| agcacagtga gaggacgaca gagagatcag tgcctgggca gacttctctc ttgtgcatac | 71100 |
| agcattttca cacagccagg actggggtga gccactcgcc tcaagtgcag aatttaaggg | 71160 |
| gcactcaaga ctcagtaatc aagataaaga atatttgtat gcttttttt tttttttttt | 71220 |
| tttttaaaga cagagtttcg ttttgttgc ccaggctgga gtgcagtggc atgatctcgg | 71280 |
| ctcactgcaa cctcttcctc ccgggttcaa gggattctcc tgcctcagcc tcccgagtag | 71340 |
| ctgggatgac agttgtgtgc caccacacct ggctaatttt tgtatttta gtagagacag | 71400 |
| gggtttctcc atgttggcca ggctggtctc gaattcctca cctcaggtga tctgcccacc | 71460 |
| tcggctggga ttacaggtgt gagccaccat gcctggcctc agtttttaa aaataaaaat | 71520 |
| taatgcaaac aaccatggtg aacaaaatat tagaatttaa aataaagaca ggatcagtaa | 71580 |
| cagtgttgtg ctcagccacc ctgcagccca agaccaagaa aaaatcagta attctgagtc | 71640 |
| tgtccctttg tgctcagggc aagtgcctca ctcccctcac cctagtcctg acctggttt | 71700 |
| cacaccaaag gtggagtaag ttttcccctg atgtaattca gttcatcagt tggtgctggc | 71760 |
| atgctccttg gtccttcttg gaaacttacc ttcttcacag gccttgccag gtttgtctgt | 71820 |
| ggctgggctt ttatttcatc tgatatgaaa gactccagcc tgtgtttcct cccgtttgag | 71880 |

```
ggcttaatcc tcttctctgt gattgctttc tgataatccc aggtgaaaac catcttcaca   71940
acattcccag gtaatgagtg ctctgagtgg cagagatctt ggctcctgtc ctccctaaca   72000
ctgatccgtc agctcaagaa aggtaacagt gcaagccatg taccccctgtc cacttctctg  72060 tgtctgtcct ttcccaaata ggtatttgac catttttctt ccttggtctc agtatactaa   72120
tgcaagtact gttttaatgt aaatctagtc cttatcttaa aaattctaac tcatcaagtg   72180
taatttttag tattatattt taacactctg ttctgggtag tttctattaa agcctgtaat   72240
tgttaaaatt attgaaactc atattattga gctcatatgt tctacagaca tattggtgca   72300
aggtgactta gagtcattgg gtgcaaggaa cagaaattta attcagatta gattaagtaa   72360
aaaggagtgt attggataag tacaagggaa cctcccagaa cccaacagca ggaagtgaag   72420
ctagattttg tgggtgttgg aagttaccag gtctttcttc tgtctgcctc tctgtctgtc   72480
tctctggaac acacatggct gacagtagca gccatcagcc tagtctacat ggttgtgtag   72540
caccatttga ttacagttcc taggtcatca cttcggattc tcaagggaga atgcactcca   72600
ggtgtcctct cctggtccag ttagctgtgg gagggaaaga ggatcacttg acataataca   72660
tctctaatca ttattttagc ataggggtgaa gagtatgata aactaggcca atgtgtttcg   72720
tacaatgaat aaaaataaaa tccttgccct gtgagagaat atagtcctag caagaaagac   72780
tagaatgcat acaagtggga tataatcagg gtaaaaaaat caaggtgggc atgggggtgg   72840
gcattctgtt gggtgaaagt tcacagagaa gtcctggttt gatctacacc aaacttagag   72900
ctgtgagttt accagttaaa gagggggatgg acattccagt acagggtaca tacgaaaaag  72960
cacagaggca tcagagaaca ctggccaggc actctcagga gttcactgtg ggttccagat   73020
tatgattggc cttgtacatc atattaagag atttaatctt gtagatgatc aagagctaga   73080
ggagaattat aagtagggaa gcaacatgat tggatgtgct attaatttgc caaacatcta   73140
ttaatcatct accacgtgct aagcactgta ttagccctga ggattccaag ataaataaga   73200
agctctcctt gctagttttta ttttctttgg tgactcattt ttcaggtgcc ctacctagag  73260
aacagcctag aatgttgttt ttataggttc acagtatcca aaatccttac actggtagga   73320
ataacaagta tcatttctac ggcagaaaag agtggttccc tctttgcctt gtctgtctag   73380
tggagagatt aacacatcca agataatcac aatacattat gataagtgca acaaaataga   73440
gcttcaggcc acatgtatgg taatctgaaa atttgggtga ctggcaggga cagggaggac   73500
tttgcagaag aggtgttatt ttaacaattg taaactcatt ttgtcaagca gaagactgag   73560
acaggatatt ccaggcagag gaaacagcat gtgtgaacct cctgagaata aagcagcaaa   73620
aaggttaaag ttctgaaagt ttgttgggtt gggaggagca gaggtgagga agagggagta   73680
ttgagagatg aggctgagtg aggaaagggc aatattcaaa ttataagggg actgaactg   73740 tcatacattt ttggtgggag tatacaatgg tacaatcacg ttgttggtat aagaaaagct   73800
ctgtcacttt cttataaaat taaacatata cctatccagt gacccagcac ttctactctt   73860
aggtatttac cccagagaaa taaaaatatg gcacaaaaag acttgtacaa cagtgctctt   73920
agagctttct ttataacagc cccaatctga ataacccac gtgtccatcc gtaagggaga    73980
ggacaaacag atttattcaa ataatgaaac actagtcagc aatgaaaatt aacaaactac   74040
taatacattc aacaacataa acaattatga tgagtaaaat atccttacac aaaaaagcac   74100
ataccatatg agtctatttt tctgaagttc taaagtaggc taaactaata atacatgaaa   74160
acaatcagaa cagcggttgc ctatgggagg atttgggtgg gattgtctgg aaaggggcct   74220
```

```
gagggacttt gtgtgagatg gaaagatttt atattttgat gggggtttgg gttacctgag    74280
tgtgttcact taccaaaact catccaatag cacactgaag atttgtacat ttcactgtaa    74340
ataaatttta tttaccctca tccccaaaaa gaatgatgaa ccctgaatac taaagatatg    74400
tatgctgaag tatttagggg gaagtgcact gaggtttgca actgactggg aaatgcatca    74460
aaaatgagat gagttgatgt ttggatagat ggatgataaa cagctgataa aagaagtata    74520
gcaaaatgtt aatacttgta gattctacaa gtggtgggtg tatggatgtt tgcagtttga    74580
tcttttcaac tttactgtat gtttgaaatt tttcataata aaatgggaa acgtataaag     74640 gctcttatat tctgctgcat taaggaattt ggactttcct ctggctcgaa gggactaatg    74700
aatgctttta agaggagtca ttccatacaa gttttagaaa gagactggag gcacagaaac    74760
ttatgactct attttagttt ttcagtaaga aaagaggaag gcctgagcta agggcatca     74820 ggggtgcagt agaagggatg gattctgggt ttggggatag aattcttaag actcagtgaa    74880
atcaacttgg caatggtggg agttggggtg gggaggatat tgtgagctgg tgcccagtcc    74940
tgattgaagg accacgacct aggggctgat ggatgacagt tgtgtggtca gatagcctga    75000
atgtcagagg aaaggcttta acacgaagtt aagttagaat gctctgtaac taatggttgg    75060
gagctaagaa aacgtcagcc tgcttttcag catgagagcc catctttcag aacataggag    75120
ggtcagggca gataggatg acctggaaaa agtagttgtg tctggagacc agttctaagg      75180
aaacctaaag agttgaaaac aagcctgggc aacatagcag gatcctgtct ctacaaaaaa    75240
tttaaaaatt agttgggtgt ggtggcatgc acctctagtc tcagccactt gggaagctga    75300
gctgggagga tcacttgagc ctgagggttc aaggcttcag tgagccatga ttgcaccact    75360
gcactccagt ttgggtaaca gagcgagacc ctgtcttaaa aaaaaaaaa aaaaaaaaa      75420 gttgaaaaca tttatatacc tttgatgcca gtgcgtattc cataacctgg ctactaaact    75480
cacatcatta cactagaaag tgctcaggat tcacagttac ttaacccgat cttcctacaa    75540
aagcagtaag tgtggaaaac tgtgtaagct ttgaagcatg aagttgaact ggaatgttct    75600
cgaattaaca tttgggagct gagagaatgt cagccggaac ttcagctttg ctgagtctcc    75660
cattctcttt tggagaatgt aatccactaa catatggtgt cctggttgaa atgatcagag    75720
ccacagcttg aaggtctgta gcatgggtgg ggactgacac atgtgagcac cgatgctgct    75780
ccctccggct gacctctgct gctctgtttg ctcatcactt actaggagat tgtggccccg    75840
gtggattaga gggatgagca caatttatgc ccaagaggct ctccattcct ttaggcaagg    75900
gatgcttcag gatcgagcat gggggtgttc atttcttttc cctctcaact gaagagcgtt    75960
ttgatttcca gcacaattat tatttttgaa agaagcaata gtgtgtagga caagtattta    76020
ttattgtgac agcagagaga tttctgtgaa gctcccctta aagttccacc ttgagcactt    76080
gccctggggt gaagggttca gtcctgtctc acactgctca gttgtgccag gctgagcagt    76140
gcagggtttt tctaccttt caccaagagg atgttctctt aatatatgtc ccttctagtc      76200
catactagac tctaaccttc tgaaggtctg gtaagggttt ttgttgttgc tgtcattgta    76260
gttttgttgt tttttaaaa ttttttattg gtatcccttta tggtactcag caaacacatt      76320
gtataacaaa cacttgagaa cctgctatgg agcagccact gtgctgggtg acagagatgc    76380
cacagtgaat cagtcatcgt ccctgcccctt gtgcagttta gagtgtacag gggaagaagg    76440
catgcaacca ggaattaccc tataagtatt taattatatt catggtatgt cctggaggga    76500
aagtagaggg tgctgtgtat accaaagaac ttaatcatat gggagtgagg gccagggacc    76560
atcaggaaag gcttagcaag gaagtaacgt ttagcctgaa atctgaagga tgattactag    76620
```

```
gagtggctca ggccaagaat ggggtgaaag ggccaaaggg agaagcatgt gcaaagatcc   76680
ttaggcagat tggagcataa gcaatgctga agaagaaaga aggctcttgt ggctggaaca   76740
gagtgagcac tggaaggtgg aggtgtatga gctaggttgg agagagacca catcactctg   76800
ggaattgcgg gccttggtca gtatttggag ttttattcta agaggggtga gaagccattg   76860
cgaagtttca aatgatatta agttctgatg tctttcagc atatctctct acatttgcca    76920
gatagctaac tctgtggcag cagtacggca aaggtggggg cgggtagctt gtggaaaggc   76980
cctttcttgg ttagccttag ctgatagccc aggcccaatg tgctgtggtt ctaggtgcag   77040
taatcaaaaa gtctctggta tatgtgaacc aacttgattt cttaaactct tcccttttgt   77100
tccaggcaag tattttcct ggaaaattaa ttttgagag gaggagggag actcttgcca     77160 aaccctaaa aagaacctcc tgagctggag atcctcccca atcaatcata acagtcctgg    77220
agagaaagaa ccaatagcca ggccagtgtg ccatgttcag cctgggctgt ggcctcgatt   77280 gggtctgtt gatgtttctg taccacctcc acaaccacca ccgttgcca gtctctgatt     77340 ttgtgcccac agcttgagtg gggagagagg gagttgaaaa cctcaagtca tcccccatct   77400
gggtgttcta tctgctgggg gaaaggactg cttttgacatg ttctccagaa ggagctggca  77460
catgatgatt tttaattgag gcaagtgagg agagattgac attaaaaaaa caaacccaa   77520 gcccccactg aaatcagtgt tgacacatgc tttgcattga ccttttctcc tggaaaaagc   77580
tttgctgtgc tccttgccat ctgttctaga gttttgaaaa cttttgttcc ttccgaagct   77640
tttggcaaag ttgtcttcaa tgtaagttgt ggatgggtgt tgatcagcct cttggggggtc  77700 attccttgtg ggagctcaca gatgctgtgg atagagcacc caagttctca ccatggagag   77760
gacactctcc cacttgaata gtgcacccag gttctcactg tggagaggac actctgccac   77820
ctgaatagtc cacccaagct ctcaccatgg agaggacaca ctcccacctg aacagtgtac   77880
ccgaactctc actgtggaga ggacactctg ccacctgaat agtccaccca agctctcacc   77940
gtggagagga cactctgcca cctgcatagt gtacgcaagc tctcactgtg agaggacac    78000 tctgccacct gaatagtgca cccaggttct aactgtggag aggacactct cccacctgaa   78060
tagtgcaccc aggttcttac cgtggagagg atactctgcc acctgaatgg tacacccaag   78120
ctctcaccat ggagaggaca ctctcccacc tgatcagcta gacaggcaga gctgtgggca   78180
gtccctcttg cctttcactg tgccatttct cttctccctt ccctgggagt ggaggtgttc   78240
ctgcatgatc tgctgctgca gggaggggac ggcagcttga gaggggacac cagttggcac   78300
ccttgcagtc tagccctggt ccggccacta ggtggcagta ctaaggagga tgcttaggct   78360
tttcactgtg ttttagtttc ccagttggtc aagtggaggt tgtagtacat gacctgctga   78420
cttcacaggc ccttgtaaag atggaagcag ggctgtctgg ttcagtccta gcttagaaat   78480
gtgttttcat taaactgcac aaggtttaag agattttaaa agtttgttg cctgatttttt    78540 aaatcaggag ctctcaccta aagatccagc tgttttagc agtcaaaaga cttgacaact    78600
cttagcccac gttccttcgt gacagcaatt ggctggcatt gaggaatggc tgccccatga   78660 gcagggcat gaactttctc agggccaccg gccccactcc tccctgtgat cttcctgaca    78720
gtgagtctgt gtcatcacac accctccata cgttttgtta aagctggact gtgtcactcc   78780
tttatgtgat ctccctggct cttcaggcat ttgggtttgt gctcttgatc tcgagaagat   78840
attccagatt tagaattta tgataagtaa tgtatcatac aaatacaaag tggttttgc     78900 agggaggtgg gggtggaagg gaaaggcagg aacaccttct gtgtgctagg tgctttgctt   78960
```

-continued

```
atcatttgat catccccaaa gctttgaggt aggagtgggg gtggggagga tattgtgagt    79020
tggtgcacag tcctgattga aggactatga cctaggggct ggttgataca atcacgtggt    79080
cagatagcct gcatgtcaga agaagggctt tagcatgaag tgaaagccct tggcaggtaa    79140
gaggacagcc tcagggaaat tgtagcttac ctgagccagg attcgaactt aacctgttgg    79200
gctctaaagg aatactacat gtctcaaggt gaagcgggge atagctcctt ccctaaaagc    79260
tgcctgtaca catctacacc ttcggtaggc atgtaagtga gggctatttg catgacttgt    79320
agtggtgtag tcttttttgtc tttataaaat acttatacct agagctgtag aatatttggg    79380
gggtaaattt ttctctcctt tgtagcagaa ttgctccttt ttttttttct agcctttctc    79440
caaaattaca cagctaaaag tagagctact ttgaaggtga ggaggaagca gtatacagag    79500
ccctacccett gtaagggagg gaggtcagtt tttcctcgtg cagccactga agtaccttct    79560
gtaatcctag ggcttggagg aacccagttt aaatagtagc actcatttag tcttaatttc    79620
ttttcttttc ttttttcttt tttctttttt ttttgagatg gagtctcact ctgtcactca    79680
ggctggagtg cagtggcgtg atctcggctc actgaaacct ccgacccect gattcaagca    79740
attctcctgc ctcagccttc cgagtagctg ggattacagg catgcgccac cacacccagc    79800
taattttttgt attttttagta gagacagggt ttcaccatgt tagctaggac ggtctcaatc    79860
tcctgacctc gtgatccacc tgcctcggcc tcccaaagtg ctgggattac aggcgtgagc    79920
caccgcgcct ggcctaattt agtcttaatt ctgcccatg aggaaatgaa ggccagagag    79980
atccagcaac ttgttcagtg ttcatttacg tctcctggat gaaacccact ttaactgaat    80040
tatctgtctg attccttaga aaagcttcag aacactatta ttttatgctt gttttctgct    80100
ttaagtaagc agcatctgtt gagtttcacc ttattttaaa agagaaacaa agagtttgta    80160
gggcagaaaa ttggaaaacg aagagcagaa aatgggcctg gatgcggttt ttcttcattt    80220
ggtatcctcc agctcttttg gcttgtgtca tcttttccatc tcagacaagt ggacttcatt    80280
cccaaaagtg tatataggac ttatgttagg agtgcagttt cctttttacct gcaagaaata    80340
aacagttggt gatttcagtg cctagaatct aggcctgatt ttaaaatatc cagcaaacct    80400
ctttggcagc aaacccagaa accctgtctc agcaccatga tgggcttctt tgtctcatat    80460
tcctagtcta atcattctca ttatttgccc agctgtttcc catcacttct cagataatca    80520
ctttggtgtg tttctcctct tcctgctcac cttaccttcc cttccctcac ttttccttgc    80580
aaagtggaag tcactggtgt cctgattcat tcagaacagc cctgggact tggcaccctc    80640
taccatgatt cagtgtttga atatagagcc agaagatata ctacttgctt cttcttccaa    80700
agccccattg ctgaattgaa tatcatggtg acgcccccaa ggagagtgtt taaatctttg    80760
tctttattta tttttctaca gacagggagg gtctcgctct gttgctcagg ctggagtgca    80820
gtggtgccat catagttcac tgtagcctca acctcctggg cccaagcaat cctcctgctt    80880
cagcctcccg agtacctaga ctacaggcat gcaccagtgc acctggctaa tttgtctgtt    80940
tatttgtttt gttttttgaga tggagtctcg ctctgtcgcc caggctggag tgcagtggtg    81000
cgatctcagc tcactgcaac ctccgcctcc caggttcaag caattctcct gcctcaggct    81060
tccgagtagc tgggactaca ggcgcacacc accacgcctg gctaattttt gtattttttag    81120
tagagacggg gtttcatcgt gttagccagg atggtcttga tctcctgact tgtgatctg    81180
cccgcctcga cctcccaaaa tgctgggatt acagacatga gccaccgtgt ctggcctgtc    81240
tttgtttttt aaagtctgca agaccatgat ctcatgttga tatcagaagt aaaagagatt    81300
ttagaattta tgtaatacccc tcctctgtgt attgcaaatt ctcactcact gtcttctccc    81360
```

```
agcaaagaac taggcacttc tgtcatcttt gcttatttag caggtagaag tccaagttat    81420
ctcagtaatt tcattggtga ctccatgatc ctatgcttat taaaaccttt tatcaggaaa    81480
gtgatgggaa gctgctaatc ctaggagttt aaatgttgaa ggatctatag ggaagtgcaa    81540
attaaaacca caacaagatg tcactacaca cccactagaa tagctaaaat gaaaaataca    81600
gcaccaagtg ttggtaagga tgtggaacaa acagaactct cgtatgtggc tgctgggagt    81660 gtaaatagc acaaccactg tggagtactg cttggcagtt tcttatacat aaagggaaat     81720
agtcacttgg catatgaccc aacaattcca ttcctgggta catacctagg agaaataatt    81780
atctatgtcc ataaaaaga cttctgtatg aatgtttaat tcataatacc caaaagctag     81840
aaaaaattca catgtccttc aacaggtgaa tgaagaaact aattgtggaa tatgtataca    81900
atggaatact agttgaccaa aaaaacaaaa actacatgga acgatgaaga tgaatctcag    81960
aaatgttatg ctgcgtgaaa gaagccagac caaagcagtg tatactgtag gattccattt    82020
attctagagc aagcaaaact atagggatgg aaagcagatc caaagttatt taatacacgg    82080
ggtggtgagg gaggggaggg gagattgtct gcaaaggtac ctgaagaact atctgcagtg    82140
atggattggc tgtcgccaca gccactcgtg cgggtatata cagttgcgaa aactcatcaa    82200
actgtacacc taaaatgggt ggattgtata atatatgaag ttgatataaa aataaaaatt    82260
tctaaagatg agggatctta tctgaactct gccaccaact agctctgtgc attcttgtga    82320
aaggaactta atctttctgc atgtctttcc tgttgggaaa atgaatatga taggttgctc    82380 gcctaccta ttcagtcatt gtgtgaatac aaatgaaata atttattttg aaatgccttt     82440
aaaataagtc gtatacacat gctgggtggg aggagtattc tgtaaactca tcttgaggga    82500
agaaagataa gaactgtggt gatgaatgtc tgagctaata tttatatata tgttggaatt    82560
catttgcaaa tcatctttta actttgtgga acatgagctg tgtcacttcc ccttcttggc    82620
tttgagtaaa atgaaggtgt tagactagat cagacataga aaactggagg ctcggagatt    82680
atctaaagct tttcagatgt gttttctttg gcctctgtgc tatggtgacc tgaacagcat    82740
taatttaaaa ggtgacttgt tgccagtgtt taaatgtgga gatttcacat acaattttgg    82800
gtttctagct catctttaga aattagcaga tccgacaaaa ccaggtccat attcccacat    82860
ggcaacaatg atctggagtt gcatggtggc catcccatta catgagccat cacattcgtt    82920
tcccatattc tctgctacta tctgtatgta gccttttctg tcttctgtag acaccttaag    82980
tagagagtta gttcattatt gaatgctcac tgtgtgttaa acactatttt atggcatgac    83040
aatccagagg caaaccaaac agacaaaacc tctaaactca tggtgagcta taaatagcca    83100
tccacatctc catcaacaat taggggaga aagaccaaaa atgctatata ttttagggaa     83160
aatgggagaa aacgtgtttt cttctggaca taaaaaaaaa tcctacatat ttaataggca    83220
aagcatgtct gtgtcaaaat tatcctgcct acttcacttg cttgcttcac ataatagatc    83280
atatcctttt tatctttatg attcaataga ttcacagatg agattatctg agtgtttcaa    83340
aaaatgccag taggcagaga gactgacaca ggctactgaa tgttaagatt ttcttacctc    83400
tgtccaaacc attaggtttt tccttttaat ctagatcttg ggatgcaact caggctgaaa    83460
taaacatctc tattgacagt cttctctgtt gacagcctcc ttccgtaata gcctgaaccc    83520
tcttaagctc tggctgagaa tctcatcacc ctgatccgtg tgacagacag ggctgtgcac    83580
gagaagtatc ttgaatggca ctatctcctc tcttctaacc tagtttacat ctccatttgg    83640
ccaactacac agtgatagtg accaacatct ttagactgac aagtcctgtt aggcgtggat    83700
```

```
tttgatctcg tgatttaaat gcttctcatc tgcagataag ccctttata ggcatagatg    83760 cttgacaatg tggcttcatc tgtgttaagt aaagtgattc actgatttgc ttttagattt    83820
atcatggtca taggctttga gaatctgggc tggctcttgt cagccattgt gcttactgga    83880
ttgcatggta ggcgactgac ccatttcttc agtcctggct gtaaaggtca tcttgctacc    83940
tacaaagaaa actacactgc tcccatctgg tggtagttat ctcaaattgc agcatctgaa    84000
agagttgcct tgtccttcag cagtgacagg catcattgaa ctgtaggaaa tacctattcc    84060
caccttttgt ttcacaacat tgtcagctgt ttccttatta cctaaagggt atcacatggt    84120
tttataggaa gagagaacca ccccaccttc tgcccataac tagccatggg actcctaagc    84180
ctctcttggt ttgtctatgc ataaagcaaa acacttggac ttaatactct ctaggagtgc    84240
cactcttgtg aagtctgtag ttccgtgatt ttttaaaaaa ttctaaatat caatgaagtg    84300
aatcctactt atactattta caaaacaatt atgaacatac atagaaattt tgtaatttac    84360
actactattt tcctcaattc tgattaatta taagagaaca tcatggattt ataactttg    84420 gcaggggtg gggggaagaa aagataaata ccactgcatt aaatgcacat ttttattaca    84480
agacattctg ataccctaaa aagcaaaatg taaaaaacat gcattttaga attgaggaga    84540
gagagagtgt gtgtgtgtgt gtgtgtgtgt gtgtgtgtgt gtgagagaga gagagataga    84600
taagacctct aagtgtcaat gctacttttg aaaatggaaa atgttattga gatacaaaga    84660
ttagagagat gacagttaaa attaaagatt atatgataaa ttttagtgtt tatttgaata    84720
ctgaggaaca ttgtaacagg aaatatgcaa acatgcagtc tctggtaaat cattatcaca    84780
gtccacattc ggaactgaag cccattaaat ttctttttac aaaattaggt gtgtatttta    84840
tgaaaacgtg caatagtgct ttatgataaa ggctctttat ggttgcaagg aacaaaaacc    84900
tactcaagct aacttgaaaa gaataactat gtaaagatac agcaggaaat gccatgggca    84960
tcaacagaca ggtactaaag tgccgctgag ccttggggga attagaaggg cataatcagg    85020
acccgaggct ttatttctca gaggcctaag atctctgtaa tggttgttta ttgatctgta    85080
tcaattttgc atgtggctcc taacccagta ctatgtcata accccaattc aaattcccat    85140
actgaagact tacctctgtg ttcacctcta tacaattagt gaccacctct gtgcaagaat    85200
ggcatactga ttttttttgct gaacagagtc aatggacagg atattcaagc taaatgatga    85260
caatgtacaa ggcaggcaga tggactgagc gtccagtgta actgctactt actccaaagc    85320
cttcaacttt gacagctttg cctcactttg tctaactcct gtcaccaatg gcattgaaca    85380
cctcatacag tgcttaggaa gtgaggatga ggttagggtt ctaagaattt ggggaatgct    85440
gtggtgtaac aaatttagag cacttgagaa ttcctgtaga gttatataca ttttttttt    85500 tttttgaga cagggtctct ttcacccagg ctggagttca gtggcgcagt cacagctcac    85560
tgcaacctcc acctcccagg ctcaagccat ccttcccacc tcagccttcc aagtagctgg    85620
gccataggtg tgcgcccacc atgcctcgct aattttgta tttttgtag acacagggtt    85680 tcgccatgtt gccaagggtg gtcctgaact cctgagctca agcgatctgc ctgcttcagc    85740
ctcccaaagt tctgggatta caggcatgag ccaccacacc tggcttatat atttctgtta    85800
atgaattgtg aactgtcttt tagagaaagg tcagtgtgga cattaaaaag tctccccaat    85860
aattgtcata cttgccttgt gtatgctatg tggaatagca cttcttacc cttatcatgt    85920 atcttctcaa cagcccagga ggtagggagg tccggaagaa tctttaggtc tgtttctaga    85980
ttcgaattga gtgataggat gagaagaaaa gaagaggaga ttcttgaaat taattgacaa    86040
ctatttataa tagaaattag tgaaataatt tcctagcctc tctggtatga gggaaagtgt    86100
```

```
gctccactta tgcttttaaa aatgttttg gtttgaatca gatgtctttg agcctctgta  86160
ttcttcagct ggtaattgtt taaaggggaa aataacaccc aatctcacag aactgtgtta  86220
agaattaaac aagagcatca aaatacccaa gacagggctg gtacagtggc tcatgcttgt  86280
aatcccagca ctgtgggagg ccaaggtggg agcccaggag tttgagacta gcctgggcaa  86340
catagcaaaa gcacttctct acaaaaaagt ataaaaatta gccaggagtg gtggtgtaca  86400
cctgtaatcc cagctactcg ggaggctgag gtggggaggat cgattgaacc caggaggtca  86460
aggctgcagt gagcagtgat cacgccactt catgccagtc tgggccacag agggaaaccc  86520
tgtctcaaaa aaaaaaaaa aaaagtacat aggatagtac ttgtaatgta gtactaccca  86580
tttatctgtt tatttgtagg ttatttggaa ataattact attcttttgt tatcctaaga  86640
taggtgtttg ggaacaattt ctctgactct tgccacccac tcccacaagt aatatctcca  86700
agttctgaga atctaagaat gtgttctaca acaggctagc cctaaaggct ggctggcagt  86760
ggcattagta ccattagcag tgacagtggc aacctccagc caccacagtt atgtggctga  86820
cttttttgaac attgactcaa aagagcttgt gtgtgtttct ctcacaggtg gatttgctat  86880
tgtatttctg gtgaggacaa gcaatgggat gaaatgtgcc ttgaaacgca tgtttgtcaa  86940
caatgagcat gatctccagg tgtgcaagag agaaatccag ataatggtaa ggctgcccct  87000
tggacttggg actgtttaaa atggaggcag agattgtacc ctctcataag aaagccaagc  87060
ggggtttgtt cccttccctg agatggtaca gaggcctctg tacaaaatgg gactcaacag  87120
ccatgggata taggacaccg cccttgcctt ggtcactctc agctggaggg cagaggaaaa  87180
agcattttga gagaactgac cagttttag gtcagaaaag tcattttggg cattgggaaa  87240
agcttactta acaacatggt tcccagaaat taactgtgat atttaatcca gaaagcctaa  87300
cttttccaatg agcctcttct tctggtcttg tctctctctc tctctgttac caatcccag  87360
tctcagttca accctcctga gctcttcaaa atcctgtgaa catatcctta tacaacttaa  87420
tattttaca tgtagttctt tcgacctgga atgctttccc ccttttttgg cctggaaacc  87480
tagaccaaaa cctagaaacc tcatatatac tctatgaatc tatttataga agtccaagaa  87540
caggcaacat tatctgtgga gatagaaatc agaacgtggt tattcagggg tgggaagttg  87600
actagaaatg ggtatacggg gactttctag gccgtggaaa tgttctgtgt gttgttttag  87660
atagtggtta cacagggtat atatgtgtca gaactcaatt gaacaccta aaatctgcac  87720
attttgttat gttaattaga cttcaattct taaaacttac tcattttca agatgcagat  87780
ttatatgttt aaagaaagag tccatgctga aatatatatg gaggaaataa tataatgtcc  87840
ttagaacaat gagtgagttt agaagataaa taagattggt caagagttga tggtgatcaa  87900
agcagaatta tgagtatatg ggaatttgtt agagtagcat ctttcttta cctctgtttg  87960
acattataca taatattata cctaataata taataatatg taatattata cataattata  88020
cataagaaac tttgaatata tagccttta ttcctttgtg cttccacagt gcttttgttt  88080
tataccaatt atattgctta acctgttata ttgtaagcag ttctgctatc aggaagtaag  88140
ttatttaaaa tcagaaattg tatgctccaa catactgctt gacatgaagt aaatgcttaa  88200
taaactttgg aagaaattag tatttgaata atggtaatag cagatacata tgttcaccta  88260
gagatgatga ttccttttat gccctggatt ttaatgcttt ttaaagagca gaaagggatc  88320
caacaatgga gagggtggca ttgtaggtat cccatcaggc tccgcttgcc cctgttcacc  88380
ctatgtggcc ttttcagtgg ctgcttagag taactagtta ggctgcagtt ggacttctga  88440
```

```
aagtactcag agtgttagag agcctggcac tactctagat tttagaaagc caaaactatt   88500
tgggaaggaa ctgtcagcac tgcacaacaa accagccaac tcccaagggc catatacata   88560
cagtcaagac cacgtgggcc tgtctgtaag gcaccaatgc cttccactcc cctgcacata   88620
gctccagatt cctgttcttg ctgtatcttc cttcacacac gcagtgggtt ttctggctgc   88680
ttctcattat ttgtcttcct ccctccttgc ccatgcttgt tcagctctca cacgctttgt   88740
ttcctgtctt tgcttctgct gtttcctcta tctggaatgc ccttcttgct catttacttg   88800
tgttacaaaa gcaatcccat gatttcactt tctcctcctt atttaaaaac acactgagag   88860
cttacttggg ctaggcaggc attgtagtgg aggaactaag aagcacaggc ccatgaggag   88920
ctcacaaatt aatgggcctg attaagagtt aaatcacaca ggttcaagtt ttggcccaga   88980
ggcgtattag ctgtgagagt tttgtttta gtttatattc tttcaaagct ttaatattca    89040
aataggtgaa ctaagcttgt tacaaaaaac gtcaagcaat tccccaaggg gaactcctat   89100
gccattacaa ggtcccagcg gcaacctctt taggtgattc ttttgatgtc tttctaaata   89160
acatgctaat attgctagtt cttgattttt cttccatttt aggcattatc tcctatggga   89220
agtaaagacg taactgtcac ttacttgctg cttgcctctc tccccaaata cttgcagtat   89280
tctcatcttc cattctttga aaacaccagt aaactttggc aatatgtagt ttatatgaat   89340
attagttttt acattattat ataagaaaac tatttcaact gaattcctgg tggactatga   89400
ttcctatgcc tttcctatgt aactttgctt tcactaaaat tattaatggt cttgtttttc   89460
ctctcttggt ctgagttttc tttgtacttt ttaacagttt aattcccaat tttccttaag   89520
ttgtgtaaac cattttttga atttttaga cgcatttaat ggtgtctgtt ttatcatctt    89580
caagatttct ccctcagtct tctgactgag gaacctcggc tgattattct ctgactaatt   89640
tacagtcgaa tcttggaatt tcctggacat ttcctttgcc tctctttttt gttagaaccc   89700
gtaattcctt ttttggctaa cttcctcatt ttgttggagc cgatcctcca gtatcttttt   89760
tttttctct tttgagatgg ggtctcagtt acccaagctg gagcgtagtg gcacaatcat    89820
agctcactgc agccgccatc tcctggtctc aagcaattct cctacctcag cttccccact   89880
agctgggact ataggcacat gccaccagac ccagctattt tttttttttt tccttagaga   89940
caaggtcttg ctatgttgcc caggctggtc tcacactctt gagctcaagt gatcctccca   90000
tctcagcctc ccaaagtgct gggattacag gcatgagcca ctatgcccag cctcagtagc   90060
tttttgatac atggtagata aattttttg aactttcagg tctaggccgg gcacggtggc    90120
tcatgcccgt aatcccagca ctttgggcgg ccaaggtggg cagatcacga ggtcaggaga   90180
tggagaccat cctggccaac atggtggaaa cccttgtcta ctaaaaatac aaaaattagc   90240
tgggcatggc agtgcgtgcc tgtaatccca gctattcagg aagctgaggc aggagaatcg   90300
cttgaaccca gaaggcggag gttacagtga gccaacatca cgccactaca ctccagcctg   90360
gtgacagagc tagactccgt ctcaaaaaaa aaaaaaaaaa aaaaaaaaca actttcaatt   90420
ctagaagtat ctttattta tgttcgcaca tcatagtttg agtacagaat tctgagttgg    90480
aaatcatttc atttagattt tttaaagcac cgttctacta tattttagct ttcagtgttg   90540
ctcttgggaa atcctaagtc attctaatgc ctagtccgtt gggagtgacc catatattct   90600
accaggaaat ttacaaattt tctctttgtt tctaatgttc tgaaatttca tgatatgcct   90660
ttgtgtatgc atttatttat tatgttaggt gtttgtggtc cctttcaatc tagaaactca   90720
tatccttgca ttctggggga ttttttagtt tcattttttt ccccttttc tgaaatttct    90780
ataatttgga tattggttct cctgaattga ttttctaatt ttcttgtttt ctcccttctt   90840
```

```
tttatatttc tttgtcattt tgctccacat tccagatttc ctcacctcta tattccaacc   90900
atcctgatga aatttattta ccagactttt aaatctctaa gatctttttt gttttgtttt   90960 tattttaat ttcgatgagt ccagtttatc aattgttctt tttatggatt gtgcgtttgg   91020
tgtcaaacct aagaaatctt tgcctagctc tcaattctga agattttctt ttaagttta    91080 tagtcttaca tttaaaccta tgagccattt tgagttttt ttttctttt ttgagacgga     91140 gtcttcttgc tctgttgcct aggctggagt gcagtggtgc aatcccggct cactgcaatc   91200
tctgcctccc aggttcaggt aattctcctg cctcagcctc ccgagtagct gggagtacag   91260
gtacgcgcca ccatgcccag ttatttttgt attttagta gagatggggt ttcaccatgt    91320
tggccaggct ggtcctcaac tcctgaccca agtgatttgc ctgcctcagc ctcccaaagt   91380
gctgggatta caggcttgag ccactgcagc tagccatttt gacttaattt ttgcataatg   91440
agtcttaggt tgcggttcat tttttcctta tggatatcta attgctctta gtaccattta   91500
ttgaaaaggc tgtcatttaa tatcttggtt aaaaatcagt tgaacttaat tgtgaaggtc   91560
catttgcagg ccttttctcta ttctctattc ccttccatta atctatgtac ctatccttct  91620
accaatacca cacagccttg attactgtag ctaaataagt tttaaaatgg actgaatttt   91680
cccacttttt ttttaatttc ttactgtttt aaatctgaag tcctatgtaa cattttaag    91740 cccactaagt ctcagacttc tgtcagatag aagccataac cccagcccta cctctctcag   91800
tgactctaag aattgtgaag ggaatcagaa gatgtaacat gctgtgtaat atgctgaggt   91860
ttgggtgttc atactcaaag aagcagattc ctctctactt ccagtggcag aacaacgggc   91920
acgttgcatc caaacgcaaa gagaactgtt agcggtttca ctgagtggtt tcacgtttta   91980
ttttgataaa tgctgtccac catgtactgg agtcttgtct gagttctttg atccatatgg   92040
gatgtgtgct ctgatagagt cgaagggatc tgacttctga tggacatttg gagggtaggt   92100
tttggacttc tgatcccttt gcctgaaagc aggaaaagat taattatctt cagacctaaa   92160
ggggtaagaa cagtgatagg aaatagctac agctccagat gtgtcaaggc tattctgtgt   92220
tcacatcccc tggcccagat ggattacatc ctcattgagc ttgataatga ggacagtaag   92280
ctgccaccag tgatgtttga ggatttgctt cgaagagatc agatgattca aagcaggcaa   92340
atggtttctt attctacaaa gggtggaaga tagatcctgt acagtaggaa gctcaggatt   92400
gttctgggac aagaatctgg aacagattat tttatttttt tcttcaactt ttaagttcca   92460
gggtacatgt acaggatgtg caggtttgtt acataggtaa atgtgtgcca tggtggtttg   92520
ctgcacataa caacccatca cctaggtatt aagcccagca tccattagct attcttcctg   92580
atgctctctc tccctccacc accccaccg gccccagtgt gtgtcgttac ccgctatgtg    92640
tccatgtgtt ctcatcattt agctcccatt tataagtgag aacacagatt attttcaaag   92700
atgctttgat tatatctttt gtgtaagaaa gttggggtgt gtgtgtgtgt gtgtgtatac   92760
ataatacata attgtttgaa tttgcctgaa aaaaaacac aggaagcatg aaagaaagaa    92820
acaataaatg tggttcacta tagggggtgg ggattggagt aggaaaaaaa ttgtctagta   92880
ttatgaacta tttgaatgtt aatatattac acactttaaa aatgaatgac ggctgggcac   92940
tgtggctcac gcctataatc tcaacacttt gggaggccga ggagggtgga tcatttgagg   93000
tcaggagttt gagaccagcc tgtccaaaat ggccaaaccc tgtctctact aaaagtacaa   93060
aaattagccg ggcgtgattg tgtacacatg taatcccagc tactcaggag gctgaggcaa   93120
gagaatcact tgagccgggg aggtgcgggt tgcagtgagc caagattgtg ccactgcatt   93180
```

```
ccagactggg cgacagaaca agattctgtc taaataaata aataaaaatt ttaaaataga    93240
aaaaaaaaag aggccgggca cgcagtggct cacgtctata ctcccagcac tttgggcggt    93300
cggatcatga ggtcaagaga tgagaccatc ctggccaaca tggtgaaacc ccatctctac    93360
taaaaataca aaaattagct gagcatggtg gtgcacgcct gtaatcccag ctacttggga    93420
ggctgaggca ggagaatcgc ttgaggctgg gaggcagagg gtgcagtgag ctgagattgc    93480
gccactgcac tccagcctgg tgacagagca aaataccatc tcagaaaaaa aaatgacatt    93540
ttaagctgtt ttatagttac ttggatgagt aagcagaggt ccagagagcc ttcaggttca    93600
ataagaacaa accatgtcat aacaacatcc tgttctcctt tgggaagatg tctggataga    93660
gagctcagtg cggtgcagta gatccagtat ctgtggactt tggccaggtg ttttgataag    93720
gacactcacc agacatctgt cagcaaaacg aagagtctag gctggattgc tactggttat    93780
aaaggtttct gataagtggt ttgatattaa tctggaggaa actttctaaa aagaaagcat    93840
tgtggcttac cattaatttt atgttatttt acatttaaca aataactcgt ttaaagaaat    93900
agaagataca ttgatcaatt atgtgccttt ataaagttgg aagatgtagt aactgcattg    93960
agtcatagaa tcaggctcca aaatggttct tataaattgg agcagtggac tgattctaat    94020
gaaatgaaat aataaggtaa gatcatacac ttgaaatttt attctaatca actttacaag    94080
catagttctt gggaggcaga gattaaaagc agcatgagtg gaaaagactt aggtatttaa    94140
gtggtcagtt aattcagaat gcatgtatag tatgatgtgg gtgccaaaag acaaaaagaa    94200
tgtaatgttt agctgcatta atagaattat agaaggtgat agtgctggtc tactctgcat    94260
gagtcagacc aagcctggag tatttcattc atttcctggg gccattctta taaaagaat    94320
gtagcagagc aaagcatata aatgtaggag cagccaaaat ggtcttaaaa accatgtcag    94380
agaaagaggg gatgtttcac atggagaaaa gaacactcag tctaaataat gctatttcac    94440
ctgtttatta tattttactt tttatttatt tattttgag actgagtctc actctgtcac    94500
ccaggctgga gtgcagtggc ataatctcgg ctcactgcaa cctccacctc ctgggttcaa    94560
gcaattctcc tgtctcggcc tcccgagtag ctgggactac aggcgcatgc caccacgcct    94620
ggctaatttt tgtgttttta gtagagacgc ggtttcacca tgttggtcag gctggtctcg    94680
aactcctgac ctcaggtaat ccacccacct tggcctccca aagtgctggg attacaggcg    94740
tgagccaccg agcccagcct tacctgttta gaaagtggaa aaatagacta gacttgctaa    94800
ttttgctctg gaaaggacca tctagaaaat caggaggtgg aagattccag ataggtaagg    94860
aagaactgtc taacgggtga gggctgtctg tagattggct gagggcctaa ggaagtggca    94920
ttattctaac aaaacagctt gttggccggg tgtggtggct cacgcttgta gtaccagcac    94980
tttgggaggc caaggcaggt ggatcacgag gtcaagagat cgagaccatc ctggccaaga    95040
tggtgaaacc ctgtttctac taaaaataca aaaattagct gggtgtggtg gtgcatgcct    95100
gtagtcccag ctactgggga ggctgaggca ggagaatcac ttgaacccag gaggcagagc    95160
ttgcagtgag ccaagattgt gccactgcac tccagcctgg tgacagagca agactgtctc    95220
aaaagaaaag aaggaaggaa ggaagggaa gaaaagaga gagagagaga aagaaagaaa    95280
gaaaagaaag aaagaggaag gaaggaagag agagagaaag aaggaaggaa gaaagagaga    95340
aaggaaggag agagaaagaa aaagaaagga aaaagaaag aaaaagaagg aaagatagaa    95400
aaacaaaga aaacgaaaga aaagaaaaga aggaaagctt gtcagaaggc tgtagtgggg    95460
attcagatat gggctgcctg gttgctctag atcagtgtta ctcaaaggat cttttttcct    95520
tatgcttttc tcctcctgtg tgttgactta caaaaaatct attttcctcc cagtctgtca    95580
```

```
tgttactttt gtgtgtatac aaattgagat aaaatttacc cttttaaagc atacggtcca   95640
gtgattttta gtatattcac aaggttgtgc aaccatcacc actatctaat tttagaacac   95700
ttttttctta tcccctgaag gaaacttcca gcctgttagc agtctttcct tattccccct   95760
ctccacagcc cctgataacc actcatgttt ttactgcata ttctagatat ttcatataaa   95820
ttgactcata caatatttga cctcttgtgt ctgttttcac ttagcatatt gttgttaagg   95880
ttcatcctta aaaacatgtc cttgatacat gtcatagcat gtatcaatat ttcattccat   95940
tgtgtggctt gtgatattct gttgtatgaa tgtaccacat tttatttatt catttatcag   96000
ttgatggaat tgggttattt tcacattttg gctattgtga ataatgttgc tatgaacatt   96060
tgtgtagaaa tttttgtgtg cctataatat tttcacatct cttgggtgaa attgctaggt   96120
catatgataa cttgactttt tgaggaactg tcagactgtt ttggtagctg catcatttta   96180
tatttctact agtaatatac aaggattcca attttcacct ccttgccaat attttttatt   96240
atttgttttt tattatagcc atcttagtgg gtgtgaaatg gtatttcact gtgatttttt   96300
atttatattt ccctaatgat tgattatgct gatcatcttt tcatatactt tcgggcattt   96360
gtatatgctc tttggaaaaa tatctattca gatccttttgc taattttac ataggttgt    96420 cttttttgtt gttgttgagt tgtaagggtt cttcacatat tctggacact aaatccttat   96480
cagatgtatg atttgtaaat attttcttcc attccatatg ttgtttttag actgtcttaa   96540
tagtgccatt tgaaacacaa gttttaatt tcaataaagt gcaatttatc gcttttttgct   96600 tgattgcttg agctttaagt gtcatatcta agaacccatt gcctcatcta aagtcacaaa   96660
gatttgcacg tatgttttct ttgagggatt tttagttctt tgatccattt tgagttaatg   96720
tttgtatatg gtgtgaggta gggatccaaa taattcccac ttgtcccagc actacttta   96780 aaaaagacca ttttcaccc attgaattgt cttggcaccc ttgtcaaaaa tcagttgagt   96840
ataaatgtac tgatgccact caaaggatct tgtgccataa tataaatcaa tgaactgctt   96900
ccctcacagg taagatcttg ctgggggag aaaagagagc ttagtgattt gattgattta    96960
tgtgctggag caagctcctt atttccttac cttctggtaa tagtttatta accagcagat   97020
gttaaccagt aacatctgct ggtaatagtt ttattaacca gcagatgagg gctctgccct   97080
catgacttaa tcacctccta aaggccccac ctcttaatac gattgcattg gggatttaag   97140
ttttaacatg aattttggag gggacacaag ccttcaaacc atagcatggt tctaccaata   97200
ttttgttgct ttttccaga tgctttatta ttcctcttag gatgagacca actcagaggc    97260
aacattgctg attcttttc aaatagttaa atgtagggat atgagtcttt cattcatctt    97320
tgaatatttg gaggatatga tccttatttt ggtttcaaag aacttctctc cagttcttcc   97380
tactttcagg aatgtgtaaa tggaaatgag ttctagatgg gttgatgatg agatgggaaa   97440
gcagagggaa ggataggcca ctaaaatgtg agtcccaaaa tcatttctg tttgggaaaa     97500 acttgaatta tagagattgt gtgtcagctt catcatctcc cttatgtatt atccaaagca   97560
gatgcagtaa gtcttttgtc tcatcaaact tctttgtcat tcctatacat ttaggaaatg   97620
accttgttct ctaccaaaaa taaaacaaca gatacgaact catttgagtt ctctttttct   97680
tccgccttaa accagcatgc acagccatcc ttgcctcctt cctgcttgcc aggggaaaa    97740 aaaaaaagtt accctaagac cagtcccttg aacagtactc ttaatcccac ccttctactt   97800
ataggacttt ttccgtcaat tatcatcatc ctgtcctgta tcttaaagct ctcttctctt   97860
ggctccttcc tctttctggt gctcagtttt ctcccattct aaacacccttt tcccctcaat   97920
```

```
gctgctgcct taggcacaaa tgttctgcaa gagtaatctg tagaccctgg ccctacttgc   97980
tcaactctca ttcattgcaa gtccagtttc attctcacca ccatcccatc tgttctgtga   98040
aactactctc acgtaagtct ccagtgactt ccatctgcca attccaaagc ctttctactt   98100
ttgtctgaac ttttgttgca gctgccattt ctgaggcaat agtcattcac aatccatcac   98160
tcagaggaag actctaatga gttttaactt tgatgcccag ggttcaggtg tattcacttc   98220
ataccatggg gttttctctt gttttgttat gaaatttgtt tttcactgta aacagctgaa   98280
tctaattaga gtggtggtag tttctgttct cacggtccaa actgctaagt tgtatggtg    98340 actctcaggg gaccacatgt tttccttccc cctgaccttt tgaaacaaa atcagacaa     98400 tttattaaaa ctagtttaaa aaataaaacc ttaccttgca tttgtgcaaa aatcatatca   98460
cccagcttgc cttcttttc tttcctcaac ttacttctta attacttggt tttgaatatc    98520
atcattacaa agagctgcct ctctggagat gtttaaagga ctataccaaa atgtgaggcc   98580
acttccagtt cctagatggg tcctgacaca taggaggtgc tcaacaaatg ttggttggat  98640
gaatgaattc atccaagcag ccctaagaga tcacatgcag ttccaactga agagctgaa   98700 acatgcccat cttatatccc agttggttgg cttgaaaggc ctgattatga acaaaatgct  98760
taggtctgga tgctattgta gtcccttcaa gactttgtaa atagcttttt ttttttttggt 98820 agatttccca aaaggaaaaa aacagtacga actatttaaa agtcaagtta aattcatttt   98880 tgccctaca accaggaaaa acatcaattt tattttcttt aattagaagt tcacatattt    98940
aagtagttca cacggtctct ctactcttta ccccctgcag tgtttctgga gaggggagtc  99000
tttgcttcta gtttacgtgg agcattgatg cagtaagcaa gtaggcactc tgtgcatttg   99060
actctagaat ttaggttctg gagtgtgctc tggtttagta gggttatgga attgctattg   99120
aagatctagc agtgaatctc agggaccact ggaaacctgt tcttgacttt gctccttagt   99180
cttctctgtc aacactgtat catctctgta tttaaattat ctgtgctaat ggaactgact  99240
ggctaattct gtcctattgg catctgaaac taacaatata tttctcctct cttgttcaca  99300
gagggatctt tcagggcaca agaatattgt gggttacatt gattctagta tcaacaacgt  99360
gagtagcggt gatgtatggg aagtgctcat tctgatggac ttttgtagag gtatgtatat  99420
gaaccattcc cttaagctgt catttctcta gcattttgat tgtcatggtt agggtggtca  99480
tttcacttaa tgtgcactgc actctatgat atgttctggt ttgacagatg agaaaactaa  99540
aagatacagt ctgctgtcaa ctcttagtta ttcttataac ggtacaaacg tagataatat  99600
agaactccat ttttgttagg tttgggaagg tttggtgttt gtatataaat gaagatgtgt  99660
aagaatgaga atgaatatgt tctttgtgat gctttataac aaatgatgaa ggcacataat  99720
aaaggctgaa ctccagatgg atgaaagaaa cagtgcagct tccccaactc cctcacttgt  99780
gtgttctctt tcccactcat gccatcattc atgtgttacg gggtaaaagc atccttttg   99840 tctaatggaa gtgaccctcc tgtccctact ctaaggctat aattcctagt aaggtgaggc  99900
tatattcaaa tgatgcagct gttaacagtg gagtaaagtc attgaaagct tcaagtttca  99960
aaaaaacatt tatcttggga aattcagact gtagcatgaa tttttttcag agttaattgc 100020 atttatata accattgttt ggaggtttgg cttaggtcag tgccttactg tttggtgctg  100080
tgttttgtaa tcacccttag ttccattaac attttcctta cgcttaagat actatccata 100140
ggccgggcgc ggtggctcat gcctgtaatc ccagcacttt gggaggccaa ggcgggtgga 100200
tcatgaggtc aagagatcga gactatcttg gttaacatgg taaaaccccta tttctactaa 100260 aaatacaaaa attagctggg catggtggtg cgcacctgta atcccagcta ctcgggaggc 100320
```

```
tgaggcagca gaatcacttg aacccaggag gtggaggttg cagtgagctg agatcacgcc   100380
actacactct agcctggcaa cagagtgaga ctctgtctca aaaaaagaa gatactatcc    100440 ataaattaaa tatgttgcta atcccaaaaa tgtgatgtta accagtaatt ttagcccta    100500 ctgtattaac tatttacctg atttcctaaa gtactaacaa atttgaactt gaccgtttgt   100560
ttcctcctgc tcatttcctt tttggatact aaaatgttta gagatcaggc agtaggagca   100620
tccaggcatc tggataatgt tgtaagtgag gtcatcaatc ttttggtcct ggagattaat   100680
tgttggtggt accatttctg caagccaagc agtaagcagt gaagccagag agactaagct   100740
gttcttgaag ttcaaagtat aaaaccatct tcttcctgct ccctggacct attgtgccat   100800
ctgattctta ctaaaagata tggcaagttg aggctgtggc catgtctcat acacaacgaa   100860
cacaatataa ccaggcaact aaagcaggac catattgtca gttctactaa cctcgaagac   100920
ataatgaggg cagctcacat ctggggtgct ttataaaata aagaaactgt ttttgatgca   100980
ttagaggaga cactgaatta taagaaaaca aatcccaagc tgggagtcaa gacaactagg   101040
ttttaatcct ggctcagtca gtggtcagct ctgttacctt agtccagact gcttctcttt   101100
ggacgccgtt cattctctta gactaaatga caagtccgaa tgtttataac gtctcctttg   101160
ccctgtacgt acccctcag gtggccaggt ggtaaacctg atgaaccagc gcctgcaaac    101220
aggctttaca gagaatgaag tgctccagat attttgtgat acctgtgaag ctgttgcccg   101280
cctgcatcag tgcaaaactc ctattatcca ccgggacctg aaggtacaga ccacactctt   101340
tcattacggg cattctactc aatatttct gtctgcccca gggatggagt agatactgtg    101400
gggatatgag agaaatttaa gatatggtcc ctgttttat gtttatattc tgcctgagga    101460
gagaaaataa caaggaaaaa agtacagtac aggtgtaagt tttattactt aagcagcctc   101520
cagaaattct ttataattat cacatgcctg agcctgtgtt gttttgttt ttcctgatat    101580 actccccca ctttttcagg attgtgaaaa gtaatacttt taatttaaat acttagtaaa    101640
caatgatgct tggttttaa agtcttattt catattttgc aaaatcaact aattgatttt    101700
ttttaattgt cctaattgcc atcaccttgc actgtgcctt tcatattgta gtcacttgac   101760
agtgtttgtt gaatggaatt ggcaccttgt tagggttcaa cttagcatgt attgggcacc   101820
aattacgtgc catgtactct actacgttt atgtacagtg tctcttcagg gggagacatt    101880
ctttgttacg ttttatagtt gaggaaacta agaagcagag aggttatgtg acttgcctaa   101940
agtcatataa ctaggaagga cagtgccaga atttgaatcc agccttcaga ttctaaatta   102000
caatttcttt tcattctacc gtgtttcagg aaacatgctt catagctaat aacttgaatc   102060
agcatcccct agcatgcttg ttaaatgcag gctggtaggt tccacactga atctcttggg   102120
ccaaaatttt ggtagtgaca tcagggaagc ccaagaagcc atatcttaat aagaacactg   102180
ggtggttttt gtatactcta aaggttttgg gataaagcag catacctgca tttcttttat   102240
ttcttaactt tttaaaaaaa attgagacat aattcacata ctataaaatt tactgcttta   102300
aagtatataa ttcaggccag gcgtggtggc tcatgcctat aatcccagca cttcaggagg   102360
ccaaggcggg cagatcactt gagatcagga gtatgagacc agcctggcca acatggcgaa   102420
accacgtctc tactaaaaat acaaaaaatt agccgggtgt agtagcgcat gcctatagtc   102480
ccaggtactc aggaggcgga ggcatgagaa tcacttgcac ctgggaggca ggggttgcag   102540
tgagtggaga tcacgccact gcactccagc ctgagcaaca gagcgagact ctgcctcaaa   102600 aaaaaaaaa aaaaaaaga agtataaaat tcagcagttt ctagtatact tacaaagttg    102660
```

```
tgtaaccatc gctactatct aattccagaa catttcatca tccccaaaag aaaccctgta  102720
tccattagca gtccctattc tgtctcccct ttccctctct cctggcaacc cctaatctac  102780
tttctgtctc tgtattttca tgttctgaac atttcatata aatggaatca tcatatgtga  102840 cccctttctgt ctgacttttt cacttagcac aatgtttttca aggttcgtca atgttatagt  102900
atgtatcagt acttcatttt catagtttca taatattctg ttgtatggat gtaccacatt  102960
ttgtttatcc attcattcac tgatgaacat tcgagttgtt ttcactttttt ggctattatg  103020 aataataaca ctgctatgaa cattcatgta ccagttttttg tgtggacata tgttttgaat  103080
tcttataggt ctatacctag gggtagattg tggggtcata tagtagctct gtgtttaact  103140
ttttgaggac ccttcaaact gttttccaaa gtagtcacac tattttacgt ccatcggcaa  103200
tacgtgaagg ttccagtttc tccacatctt taccaacact tgttattgac ctttttttgtt  103260 ttagccatcc tagtgggtat gaagtggtac atcctggcat ttctatatta aggcagttag  103320
cttacaggag aatgagtata tacctcccaa aggcttagat agctttctgt agtgtacctc  103380
tgcgcacagt cagccctttt tttctaagta gaaatagagg aatgtggccg ggcgtggtgg  103440
ctcatgccta taatcccagc actttgggag gctgaggcgg gtggatcacc tgtggtcagg  103500
agttcgagac cagcctggcc aacatggtga accccatttt ctactaaata caaaaaatta  103560
gctgggtgtg gtggctggca cctgtaatcc cagctactta gcggctgag gcaggagaac  103620 tgcttgaacc caggaggcgg aggttgcagt gagccgagat tgtgccacta cactccagcc  103680
tgggtgacag agcaagactc tgtctcaaaa aaaaaaaaa aaaggcaag tggggcaggg  103740 aatgcatgtt gttgaatatt tattataagc ttagcatagc acaagtacat aattctgtgg  103800
ggatgggaca aatataacat tgttcctacc ctcaagatat tcaaagtatt gttggtaaga  103860
agataccaat gaaatattta gacttgaaac agaaatagat gaaatataaa actctataga  103920
agaaaatgat gaatagaaga taatcaaggg gtttaatgta tggccagata gtgagatcag  103980
gcagtgatga ttgaatttttt ctggaaaagt gggattttga aggcctgata ggaagtaagt  104040
ggtcacagag aggatgaaga acattctggg tagagagtag agccagaggg ctccctgcag  104100
aagggaacag caaggtgtgt ggggatgaga aggtgggtca gagctccagt gtgtggccag  104160
ttgcagacca ggctagagtg accacaggca ttgctctgaa tatgtattga cactactcct  104220
agttgccttt aacaatgagt aaaattttttg tttaaatcct gttagcatgt atttcagaac  104280
aggcagtggt accaaaactt aaggacctga cccctggcct tgctgcctgc cttggagaag  104340
agtgtgagag gcatagaaat aggggagaaa tgtggctggt gggcaccgct cttatgatcc  104400
atgtgacctt ttgcctctct gtagccccg ttctgcaccc cttccatgtc aaatggggtt  104460
agagttcatc ctgtgaactc tgactctgca ccaccgtgtg actcatactg acggaattac  104520
aagtgctgtg agaggtgagc ataggcagct tcctccgtat tgccaaatgc agagaacatt  104580
ttccagtccc tgtcttattc cccctgtggc ttctggctcc tttgtgactg tctctccctt  104640
gacctctatg atggtgtctt ctcccagct cctcctttcc aggctccttg gctttcttct  104700
caaatcacta gcctctccga gcctgagttt catcatctgt aaagtggagc taacagtgcc  104760
tgctctgtta gggtggtggt gaggttgaat gaggagtgc ttgtcaatct ctaggcgcac  104820
atccctggca tggtaaatgc ctgaaagggc tcagaggtga ggacaaggga aagagcagag  104880
ggacacagag gatcctttta gaaagtaata ttcccatgtt ctcagagtct tcctttatat  104940
taactttgtt ttttgttttt ttttgagatg aagtcttgct ctcttgccca ggctgtagtg  105000
cagtggcaca atctcagctc actacagctg tcacttcctg ggttcaaacg attctcatgc  105060
```

```
ctcagcctcc cgagtagctg ggattactgg tgcccgccac cacgcgtggc taattttttgt    105120
atttttagta gagacggggt ttcaccatgt tagcaagact ggtcttgaac tcttgacctc    105180
aagtgatccg cctgccttgg cctcccaaag tgctgggatt ataggcatgg gccaccatgc    105240
ccagccctct ttatattgat tttaaacac ttactggatt aaatgaagcc tgaatgatag    105300
tcatgtcata ccagtaaata acacctgtcc agcttacgta gttaccagga tagcactgcc    105360
tggtgacatt ccctgtgcta cagtgaggtg ctgggtcagc atcacccagt gatgggccc    105420
tggagacaga gctcagtgtc ttgcctggga tgctgagtag gtcggtggga gggctaaggc    105480
agcgggcccc agcctcttcc ttcactgcac tgaacagccc acaagatgtt tcagcagggg    105540
aatgcggagc aaactggaat gaaaggctag agtgaggtta ccagacttca tttccccagc    105600
cagccctcag tgctttaccc cttgcacctc agtgctccta agacggaggc agcgcaatgc    105660
tggacacaca gtagttggcc ttctgcatct gatgttccac atctgcagat tcaaccatct    105720
gtaggtggag aatacacaca gttgtccccc cttatcagtg ggttttgatg catggttggt    105780
tgcatggagg gagacgtgaa acctgcagat aaggagagct gattgtattg gactctgtgg    105840
ttgtgttttc atcaatattg aagatcatca ggcatgctgc caatttgttc actgtggttc    105900
aggagactct ttctccttta ccttggatat agggaccatg ggaagaggcc tggattgtga    105960
ttgttgcaga gaagtcctgg tcgctgttgt ttttagtcat tgactcccca gatcttacac    106020
tcgatgccat ctagatgctt tcattagcac gttagatttt attgctgtct gctagtatgt    106080
ccgcgctggg cagttacagt tgtctgcgca tctgcagctt ccccaagtgc tcctgttcac    106140
cctggctctg tcgttgcatc acatagtctc agcgactctg agctccatgt cactgtgaga    106200
accagccacc acagtcctag cagtagtcag ggccaaagag ttctctattt tcctgttttc    106260
cagagaaaat gctagttgct tctctgtgag caggatttcc attcggtgag aaggtgccac    106320
tgtgaataaa agttaatagg atgagggaaa gagcacgggc caggcctact tcgggccttg    106380
tggagccagc gccactctgc ctgtgggtct gctggttcac atgcagaact gaggaaaccc    106440
cccttgccct ccctactgcc tgtgcagcct ttctttccag tgacagagga ataaactga    106500
aagtggtccc tgtccttaag cagcttatgt tctaaaaata accatagcag aagtgctgtt    106560
ctatattgaa gatctctcct ctaatacatt attttaacac tttaatcatt ttccccattt    106620
taaattttca tttctctgag aaagataaag atcagtattg cagatcatgg tgttgtggat    106680
ctgggaaggt cacctaagcc agccctcttc tttaccagtg aggaaacctc cgcacagaaa    106740
ggctgtgacc tgcacaggta gttgagtgat caaaccagaa cggagaccac ggttttttcac   106800
tcccgttttta ttctgttgta ttataccatg ctatttgtcc aagcacttaa gaaaggagaa    106860
gaaagggtta aggcttaaca tgcacattca tgtcaaaaga gtcatagatg tctccttgt    106920
tagaatagag attttgatct catgaagtat aataggatga agattcttgt cccattttta    106980
gaaacacagg tttgaaaacc tgcattcatc taatccttca aattttgcag tggcaataca    107040
ttctctgact gaaatgccta atgccatacc tgtttggaat aatattgaga tgaagaggtc    107100
agtaggaggt agcctcttag atcttttttgc taaagctgta agcagagttt gacagtgaca    107160
acttcaattg cactcttaag ctgagaggct aggaaatggg gtcagcagca tcgcactctc    107220
aaagaatgga aaggttcggg attgtaagca gtggtaaaca atcttgagct tcaccctaag    107280
ggactttgcc aaaaacaaag tcctatgca aattctctga agctttcaga aggtggtgta    107340
cgactgtcta gttgggtttc taccttctta atctcacata atctattcac acctgcttac    107400
```

```
ttccatccct gttgattttt ctctataccc tgccctagtc atctcacacc cagactgttg    107460
tacctgccct tgttggcttc cttcttttct tctccctcaa ttttgccaag ctaattttca    107520
taaaatggct gtcttcatgt gctgctgacc tgagaaaaat gctgaatggt gcccaagtgc    107580
ccttcctcag tctgctgtct gtgtgcttct ctggtcctct cccttctcc ttcctccttc     107640
ctcgccaatc tcaactgtcc atccccctta attgcacaat gcacatcagc acggtgggtg    107700
agggtgtggt cctggcagtc cggtggcctg agcctaaata ctgccctact atcctgtgac    107760
ctcagacaag ttaggtaact tctctggcct cttttttcta atctattaag ggagacaata    107820
aggctttgta aggattatat gaaatactct aggtaaaagc gcgtggagca gtgtctggca    107880
cttaataagt gctgttagtt gctactgtta ttatcactct ggtttctatg ctttgttcct    107940
gttattagtt tcacttttgt aagtccttca cttcctccat ggctccacat tgtcttgtct    108000
cccctttcct gacagcagtg gttcatagta ggtcctttcc catgttttca gctttctttg    108060
cagtactggt actatgcata gcactattcc agccacagtg gcctgcctct gtgcctcaga    108120
cccttcaggc acactcccat ctcagggcct ttgtgctact gttttctgct tggaatgctc    108180
tttccccata tggcacatgg ctgctccttc ttcatccagg tctctgttcc ccttggagag    108240
accttccccg actatactat ttaaaataac attcgtcttc accttacata cattcacctg    108300
ctgtattctt gtcataatat ttatcactac caggcaagta taattatttt cttcttatcc    108360
ccagttggac tgtaagctct gtgagaggat agaccttgtt gtgttcacag ccttatccct    108420
agagcctaga aaagttcttg gcatatagta ggagttgaaa cgtgtttctt tgtttttta    108480
gtttttaatt tttgtgggta cgtaatgggt gtatatagga gttatatgag acattttgat    108540
actggtatgc aatgtgtaat atcacatcag gatgagtagg gtatctgcca cctcaagcat    108600
ttatcctttg tgtgaaacat gtttctttga taaatgtatg gtataacagc ttttctagat    108660
gtacattcca gcattagaag tgtagaaact gattcagaaa gcgagtgcac acatacaata    108720
ggagaagcat ggttttagat gagccctgcc aggtgcatga ggccgaggag gaagattgtt    108780
gctgaatgat gctgaataag tgatttcatc ggcaacattt aagggtccct ggcgtgtgta    108840
cagcactgga caaggtgtta tgggagatgc acaggcataa cacagtgccc ttttctctaa    108900
agttttgtat tcttacttgg gaaggcaagc ataaatacat aagaagttaa ataccaaccc    108960
acagtgaaag aaacattgcc aaattgtaaa tgattatcag tgattattac ctaccaaagg    109020
ttggcaaaat ttatttacaa agggccagat aataaatatt ttaagtctgt cataactgct    109080
cactctgctg tcagagctca aaagcagcca taaactttag ggtaagtaac aagtgggcat    109140
ggtttgatgt ggcctgaagg cctttggcag cctctgctat tgacagtaag ttctgtagat    109200
tttgtgaact ggttgtgaaa ggtttttctg aggagttaca actggagtgg agaatgagca    109260
gttgaataaa aggagcaatt gaataaaagg acaaattagg ttgtgtatgg aatgcttagg    109320
agacatcgaa caaatcagcc tggctagtgt ttagacactt cattccttat tcactagatt    109380
tctattgtgg gggcatttct gaacataaag caccaagaaa gtcctgtcct taagcttgca    109440
cccaatgcat tagacaagta ttgtctcccc tactatagtt ggaagtaagg atgggggcct    109500
tgagtaattg ctctgcttct aacctgcttc ctgtagcagg aatataattg cctatccttt    109560
ctagagtgag gttgtttagg ttcacttccc agctgtacca actattggct gtgtgacatt    109620
tagcaagtga cttaatcact ctgagcctca ttttctccat ctgtgagaga aggataataa    109680
tcatattggg attatgagga tgtagtggga taatccatgt aaaatgctga gtacagtagt    109740
actggcaata ataaagctca gaaaatgatg gctgttattt ttataacctc taaattagat    109800
```

```
tgaaaacatt agcgttgttt tgttggaatt attttaaatt cctaaagtgt gtatatgctc    109860
aggaagcttg actgtgtcac tttgtgtaaa tagattaaac tggtgagctt tataaaaaag    109920
acatagatga tggaaatatt tgcgtgcctc agccttatct caaaggaatg aatctctcct    109980
aatctttcat aaccctatgc ttaagaattg ttcatcatag aacatacctg tgcaggttga    110040
tggctgtagt tcaaactacc tatgtggctg gaaattccaa ggtcaaaatt atagattaaa    110100
gtgattccag ggtagtagtg cccccagcta caccagtata tcctctctgg aagaacaata    110160
gactttaaac ccagatctta caagcttttt acagattaag ttccaaggaa tgtaagttaa    110220
caaaaacaaa aagctcctca caacaccacc ataagcaagg tttagtagga gtaagaaaca    110280
ataaactgca gaatcagttg gcagcagaga cttcaaatat tggaattggc agatacagac    110340
tataaaatat acttaatgta attcttagaa gaattaaaag aaagtataga aacaagtata    110400
gaaattagag actattataa ttgaccagtt gttttttaaaa gaatcagtag tagtacagta    110460
gtacggcctg gatatttggt ggctcctatc ttgcgcctga cacaccaggt ttgcacacac    110520
atacacacac ctacacagtg tttttttggtt tattccattc aacatacatt ttttatacca    110580
agcattgtgt taggcactag gtagagaaga ccaagaatat gattataaga agatgcttat    110640
ctttaaggag cttatctttc agagtagact atttatagt ctactcttgc ctttgttttc    110700
caaaggtgat cagtctttgg aaggctgaag gcaaaagaca atggagacta cagtcttaat    110760
ggcctaacaa gattttttgg ctgccatttt actgcccaca catagccagg tctgtcctcc    110820
ggcatactag tcagctcagt tcacctagac ccaaaatcag tacaccttga gtacatagtg    110880
cccactattt tggagttgtc atttcatttg tagagtcctt tgataccagg gatttctcta    110940
gatttggggc tttataagct ccctgctgcc tagaactcct aactcactgc ccaaagaatt    111000
catttattta aaaaattagg gcaatacatt aacaggaaaa ctgcccattt atccccagac    111060
attttatcac attgagaagt aactgaaaca taagcaatat taattctgaa tatcctaacc    111120
tagtgtagta aagacattta tataggtact tataaggtcc aagtgaagta attcacatca    111180
tgagagaatg aaatactgaa ggacaatagg gaaagagtga catttttatct gagtgggagc    111240 ctgaaagttt caaaaaggac atggcatttg aactgggggtt tgaaatgaga ttttgatagt    111300
tggctaagga ggtggggttg tggagggcat cctggcctaa aagaagagca agagcaaagg    111360
cacaggtcag aggcttgaaa gtatgaggat ggtttctgca gaggtgagaa atgtggctga    111420
aatttacaaa aatggcactc ttgcatcccc caccgtggag tttcctcttt tttccctctc    111480
cacccacttt tccctcttac tctgcatctc ctgtgttcca cttgggatga cccctgttga    111540
gatacttgga gaggaataac ttccctgtgc acattaatga gactgccaga aataaaacgt    111600
ttatttatgt gactgtgaaa ccaaattttc acgtgcatta ctaaatgata tcttggaatg    111660
ggtggttggg gaatgttttt caggttgaaa acatcctctt gcatgaccga ggccactatg    111720
tcctgtgtga ctttggaagc gccaccaaca aattccagaa tccacaaact gagggagtca    111780
atgcagtaga agatgagatt aagaagtaag ctttttctcc tttcatggag ttttgtccac    111840
aatcagatga gcaactttac cttcagctta tggatgagaa ggtcagggtg gggagagaat    111900
ggtgatagtc agttgtcctt catctcagag catcatgttt acagtggggt tgtttgactt    111960
taagtgaaga atgaggaggg ggtttacagg catacatcag agtaaaagga aggactctta    112020
gagcacttta tcagtggtcc tgtggtcatt gtacatagat gttttgattt atgatgtcac    112080
agagcctata aaaagctgag aggtgcacac accgtaaaag tactagcatg ttttttaagta    112140
```

```
tgatcacaac aaccatgaca ttatcagtca aacagatgtg cttttttactg aaccctaaat   112200 tgctcctttc ttcctgctca taaggcgatc taagtggaaa taatggtgag taggttatta   112260
aagtctctgc agatactgaa tcacagactt tcatgataaa aagcttcttt agatttgtga   112320
ctccaataag agcctgaccc attttctcct catgtccaca atgttggatt ttttacaggc   112380
aacagcactc gctattacta ctaataagtc aacagtctag cctgcacacc tacatcctga   112440
tcttctctgt cctttcatgc gtcaccccag acaaccatgc ccggggcaag aagaacctga   112500
tcgacccaag gccctgaggg atgcctagac gtgtcccatc tgggatctag agactaaagc   112560
atcataaatc acatgcttgg taacaccaag acactcactt cgaggacgtg cttatactac   112620
ttttttctgg agcaagagat aaaactgtta tttcagcctg attccaggag caaagaggaa   112680
gggctcttga ttccatccac tcctcacccc agccagggcc cactttctgc tcttctgcag   112740
agtaccacag tcagtattac atctctgtgt tgagccacat gtaaaggcca tttttaaaac   112800
aacaaattga caaatatag tatcagtata agaattttga gaagattttg tcatttgagg   112860
acccaagaaa agttgctttt agaatttatt taatgcatta gtgtctgagt ccccacatgt   112920
tcttagacta ggaggactgc tgccagaacg ccttggtgtg atgatatgat tgtaccaagg   112980
acagcctttc attttatctc tactaatatt tcatactctc ttctgcagat tgctcccagg   113040
gattctgtta atgtaaaaag aaaaaaagta tttctgctgc tcctggtttt taattatagt   113100
attgacatat ttaataaaaa atgaatctct tgattgtaga tacacaacgc tgtcctatcg   113160
agcaccagaa atggtcaacc tgtacagtgg caaaatcatc actacgaagg cagacatttg   113220
ggtaggtgtc agtaaccta tccatacctc agatagcagc agtcttgact gtgaattccc   113280
aaggttaatg cacacagcgc tatagcatgg tggctactgt accatatcat ggtctactta   113340
cccctcaagg ttattcttga tgtgagaata ccagccactg cttcttgaag catgataaag   113400
aaaattactt ccaagctctg tgaaaattat ttagattttt tttcatgtat atgttactgg   113460
ttcttaagag caaacaggt aaatactat tatttactgg aacacgattt ggtaataatg   113520
gtagaaataa tgtaactcag ctgctaacag tggtgttggg ttctaaaact catgtttcta   113580
atacattaat agtctatagt ttttgtatct gctagtaaat gtggatggtg ccagtttctc   113640
attagatcca tttagagtca tgataaataa gccactagta gcaatctgct atctttattt   113700
tttaggctct tggatgtttg ttgtataaat tatgctactt cactttgcca tttggggaaa   113760
gtcaggtggc aatttgtgat ggaaacttca caattcctga taattctcga tattctcaag   113820
acatgcactg cctaattagt aagtatttta agtttctagt ttcatatttt tatttctaat   113880
cacaaagaat gaattggggg ataaagggat tagattccag gagtaatgag ttagatgcaa   113940
aggtaaagaa attagttgat aatgattggg aactcaaaga caatgtaact gtctagttag   114000
agtggtgggt ctttttgcta gaaatctgaa gttctgtttc acacctgagc ccagccaccc   114060
aagcagaaat cctaactgcc tggagcagta tagtgcttct atattctgtt gcagtctcta   114120
tgaaagctcc ggtaccaaag gagtccagct gactcatatc aagtgataag aaattcatct   114180
ttgcaaaact ggaagcaact caaatgaaaa tgattgcagt acattcactg gagtgaatag   114240
ataattaaga ctataaact ccgtggaacc aggttttttct tctcatttag gttaatcact   114300
ggattttgat aacatgcatc taaactcaat gctttcttaa aaatagtctt aagattcccc   114360
actatttggt atcatcatag caagcatatg tactaacatt cattaaccag atggtagaat   114420
aagtaatctt taaagaaaaa aaaaagaata atatttgcac aaagccccta tactaaaatg   114480
ctaaagaagc agagattttt atcatctttc cacattggtc aagactctta acatctaagt   114540
```

```
tttaactgtt atggattgat tataaatcct gagtaaccca tttgggtcct gcatggggat 114600
acactggaaa aaatagaagc agcaaatgtg ggtggagcat ctgacatttg ttgagggcct 114660
acttatacct catttaattc ttaaaatcct ttatgtatta agtgtaatta ttcccattat 114720
gcaaatgagg aaactgaaac tgagaaaatg taggtaactt atccacttaa catagataca 114780
gcttttaagg tgctgcccat tccattgtgc cagttttgtc aatcagcctc ttccatttat 114840
taacaaaaaa aggaggaata tttaaagggc tggattatga catttaataa ttgttggatt 114900
gttttaagag ataaagcatt atgtccatgt tagaattcca ggtatgtaag tgagattggt 114960
aggaaatatg ggaaaatggc caactttgat attagactag tattattttt tgataatttt 115020 taaaacatttt atgcagtaaa ttcatattgg gaaatacaac tctttatgaa tgtctatacc 115080
atggacatct ttcccaaact gcttgcaaac catttggcaa ctccactatc accctaaacg 115140
cacagatcta aaattaagtt tatcatcatt agccctcctt ccttcttttt accctcaata 115200
cccagttcgc ctgtcctctt ttcagtttct ctcagtggta tcaccattga agcctggaag 115260
aatgaaattt aagatttctt tggatccagc tagcaagaga ggaaaggttc agtcgtgtac 115320
tcggccatat tccttttttg gagtttctac tgttttcatt acattcttta tatgaacatc 115380
actgtcacca tagtatatac agactctgtc agctcatgcc tttactgttg gactggtcac 115440
cagcttttct cctctctttt caatccatcc agcacaccct caccaaaaga ttcctcttat 115500
aaaacaccac ctctcatgtc cctgattagg aaactctagc ggcttgccaa tggtctcaca 115560
gtagggctca gcttcttagc atggcattta agattctgat tctgattgca ttccacccac 115620
tcagacttct ctctacccctg tccttctggc tcctctattt acttgcagca ggcattctct 115680 tgtcttttctc caagtccttc tttgctcaga ctgttctctt aactagaatg tcttttttctt 115740 tgcttcccca ctgactaaat tctgtcctgc cttcaagggc cacctcaagc tctgcctctt 115800
ctgcaaggca gtcacaaggc tgcaccctca ctgatctttt tggaacttag tgtccagagc 115860 attcactttta ttatttaagc agtcagctgc cttgcgttgt tgtttgcatg tgtatgtgta 115920
tgtttgtggt cttctcaaat aattttttttt ccccctgagg attttccag cctcagggag 115980 gcagaagctt aaaggacctg gaaatagaca agtgatctat aggtcacagg aaaagtagat 116040
atgcatacgt tactttgtaa tttctttttaa tctggaaacc agctaatatt tccaacaaaa 116100
gaataataag taaattcatg aagtttgggt tttggttata attattaaga ataatcattc 116160
gtttagtaag ataagatgaa ccaaggaagc ccatggtaag accgtgtaac ctcctaggta 116220
tcggagtatg aaggtggtaa cttttcatatt gagagcttga gtccctctgg tgcaaagcat 116280
agaatatgaa ctttaagtat ctttgttaca atctatatat tttattttct tatggatatt 116340
aaatatttca ggaacattag agcttctctt tctaagggag agaaaagggg ataattatac 116400
tgtctgactt ctatgaaaaa taaaagttta aaaacaaaac attgggagta gagagaggaa 116460
tgatgcttcc tagctagtgt aataactgtt ggaatattat taaataaatt cacatgtttg 116520
ccttagggta tatgttggaa ccagaccctg acaaaaggcc ggatatttac caggtgtcct 116580
acttctcatt taagctactc aagaaagagt gcccaattcc aaatgtacag gtacgtgaat 116640
ggtgctattt aaagggagta aacattatca aattgccatt ttgagctcct ggggtgttaa 116700
tcagctgttt aaatgaattt agatgtccct tgctttatct actggggggta gtcaagcaaa 116760 gctaactgtg aagcagttgc cataaaggga atccagtttt cccatggaat ttaattataa 116820
aactgaagca attgtactga acaaaaaaat gccctaggga ttgagttgga cgctttggat 116880
```

```
gaagattgac caacttcatg tctgtcaact cttctagttc tctgagagcc acatgcctgt    116940
tgtagtcacc tggaggtgat tacaggcagg ctactttccc gaggcaatgc cttggacatg    117000
cccccatgcc tgttagaacc tacgccccct gtccccgttc tccttccttg cagcagagct    117060
ttcttgattt tgcttctgct gttggccatt tataactcac actcctcttt ctctgtcctt    117120
ccagcacatc aagccataag aatgttttct acatttagta atcctaaact ctgcactcag    117180
ttttcagagc aaaatgcttg caaatgtcct ttttacagat ttcaaatgtt gctagtacgg    117240
ctgggcatgg tggctcacgt ctgtaatccc agcactttgg gaggccgagg aggatggatc    117300
acctgaggtc aggagttcaa gaccagcctg gccaacatgg caaaacccca tctctactaa    117360
aaatccttgc atattttttca tgtcatattg tgatttatt ttcttaaata ttttattaat     117420
ggatgctata ataatagatt ctgatctgaa atgttcttgc tagttcctcc aataatgaac    117480
ttttgatttc actgctggga cttaagggtg ctgctcctct ttcactctca catttggaat    117540
cagatgtggg gttcatccat gtggagctca gaatattggc tttattacta ataagcttga    117600
gtcagaagat gcagcttgac cagtcaggct ccctagcatt agaccacat gactgaaatg      117660 taaacacctg attcctgggg gaccagctct tctttaaagg aaggagggca aagcaaaccg    117720
gaccagctca gttttctac agtcttaaca gtcacagaag tcaactcttc tccttttggga    117780 gaggaatgct tgaagaagag gaagtgctag aagttttcta gcagaaaatc tccccccacc    117840
tggaaacatg aaggaagcga gaggaccctc ctaaaaggcc agttttataa ctagtattgt    117900
gtgttggttt cccagattaa aacgagggat actgtgcagt aaccaaacat gactgtcttc    117960
ttttgtagtc ccactttccc attcataaag ttaaataatg tgaaatctaa gtggaagcat    118020
tcagattggt agctagtttt ttaaaagtac acctcacaag tcttatgtca tttggtactc    118080
agtagtggta agcacttgtt ttagggttag ggacagctag ttggtgctcc ctcatgaggc    118140
attattagat ggatagtgca gatttcaagc cagaggaact ctccttggct tgtggactga    118200
gtagtgcctc acatgttggg aagggtactg gctcagcagc catacacaga ggtggctgtg    118260
gttttctctg agcattctaa cttgcagact cagtgcaccc tggtttgaca cattgataag    118320
ctcgaacgaa gatctgtctg ggatccagaa taataccagc tacagacatt ccttcccat    118380 tccttttcata gcatcacttc taagctgtgc tataggagga aagggtact gagatcaagc     118440 cccagtgact caccatggta cagaaggtag agaataatcc gggaatgtgt gctgcacaca    118500
agctactctc tcctcttctc agatacattg cttccctgac tgtggctgag tctgatatgc    118560
atttggttaa ctttccttcc ctctaccaga cagagctcag ggcctggaag ctgctccaga    118620
agatcccaaa atgtgttttcc atcagctctc agtcccagtc aggctgctta ttctttaaca    118680
aagaaatctg tgatgtcctt ttgttttgtt ctgttttgtt tgcaattcta tagaactctc    118740
ccattcctgc aaagcttcct gaaccagtga aagccagtga ggcagctgca aaaagaccc    118800 agccaaaggc caggtaagaa atgccttcat gaacacatgt cctccttgga ttgccacagc    118860
agcagggaat gatgcctgtg tttcttgatt cttatgtatg ctgtcatgac caggggctgc    118920
acagatcagg aaagcaagct ctgtcttgcc taggcagaaa cggttctttg ggaatgcaaa    118980
aaggaatatc atgaaatatt gtgatctaca tttgaaagag aatcaagaac tctgaagctg    119040
ttttctttgc atgggaatag gctcagggc attcagagat gaggcaacag cagactttaa     119100
atattgctag tacggccagg cgtggtgttt cacgtctata atcccagcac tttgggaggc    119160
ctaggagggt agatcacctg aggtcgggag ttcaagacca gcctggccaa catgacaaaa    119220
tcccatctac taaaaataca aaaattagct gggtatggtg gcacacacct gtagtcccag    119280
```

```
ctgcttggga ggctgaggca ggagaatcac ttgaacctgg aaggtggagg ttgcagtgag  119340
ctgagatcac gccaccgcac tctagcccgg gcgacagagc aagactccat ctcaaaaaca  119400
aaacaaaaca aaacaaaaca aaacaaaaca aaaaagaat gttgctagta caagagtatc   119460
ctaaacatta ggcaggcatg gtagcacgtg cctgtggtac caactgctct ggaggctgag  119520
gcaggagaat tacttgaggt caggagtttg ggatcagcct gggcaataca gtgagaccct  119580 atctctttt aaaaatgta aaaaatatcc taaacatgtg tcctgacttt tggttagctg    119640
cattcaccac cctaacactc aacctccctt tccttcttac tttctatggc tccaaccaca  119700
ttaggaaaat gcaggtcaaa gcaccaggtc agtgaacagc agaagactct ctgggtctta  119760
gctaatcaca gtctgttcaa cctaggttct tccaaaaagc agatgccaaa agaggattaa 119820
acgaagatgt tatttggga aatgcccatg tgagggaaaa cagggaggga gccaggaaag  119880
gctgggagtg ccatcggaag gcaatgcaag tctgacccag acagagggag aagaagcatg  119940
ggtggaagtg acctagactg tctcacaact taagtaagac tcaccaaagg tgttggggtc  120000
cttgtgccag tcagccagca gatagtccct catctcctag gaattcctgt gggttggagg  120060
ttagggctgg cagcaaccta tgggaagcat ggcaccaggg caaacacaca gcagtgctgc  120120
atttagtgct gcattttggg aatgcagcag ctgagcattg gggttttatg ctccctgtag  120180
atgaaggtct acaaagcact ttcgcatggc tgccacccct tccaaatggc agattctaga  120240
ggtagcgcag gagatatta tactcctctt ttttctacca ccatcacgag taagtgctag   120300
cagcaaactg cgtcaacaaa gtaccctgga tgggaatatg tgaattttaa ttgaacagtc  120360
aaataacacc tgtatcttaa aaagttcttt aatatttatt aaatgcctgc tgtgtacatg  120420
aagttatttt agatgtgcct ctaaagtagt gagactttga ttttaataa acgtagcaaa   120480 cttgcttaac aaacaaaact tgttactttg tagtctgtcc atttccttca ctaattctgc  120540
catgctcacc tctttggaag ttgtttggg gctgatttaa gtagcttagt cctttgtgct   120600
catggctgtc ttgtactagg ctcaaacatg atatgtgcag agggtaagca atgatccctt  120660
tccccactcc actccacaaa acatactcat tgaagtccat acaaactaat attttggaca  120720
ttctacaatt aataaaacag attgacagtt actgataaca tttgatgttc acatctgcct  120780
tatgatgtag gcatatgttt ttcccttta cacataaagg acccaaagct gaaagagggt   120840
gagtgacata cccattatca cacagttact tagtgaggag ctagaactca gatatatttt  120900
tctttggctc cagatcccat tgctctaata tgttcccctc aagagatgat caacatggag  120960
gttgtgctgt ttgggtttct acagaagcct gctcacctcc ctcacccttg gcttttcttt  121020 ttttcctct ttttttttt ttgagatgga gtcttgctct gtcacccagg gtggagtgca    121080
gtggcgtgat cttggctcac tgcaacctct gcctcccggg ttcaagtgat tcttcagcct  121140
cagcctcccg agtagctggg actacaggcg cgtgccacca cacccggcta attttgtat   121200 ttttagtaga gacggcgttt tgccatgttg gccaggctgg tctcaaactc ctgacctcaa  121260
gtgatccacc cgcctcagcc tcccagagtg ctgggattaa aggtgtgagc caccaccccc  121320
agccagcttt ttcttctta cacctttctt cttttctcca gcacgtgtcc catttttctt   121380
cccacatccc ttgcccaggt tctagccccc aagatgtgat agcctttata tcaccacttc  121440
cccaaccggc acaagagcat ccctctaaca ggttgccagt gcaaagtttc tgggcccagg  121500
atggaccttg gaggtatgtc atgggaagga catgaggcca gctgctttgc ttcctgtttt  121560
acattcatgg aggctgtttt ggaaatattt tgacaaaaca tgctttggaa atattcttga  121620
```

```
aacttattaa ttttggccta acctcagtta tactctgtaa agtggagttt caaaggacgg 121680
ccaactctga tctgagttag gtagtagcta gctgcctgga ctactgtaaa tgagtggaag 121740
ttagcacctg ggcttctgca cccctcacag ggagcaagca gtcttcccta tattagtttg 121800
aaagtgtcga tctggctgtg aattacagaa agtccaaagt gacagctgcg tatagaagat 121860
agatgtttat ttttttctct caagtaaaca aagtctggag gtaagtagtc caaggccagc 121920
atggcagttc tgctccatga ggccctcagg gatctagact tcttcaagct aaccacatca 121980
ccattcctac agtgtagcta tggctgcatg gatcaatatg gcaacatctc tgctcctagc 122040
agcaggatca aggaatagtc aaagaggaag acagaggact tgaaccagtt atttcttatg 122100
gtttctggaa actgccacct gataatcttc ttacatctca tgtaatgcca ggacttagaa 122160
acaggttcac acctgttttc aaaagagact gggcaatgtg atttttactc tgggtgaccc 122220
tgtgcccagc taaaacttct gttactgtgg aaaaaagata gtatgtatat tggaagaaat 122280
ggagtttctg tgacacttcc tttttatttt taaacccttt gacttgaatt atttactttt 122340
tccttccagt tcccatgttg gattcactca tctgcatgct tttcatttta gagagaccac 122400
tttaacagct agttgcagcc aagtttgaat cctcttcgca tctgaaaacc atgtgcctca 122460
aacctctctt tgcattatta cccaaagggt attttgggaa atcctaggag gtactaggta 122520
aaagcgccac aagaagaaat aagcttgaga atgcaaagag aatactatat agcattcttt 122580
ttgagattgt ccttgcatat tcgcacatga aaagttctgc tagaaggaga gccactcagt 122640
atattttgat cagtgtgtta aaaatgtatt tgcccaccaa gcctactttc agaaggtcta 122700
gtaacaatgg catcctgtgg gagattcttt gggaagcatc gattaaacag acctggaagg 122760
tttgggtcga tgtggaagcg gaagcattgt gtcctctgcc cactcccttc cattttccc 122820 atactttaat atgaaccttt ctcttttccc tttctagact gacagatccc attcccacca 122880
cagagacttc aattgcaccc cgccagaggc ctaaagctgg gcagactcag ccgaacccag 122940
gaatccttcc catccagcca gcgctgacac cccggaagag ggccactgtt cagccccac 123000 ctcaggctgc aggtttgtat ctagattggt ttgaaactca atacacctct ttgttattct 123060
ggacaacaga gaagtcttgg aaagcctggt ttgctttagg attggactcc agaggcacac 123120
agagataaca gtgttccttg aggaacagga ggaagctgcc cttgaaattg tatggcagtg 123180
gccgggcgtg gtggctcatg cctgtaatcc caacactttg ggaggctaag gcgggtgaat 123240
catccgaggt cagttcgatt tcgagaccag cctggccaac atgatgaaac cctgttttc 123300 aaaaaaaaaa gtacaaaaaa ttagccaggc attgtggtgt gcgcctgtag tcccagctac 123360
tggggaggct gaggcaggag aatcgcttga acctgggagg cagaggttgc agtgagccaa 123420
gaccgtgcca ttgcactcca gcctgggtga cgagtgaaac tccgcttcaa aaaaaaaaa 123480 aaaaaagaa aagaattgta tcgcaaatgg ctggcaaaag gagaggcctc cttgaattct 123540
gagatggatc tccaaaacca ctaaagccct ttgtcgcttt ttctagactt ggccctgatt 123600
tttgcagttt ggaaccttat cctccctctt tatttcatat atttcccttt gccttaaag 123660 aaataagact cttccaaagt gttgagttca gtccagggca gcttccctgt tctgttaatt 123720
aaactttggg acattgaaat gggctagggg agatgattgg gtagaaagca ttatttatt 123780 catttgcctc ccagcctaca aaaatgcctg cttgggtcta atacatcaac agttaaagat 123840
gcctggaaga gacaggacta agaggctga agagcttgga ctagcagaca acttactttc 123900
aattttagga agtttggggt ctgatgggct gagatacaaa gaaactgagt tattttcata 123960
catgcctaaa aaaaaaatag aaacaagact cctctctttt gacattcaca gaagaatatt 124020
```

```
gtttctttaa tgctttgtct cttgaagtat ctaacacccc ctcatgtttt ggcattctgt    124080
ttctaatgaa ataagtaagc tttgtttcat aaaaaggatt gatccaaaat atcgagtaac    124140
tgaaccctac caggaagctg cttttggtga atttggtggc catctactta tagccacgca    124200
tccagactgg gataagctac atgtagaaca ccagggaatg atgttgtcat gctgcatgcc    124260
aagaggggca aagcttgtgc atatgtacca aaggccagtt gaatatgtag acatttgggg    124320
tgccaactaa agttgtaatt gactaaatgg gatgattaat aagggaagac tttcttaagg    124380
aggcaatatt gaaccttgtt ttgaaaaatt tgaagcacat aatttagcaa gaagatagaa    124440
agacattcca ggtgggacag agcatgtgga aagacagtga ggaggacacg aatcttgaga    124500
tactctgcac acttgtcacc ccctattagt tgttttggca agacagaaag ccattttttgt   124560 gtggaagcat ttggaaccct tacatggact ttattctcat tgcaggatcc agcaatcagc    124620
ctggcctttt agccagtgtt ccccaaccaa aaccccaagc cccacccagc cagcctctgc    124680 cgcaaaactca ggccaagcag ccacaggctc ctcccactcc acagcagacg ccttctactc   124740
aggcccaggg tctgcccgct caggcccagg ccacacccca gcaccagcag caactcttcc    124800
tcaagcagca acagcagcag caacagccac cgccagcaca gcagcagccg gcaggcacgt    124860
tttaccagca gcagcaggcc cagactcagc aggtaaggtg gtcagagtgt ggcccttgct    124920
tgcatatctg agtcatgact gtgaaaaggc ccactaggta aaggtgtctt cccagagagc    124980
cattaaacat tacatcactg tttctcatag atgtagatac taaagcattg agaagcggat    125040
ccatcactca caccccttttc accctttttac tcaggccatg aggaatctgt catctgattg    125100
aggaacatca gtacaagagc tatttttttg gccgggtgca gtggctcgcg cctgtaatcc    125160
cagcactttg ggaggccgag acaggtggat cacgaggtca agagatcgag accatcctgg    125220
ccaacatggt gaaacccctgt ctctactaaa aatacaaaaa ttagctgggc atggtggcgc    125280
aagcctgtcg tcccagctac ttgggaagct gaggcagaag aatcgcttga acccaggagg    125340
cagaggttca gtgagccgag atcgtgccat tgcactccag cctgggcaac aagagcaaga    125400
ctctgtctca aaaaaaaaaa aaaaaaaaaa aaaactatttt tttttaagg actgcttttt     125460 tttcttcttt tttctaatac aactgtaaca ccattatcat aagagaggaa aaaataacaa    125520
tagtttctta ttatcaaata tccattagtg tttaactgtt tctgatatct cataattaag    125580
ttggcttgtt tgaatcagta tccaatacta acagattgta tttagttggt ctatattgtt    125640
ttccattatc ttttcatata tttttttcac atttttttact atgaatgtat tcattttata    125700
atgatgagta tatctgtttt tttggaggta tggtcttgct ctgttttccca ggctggagtg    125760 aagtggtgca gttatagctc actgcagcct ccagttcctg ggctcaagtg atcatcccag    125820
ctgagtctct caagtagcta ggactataag catgtgccac catgcctggc taatttttat    125880
tggtagaaat gggggtctcg ttattttgcc caggctggtc tcaaactccc ggcctcaagc    125940
catcctccca cctcagcctc ccaaatcatc ggaattacac acattagcct atgcggctgc    126000
tggctgatat atctttttaag tcccctttta tccataggtt ccctctcctc tttttttttt    126060 ttttttttgct ttttgtcatt taattttttcg gagaaactgg attatttgtc ccttggaatt   126120
tttggcattc tgggtttagc tgattgcatg ctatggtgtc atttgatgtg tctgaccgtc    126180
ttccgtgtac actggtaatt tctcgaggct tactcagtat ttgattcagt ttgacaattc    126240
tttgttcttc ctgttgcatc atgtcaggag gtctgtaatg tctctctggc ctctatttca    126300
ctgatattaa gatcagggag cgtgtacttt cagatttccc tgaagactgc gtttcccaaa    126360
```

```
aatattttta aaaaaaggaa gaaaaaaaga tcaatcggtg tattgaggtg ttgtctgtct  126420
gatccatttg tttaatgttc cccattagct tagcaggtat cactgatcat ttgccaagtt  126480
ccttaattca tcagggatgg cacagtgata ttctaacatt ccctcttcat ttgagggctg  126540
gacgttttcc atgaagaaat ttttcatca gctctttagc tacccctgagg tactgttttgt  126600
acagaaaagg caggaaaaac acttgattct ttccttttgt ttactggttt tcagagtaat  126660
aaatttgttc cctcttgtca tccaaaggtg aacagtgacg tttttgtttt gtttagttta  126720
gttagtatca ttaggaattc ttagatttta acatatttga tatctttgaa tacattgctt  126780
tttttgtttt gtttttacta gaggtggggc cttgctgtgt tgcccaggct ggagtgcagt  126840
ggctattcac aagcaggatc ccactactaa tcagccctgg agttttgacc tgctccgttt  126900
ctaatctgcg ctggttcaac cctccttagg ctactggtcc cctgctcccg ggaggtcctc  126960
atactgatgc tgaccttagt gcagacaccc aactagcata gcatactaca acccttgact  127020
tcctgggctc aagcgatcct cccgcctcag ccttccgagt agctgggact acaggtgcac  127080
accaccatgc ctggcatatt gcagttttaa aaaatgtatt tattttaaag ctcagattgc  127140
cccaactttg gccagtggaa gtctcttcaa attggctcct aaatcctttg aatgtaactc  127200
cagtggtctt taatgatttc cttgctatct aggatcatgc tgccctctag gatcatgctg  127260
ccctcaactt gaaatcatcc attttcctta ggagctctgt ttcttttttag tgcaaataat  127320
gtttagaaac cacagttttg atgctagaaa taccatttgc ctaatggatt gcttgttgtt  127380
tctaggcctt ctcagtggac aattagaaaa tatattttgt tttgtttttgt tggagaatag  127440
gcattatgaa ttcggattta tattcctaat ttggatttgt aattactgga tttctgttta  127500
acttcttgga ttttgttgtt ttttttttt tctggaaatc ttgattctta acagcattaa  127560
catagataat taattgttct atcgttttaa gatagcaata accatatgat tactgaaaac  127620
agtttaagat ttccttgccc attttacccct tagaatgttt agcacattat tttctggcgc  127680
gttcagctac caatttgata caccggttta tatgcattgt ttttgctttttg attttttagtt  127740
attgcttttt aaattttagt ttaattctgt tttgtggata tgtgaaacat ttacatagtt  127800
tcagagttaa atctgcaaaa gtccatcccc accaacccat atatagtggt attgctcatt  127860
cttatttaca acttgagagt attctattag atatttcctt caggatatat ctatcataaa  127920
tatttaatca gccagtctcc tgttgataga catttgggtt gtttccagta ttttgctgtt  127980
ataagtaggc agctattttt tttttttgac atcttctaat ttgttaaccc tttaactttg  128040
ccccagtaga caaacagtat cctcccaatt gactctaata actacgtaaa gtatacggga  128100
tgttcaaaga tacagtgttg accttagttc atcagcaggc cctatttttg agctctgttt  128160
gtgtatgtag cacatagccc ctaacagtgg ggattagaga gacatataag aagtgtgggc  128220
cagatacagt ggctcatgct tgtaatctca gcatcttcag aggccgaagc gggaggattg  128280
cttgagccca ggaggtcgag acagcctggg caacattgtg agactgtgtc tctacaaaaa  128340
ataagaaaaa aaattagcca ggcatggtag tgtgcacctg tgataccagg tacttaggag  128400
gctgaggtgg aatgatcact tgagcccagg aggtcaaggg tgcagtgagc cgagattgct  128460
tgcaccacta catcccagcc tgggcaacac agcaagacac tatctcaaac aaacaaacaa  128520
aaggaagcgt catagagcac actggctatt ttgaatgttt aaggaagttt aataaaaatg  128580
gagctcttgg gaaataattt ttagtaagac ttgagatgag tcttaatagt tgagttaaca  128640
tttaggttat tcttttcagt gtcatcattg cttcatcctg ttcaggtagg gaagcatttt  128700
aatcttggct acttcaaatc cctttataag aaggattacc tctatgatta ggagatcgtt  128760
```

```
tattagctcc tgctatactc tagcttatgg agtcacatga tgtttagtca gatagcttcc   128820
cttaggcaag gcccagaaac ccacttggaa ggccagtctg tagtgcagga ggcagcctgg   128880
tgcaatggat ggagcctagc agtgtaaggg actgctgctg tgttgtattt taattccctg   128940
aggtctctat catgagattt taggcctagc ctcaagactt ttctacttgc ccttgccttt   129000
ggctttagca ctggtcttca ttgtttttga cacatttgtc ttttgtgact attattctgg   129060
gacaggccct tattcatctc ctcatttctt gctcagtttc aggcagtaca tccagcaacc   129120
cagaaaccag caattgctca gttccctgtg gtgtcccaag gaggctctca acagcagcta   129180
atgcagaatt tctaccagca gcagcagcag cagcaacaac aacagcaaca gcaacagctg   129240
gccacagccc tgcatcaaca acagctgatg actcagcagg ctgccttgca gcaaaagccc   129300
actatggcag caggacagca gccccagcca cagccagctg cagccccaca gccagcccct   129360
gcccaggagc cagcggtaag aatcaaccag agctcagagc acaaaagcag cagaggaatg   129420
tgcagcgaga gctaggggaa gggtgggaaa gatggcagca gctgatgagg gtccaggttg   129480
cttccccacc tgggtggttc aattatttga tcttccttg atatatccaa gaatagtatg   129540
gatgttctat agaagataga ggttttttta aaaaaggatt ctaggctact gatgaagagc   129600
cttcttaatt tttatcactc tgaaactagg ctagcaggaa gatctgttca tcatctctgt   129660
ctgtgtcact ttgaacagtc aaggacctag gcaggattaa agctaatccc tttctcttct   129720
tcaaggggca gtttgatcca ttgtgccctt tccaggccct gggtcctcca tgttgtgttt   129780
attctttgtc ttggatgaca ttactaatca cattatttaa gtttaccatg cagctcccgt   129840
caagggcctg cttacctgag accattcacc ctggtgtaat cccctgggt accagagcat   129900 ctgagtatcc agtcatttga gccatcttat caatttagaa attgggcatg tccactttta   129960
gatattggct gagtatggca tcagaacccc tcgtctgatt gtcctctaca gtttcaacac   130020
acacgggcac atcatgcttt ggcctgtgat aagtggattt ttttctgtac tcttattttt   130080
ctgagtgata gtgatagaaa atgttatggt gttagaaaaa gacattttgc atacccagct   130140
ggtagagtgt cacagctacc ctgttactcc cagggaagtc taactactag aggaacaaag   130200
gaaaagtaag aagccatctt tctgctgggc acagtggcct cacgcctgta atcccagcac   130260
tttgggaggc cgaggcgggc ggatcacaag gtcaggagat cgagaccatc ctggctaacg   130320
tggtgaaacc acgtctctac taaaaataca aaaaaaaat tagccgggcg tggtggcagg   130380
cacctatagt cccagctact cgggaggctg aggcaggaga atggcgtgaa cccgggaggt   130440
ggagcttgca gtgagtggag atcatgccac tgcactccag cctgggccac agagcaagac   130500
tccatctcaa aaaaaaaaaa gaaaccatct ttctgaggat tgatttctaa tagagttttg   130560
tctcccatct taaccagaa aacctacatc gcttcgaaag gaagcagtgc cgtagattgt   130620
cttctttaag tcttagctaa gtgtgtgttt agtgtcttta caccttcgtt tctaaaacaa   130680
ctcagacttc ctgcaggcat ggagtagaca gtgagtctct gtatttttaa caagaggtaa   130740
agttcctctt cttcatggaa aaagagttt taaaaaaatt agtacatgag atagctagaa   130800
gggaccttaa ttattcagtt cagcctcctc attttacaga attggaaact gaggcataga   130860
ctagaaagtg gttgcccaag acatacgaac tgatggtagt ggagctgggg caagaatcaa   130920
agaatcctga tctgtgttta agtttaatta taacaaatgc tcatccaggg tgataaaatg   130980
atcaactact actgactaca cttccttatga ggttccccta tgcttctcct acacaaaagt   131040
gtctactccc ttgggaatga attatgaact ttctccgtgt tctttggatg aaaaaacact   131100
```

-continued

```
ttgaacactt tgctctggga tagttggttt tggggacaga gaggaaacag aaatagacca    131160
tgctttggcc aggagccata gagcttctca gctttgaccc atccttgtct ccgctgactc    131220
ttggcagggc taatctaaag aagcaagtga atgaaggtaa agcgtaccct gtagccatct    131280
taaagcaata attagcaaag gggaaatggc catttgccct agatgtttat tgcagtctta    131340
ttaataatag cccagagaat ttggaagcaa cctaaattgc tgagaaaccc aactgtgcag    131400
ccattaaaaa gcacggttat aaagtctgta caacagtatg aaaagaaatg ctcatgaggt    131460
aatgttaaag gaattgtgaa attacggaaa aactatacac ttgaaaagag acttaaagta    131520
taaggtacca aaaagataag gattgtatct agttgtatta gagtgatgga ataagaagtct   131580
gttttctata ttcttacatt tcttgatgtg attatactcc ttttataatt acatttttaa    131640
aaaatcgtca gcaaaataga catctgagtc ttttttattcc ttctcccgtg gtctctctgt   131700
ccctcctccc actttccaat cctgtttgga tgggatggca tcatggggca gaaaagagtc    131760
ctgagccaca gtcaggagac atgggctctg cttccagtta accctgtgac cttgaatgag    131820
catttggcct cagtgcagga gttgaaatct gcattttcta aggtcccttt aaactctcac    131880
attctttgat tctaagtgga agtataactg tctgccaggg ttgctgggag gcgtagctga    131940
acagatacaa accacttagt gtctgtagat tgctgttata gggcaaggtg tcctgaagga    132000
ggcatctaat cttcagtgtg ctgcatctgg agaacagaag agaaaaatgt tctccaagtg    132060
gtaagaaaac tatccaactc cttccttta tgccatcaac ctcgagacaa aacaacttcg     132120
gatgtaaaat gccctggaga tttcaccatc ccttccctcc agtccttcat ctcagaatag    132180
agttgtcact ggactcttca aaataaaggg acccaacagt ttagtattct tttcagatta    132240
atgaatgtct catgaaataa gcccattcag tgtatcctca aagccctctg accctatgt     132300
gtggtagtat tcagccagct gttacaggca caactctgga cccccagagg aagttgtgga    132360
gctggagctg tggttgtctt cacagagcac tctgcctctc cttcagcagg gcagctttgt    132420
tacccttcta acctctgatt gatattagaa ccttatattg taacattcag cctgttggtt    132480
aagtggatgg aatactgaca tgtgtacata gtctacctta ataaattttc caagtcctga    132540
ggacaagatg agggcagtca atatcccaag ctagaagcat cctgacccag gtagctggat    132600
agtctagttt ccttaaactg tctcagggcc tgcctttgta gacactgaga ctgcagctga    132660
actgagttgc agcatggagc agcaactcta atctgagaag agggactgga gggaagggat    132720
ggtgaaatac ctggggcatt ttatatccaa agttatttta tctctaggtt gatagtgtaa    132780
aggaaagggg ttgggtggct ttcttaacat tttttgttca ttttccttga tataggtgac    132840
ttatgcttaa ggaccactca tgtggtcaca aggatattct caccggtatg ttgttctgtg    132900
gtggcagttt ggcctgtttt gaaaatggcc cacatcacaa gagtccttgt attattagct    132960
cagtcatcat caggaccttt ttttctttc ttcttcttat attctctgcc agttcttcaa     133020
tattatgtcc aaactgaaga ttgaaacaag ttaatcccac taaactaatg ctacatattt    133080
tcttaggagt tgccacagaa ataggatctt atatacccat cccatcagtg aaataaagag    133140
ccttaacaac aaaacaaaaa agggaatgct tatacattct tgatgggagt ataagttagt    133200
tcaaccattg tggaaagcag tgtggcgatt cttcacagag ctaaaagag aactactatt     133260
caacccagca atcccattac tgggtgtata ctcaaaggaa tataaattgt tctgccataa    133320
agacacatgc atgtgtatgt tcattgcagc actattcata acagcaaaga catgggatca    133380
acctaaatgc ccatcaatgg gagattggat aaagaaaatg tggtacatat ataccatgga    133440
atactatgca gccataaaaa agaaggagga tggaggcttt gcaagaacat ggttggagct    133500
```

```
ggaggccatt atccttagca aactattgga ggaatagaaa accaaatagc acatgcactc   133560
acttacaaat gagagctaca tgatgagaac tcatggacgc aaagagggaa acaacagacg   133620
ctggggcctc cttgaaggtg gagggtggga ggagggagag gatcagaaaa ataactctt    133680 gtgtactagg cttagtacct tggtgacaaa ataatctgta caacaaaccc ccgtgacacg   133740
agtttgcctg tttacctgta taacaaacct gcacatgtac ccccgaacct aaaataaaag   133800
ttcaaaacaa acgagcagta acatttatta atcacagtag aattttctct gactcactcc   133860
caacctgtgg tctcgctatg gcagagagtg agggatctct tagcagaaat cattcagctt   133920
aaatgtgttt cgctggagat acgtcttcat tggcctttac ctgtagtgat aggatctatt   133980
gcttgccctt tgaaagcatt ctgaatgagt ttgtatgtga ctccagaaat agaaagtggt   134040
cctttatgat aaattctaga tctttacagc tggaatagct tctgcattct tatgctttga   134100
gctgaatatg gttaacatat ggttaccta tatattatcg ctgataaaga ttgaaattta    134160
tgtgtatcag gcaaatacca tgttgttatc agtctcaaag ttgcagcaca gattgtcaaa   134220
gcctggattt ttcttctgg gcattattga taaacttagc catgtgagtt tcatgttagt    134280
gcttatgtgg cattttttgt tgttgttgtt acacttatct gtttgttttt cctttaactt   134340
ttttttttaa tttaatgaaa cactttccgt ctctcttcct agcagattca agccccagta   134400
agacaacagc caaaggttca gacaacccca cctcctgccg tccaggggca gaaagttgga   134460
tctctcactc caccctcatc ccccaaaacc caacgtgctg ggcacaggcg tattctcagt   134520
gacgtaaccc acagtgcagt ctttggggtc cctgccagca aatcaaccca gctgctccag   134580
gcagctgcag ctgaggccag tctcaataag tccaagtatg tggtgcttcc tctttgttgt   134640
tcttacctct gtgggcaaag tctgcctgcg gctgttagtg tgtgattctt tgcataagtg   134700
tgtagatgtg tgtaatgcaa atacagtggt gtgtacttgt gtttgtttat ttttctggtt   134760
tgtttatttt tctggctcat ttcatcttgc atgtacttgt gtttaatgag cagctgtgaa   134820 tttgtctta gtgcatgggc catactaatc ttaagaaatc ttttcctact tggcccactg    134880
ttctcattct ctcacctgtt ccatgctcta cagtgtgttt tctgaactct cgatctgacc   134940
gagtctctcc acgctgaaaa gtctttcact ggctcctcat gatagctgag cacactgctt   135000
aacatagcag ggcctgttgt gtttcacagg cagacttgcc attcttcacc ttcccgagcc   135060 cttttgttcct cctgtgccct ctcctgggac tgctatgctc ctccttgccc acctaggaa    135120 tgttcattta ttcatcaaga tccatgtcag aggttgactt ttccttgacc cttcctctga   135180
tatgatgtat aattttttgtc tgaacatttt tttgagctta tatgacattg tgttgtcgtt   135240
aattatttgt atgtctgacc gaactggttt gtgagttctc caagacaatg accatgtctt   135300 agtcaaccttt tggaaatcca gtgactggtt ctgtgcctga caagtagatt ttgatgagtg   135360
ttgagtaaat gcagtttcag accccttaact gtcttagaac catacactct aaagttaaaa   135420
tctttcaatg aagttaagag agactttata agaaaattat ataatgatac ttagatgcac   135480
aaagtagtgg taactgtctt tatttctttt taattgtgat ggtggcccctt aactctatgc    135540 atgctggatc ctgagagatg agaggcagcc taaatagacc tctttcctgc ccttccagag   135600
gtcagttatt gtggatgtta tggtggtcac cacaagatac acaagtctaa gaacaggttg   135660
cttttagatc ctgaactgaa acaacttgca gataagactg aaaacttaag caagagatta   135720
aggaagtagt gggaggtagt gagtcatgaa ggaaaggaga cattcatttc acaaagtgga   135780
atgggtatct gcggaaattc ttcaggtgct gtggaaagcc cttttaggaa aacactgtgg   135840
```

```
gctggatgca gtggctcacg cctgtaatcc tagcactttg ggaggccaag gcaggtggat   135900
cacctgaggt caggagttca agaccagcct ggccaacatg ttgaaacctt gtctctacta   135960
aaaatacaaa aattagccag gcgtggtggc atgcgcctgt aatcccagct actcgggagg   136020
ctgaggcagg agaatcgctt gaacctggga gacggaggtt gcagtgagtc gagatcacgc   136080
cattgtgctc caacgtgggt gaaagagcaa aactctgact caaaaaaaaa aaaaaaaata   136140
ctgtggtgga aaatgatggt ttgacccaga aaataatttg attctgaaac agagaaaata   136200
agttgaccct ttttgttttg ttcaactttt atatcttttt gtttcgtggg ggtgggaacc   136260
tacctaggtc tgcaaccacc actccatcag gctctcctcg gacctctcaa caaaacgttt   136320
ataatccttc agaagggtct acgtggaatc cctttgatga cgataatttc tccaaactca   136380
cagctgaaga actgctaaac aaggactttg ccaagcttgg ggaaggtgag taagctgtgt   136440 cttttttgt gcttcttgat tatagattct ctgtgctaag aaataaccag gaatgagaaa   136500
gaatcgtaac tctagaaggg tatgcatgtg gaaacgtagg cttgggcctt tgcataaggc   136560
ttgatttcaa agtatgcata caagtcagtt tttatttta ccatgggccc tgaagtcctc   136620
atcttcagga aatcctgatc tattgtgggt ggtagcaagg agagtgtgat gcttagggaa   136680
gaaacttgta gaaaaggttt gtgacatagt ccaggataac agcatcaggc atggtccctc   136740
cttggaggag tgtgatggtt ctctcatcct aggttggttt actgtcccag aaagttgcca   136800
ctgcttgtcc atgaatgtgc cttcacatgg acactgaatc tttctttcac tatagtcaga   136860
gttctgtatt actgtactac acagaaagat gattaaataa atagaagata tacttctgcc   136920
tgaagaacag tctactttgg aaggcaggac acacacacac acacacacac acacacaggc   136980
acatgcacac actttggaac aaattctaat atgcataatt ctaataattc taataatgtt   137040
agagagtact ctaataaaaa gtactctcaa tgtagataag ggcgcaggat aaaggaatga   137100
tgagaaccaa ttgagtggta tgaactattg gccaaacatt ttggctttaa ctatcatttt   137160
atagaaatct tttaaaactc caatccaggt gtggtggctc acgcccgtaa cccagtactt   137220
tgggaggctg aggcaagaga atcacttgag cccaggagtt caagaccagc ctgggcaaca   137280
tgccaagatc ctatctctac aaaaaatttt aaaaattagc tgggcatcct ggcacacatc   137340
tgtagtccca gctacttggg aggctgaggt ggaaggatca cttgagccca agaggtcgag   137400
gctgcagtgg gctatgaatt taccactgca ctctagcctg ggtgacagag tgagaccctg   137460
tctgttgaaa aaaattccta ttactttctt gcttttttaa acagaagata gggcatagta   137520
cttaactttt ttggcaactt tgtttcattg ttatgtatac cagttgttat tctggactgt   137580
aaatagaaat acctctatag actactgaaa attgtagtag ttttgtaccc aaataactag   137640
cccctgagtt ttaataattt cctctcccett ttcttactgt tcagctgtca gctttcacat   137700
taagctactg tcattatgct tgtccctcat aacgtctcat tattgccatc tccaccactc   137760
cctcttctca tttgctctcc taaactgctt ccaacatgga aagcagatca tcaaactcat   137820
tagagctgta taaagtgaat agattacaag tgagggcggg aggcattaaa tgtgcagttc   137880
cgtagtgtta agtacattca cactgttgtg caaccaacca atctccagaa cgcttttcat   137940
tttgcaaaac tgatgacatg ctctcttttg attcttaaca atttccttt ttttctcagc   138000 cgttctctca gttattgcaa tgactagaca aggacctttg aatgtgtcgc cataatgcag   138060
taaaagtagt caagtccaga agtcagttca gagaatgccc cttacctctg ccatgtgtgt   138120
gtgcctcgca agattctgct agaatgaact gagtggtgtt ttgtctctcc aggcaaacat   138180
cccgagaagc ttggaggctc agctgagagt ttgatcccag gctttcaatc aacccaaggt   138240
```

```
gatgcttttg ctacgacctc attttctgct ggaactggtt agtatggcaa atacctggaa   138300
cgggaggttc actgttgtta ccttcacact gttttttact ccacagataa ctctagcatg   138360
ccagtgaaat ccaaatcctg gcagtaccgt gtatatatat atatatgttt ttcatggtct   138420
atttaattta aaatttactt tttttttaatt caaaagcttt ctgatcaaaa agggataaag   138480
atctagaacc actttgaatt aaagtggcag acagtctgg cagtaatatg caggacttgt    138540
tctctctagt ccacaggcac gtcttaaaca aatatttcta gatttaagaa acacccagtg   138600
ttcattgctt gtaatttctt aggtttctga gattacttga agaattttaa aaattaaata   138660
ttctgttata gctaacactc ctctaaactg tgtgtgtgtg tgtgtgtgtg ggtgtgtgtg   138720
cgcacacgca cgcacgctgt tggggagaag gagggaggta ttttttaatg agacttctaa   138780
aaaaggaggg aggtttttt aaatgagact ttgttaaaag tatagaagca atcataagag    138840
acaaacttt ccttctatt aataaaaaat tatacatttt gattatataa aagttagtaa     138900
tttatagaga agaaagttaa aattctccat gacctcacga ccaagagata gtctagggat   138960
actatcttga tatctgttag aggcattaa ccttttgaga gtcacagata tctttgtgaa    139020
tctaatgaaa gttataggtc tccctgacca gaatacacat gaccacaatt ttatttttg    139080
agatggagtc tcgctctgtt gcccaggctg gagtgcaatg gctcaatctt ggctcactgc   139140
aaccgccgcc tcctgggttc aagtgattct cccgcctcag cctccagagt agctaggatt   139200
acaggcacct gccatcatgc ccagctaatt tttgtatgtt tgtagagacg ggatgtcacc   139260
atgttggcca ggctggtctt gaactcctga tctcaggtga tctgcctgcc ttggcctcca   139320
aaagtgctgg gattacaggc gtgagccacc atgcccagcc atatgaccac aattttgtac   139380
actcttggc cccctgctta agactctgag actctgatat gcatcttttt tttttttttt   139440
ttttttttga gatggagtct cattctgtcg cccaggctgg agtgcagtgg cacagtctcg   139500
gctcactgca aactctgcct cccaggttca agcaattctc atgcctcaag cctctcaagt   139560
agctaggact accggtgtat gccactatgg ccggctaatg tttgtagttt tagtagagat   139620
ggagtttcac catgttggcc atgctagtct cgaactcctg agctcaagtg atctgcctgc   139680
ttcggcctcc caaagtgctg ggattacagg catgagctac cacacccaac ctgatatgca   139740
tcttatagt catattttga agcctaattt tttcacttaa tgaacctggc acatatctcc    139800
tacatcatta aagaagctcc taaaatataa tttttttttt ttttttttaga cggaatttcg   139860
ctcttgttgc cggggctgga gtgcaatggt gcgatcttgg ctcactgcaa cctccacctt   139920
ccaggttcaa acgattctcc tgcctcagcc tcccaaatag ctgggatcac aggcatgtgc   139980
caccatgccc agctaatttt gttaaagtat aattttaaa aattattaca ggtgcggtgg    140040
cttacacctg taatcccagc actttgagag gccgaggtgg gcagatcgct taaggtcaag   140100
agtttgagac cagcctggcc aacatggtga aacctcatct ctgccaaaaa atacaaaaat   140160
tagccaggca tggtggcgca cacctgtagc cccagctact caggtggctc aggtgggagg   140220
atcccttgac cccaggaggc agaggttgca gtgagctgag gtcacaacac tgctttctag   140280
cctgggcaac agcgtgagat cctgtctcaa aaaaacaaaa acaaaaacaa aacttctagg   140340
atacaccaga tgtatgatat atcctagtgt atttaaccaa ttgcatcttt tttaacatta   140400
actttattcc agtatttact attataaaca cttcagcaat gaatgtgagc ttttgaaagt   140460
attcttaca agatgtagaa tttggcatgc ttctaaaagt gatctttta attatactga    140520
ttagtatcta cttttaaccct tatcatatat tctttctgcc tgctttcttt aggaatgtta   140580
```

```
gtagtttttc taacctcata aatttatttc tgaatagaat gttgtcattt aataatattt   140640
gatatgtaat actctcttat tcttattatc tggatatttt taaatagaag tttcaatttt   140700
ttctttaatc aaaagttact caggttatgt tttcattgca ctatgaccaa tatgccctgt   140760
gcagtctttg ctgtaaacta tactgaaggg ctgtctgtgg cccagtttgt tattcatttt   140820
taaatgtcct ctggaaatta gcagtttcca cgtcaataaa tattaatcta caatatgatt   140880
gttcatggaa gaatggcaac atttatttaa tatccccttt tatgaatatt tacattgtta   140940 ccaattttc accatataaa tattcttgaa gctaaatttt tgtttatatc ctttacagtt   141000
tctctaagat aacttctaag agactatgtg ctaaatcaaa agtatgtata ttttaaggtt   141060
ttttatacat attttcaagt tgtagtccaa gaaagctata taaattttgt ttcgattaat   141120
agtgaatgag agtcattttc cctgccattt ctccacccag ccagcacagc ccaggccaaa   141180
gactgtagac agagaaacctt atttttattt tatttattta ttttttgaga cagttctgct   141240
cttgttgccc aggctggagt gcaatggcac aatcttggct caccgcaacc tctgcctccc   141300
aggttcaagc gattctcctg cctcagcctc ccaagtagct gagattacaa gcatgcacca   141360
ccacaccagg ctaattttgt acttttagta gagacagggt ttctccatgt tggtcaggct   141420
ggtcttgaac tcctgacctc aggtgatcct cccgcctcag cctcccaaag tgctgggatt   141480
acagacgtga gccaccgcac ccagccagag aaccttattt actgacccat ttttatttct   141540
ttgagattgt attgttgtg tcctttgcct tttagattca ttttgtaagc attcttcata   141600
tgtcacatat tatctttcc tagaaaatca tctgcagttt taaaatttt cattaaagta   141660 caacaatata tatatatc ttttaatatc tgtgtacatt aatttaatt gtatgtattt   141720 gtgttcctct ttttcttggt aactctagcc agaggttgga tgttttatta tattttcaga   141780
gacaacactt agatttataa aatcttctgt tttcttttt attctttacc ttttgctttt   141840
atctttatta cattttcctg tttgtttgtt tgtgtgagat ggtgtctcgc tctgttgcct   141900
aggctggagt gcagtggtgg gatatctgtt cactgcaacc tctgcctcct gggttcaagc   141960
aattctcctg tctcagcctc ccaagcagct gggacaacag ttgcacgcca ccgtgcccag   142020
ctaatgtttt gtattttag tagagatggg gtttcaccat attggccagg ctggtctcaa   142080
attcgtgacc tcaggtgatc cacccacctc ggcctcccaa atgctgggat tacaggcgtg   142140
agccacctcg cctggccatt ttcttgtttt tcttatattt ggtgatatta agaggaacac   142200
atagtaacat attttaaaat tctttttaa aaaataaagt acttgggctg tgagttttc   142260 ttcacaattt gacagtcatt ttcacccagc acaaaagtgg ggagggaggc taattataat   142320
cttcagggag gctttgtcat gtgaaaatat tccaatgtcc tccttcctct ttctccagtt   142380
gcctcgcttc aacctttgaa gattacactg tttattaaga atgctttcta atgagtgtgt   142440
atttccctag taaaaaaaaa aatggggttt tgtggagctt aaccatagct cataaatatt   142500
cgtatgatat tctcattatt attttggagt tatgcttttc atcattaagt agttaaaaat   142560
ttttgtttca cttttagctt tgtttgtgta aattgtataa gtatattgat attttggtga   142620
aatttgaaaa tgttccaaaa ccagttcatg ctgcttgaag tttgatgtgc cacatagttg   142680
accaaacata tcaaatgtgt aaagcattga ctgttgtctt tgaaatagaa catcaaaatg   142740
atgattagcc atggacctgg gtaggatata gtttgtctgg aaagagggtc acagaataag   142800
ccctgagagt cttctttgct gctgagtccc agaatttggc acgatgtttg gctccataca   142860
gacgtgttga atgaataaga agagttgctt tgtgccaaag cttaggacct tggattcagc   142920
agcgttaaca atcgaggtcc ctgatcattt tccatctact caccctacca accccagttt   142980
```

```
taatgcctag ttttcatcta ttacacatgg ttatgtttca ctgtttgtat gagctgtttt  143040
ttaatgaggt ttattttgtt tttgtttctg cctttccact actttatatt tactccaaag  143100
gctgcaaatg gttgtgtgtg tgtgtgtgtg tgtgtgtgtg tgtgtgtata tatatatata  143160
tatatatata tatatatata ttttaaggga cttaaaggca cagctacaaa cacatatttg  143220
agtaaagtta tgacagtaat aacattgaac atgtatcaag cacttgaggc atgttaaacc  143280
cactgggtaa gcacttttct tgctcattat ctcaggtgat cctcacaaag accacctgcc  143340
caagggcaca gctggagaat gacagaatag agatttgtac ctgtagccca gctcaaaaac  143400
tgtagttata accacatctc aggaatctca taaaccagca acactaagct tttacaaaca  143460
ttaaaaagtg tcttcatagt ttcctcagtt tatctggtct ttttctatca acatttgata  143520
ttttcccctc tctcttgttt gcagtgtaaa tgtttctttt ctgtgacacc ttcattcttt  143580
acaaatgaaa gaaaattaca tctagatccc aggaactcat ttgctctcgt ttgtacaaag  143640
ggcaagatga catcattttc tataaatttt ctaactgaac tcagactgtt tacagatttt  143700
aaaccttctg attgatcaaa ggagaaacta agcaggaaat gtcataatgg gttcgggagg  143760
atggcacggg gctatattaa acatttgtat ggtaaaagct gcaaaaatga cagactgtgt  143820
ctatacattg gaggagaaac aggcaaacat ttaaaacttc acatggtgcc tctttatttt  143880
catatgtttt cctgtgtata atttacacat gttcatttat aaaaatgtgg agaaatgaat  143940
aaggcccaaa gtaaagaaaa taaaatctta taaccccacc ttgagagaag agcatttgct  144000
gacattttac agtatttgta tctagaattt tatttctgca tataaatttt tttcaaatat  144060
gacttacacc gtatattcag ttttgcagtt tgcttttttt cttttaaata tgtttcattg  144120
tgtcgtttta aaatatttca aggacttaaa agcagttatt ttatccttct tttcctcctt  144180
ctacctttaa agaaacttag tttaaaaccc actttaataa caaaattata gagactgaga  144240
acagaatagt ggtttccaaa gaatagtaac aggaataagt ggtgggtgtc actacaaagg  144300
agtagaatga ggaggtcttt ggtttcatgg aacagttctg tatcatgatt gcagtggtgc  144360
tcattctaat ctatacggag aatcaagttg cgaagaacta tacacacagg ttggggaag  144420 tgaaagtccc agagggaact aggggcccca gaagggagtg ctttaaaggc tgagaaatac  144480
ggtttgaatg aggagttggg ggtcctagaa gaaggttgaa ggtccaagaa gttgagtgtt  144540
ggaaggtgtg agattaggat cccaaggagt gttggaagtc caaggaaggg ctgagggtta  144600
gagagtggga attcagagtc caaagaacag tggggttagt agtgtgtcag tgggggttgg  144660
aggtgacctt ccatcccatc cccacttccc agggcaggcc tggagatgaa gagggcagat  144720
actcacagtc ctgagagttc agtgtgccag tcactgagct gggtctgata gcagctgctg  144780
gcacactggg gctgaccggc cactgggtag gacatggctg tggagatgat ggaggaggtt  144840
acccactaag gggatgccac tgcacctccc cattcccttc tgccacatct gggtattaac  144900
accccagtct gtccctattg gcccttgcct gttaccatc tagttgagct ggggctggga  144960
agttcctgca cacctgagga atggtaagca tcacacatgc caccacctcc atatctgggc  145020
ctggggcact gggttcccac atttcaaggg cctctggagt gaaagcaggt gccgtatgtc  145080
tttgaagcca ggatgtaaag gaggcggcca gattccaggg actggaaatg tcgccggtcc  145140
atccagcaat cccacctttg ccttccactt tatcatgcat ctcagactat atcttgcgtg  145200
ccctgaggag gtagcattaa gggtggcaga ggtggctgct gtgacagtgg cagagtgtat  145260
tcaagagatg ctgggtactg agtaggcgag ggcaagggac tggggcactg ggctctcggg  145320
```

```
ggcaggggag gtgggagaa agaggcccgg tcagccactg actacgagaa atgtggaata    145380
gaggtgggtg gggtggaaac tctcccatgt catcacagct gcccagtaga ccccagagca    145440
tcctcctcat gccagaggca gaactggaga gagaccaaga ttcagagaca ggtaaagtcc    145500
aagacaggga aagaaggaaa tcagagccag ttgcccacag agatgctgcc agtgatgccc    145560
acacatgctc agcactttga ctcctccaca agcctgtttt acagacagaa cactgaggcc    145620
aagagaggta aaagaaatg tcccacattt gatggcccag gccaagggga ttagtagagg     145680
ggatgctgag ccccatgatt tccaaattca acccagcacc actcaggctg agaaggaggg    145740
attcaggggt cattgagaaa gacagggatg tccaggagc gagatgaaaa gaggcagaga     145800
gacatgagtg gggtggggtg gggtggggtg gagggagaac agagcagagg gtgtgggtgg    145860
ggtcccagag ccagaggtat gggtgacatc ggcactgagg ggagaagaaa agaacagtag    145920
acacatgcac aaatagggcc acgtaacaac tggtgagcac tgaggagcct agggccgcgg    145980
tactgtgctg gagtcggtga tctcaggcta cagtttatat aagacatcac cactggggga    146040
agctggttga agggttcaca ggactgtatg tgcaggaact tcttgtggtt ctgtattact    146100
tcaaaataaa acgttttta aaacccact ttatagaaac aaaatgaggc tttttttttt     146160
ctagaaagac agctgacaaa caaaatgaga ttttaattaa cgaacaaact gaatactgaa    146220
atgcaaagta aagaatgatt atgtatggct gggcacggtg gctcacgcct gtaatcccag    146280
cactttggga ggccgaggca gttggatcac aaggtcagga gttcaagagc agcctggcca    146340
acatggtaaa accccgtctc tactaaaaat acaaaaatta gccaggtgtg gtggtaggtg    146400
cctgtaatcc cagctactcg ggaggctgag gcagagaatt gcttgaacct gggaggcaga    146460
gcttgcagtg agccaaaatt gcaccactgt actccagcct gggcaacaga gcaagactcc    146520
atctcaaaaa aaaaaaaaa aaaaaaaaa gaatgataat gtaaagctgc atgtggtggt    146580
gcatgcctgt aatcctagct actaggctac taggctgagg tgggaggatc gcttgagccc    146640
aggagtttaa gtccagccta gttaacatag caagacctca gtctcttgga gaaaaaaat    146700
aaaagaatg ataaagtgga aaccaagaaa cctggcttct gatcctacct ctggctagtc     146760
tttaacgttt aggcttcatt ttcttttatg gggaaataag aaaattgtgc cagaaaattc    146820
tgagaccacg tcaagctctg ttattccata gggtgtatag agttctgtaa atctatattt    146880
tgccaaatat agaatgaatg ccaatagtat gttaagtata gtacagagat tagggcttgt    146940
ctaaccttgg aataggcaag aagtctattt ctgccccttt ctgtgtgtct gcctatcact    147000
atattagaca tcatggtgat acagtaggac ttagtcctta aaggacctca agagggtgat    147060
agatacatag gaagtaccta tacacatgct agattacaaa acagatagtg ttatatctgt    147120
ttatgtgcta aaatgtgtga tatggacatt acctcctctc gacattctga aagagatact    147180
gtagactgca gtatatccaa gaaaggagtg gaatttcaga catatgaata ccctggtttt    147240
attgttaatt gcatctcata atatgttgca aggaccaggt tgagctgggt gcggtggctc    147300
atgcctgtaa tcccagcact ttgggaggct gaggtgggtg gatcacctga gatcaggagt    147360
tcaagactag cctgaccaac atggtgaaac cctgtcttta ttaaaaatac aaaaattagc    147420
tgtgcgtggt ggcaggcgcc tggcgactca ggaggctgag gcaggagaat cgcttgaacc    147480
gggaggcgga ggtttcagtg agccgagatt gtgccattgc actccagcct ggtggacacg    147540
agtgagactt cgtctcaaaa aaaaaaaaaa aacgggccag attgagtatc tcatagatac    147600
tttgctgttc actgagctac agccactttt attctaggct tagacttact ctgtagtttg    147660
aactgttgca ttaatagagg gtaaacttac ctagatttac ttggtgttat tgcttttctc    147720
```

```
tttttttctc tcctgactcc tccttcccct ccaacctaac tccagctgaa aaaaggaagg  147780
gtgggcagac tgtggactct ggcctcccgc ttctaagcgt gtctgatcct ttcattcctc  147840
ttcaagtacc tgatgcacca ggtaggtgaa cagaactgtt ctgaggttaa gcagcttgat  147900
ttgcatgtcc caggccttgt agaaagttct gccttaaata ccccgtgaaa aggatctgaa  147960
ttccaagccc taataatagg ctgctgttgt atattttac tgtgtctcaa taagaggagt   148020
aaacttgtcc tggagggtac cagcccttag caaagataaa atcagttcag gttataccaa  148080
attgatttcc atattatatc aatgttcagt ttttcatcct tgattgtgtt aatggtgacg  148140
tgaggggcct ctgtattgga aagaacatta gtccaatatg attttaacaa tggtggggag  148200
gctgtaagca catgataaag tgatcaaaat atgaatagtg gtgatagtgt gatcatggga  148260
ttgtgggtga ctgctgttca gttcttttct ataatgcctt tttatttat aatataaaaa   148320
cacataatga taattaggga atgggataat aattaatagg gaatgtgcgt caggagacct  148380
gggttccctt ccaggctctg ccgctacctg aaaaccttct gggcttggtt cttcatcagt  148440
gaagtgtgtt ggactgcagg agtttgaata tctcttgtag tccaccatat ctcaatttta  148500
agtagcagtc taaaaagtag aaagtggttg atgtgttctg aaagagcttt tggaacagtg  148560
attggatgct tcccagttgg agttcaagtt gccaaagctt ttccttccgg ccttccttcc  148620
gtactctttg gtgggaggag tggtgtgggg aagagaagcc gcccttctc ttatctgtca    148680
gtctcttcac aaaagcaaat tgttccagct ccttagaagc agttgacagt tgttttgctt  148740
ctgatcattt ttcctttttt cccattgttg cccctaccaa ctcttgacct tgaactgaca  148800
ggactggctt ggtttttttt ctctcccaaa atgttaaagg tatttgattg cttgcttcaa  148860
gactggaagt gactgcgatg ttcatatcct ttaccaagtc tgcccaccat cactaagaca  148920
gactgcagct agggtaccaa ggcagttttt atttttatt tttagacaaa tttgtttacc    148980
cctctaagga gaagcaaaca cttgccttga tcaggtagta ctgtataact ttatagctta  149040
ctggacctgg atgtagctta aaaatatcga aaaccactaa ggaatgattc aatacagggt  149100
agttaaaagg gaagaaagga atgaaataga ggcgcttttt tcctttgcac ttttcaggta  149160
tgcctggcag tacttggaca agttcatttt gaatagaagg ttagaaaagt gtgggctgta  149220
aactccagct ggggctcact gtcttttcct ccctgttttg gtaatcatgg gatcagacaa  149280
gggaaagagg tgatggaggc attctccttt tgacaccct tcaggttctt gctttgctgt    149340
tgcttaggta gcccatgggc tgcagaagcc aggaagaagg cctctttgca cagggcagag  149400
gatgagggcc ctcaggcaag taactgtcct gtgcagctgt cacaggagtc ctctggatca  149460
gggttgaaga gccaggcaca tgccccaggt ggctcaggaa atcggcttca gcttgtggaa  149520
atgcgtctgg ggccaccaga gccagctggc tgccatcctg cctgccttct tgtcatcttt  149580
cctgtctcct ggtcctccat gcttctttca tcctggtgga ttcctgctga aatgttactg  149640
gtatacactt taataccaat taagccaaga cctctcttgg gttcggtgg aaagatcaac    149700
taaaatgaga cattttaata gagaactgca ggagtgtatt atttactttc tgatctgtca  149760
gaccagactc atctgttgaa aacataagtc agacagttaa ctcttctgtg ctttggtgaa  149820
ttctcatatc actgagggg cataaaatcc aggctgctta ctgcgacctg caaggcccta    149880
agtggtgtgg cccttgccta cccctctaat ctcagctgag agcgctgttc ccctccatct  149940
tgtctttcct ccaacaagct aagcttgttc ccacctggg gactttgcac ttgctggtgc    150000
tcagcttgga aagccttccc ttcagttttg ttcccttgtg tcattcaacc tgtgggtctc  150060
```

```
agcttaaatg ccgtctgctc agaaaggccc agtgtggtcc catgggcact cccagtcaca   150120 tccccteggca ctttttcttc atagcccttta tcaggacata gtctgtcttt cctcatccta   150180
tcactctctg agggaggggc ctcatctgtc ttattcatca cctgtatcag ctgtgccaac   150240
gacactgtct gtattcactt agtgagtatt tacagatccg acaaatgaat gaaataaaac   150300
cagaagctgg aagcctttag gtggccccat taccctgcat ttctgtccca gctcccaggc   150360
accagacgac tggctccata gccttccatc tgcacctctg ccaactccca gccagtcccc   150420
ccacacccac tctttgagag tgaataaagg aaggcacagc ccacagtgtc aggcagctgc   150480
cagtccctgg gctgatgaga atagtagcta ggctcagcag gtcgtttagc cccgtccttt   150540
cacggtgtcc tgcagaattg tgctaagtat gttatattac cacggtggct ttgactattc   150600
tgcttatttt aacattcagc ctctagcaca ttcagttaca cagcttctat atcaaggcca   150660
ctgcatcctt tttttttttt tttttttgag acggagtctc gctctgtcgc ccaggctgga   150720
gtgcagtggc gcgatctcgg ctcactgcaa gctccgcctc ccgggttcac gccattctcc   150780
tgcctcagcc ttactgcatc cttttttaac atttttgaat attgagtgag gaaagggctc   150840
agggttcagt gtctctagaa cctgggcaaa ctacaaatt ggttttaccc cgcaaaaagc   150900
aagtagtctg tcacacctcc agcccactat ggacaccagt caagtttttt gcctgatttt   150960
ctttgttttg catacatgct catcttctac tctcagccat actgatgata agaatcatga   151020
aaggctgggc gtggtagctg acacctgtaa taccagcact ttgggaggtc gaggcgggtg   151080
gatcacctga ggtcaggagt tcgaaccag cctgaccaat acgatgaaat ccctgtctct   151140
actaaaaata caaaaattag ccaggcgtgg tggcatgcgc ctgtacttgc aggtactcgg   151200
gagactgaga caggagaatt gcttgaaccc gggaggtgga gttccagtg agctgaggtc   151260 acactcctcc actctatcct gggcgacaga gcaagactct atctcaaaaa aaaaaaaaa   151320 aaaaaagaa ttggccaggc acggtggctc acgcctgtaa tcccagcact ctgggaggcc   151380
gaggcaggtg gatcacctga ggtcaggcgt tcgaggccaa tctggccaac atggtgggac   151440
cctgtctcta ctaaaaatac aaaaattagc tgggcatggt ggtgggcgcc tataatccca   151500
ggcactcagg aggctgaggc agaagaattg cttgaacctg ggaggcagag attgcagtga   151560
gctgagatcg cgccactgca ctccagcctg ggtgacagag caagactccg tctcaaaaaa   151620
aaaaagactc atggactctc agtctcctga agaccatgcg tttcaatgac ttttaacttt   151680 tttatttttat gcttttaaaa tgatttcacg tacaagtacc tttgatctta tagatactgg   151740
ggagtggtag gtggtagata atgtcaagta acgccctcat ggtgtgggtg aggaagtgag   151800
tccttagtgt tgtttggact gtgctcagcc acacattctt cttattgccc acactcccca   151860
aacagtggag ggttcttta tctttgggac agttctcaga tcaataaagc ctttgaccag   151920
agagctaaat ttaaggcttt gggaaatata aaaatagatc tgaaactgtt agtcctgagt   151980
tctagccatt agtggctagg tgattgtggt caaatcactt aaattgtgtg ttcttatcct   152040
taaaattggc aatactaaaa cctaccttat ggggtggtca caaggttaga tgaaatcatg   152100
tatttgaaat ttctatgtga attttaaatt actataaaga tgggaaatgc tgtttcaact   152160
ttggttctac atcccctattc ccagtgggc agtcctagtt atcataaaat gatatttttc   152220
tcttgttgaa attaaacttg ctcttatgac ctttaacttt tgcacaactg agaaccatta   152280
aaatagattt cctggataca gtgattgtca aactatgggt aaagggcact ggataattgt   152340
aggttggttc gttggtttgt tttaaggaat attttatttt ttcaaagcac tataaaacaa   152400
attttcttag aaggtctgga atatgaaaat catagccatg aacatttgta tgcttacaaa   152460
```

```
gctgccaaat gatgcatggc tagtgagtct cagagtattt cactgatgct caaatgctgc   152520
ttgtccattt atttgccttc tgtatgcatt aggaaacaga taagctataa gtagtaccag   152580
cattttaaaa tatggtagaa aagaggctgg gccaggctca tgcctataat ctcagcactt   152640
tgcggggcca aggcgaaagg atcacttgag cctgggagtt cgagaccagc ctgggcaacg   152700
tggtgagacc ctgtatctaa aaaaaaaaaa attttttttt aattagccag gcatagtgct   152760
gcatgcctgt agtcctagct acttgggagg ctgaggcagg aggatccttg agcccaggag   152820
tttgaggctg caatgagcta tgatcacact actacactct agcctgggtg tgacagagtg   152880
agaccctgtc tcttaaaaag tgtgtgtgtg tgtgtgtgtg tgggtacaca catagata    152940 tattttagaa agattgagga attttctctg aaaactgggg acaatatttt taaatcattc   153000
ttttaaattg tagtaaaatg tacataatga gatttaccat tttaaccatt tctaagtgta   153060
cagttcagtg gcattaagta tattctcatt gttttgcagc catcactacc atccatccac   153120 ccacctttt  tcaacttgtg aaactgaaac tctgtaccca ttaaacaaca actctctatt   153180
tcccctcccc ccagcccctg gcaaccacca ctctattttc tgtctctatg aattttacta   153240
ctctaggaac cgaatgtaag tggaatcata cagtatttgt cctttgtga  ctggcttatt   153300 tcatttagta tcatatcctt aaggttcatt catgttgtag gatatgtcag aattttcttc   153360
ctttctcagg ctaagtaata ttccattgta tgtatatacc acatttttctt tctcctttca  153420 tctgttaatg gacacttggg ttgcttccat cttttgtctt ttgtgagaga tgcctctgtg   153480
aacattgagt gcacaaattt ctcttccaga tcctgctttc aattctcttg ggtatatacc   153540
cagaaatgga attgctggat catatgctaa ttctattttt aactttttga ggaccactgt   153600
tttccataga ggctgcatca ttttacattc ccaccaacaa tgcccaagga tttgaggaaa   153660
cgatctttat aacaagtctg cagtactgat ctcggcgttc cacagactaa gcaagaagac   153720
attcgttgcc ccatcagtgc tgcttcttag aattaaaaac ttttttaaaa aagtgcctct   153780
tggtttatgg caattcatca tctcttgaga agttaagcaa gagaagctgt gttttctcaa   153840
aagtttatag tcaagacggg cattcttctc ataactttttg gcctggcctc ttcctcattt   153900
ccaactgctg tctcgtgata ctgagaagtc caaggttgat cataatatgt gttttactc    153960 tggaaagctt atctttctgc agatttaatt ctctaaaatg aacttggaat ggggcatgat   154020
gtttgacttt tgcttccaac ttgcagatgt cacaaatggt ttctcaatgc taagaactct   154080
ttagagtgac tagatttcat tttattttat ttctttttta gggtgactag agtttttaaaa   154140 catcatctct cgtcatgaga cttcagggct tacaccccaa ctcagacaga acatagattt   154200
ccaaagccac aaggctggag tggccgtgtc ctctttttg  gtggggctgg tattcggccc   154260
ttccatgtct gtgagtcctg ccgttctact cctcctgctc atattcctaa ccagagtcag   154320
aatgggcctt gagaaagccc ttggttttat tagcctgtat aagtagatac ctgtcctctt   154380
tttttttttt tttttgagac ggagtctcgc tctgtcgccc agtctggagt gcaatggtgt   154440
gatctcagct tgctgcaacc tctgcctcct ggcttcaagc aattctcctg cctcagcccc   154500
ccgagtagct cagattacag gcatgcgcca ccacgcctgg ctaattttg  tattttttcgt   154560 agagattgtg tttcaccatg ctggccaggc tggtcttgaa ctcctgacct caggtgatcc   154620
acccgcctca gcttcccaaa gtgctgggat tacagggggtg agccccatag ccggcttctc   154680
ttttgatatt ttaggagagg ggctggatat ggtggctcgc tcctgtaatc ccagcacttt   154740
gggaggctga gttgggtgga tcgcctgagg ccaggagttt gagatgagac tgggtaacat   154800
```

```
acagggacgc cattttttca aaaaaaaaaa aaagttttaa gttagccagg catggtggca  154860
tgcatctgta gttccagtta cttggaggct gaggtaggag tgctgggatt acaagtgtga  154920
gccactgcgc ctggtcagtt tatcttcatt ttgtccataa gagaacttca gtctagaaag  154980
agtaagagat ttgcccaaag tactacacaa acttagtgta gagcaggtct cctgtttctt  155040
agtaccttgt gtacctctct gttagaccat cctgcctctt ccccacctttt cactttattc  155100
taacagttct gcttattctg ttctcaccca agacatttga gtaaaatatg gaacttgacc  155160
catattcact actgtaatca caggcacctg tggcttggtg acccctagc ccatttagtc  155220
ctcttactta aaagagacgt taatcccctt ttatgtacca aacactttat ttatacacac  155280
gcattaattc tgataaatac acccttttaa tcccaacaac actttaaagt agttcttaat  155340
ctgtttacag gtgagaaaat tgcttagaaa atcaggcaa cttaaattca ggctctttta  155400
ctctttactt tttgggattt tgcaggcccc agctaaaatt caaaaaatgt atagtatcac  155460
aataaaaggt aaaaataaat caataaaatg atactctcta tcttttttta aacttcaac  155520
ttattttcta gatttagggg atacgtgtgc atgtttgtta cctgggtaca tagcatgatg  155580
ctgaggtttg gggtacaact gatcccatca ctcaggtact gaacatagta cccaatagtt  155640
attcaacttt tgttcccctc cctcaaacac acacacacac acacacacac acacgtcc  155700
acacacacac gtttagagtc tggagtcagt tctaaaaata tcagagtaag cctaaaaact  155760
aatgcaaaac ttggccgagc acagtggctc acacctgtaa ttccagcact ttggatcacc  155820
tgaggtcagg agtttgagac cagcctggcc cacatggcga accccatttt ctaataaaaa  155880
taacaaaaat tagctgggcg tggtggcagg cgcctataat gccagatact cgggaggctg  155940
aggcgggaga attgcttgaa cctaggaggc ggaggttgca gtgagctgag atcgcgccat  156000
tgcactccag cctgggcaac aagagtgaaa ctctgtctca aaaaaaaaa aaaaaaagc  156060
aaacaaacaa aaaatactaa tgcaaaactg gaccattttc ttctcttcag aattgtccaa  156120
ttgcttttca caaacatttc ataggaagat taaatcatta ctaaaataca atttatgaat  156180
aatttggggg tttcattggt ctatcccctt aaataattga gaataacagt gtcagtcttt  156240
gtacatttca ggtatgaact gtcccagaag aatggctttt gcctttgcat ccaaagaagt  156300
cacttctcat aactcatggt gaaaaaaggt ctttgttcat tagacatcac taagtcacga  156360
tatgctgatg tgaagcgtga ttgatgtttt tggatcttaa ggaacacttc tacagttttcc  156420
tacattcacc actctcttct ctgtgctgtt cttctccatg ccccatcatg atacttggct  156480
tcggtgtgtt tctattaaac tgtaagggaa aggacagaat ttataaaaca aaggatatca  156540
gggccagccc ttgatgcaga tggaaggcct ccaggctcca tgatttatag actgtcagca  156600
tcctatagcc tttcttgtgc ctcccattac atccttttct caagttcttc atttacaatg  156660
accaaaaatg accagtaata gctttagatg tgacctcttc taagagtcct tacatttttaa  156720
agcaatcaaa actttagtta aaccagaaga atgaaactcc agtgtggtca gatatctgag  156780
tcttagtatc agctagctct cttgcttgct tgctgtgaga tctttggcaa gtttctttaa  156840
ctttctggag ctggtttctt cattcataga ggagaaggct gaattagata agatatgagg  156900
ttctttccaa tgctaacctg tctgataaca ttaccgttgt ccctgggacc atgtctatgt  156960
gaagactcat attcctatat tgatggagat aggcagaccc ctagacagat acagagagaa  157020
cttcagagac aagtccaggc tctaccatgt ctaatctgtg actttgggca agttgcacat  157080
tctcatagtc tctgatcttc attctttttaa actgtattag tattcccaaa cccagggggtt  157140
tttgaataat gaatgaaaat atttgatatt aagctctaca aatgtaagtg acgtccatca  157200
```

```
ttgtgatggc acctggaggc caactgagtc actgggagcc ttccttccct gtgagagtcc   157260
tgggagtcca agtagctttt cgcacagctg tccaccttac atagacatgg cctgtgctct   157320
cactcccagc tttgtgcctg gtattgttct gtctgcagct cctccctccc acatttctgg   157380
tatttgagta ttcccaagca gccgtgacca tacaagttat ctatgtgaat agcttgttac   157440
tttgaggttt ggtcagaaaa taagcccccc taaatcaggc agtttacacc attctgtctc   157500
accacacaac acgtgtacac tcatgtactt ctttaccctc ccacgtgctt tttgctaatg   157560
acttataaaa atattagatt cttgagccag gttcagtggc tcatacctgt aatgtcagca   157620
actcaggagg ctgaggcagg aggattactt gaggccagga gcttaagatt gtcctgggca   157680
gcatagcgag accccatctc tactaaaatg aaaaataaaa atattagcc gagcatggtg    157740 gtacatgcct gtagccctag cttctcagaa ggctgcggct gaaggatctg ttgagcccga   157800
gagttcgagg ctgcagtgag ccgtgatcgt tccacagcac ttcagcccgg gtggcagagc   157860
actatcctgt ctcttaaaaa aaaaaaaggc caggctcagt gactcacatc tgtaatccca   157920
gcactttggg aggccaaggt gggtggatca cctgaggtca ggagttcgag accaacctgg   157980
ccatcatagt gaaaccccat ctctgctaaa aatacaaaaa ttagccgagt gtggtggcgc   158040
acactcgtaa tcccagttac tggagactga ggcaggagaa tcgcttgaac atgggagagg   158100
gaggttgcaa gtgagccgaa attgtgccat tgcactccag cctgggcgac aagagcgaaa   158160
ctcccatctc agaaaaaaaa aaaaaagaga gattttcttc aattcctgtt ctttccacct   158220
ccccagtcaa gccaaaaggc atagatgtgg cagggcatct gaggggaaac caagaactgg   158280
gatacaaagg ttcgtaagac ccttccttac cttcagtcat gcttaagggc tgcgagagaa   158340
ttgagtgcag gatgctccag aagattcctg atgtggcagg aaggtgggga aaggcttaca   158400
ggagatagta ttgagtgaca agtacaaaaa agtaggggga ggcatctcca ttttacagat   158460
gaggagataa tgtcagaagg ttaaggaact gtgccagagt cacaacatgt caccagagag   158520
gctagaattc agaatctgaa agaatgctag cctgaggttt tgcaccaaga taaactgctg   158580
catgaaagac aagcaagtaa ttttgggtct ttacttttta tccattgctt ttcaagattg   158640
caaatatatg agtgctaact taaaagaagc aagtaatttc atttttttaa gtgacagttt   158700
tttgaggaga gaggaatgaa gcaaaaacta gtgtttggag caatgcaaag ttagactttt   158760
taggaaaacc atcttatttt taccagtatg ctgaaaatta ttagagatat ttttaacatc   158820
ttataatgtc atatacagtg taaggttaat gctaatataa ttacacttgt atacttggtt   158880
agtgccctgt gagggttttt ttcctgcaac tgaaaaactt ccttttttt ccttcctttt    158940 ttttatgttt ttatttatta ttattatttt ttttttgag actcactctg tcacccaggc   159000
tggagtgcaa tggcatgatc ttggctcagt gcagcctccg cctcctgagt acaagcaatt   159060
ctcttgcctc agcctcctga gtagctggga cttcaggcat gcgccaccac gcctggctaa   159120
tttttgtatt tttagtagag gcggggtttc gccatgttgg tcaggctggg actataggca   159180
tgcactacca cacccggcta attttgtat tttaagtaga gatgtggatt tccccatgtt    159240
ggccaggctg gtctcgaact cctgtcctca ggtgatccac ccacctcggc ctcccaaagt   159300
gctgggatta caggcgtgag ccactgcacc cagccgtcct tccttttttt aatataaacg   159360
aggtataaat gagatatgta gcttattgtc atttaattca aagttatctg cattccgtag   159420
actccagaga tggtgaattg gctttacata taagtcttt tctgcagtgt gttaattata    159480
ctaaagcaaa ttatcttgcc aagactctga aatccattct tttgtttgac ctgtgtagtt   159540
```

```
acagatcacc taaattgaag atcacctaaa atttggttcc tgttttcca tgaatatcaa    159600
tttatttctt gcttatctca attcccaaat ggcctagaag aatacagatt tattacaacg    159660
ttatatacac gttcttggac tttaagtcac ttctttttct caagcaaaca ttttaatttt    159720
agttctctta atgacatttc catggtttaa aagaacgttg ttgacatgtc tttaattggg    159780
caagttacag aatttatgtg atctaagtct cctcttaaca ggaaatgtga gctctaaatt    159840
cccttcttcc tataagattc tatgattcat tattttgttt caagttaatg ctttaccttt    159900
aatagcttaa aggtaaatag agggttcttg atggatcggg ctaaaagaat tgttttggaa    159960
ggaatccaaa tgtgcacaca ttgtcaaaca ttaagttacc aggtgtgaca agtctggtgg    160020
ctcaggcgtc cttttatttc ttggccagaa gacatcaaga gtaatccatt tttgggctta    160080
agtgaatttt gtgatatttg accatagaat aaatatgactg ccagcatgtc acaggtgcat    160140
agttggcaga caataaatga tcgttgaagt cagcttaggt gtggttgaat tgattatctt    160200
ggtgagttat aaactgtttc taaataaagt cccccccaac cccgaaaaa agagagagat    160260
tcaaaactaa gcccgagaag gaaaatgaac atacaaagat ttatatgcaa atgtttatgg    160320
cagcttattt tttaccagct taaaaactgg aaacaaccaa atgttcagtt ggtgaatgga    160380
tcaacaaagt gtggtacagc catacaatgg aacaggactc agcagaaaaa cagagcaaac    160440
tattgatact tgcgaccaca cggatgactt tcatctcaaa ggcattatgc caaggaagg    160500
aaaccacaca caaaagacta catactctgt ggttccattt ataggaaatt ctggaaaagg    160560
caaagctgta gggacagaaa gcagatctgt tgttaccagg gtctgtggtg agaggaaggc    160620
actgactgta aagggttatg aaggaatttt ctcaggtttt ggaaatgttc tgtatcattt    160680
cagtggtaat gatatgaatg tatacatttg tccagactaa ccacattgta cacttaaaat    160740
gggcgacttt tattgtatgc aaattacacc tcaaataaaa acaagcagac gcacccagga    160800
cagcatcttg aatgccttac aaagtgacta cttcacttga ggaagtaatc attttaaac    160860
ttccaattt gaaaacctgt tgttaacaag atattaatag cattcatttt tatggtgaac    160920
ctgtaccaaa tattgacccc taaaatgtgt ttgcttaaag aatagtgaat gatccgctgg    160980
ctttaatatc ttactacatt tttgctttct ttttgtctct ctgcccaacg tagaaaaact    161040
aattgaggga ctcaaatctc ctgacacttc tcttctgctc cctgacctct tgcctatgac    161100
agatcctttt ggtagcactt ctgatgctgt aattggtaaa gtcatcatct ctgtttcttc    161160
agtcatgcat gatatgtgtg cctgtttcaa gaatgacaag tacctagtta accaatccct    161220
ggggaatagc cctgccaccc cagaagccaa ggctatttaa tctcacttgt atcactccaa    161280
atgaagtgtt ttccttgctt ttcgggggta caacgtctat ttttttgcctt tcttgatatc    161340
tggagatttc tagagtggat ctcttatgaa tgaggaggaa tgtggaaagt ttcacattta    161400
gttagaagaa cttttaaaaaa ttggtttcta actagactac ctttactgaa cttaatgaaa    161460
tttagcagat tcttctttt tttttttttg tttgagacag agtttcactc ttgttgccta    161520
ggctggagtg caatggcaag atctcagctc actgcaacct ccatctcccg ggttcaagca    161580
attctcctgc ctcagcctcc cgagtagctg agattacagg catgcaccac catgcctggc    161640
taatttttat attttagta gagatagggt ttctccatgt tggtcaggct ggtctcgaac    161700
tcctgacctc aggtgatcca cctgccttgg cctcccaaag tgctgggatt acaggggtga    161760
gccaccatgc ccagcccaga ttcttcttta gaaggcccat gtacatccag ctgcagtggg    161820
acgagcctgg gaagcatagg aagacccat ccctacaaaa aaaatgttgt tagttagcca    161880
ggtgtggggg tgcacacctg tgctaccagc tcttttggag gctgagacgg aagatcactt    161940
```

```
tgagccaggg ggtttgaggc tgcagtgagc cctgatcatg ccactgccct ccagcttaag 162000
tgacagagac ccatcttaaa caaaattaaa aaatttaaaa aggtccatgt atataccaag 162060
tatcagtaac tgagaaaaca ttttgcccac tggttaagcc ccataaatag aatccagggc 162120
aggggcttgg tctgcttcct ctctcacatt ttcctatgtt ccaacagcaa ggcaggcaag 162180
atttgcaaaa tgtccaaggc ccctgtactc caggagggtc caatcatgag gcacctaata 162240
atgcctttgg gcagaaagtc ctagaactca gaagtgccat gaccttgcat aggggtaggc 162300
ctgcagctga ggggtgtcac gtggtgcaaa aggcctccca gctacatcct gggatggggt 162360
ttgagatgga ttaatggcct ttgcatggca cagaggatgt tgcccccag gtttatccct 162420 taataaaagt gaaattacca gaaaaaatta aggtgccttt cagcccatct cttctgacat 162480
ggaagaggtt tgctgagcgg cttatgttct gaatttgttt atgagaactg atcattagtg 162540
agactggcca cagtatttaa ccttgcacat gcatgctcag tgaagcctag acattcagag 162600
cagcagaaat aaagtaactt attttctctt ccaccttgcc tgagactggc attttagaga 162660
cctgttaaaa gaaagtcttc acatggctgg gtgcagtggc tcacacttgt aaccacagga 162720
ctttgggagg ccaaggtggg atagatcgct tgagctcagg agcaagacac catctcaaaa 162780
aatgagaatt aaaaaaaaag aagaaagctt cacagaattt cctaaagaaa cttctgactc 162840
cctttccctt acccttttcct cttcttaatg ctctgttacg aaagaaaaag ctgatgttgc 162900
tgttgagagt ctcataccag gactggagcc cccagttccc cagcgcctcc catctcagac 162960
ggaatctgtg acctcgaatc gcacaggtca gtcaggtgtc tctgcagctg cagggactgg 163020
tcggtgtggt gaacctctga gccagtcttt tcacctggct cagtcgttcc tgggcttatt 163080
ttgaagccca ggtagttcct cctgaaatgg acactctgaa ttgtcacagc cccggcttct 163140
agatgttgag tgatatattt ccttgctaaa gaactgagta ctttttggag ccatgttctc 163200
tgtggagtga tctctgggct ttctctggtt acagtatttc tttattcaaa attcttttca 163260
ctggtggtgg gatccctcta tgtccttaat taaagaactc tgccgagctg taaggatacc 163320
cttaaccctc cagattgctg tacatctttc cagtctgcca atgccagtga tgtccgtgga 163380
gctcatcttc tatatattga tgttccgttc ccagcacagt gctttaatcc tgtataggta 163440
atttgctgta aaattgtagg caaagttgaa gtcttcccta gatgtagtat tacttgtacc 163500
ctaatttcaa aattcagtct taatagaatt tcttaactgc ccacaaatac agatttggta 163560
accttcttct tttttttttt tttttgtcca taattccctt gataaaagta tctggttttc 163620
aaacttggat agaaacaatt agaagcctag gaaatgtgag gataaattca tgcaggtgaa 163680
aaaaaaatta cctccaaaga cattatgatt tattttcctt atcctcattt gaatgttttc 163740
tcctagaaaa cttctcagaa acaatccct gtgttaaaat gcttaaactc aggctgggtg 163800
ccttggctca cacctgtaat cccagcactt tgggagactg aagtgggcgg atcacctgag 163860
gtcgggagtt tgagaccagc ctgaccaaca tggagaaacg ccgtctccac taaaaataca 163920
aaattagccg gttgtggtag cgcatgcctg taatcccagc tactcaagag gctgaggcag 163980
gagaatcgct tgaacccaga aggcagaggt tgcggtgagc caaggtcgtc ccactgcact 164040
ccagcctggg agctggagcg agactccgtc tcaaaagaa acttaaactc tgagttttg 164100 tcttggtttt ctgaagtcaa aatcatgttc aaagggccaa tttcaatgta aagaatacta 164160
gctagaggca ttgtgggtgg gaacctggtt gagttctaga aggtactgtt taatcttgtc 164220
acattctgct aataataagc cagaggcaac cctctcctaa tcagtttgga tactttgtcc 164280
```

```
tatagtaact tccttctatg agtgtttagg gaaagtttaa gtgaaactct aattgtaaag    164340
ttttttctcc caaatggcat tcactaagaa ctgaggtgct aaagttagct cagcatccaa    164400
atcacagacc tatttaacca gcaacctctg agcaaaaaat tatcctctat ttctatgtta    164460
atgttaagag gaatctagaa agacatgttt ctatagatga aaatccagaa gcctccacac    164520
atttcttttg gttttcattc tcccactttg gcttgtatgt gtaacgtgta aatgcagtaa    164580
cttaaaagct aagatctaat ctcatgatac agatgaaaat ccagaaggct ccacacattt    164640
cttttggttt ttattctccc gctttggctt ttatgtgtaa cgtgtaaatg cagtaactta    164700
aaagctaaga tctaatctca tgatattgtt gtgtgtgcca cttaatgcca tcactgacct    164760
gggatgctgt taatctggac tcagattctc tcaccgggga agattccctg cttgattgct    164820
ctctgctctc taaccctact actgaccttc tggaagagtt tgcccccaca gcaatctctg    164880
ctccagtcca taaaggtaaa tgcttttcttc ttctcaggcc cacatgtgtc cttagagggg    164940
aaagaactaa acaacttttg aaagtttttc ttatcaaaag tctttactag tgaagtttta    165000
aaactacctc cttgtatgga aaacttgagt atctcctaga tactgtgtta taatacctct    165060
cagtgagaat atttactaag acttagacga ccggccagtt gtggtagctc aggcctgcaa    165120
tcccagcact ttgggaggct gaggtgggag gatcacttga gcctaggaat ttgagaccag    165180
cctggacaac atacggagtc tcagtctcta caaaaaaatt ttttaattag ccagccatgg    165240
cagcatgcac cggtggtacc agcttctcgg gagactgagg tgggatgatt gcttgaggcc    165300
cggagggcaa agctgcagtg agccatgatc gcaccactgc actccagcct gggcagcaga    165360
gcaagactct gtctaaaaaa acaaaaaaaa tagcagacag gtactaaaaa taaataaaat    165420
taaatctgaa aaaagcccta gacaacagat tggtgaaagt attgctttct ggcaagaaca    165480
tagaatgcag atattccatg ttacctttaa gagctagata cctttgcagt caattcaagt    165540
agatggttga agtgactatc tactgcctgc ctataatgat catatgatgc ttgttggcct    165600
tagaatgtaa aatggtttta tcatatctga ttcaaagtta ttgcatagtg atgactgcaa    165660
taaagaaata agcatctttc ctcaaaagtc agtccttgca aggttgaact tgtagaagtt    165720
ttgaatttta gttcacccttc aagtcatgat tggttactgg attttctcttt ctaatctact    165780 attttcattt ttcagtcttg ggttaatagt ggtctgaaat cctggacaga ggtagcttga    165840
atcagattct attcaatgag cagtttgtga cagtgtcagg ctcaatgcct ggcttacttt    165900
gttactgaac tttctgtgat tgggtagtga aagtagtctt ctggaaagag aaaatgtgta    165960
gaaaagaaag agcttaagtc ccttcaggag aaaattcaag aaggaagcct ccccagaatg    166020
actaaaaata atcacctctg tggtttgcaa tggtaatagc tgagttttttg ttttttacccg    166080 tgatgacatt aaaatgatta tgttttttata gattatgtag agggaagtta cctatttaga    166140
cagtgatgtc tggcaggagt atgtcagcag caatgtagaa ttacagagaa gcatcatttg    166200
caaaataagt gctcagccag cacttgcttg ctgttagggt agctttaatt agaatggaga    166260
agactattct aacaaacttc tacttgaggc ctcagtgcgt gtgatcttgt gcctcagcgt    166320
tccctgaggc ttctgagttg tttcagtgtc ttttttttccc agtcacagtg cagtgagtcc    166380
ttccagcagt attttgtttg cattatatac agtggttact tcttaaagag ccaccaattc    166440
tcttcctcct cccctgccct gccccccaagc cccggttttg agttttttcaa atattgtttg    166500 gcctctgttc cctcagtgaa gacaagtgac ttattcctat gcctttgtgg attagtgaca    166560
atgaagagat acctcacaat aattataatt aatgtcttat aaataataga attcttccaa    166620
gaaccctttt ccctaatcat tataaaagtc aacatggcca actctaaagc atttttttct    166680
```

```
atatctctgt attttccagt tttgctattt ttatttcaac tcagaaagat aaatcctttc   166740
acctttgaaa ataacagggc tgtacagttg agatctttgt gcctctttca cattctctca   166800
tttgctaatc tctgcctctg ttgtttctgc ttgtgtactt gcattctgta ttaagctgca   166860
gaagatagta atctcatctc aggttttgat gtccctgagg gctcggacaa ggtggctgaa   166920
gatgagtttg accctattcc tgtattgata accaaaaacc cacaaggtaa gaaaaaggat   166980
ggggaaaaga gaagagcttg gcctcagttc tcttcaaaat agtcatgcac ctaatctgca   167040 aggggggaaga aaagcatcaa catttaatga aggacattgg gtgtaatgag aatcattgta   167100
ggctggacca atagagatag atagagatag gtatctttaa agtttgaccg tggtgtttat   167160
ttagagagaa gtctttaaca gttggccaaa agttagtttt taccatgaag ccaaaagcaa   167220
aatgatcttt agtcagtgga aacctgaagg tatatatcaa aagcacatca cattttttat   167280
catgattaga ataatccata ataaatattt ttcccaaaga gattaacagc tgtgttttgg   167340
tatcattcac atctttttga cattaatgga gcatcctttt tcaactttga tggaggaaaa   167400
tcatgtgaac atgccataaa acactaaatt accatgggac catctattta tttttaaag   167460 catgttctta ttgcagtatc ttaataacta gtttctcccc aaagcaaaaa ttattgattt   167520
ttactttatc aaagggagat ggcttgatat tatcaggaag ttggtatata gccagcaatt   167580
ctcaaccaaa aaaagtattg atttgaaaat agtgccctct ttgcaagatg tcctacctat   167640
actgtggtgt gcacagagtg cctgagcttt tggtgggagg tggtggacag ctaacttaca   167700
tgtttcaaaa tcaacgtgta aggggtttgca aatgtaaaat attgcttctc tagggtttgg   167760 ttttttttggt ttttttttgt tttggttttg gttttggttt ggttttttctt ctttgcttgc   167820 tctgcacatc taaaccttaa ccctctatgt tttgtactga attcctatct ctccacttcc   167880
aggtgggcac tctagaaaca gcagtgggag ctctgagtcc agtcttccca acctagccag   167940
gtctttactg ctggtggatc agctcataga cctgtagccg tgacccagta gcagatgcag   168000
ttctgtaacc ttcataccgt aaaatacatt ttcattacgg agttatgaaa aaatgatttt   168060
ttttaaaaaa atctgcaaat aaggggcccct ccagcccttt tctcctaccc cttgccttct   168120
cctgtagaaa tgataaggaa agaaaatcac tttggccctc cagatattcc ttggccagtt   168180
cctccttgtt agtttgctgt gttttctcat taccttctt caatagcatt atcttaaatc   168240
aagcactaga tgccatgagc ttcacctctg ctggaatcaa ctccaccaaa agcttaactg   168300
taactgaaac tagtgaattg acactttgt ctcgttcttg ctaggaatgg cctcccagat   168360
caattctccc aaccccgtc tcctttggcc agatgctgat gaatgtattt ccctgttttt   168420 gcttttttatc ctgatgcatt atcatgagga catggctact tcagttggtc ttaactctag   168480
gcagtagcct ggagatgggt gtgtggttta agaaagggta aaacttactg actggtagta   168540
tatatttgag aagagaaatt gagcccagct ctagccaacc aactttgacc ttgtttgatc   168600
atagacttag ccaagggatt ttacacccca tgcaacctgc ccagcattcg tccagctttc   168660
tggcttccat tgaaccgtga tttctcagat ctggagacgt gactgcaagt atttgagatc   168720
cttggataca atgtgtacgt tatataaatc ccaagtattg ccattccttt tcatgttaac   168780
tgttccaagt gggatctcag aattagacca aaacaagacg gtggtaatat gatacctttt   168840
attagaagac ttttcactgg ggcggggggtg gggggaggat gggggagggga aggaattgta   168900 gcagaaacag atgtattttt cttgtgattt ttattttgaa tcaaatattg taaattgtgt   168960
ataaatgaag atgctgaata gttctgtttc cacttggcat ttcaagtctg atatcaggtg   169020
```

```
tctgtacagg gttttgattt ctttcccttg tataactaca caacaatcct acagtgtaac  169080
atatggaatc attttgaata gacttgtgtg ctataagctt tcagcaggtc ctctgtctct  169140
agaataagca tgttgtttat tttcagataa tcagaaataa gtgtgctgac aagctggaca  169200
caatctgggt gtgcccagct tacctttctt tctgatgttt aaattgaagg ctgcagccaa  169260
tggaatatgt tcagctggtt ttccttggct tcctagatta aaaaaaaata ataaagcata  169320
gttctttatt aacttaggga tattgttcat aaaataaata aaggcccctg cactaacatg  169380
acaacatgcc tcatggtcac cctctctata tgtacttact cattaaagtg tattttattt  169440
ccttatgtgg aaagcacttt tataaaatca ccctttttgaa aagaagtggg cacagagaac  169500
cccactcctg ttcttttcct ctagtgccat tgtccatcat caaaagggaa actcttagtt  169560
aatcagatct gtacaaataa aattccaagt ccatttgctt gttttgctat ctagtacttt  169620
tgtttcttct tcctcacatt tgcactttat gggggaaaaa agtttaacag caacaacagc  169680
ctataaaaca ctgcattctg gagggcaagg tttgaccta ggaatgtgcg agtagccttt  169740
gaaaggcatt ggaggaaaag tctgaatctt ccagccttcc ttctgtcttt aaatacttcc  169800
cgtgctggct gaaacaagat gagctaggta aaggcctcta gttgaataac agaccatttc  169860
caaaactgag agaggcacaa gcttcctgcc gaggattaaa aagcaaaaga tatccacgaa  169920
gggctctctg tggttggata gcagtgaaaa taggacttgg tttacccctt tatggacagg  169980
aaaattgctg caggtcagaa ttgtattctc tttcctggac atagaaagaa tgtataaatt  170040
aatgaaggaa atgtttattt ttaaataaga ataatgtttg agttctatgt tttcatattt  170100
gatttttttc gtatatacat gttagaaata taatgaaata tctagtttct caatttaatt  170160
gaaactatga agagtacagt ttagaaatta ggtatctcta aattgttctt ttcatatatt  170220
acccataatt acattgaaat atattatcta gtcatttggc tcagtaaagc ttaatggagg  170280
cagttaatga aaatgagcag actagaagcc agagacggca gtagaagcct aagggagata  170340
atgacaagaa attgtcttgg gcttatttag agtaaggcct cctcaaaggg gagaactatt  170400
tttctgttaa ggaacacata tgagtgcttt ggtaaacgga gccttccttg gtttagagca  170460
tcatccctga gctgaaagag tttatttgag ttgagcatag tgtcctggta cctgtggaat  170520
catagcctga gctacaaagg gacctttgag accatcctct agtccaccat cctcttcatt  170580
ttacaggtgt gggacctgag ctggattgaa cagggtcggg ggagaagagg cctgggcagg  170640
acaggccacc tgggatctca tcctggccct tgccagccac tggctgagtg accttcagca  170700
ggcacttcac ctctcagagt tgctgttcct tagagttata cgatgggttt ggactagatg  170760
gtctttaaga ttatagaagt atagggtcct aagtatatat tattatattg agaagggcta  170820
tgaaggattt atataatcct gatgttcttc agttatcttc tgtagttcct gctattacgg  170880
tagcagtgtt tacattttaa agaattataa tgggctttta ctaacttgct ctttcttgat  170940
tatctgaata gaagcctaaa tcataatctt agagattttc cttttttaagt attacagaaa  171000
cacatgcgtg gacacacacc tacctattct aataaaatgg tatcagaaga tttcttttta  171060
aatgtataat caggcatcta ccagtttaaa acgggcaaat actataagca tatgtttctg  171120
atttgctttt attccagcta tgtaagagga gtaactatag cagaaaacat gacaaattga  171180
ttttccctt tacaacattc aaatgagtcc caatgttttc aaaaatacat acctcagagg  171240
agataaggct taagtggaca cttctaagta tgattataat tattataatt aatgatttct  171300
ttagcagaca tatcagaatt ttgacatcta attaagtgtt gttcccctca atgtcatcta  171360
gttttactta agaagttaat acttattcta atgatgctgc catccttaaa gttattttg  171420
```

```
aaactcctct ccttagaaat aatatcaagg aaggtaataa ggtataagaa aatcagctat  171480
attatttaat tagtatcact ttgagaaagc acctggaagt atattctttc tttgtctact  171540
ttttctacta ctcttggttc tgagtaacat ttagccattt ccagaaagca aattcaaccc  171600
tgtaagatga agagtggtta ctgttgaaga cagtaaaaag gataatccac aaaaaattct  171660
cagagaggac cttataatag aaagtgaaca tgattaagac ttaatttctg taattttctg  171720
aataaggaaa cttctgtgat tccttagtct ttagaatggt ttaaaacatt gaaagatatg  171780
ggtattaaaa cacctctgaa agaagttgtc actttgttca gtgttatttg atattggact  171840
tcgctcttcc tgaattagaa ttacacaact tggattgcta atacttgtgg aaaaacaaac  171900
ccaagaaacg aactactttc tcaagatgta atatttgttt tattattaat acttttggtt  171960
gttttgatta cttatttcct actctcctga cagataattg atcaaccaat ataaccttcc  172020
ccaggttagg aacagttctg ccttcagcag tgctgtggga atgaagggat ctttggggct  172080
gacagcctat gatgtggagg gatctgcact cagctaaata aatacatgct atagatacct  172140
tgggccaaaa taaagtctct cttgataagg ttttttctgtg atttcccaga gtccttaacc  172200
ttctctgtct gcaagattat caggctccca tagccactaa ctttgagctt tgggatgaaa  172260
atgacaggat tgcccagtgt gccgggttaa gcaaattaga ggctgcctgg cagaacagaa  172320
aaactatcac atgaatattt agaatggaag ctttcctgaa acactccaga tactgcaaag  172380
ctatctttat tcctctctaa aggctataat tttatcaaca caaagtcagc cttttctttt  172440
tccacattag taatgtttct gaagttggat gtgcttagat ttcttaaatc agaatgagtg  172500
ctaggaaatc tataacaaga aacctctttt gcttctccca gatttccttt cactaatacg  172560
ggatagggag gctccttggg taatgctaac ctatgcaaag aagttaccaa atggtggtag  172620
ttgctagaat taaagacacg ttcttggttc acactttgat gtagtgacct gaatttactc  172680
ttttcctgtg agtattctac tctgccctat tgcactctcc tttgtcatgt ggatgtgtgt  172740
ttatcatagg tctttaacgc gtccttccca agaagacaaa gcatacagtt gtacatgaag  172800
atatcttatg cagtaaaaac gtgaaatttg aacattgctg cacaagtatt gtataaaaaa  172860
aagtctgtaa agaactttct tatgtaaaca tacagggaaa taaagacttt tatctgttca  172920
aatgggagca tgatgtttag agatgtaaat aacttaaaat aagttgctct tttcctgagc  172980
tgaaaaccca ctttttttgca gaaaggattt aatcacagta ttgagtgaca ataagtacct  173040
gggcacaaga aaagtatagc tacacactga ggacatatta atgaatcatg gctacctgag  173100
agagtaaaac ccctgtttta gtctcaagga gaataagacg cctgccagcc tacactggat  173160
atgaccagac tcagggttgt aaaatggagc gcaggtttgc agcttccctc ctctaactta  173220
atccctaata tacccaggcc aacttaatta aacattttgt gttggcaaga ataattttat  173280
ccccagtgag aaaactcact catttaattg cctcattggc ctgagaggca cagctggcca  173340 ttttggctt ccatgaggtc cctcatttcc cagtcgtggg ttaatgca gctacctaat  173400 atatggtgga accaaatgct taattttgtt atgtgagcta aaggtcatg gtaattatta  173460 gtttgatgta cgtctcttga tttccccagt ttggttctaa aattttacgt ttcaattgct  173520
gctgcatttc caagttcttg tgaagggata ttttgctttc tgtttactaa ctatatgtga  173580
gaaggcttct tctcaatgct ccaagtcttc gttttctgtt tttggcaaga atcatatctt  173640
tgatactccc tgtaaccgtt cttcagtttt tggtatgag gaaagtaaa cttcggtgt  173700 tgtgtgatgt atttcattaa ggaatatcca gcctgacatt taagtcttca gattttaatt  173760
```

```
ctgtagggag cattctgatg gccctcacta tgtcaatcag atggagtttc caggggaaac   173820
ccatcctaaa tgattcagca cttttgggttg ctttggaagt gaatagggag ctggtgagga   173880
tagttgccaa gttgtcaggt attttaggaa ctccttctct tccctgaagc atgtgagttc   173940
ttgctgaaat ctacataatt tggagcctca aaatagacta atatgagtt acccatattg    174000 aaagtgtcaa cgtgcctaac ctggcacaca gtcctacatc agagcaagaa aagaagtat    174060 gttttgactt cttgcttaat tttatgtgtg aaaccaaaat aaaaagaggc atgatccagt   174120
ttgagggaat tataacaaaa ccctacgtta ggctctatga taagtaagac cctgtgcaga   174180
ctatgaagcc aggccctggg ctttagcccc tgaggtacaa caggcagtgt ttactgagct   174240
ctatggccac agggtatctg ctatgacgtg ccattggtta ccaaaggaac tgggtcaagg   174300
catgtggtta ggttagtata aatccttcaa tgctagtaaa gagactgctt caaacacgtt   174360
ttcttgttga cacaatgcta ccttcatata aaggaactgt tcaccctgaa aacacatttt   174420
ccctgtaaga acacattcac atactcaaaa aaagactttt atctgccaac aagatttaat   174480
ggttaccttc tgtttctagt atatttggaa tttatccttc tctcgactac cttgtttctg   174540
gtgctgccac caccagaatt ccttaaggga atgtggaggt ctgggcttcc cccatattct   174600
ctggcatttc tttgcccttc agagtgccag gcctggagag ttgcaaagtg tggttgctct   174660
ccgcctcagc cacactgtac ctcctctaac aagaatagaa aggttaaggg acttggcctt   174720
ctcaggacaa ccctttaaat gtacttttcc attcctacaa agcctgttga tgctgaaaga   174780
aagataggaa atagctcttg tccttgtttt gaaggacagg agactaattt tcccttcaaa   174840
cttgatattc tggtgttttt gtgactgttt ttgtaaatta ttcaaagttg ttggaatttt   174900
aagtctgatt ttcccagtac tcatcatgaa ggtcatagaa tatgctctga gttggaaggt   174960
tttccaaatg ggttctcgac caaaaaccca cttttaaca aataattttg atgggttaga    175020
catgttcttc catcctctcc aaccctgaat atgggcacat acacacaccc cttggtactt   175080
cctagttctc aaaatgtaat ctagcacttc aggcatccaa agtgccctg gttcaataga    175140 tagctgcttt tttgccagtc tctgtgcaca aattgtttta actgaattca gtttaaattt   175200
ccaaaaaaca ctgactctgt tcaaactagt gttcattgga ttattgacct gtatgatgcc   175260
agagttggtc actggcttga ctaagttttc cattttttt ccctaagaga tattttgctc    175320
tcctgcagaa caagcttaat aacatcaact ttcaaggtag ttttggaaga tgagaaattg   175380
tgcttttgtt ttggcaactg aaaactttgt ccaactgata ctatgtgagg aaggtggttc   175440
aaggagtttt agggccctct tgtccttctt taaggctctg caaaccttat tttggaaaac   175500
ttatttttct ccctttttatt tgaatttcct cccagaaatt atcatcttgg tatcactgag   175560
acaaatctaa tatcaattta cttgcctgag aaattaggat tatgtctgtc cacataaatc   175620
gcaaggaaga aggtattctg tttatttcct gtccactgac tgatgctttc gtatcaccat   175680
gtagctgcac atactaaaat tataatacaa ggaaaaattt attctttca aaatcttatt    175740 cttcaaatac tattctgaaa gccatttggc accagtacaa aatttaactt aacgccccaa   175800
tctggaattc actgaacgca ttcaaactgt tagaaggaa ataaaaatg gaggacaaac     175860 acatttttgt tctgtttctg aaaacaatat ttaaggtcag aactgtttaa aaagaagcac   175920
tgctaaaaag ttataggatt cagagaaaca tagtattttt gtacagtatc ttataaatg    175980 ttcagacctc tctctacatt ctcttttacaa tgtaatgtct ctaagtgact ggtttcccaa   176040
taaactgatt ttaatgcctc ttctgctgtg gtctgtgtgc ttaattcatg cagaaacttt   176100
agcaggggat aatttttggc agaaatttct gctagctaat ggtttgcata ggaggggaga   176160
```

-continued

```
gggtcagtat gggaagggga tcattgagtt ccatctctac agaggttctg ggtcatctat  176220
ggctccaaat cattgtatct aatattctta tcctggtggg ttgggaaact ccagtagtat  176280
ctctttactg agcccatgat gaaatgatac ctttacccc  aaccaccctt tctctggatt  176340
cttcttgctt agttacatat gccttttcc tgccctcttg ctaacatgtg cccaatgaca  176400
tacttctaac ctgctaatat ttcttggaag gtaagctctc ttgcattctg ataattgtct  176460
atttgatttt aaaagccaga gcaccctgag gcacctctac ctagatagaa atagactagt  176520
atattggagt ttgctaatgc ttctgtaatg gcccatgcat tttactcctt ctgcttaaag  176580
aactttatgg cagattcatt taagcagagg agatctttat gaacttagaa gactgaaaac  176640
aaaattctgg ggcaactcca gctgaaggtg atttatttgg tctgattttg atgctgtatg  176700
ctcccctcag aaggtacctt cagtatttat attttgggca ctcgtatgct ctttgagtag  176760
tgcttgtgat gtaagtcatc aagtaaactt gcatttatca agcagccaca ttctgcttct  176820
tttcagagag tttgtccctc tgcatgtggc gcggatgacc acatgccaga ttctgaattg  176880
agtcatcccc agacagtgtt tctacataat ccaaaactgt catggtatat gtggagatga  176940
atgactgggt ttgttttcat tccataatga gccagtgcca ggtagagcag gtgtccgtgc  177000
ctggccctgt gtgtaggagc attgcatagt tacgctgaat gtctgtgtgc ctaacatctt  177060
catctccttt cctgtacgtc gtgcctatca tgttccaaaa cgtgagacag tggttgattg  177120
tgttccagtt tgtgtgcagt ttccttgcct gactttatt tttatgtttt tcctgttgca  177180
ttttcaacat ctattatttg gtcccacaat gttttgccg cgggttgacc attaaatgtt  177240
ccaaatagag ttgaattgac ctacacatta attctgcatt ttatgctttt ctagatctcc  177300
agagggagtc caatccctgt cctgtaataa ctgtagagca ctttaaagaa tcactgggtg  177360
ttaaaggcct tccgctgtat ccagacccct ccagagtacc tggcacaaag actcagaaca  177420
acttagaatc tgactacttg gccagagatg gcccttcaag caacagctca ttccacagca  177480
gcgaagagga agggactgac cttgaaggag acatgctgga ctgcagtggg tctcggcctc  177540
tccttatgga gtctgaagaa gaagatgaga gctgcagacc ccccccgggg aagctgggag  177600
gagccgttcc attcgctcca ccagaagtct ctcctgagca agcaaagaca gtgcaaggtg  177660
gaagaaagaa ccagtttcaa gccttcacac agccagccac tgatgggctc agtgagccag  177720
atgtttttgc catagctccc ttcaggagct caagggttcc aaatgatgac atggacattt  177780
tctccaaagc cccatttgtc tccaagagca gtatggctcc ttcccagcca gaggagtcag  177840
acgtgttttt gagagctcct ttcactaaga agaaaagcat ggaggagtta acagttatcc  177900
aatgcacctc ccaggagctg cctgcacaga ccggtctcct cagtcagaca ggtgatgtcc  177960
ccctgccgc  gggccgtgag agagctgtgt acacctctgt ccaagctcag tattccacag  178020
ctggttttgt gcaacagtct aacctcctgt cccattctgt acaagcagca gaccatctgg  178080
acagcatctc tcccagggga tcctgcctgg aatctggggg tcattctaat gacagaaaca  178140
aaggacctca gctccagaaa gaagctgtct caggccccat ggctggcaaa ccattccgcc  178200
cccagtcctt atccaagtat tcccgtcact atagcccaga agacgagcca agtccagaag  178260
cccagcccat tgctgcctac aaaattgttt cacaaaccaa caagcagtcg atagctgggt  178320
ctgtttctat cacatcccct tcctccagga ctacggagct gccagctgct gatccatttg  178380
ctctagcacc cttcccttca aaatcaggca agaaacccta ggagcaaaac ctgagcctca  178440
agcctcttgt ctctatccca ccctcaatac ccgccatggc actcccagct tagccttctg  178500
```

```
aagaagaaat attatcagtt cttatatttc aattccctgc gtcagagcag aatttcttga  178560
gtcaacaaac tcagttgcag tgatatttag ttgaagcccc tttaagttat gttcattttt  178620
gtttgtttgt ttgtttgttt atattgattt ctggacttgg aggcattttc atctccttca  178680
cagaggtcat ccacttccac caagaactct gctttccccc cgccccaccc acagaaactg  178740
tttaaatcct gaaatacttc ttcaccccaa tcccaagggg ccctattgt tgctagtttt  178800 aattcctgta gctcctgttc taagtcatgc ccatcgaaga atcaagatta gtccctccac  178860
taaatcaaga tttagtactc ttgaaaaggg gagatgtctg gaaagaagag caagataaaa  178920
accctgcaca tcaacaggaa gtataatcct gcagttacta ataattcctg tagaagcagc  178980
agctctagga gtctccagat ctgattctca gtctgtgtgc aagccaggct ggctctcgtg  179040
catgactgtc tatgggtgtg gaatgtacgt cagagcctgt gtagagatac aggcagatgg  179100
gctaactcct catgtctagt catgctggca gggctttccc cacatccatg cttttgaaat  179160
tagtgtgagt gtacaggttt gtgtgtgcat gtatacgtgt gtgtgcacag gaagcatttc  179220
cacttgaggg aaatcctgcc ccatcatgcc tacctccaca atgaaatcac tcgttttttg  179280
gtgtttgctc gcctaactga cttgaacccc attttattta tttagttttt ttctcatggc  179340
aaagtagaat acgttggaag gtgtagggaa atcctgctgg aactggtgtt tcagagtaaa  179400
tcttttttct ctccggaatt tcttgttttg ctattaacaa attatattta cctgattatg  179460
aaaaattaat tttccttata cattttcccc ttacaacact agaaaagagc accttgttac  179520
agttccggcc tctcagtatg tgggctaaat gccagcatta gggaattcat taatcatgag  179580
actaggctac aaactaggct tgcttgtttt ggggtggttt tgttgttgtt gttgttgttg  179640
ttgttgttgt ttccaaatct ctactgcctt ttgaggaaat gtaaatctga gacatggaaa  179700
taagtgtttg ggagaatgga aaagagctga atcaggtagg catgaaaact tttacattct  179760
ctatcctctt tagatgttga aataggccag acaggttaac tgatgttttt taaaattgtc  179820 ttttattttct ggaaagatct gacttattcc tagcttttt catacccttt attattagtg  179880
ccttaaaata aagctggcca ggtgcagtgc cacacacctg taataccagc attttggaag  179940
gctgaggcag gaggatcagt tgagcccagg aagttcaaga ccaactctgg caacacagcg  180000
agaccctgtc ccttcaaaaa ataaataaaa aaataggctg ggcatggtgg ctcacacctg  180060
taatcccagc actttgggag gccaaggtgg gcagatcaca aggtcaggag tttgagacca  180120
gcctggccaa catggtgaaa ccccatctct actaaaaata caaaaaatta gctggacgtg  180180
gtggtgcaca cctgtagtcc cagctactca ggaggctgag gcaggagaat cgcttgaacc  180240
cgggaggcag aggttgcagt gagcagagat tgcgccactg cactctggcc tgggcgacag  180300
agcgagtcta aaaataaaa ttaaataaaa taatgaaaaa aattagctgg gtatggtgac  180360
atatgcctgt agctactcag gaggctgagc tggaaggatc acttgagccc aggagtttga  180420
ggctgcagtg agttgtgagt ccagcctggg tgacagagtg agacactgtc tccaaaaata  180480
taataataaa aataaagcct gtatctcaat gggaagattt ctgctaaggc agttcaactc  180540
actggaaaga actgctgcat taggtttcaa ctttaatgct ttctgttact tctagtaaag  180600
gttaagtgat ttttccatta gctgtagaag tttggagagc tatttaccaa gccagatcaa  180660
tgatttaaaa attattggaa attcatctaa gaatcaagtc tgaatgccca attctattgc  180720
ggttgattag gtgtgatatt ctttaaagtt caggaatatt ggcagtaaaa aatgagcagc  180780
tacttttcaa tactttgtcc ttttttggtg gtctctgcct atttcaaatg tcctgatcaa  180840
aagataaata attggcactg tgccaaggtt tggttttcca actaaggttt caactgtgcc  180900
```

```
agaaacctat gtccttcact ttggtggatg ctaaatgtta ttctaagaat atgcttttc   180960 ccaattctcc tttctgattt ttatgtatta gtggatgcaa aattgtcttt ctagttgaat   181020
gaataatttc ggctaatgca cgtggaactt tgcaccccag attcttccca tggtcattat   181080
caagtgaagc cctcaaaaac atgagcgaag agcctagaaa tactcaggga gatttctcac   181140
cccaactcag aaatttttt ttttttttc aagacggcgt cttgctctgt cgctcaggcg   181200
ggagtgcagt ggtgtgatct cggctcactg caacctccat tttccgagtt caagcgattc   181260
tgcctcagcc tcccgagtag ctgggattat aggcacacac caccgcgcct ggctaatttt   181320
tgtattctta gtagagatgg ggtttcacca tgttggccag gttggtcttg aactcttgac   181380
cttgtgatcc acccaccttg gcttcccaaa gtgctaggat tacaggcgtg agccaccgca   181440
cctggcccag aaattctttt tttttttta aattattatt atactttaag ttttagggta   181500
catgtgcaca atgtgcaggt tagttacata tgtatacatg tgccatgctc gtgtgctgca   181560
cccactaact cgtcatttag cattaggtat atctcctaat gctatcccgc cccctcccc   181620 ccaccccaca acagtcccca gagtgtgatg ttccccttac tgtgtccatg tgttctcttt   181680
gttcaattcc cacctatgag tgagaacatg cggtgtttgg ttcagaaatt cttaaagtaa   181740
gagatcattc taattcccct ttccaaatat tcaggattat ctctgtaaca gcccagcaaa   181800 atgttttcc tttggttatt tgataattcc cttctaatca agtgactatt ttaattctca   181860
aggtgcaaat caggataaaa tcatggtgat tttactacat agttgaatac ttcgtcaagt   181920
atgagcttgt atcctttta aatttttcac tggaggccag gcgcggtggc tcacgcttgt   181980
aatcccagca ctttgggagg ccgaggtggg tggatcactt gagggtagga gtttgagacc   182040
agcctggcca acatggtgaa accctgtctc taccaaaaat acaaaaagta gctgggcgtg   182100
atggcacgca cctgtagtcc cagttactag ggaggctgag gcagaattgc ttgacccagg   182160
gaggcagact ttgcagtgag ccaagattgt gtcattgcac tccagcctgg gcgagaagag   182220
caaaactccg cctcaaaaaa aaaaaaaaa ttgtcactgg agacatgatg ggtggagact   182280
ctacatacct tctttgaata cagaaacgga tgcaaacaca tgcaaattac tttttttttt   182340 tttttggtg atgcatgaaa aaactttgac ttgtggatta cattaattat tagtaacagt   182400
tagattctgc cgacttgtat tacagtaggg tcttatttcc ttaaagagaa aaaaaatac    182460 agtcatgccc cacttaatga tgagggagac attcagagaa atgcatcctt aggtgatttt   182520
gtcattgtgt gaacatcaca gagtgtactt aacacaaacc tagatggcac ggcctactac   182580
ctacctaggc tatatggtcc agcctgttgc tcctgggcta caaacctgta cagcatgtta   182640
ctgtactgaa tactgtaggc agttgtaaca caatggtaag tatttctgta tccaaacatt   182700
ttagacatag aaaaggtaca gtaaaaatat ggtataatct tatgggacca tcatggtata   182760
tgtggtccat cattgatgga atcgttttta tgcagcacat gactgtatat aatcaacaaa   182820
caactctact ttcttgtttt cgtttgttgt gttttgctt tacacatttg atagggaaca   182880
tagaagttgt gacctttcat ttcagtggaa agcattgagc cagaatatat ttattcctaa   182940
accatcgagc cacacatgca ttgatgaacc ctgaaagaat ccacagtaat tgactaacag   183000
gcagtactga atgaaagatg tcatatgtgg tgaaaaatat ttaatatatc agtttcttgg   183060
gctcacatac agccctttag ttccaagtgc ttggttagat tagaaaatgg gatgaacaca   183120
atttgatgct gaagcagctg ctgagcagca cccaggagt ctaggtcata cgccctatat    183180
tgttttcggc ccacttattg ttgagttgaa aagtctcata tttgtagact agagtgtatg   183240
```

```
tgtttagagg ctcatgttgt atctgagttt tctctggcaa ctaagatctc tttctaaacg   183300
ttctagaaag atactggtat cttactggcc cattatttag taagttttag aatacatgta   183360
catcagtgtt ttcaactgct tggtggacat ttcactgatg cataatcaaa gtagcagatt   183420
ataatcatca gagtgatctg acaaggaaat tctgtatttg cttccataaa gaaaaataat   183480
caaaacatat atcagatata atatatatgc agtatatcac ataggaaatt ttattgtagg   183540
aaattagaga aggatgctac tcaattcatt ctctagcagg aagaatacag cttaaaaatc   183600
acttgggtcc ctttaataaa gaaaagtgtg attctgtgtt gtgtgtttgg aactgaaatt   183660
ggagaacacg tgccagtcga ctgtgaaatg gttgctggat aaaaccacag atgtggtttt   183720
atccgagaaa tgtgggactg aaattatttt gatgagaggt acataagaga gctgcagaaa   183780
agactgtagc ttctgaggag gcaggagtac cttgttaata tccaaaccac ccctgagttc   183840
taatgttcca actccaccta aacgaggaat tggaaacttt aaatggaatt atctaattta   183900
aattcttagt tttttctttg tctttctcag ctgatacttg tagttttgtt ttgtttttta   183960
accaccaaga acacttgcaa gtttgttact gaaaacatca ctaaaggaaa agaagagttt   184020
caaaatgctt gaaagtagt atgtggttgg gaattgtttt tgttcaagtc cctggaagtc    184080
ctcttggctt agctcccttg ttcctgttcc cacttcattt ccttacttaa cattcccta    184140 ttttgagcat gtcaataagt gcatgatgaa tggcacagtt gaatgatcat gttaacttta   184200
attgcttcct ttgttgctgt aaacagtttc ttgttaagtt tcagccaagt ctgtgacaat    184260
ctcaccaaat aagaatgaaa tgggcggggt gtggtggctc acacttggaa tcccagcact   184320
ctgggaggct gtgttgggcc gatcgcttga gctcatgagt tcaagaccaa cctgggcaac   184380
atggcaaaac cttgtctcta caaaaaatac aaaaattagc caggcatggt ggtgcacacc   184440
tgtagtccca gctacttggg aggcttaggt gggaggatgg cttgagcacg ggaggcgag    184500 gttgcactaa gccaagatcg tgtcactgca ctccagccca ggcaatagag ccagaccctg   184560
tctcaaaaaa acaaaacaaa caaaacatga atgaatgaaa tggctcacct tccctattat   184620
gaactagaag aaaggatgaa ggaaggttgg caggacccca gccttactct gtagtgacaa   184680
cccagaggta cttttcccgg aatgcagggt caagtttatg tgtgaaggga ctctagaata   184740
gctggtaaaa atggctacat ggtaaccatt cttgacttag tccagtattc ccataatttg   184800
taattccata aatttattct cagctgtccc ccagccattt ctaatagaag gatgtgtacc   184860
ccagttttga caatgttctt gaaatcaagt tagtgttacc tgcattgcat tataatggaa   184920
ctatatgtac atgttaaagg gatccgtttg attcctttcg gcaaggaatt gcaaaaatag   184980
tttttaccaa taccagttaa aataggatag gttagacttt gggggcaggg tgagacagtg   185040
cagccttttc actctgaaat ggcaaatcag ctgtactctt tgagtctacc agagattcct   185100
atttgagtgt gaatggggtg tgtgtgtgtg tgtgtgtgct cattcatctt catgctttct   185160
tccatggtgt taattcaagc tctcctaata aaggtatcca aagagtactg agaagtgacc   185220
ataggtattt ggcatgagta aatgtagttc cttttgccaa aaaaactctc aaaagttaca   185280
actggagttc ttcgcgataa aaggttgggg aaatcagcca tggctttagc cttgttccca   185340
agtacacatc ttcttatcca caaggatgaa actctgtagg gctcaccctg agggctcatg   185400
tgtggcattg agagggtagc agtgaccaga acaccacaag gcccacaaga tgttttgaat   185460
gagggaacat ttaatgtcat ttgttaggag atagaaacca aataataaag gacaaggacc   185520
acgctcattc cgtggagaag aggtgaactc ccctctgctga ctatttggaa tggactgaat   185580
gaggaggtct ctccagccag aaggagtatt gaggtcatca ggcctcagaa aacaatgtac   185640
```

```
acataatctc gggctgtgaa caagagaaag gagggggga aacatgaaag tcaatcttaa  185700 caattttgc aatacctctt atttgcagac cattggattt atgttattgc actctcggtg  185760
tgatttatcg tatgtatctg ataggtttta tgaattgttt tgagttgtaa actcctatac  185820
cctttattaa aatggaccta attaagtgat t                                185851
```

<210> SEQ ID NO 2
<211> LENGTH: 961
<212> TYPE: PRT
<213> ORGANISM: Homo sapiens

<400> SEQUENCE: 2

```
Met Lys Lys Phe Phe Asp Ser Arg Arg Glu Gln Gly Gly Ser Gly Leu
1               5                   10                  15

Gly Ser Gly Ser Ser Gly Gly Gly Gly Ser Thr Ser Gly Leu Gly Ser
            20                  25                  30

Gly Tyr Ile Gly Arg Val Phe Gly Ile Gly Arg Gln Gln Val Thr Val
        35                  40                  45

Asp Glu Val Leu Ala Glu Gly Gly Phe Ala Ile Val Phe Leu Val Arg
    50                  55                  60

Thr Ser Asn Gly Met Lys Cys Ala Leu Lys Arg Met Phe Val Asn Asn
65                  70                  75                  80

Glu His Asp Leu Gln Val Cys Lys Arg Glu Ile Gln Ile Met Arg Asp
                85                  90                  95

Leu Ser Gly His Lys Asn Ile Val Gly Tyr Ile Asp Ser Ser Ile Asn
            100                 105                 110

Asn Val Ser Ser Gly Asp Val Trp Glu Val Leu Ile Leu Met Asp Phe
        115                 120                 125

Cys Arg Gly Gly Gln Val Val Asn Leu Met Asn Gln Arg Leu Gln Thr
    130                 135                 140

Gly Phe Thr Glu Asn Glu Val Leu Gln Ile Phe Cys Asp Thr Cys Glu
145                 150                 155                 160

Ala Val Ala Arg Leu His Gln Cys Lys Thr Pro Ile Ile His Arg Asp
                165                 170                 175

Leu Lys Val Glu Asn Ile Leu Leu His Asp Arg Gly His Tyr Val Leu
            180                 185                 190

Cys Asp Phe Gly Ser Ala Thr Asn Lys Phe Gln Asn Pro Gln Thr Glu
        195                 200                 205

Gly Val Asn Ala Val Glu Asp Glu Ile Lys Lys Tyr Thr Thr Leu Ser
    210                 215                 220

Tyr Arg Ala Pro Glu Met Val Asn Leu Tyr Ser Gly Lys Ile Ile Thr
225                 230                 235                 240

Thr Lys Ala Asp Ile Trp Ala Leu Gly Cys Leu Leu Tyr Lys Leu Cys
                245                 250                 255

Tyr Phe Thr Leu Pro Phe Gly Glu Ser Gln Val Ala Ile Cys Asp Gly
            260                 265                 270

Asn Phe Thr Ile Pro Asp Asn Ser Arg Tyr Ser Gln Asp Met His Cys
        275                 280                 285

Leu Ile Arg Tyr Met Leu Glu Pro Asp Pro Lys Arg Pro Asp Ile
    290                 295                 300

Tyr Gln Val Ser Tyr Phe Ser Phe Lys Leu Leu Lys Lys Glu Cys Pro
305                 310                 315                 320

Ile Pro Asn Val Gln Asn Ser Pro Ile Pro Ala Lys Leu Pro Glu Pro
                325                 330                 335
```

```
Val Lys Ala Ser Glu Ala Ala Lys Lys Thr Gln Pro Lys Ala Arg
            340                 345                 350

Leu Thr Asp Pro Ile Pro Thr Thr Glu Thr Ser Ile Ala Pro Arg Gln
            355                 360                 365

Arg Pro Lys Ala Gly Gln Thr Gln Pro Asn Pro Gly Ile Leu Pro Ile
    370                 375                 380

Gln Pro Ala Leu Thr Pro Arg Lys Arg Ala Thr Val Gln Pro Pro Pro
385                 390                 395                 400

Gln Ala Ala Gly Ser Ser Asn Gln Pro Gly Leu Leu Ala Ser Val Pro
                405                 410                 415

Gln Pro Lys Pro Gln Ala Pro Pro Ser Gln Pro Leu Pro Gln Thr Gln
            420                 425                 430

Ala Lys Gln Pro Gln Ala Pro Pro Thr Pro Gln Gln Thr Pro Ser Thr
            435                 440                 445

Gln Ala Gln Gly Leu Pro Ala Gln Ala Gln Ala Thr Pro Gln His Gln
            450                 455                 460

Gln Gln Leu Phe Leu Lys Gln Gln Gln Gln Gln Gln Gln Pro Pro Pro
465                 470                 475                 480

Ala Gln Gln Gln Pro Ala Gly Thr Phe Tyr Gln Gln Gln Gln Ala Gln
                485                 490                 495

Thr Gln Gln Phe Gln Ala Val His Pro Ala Thr Gln Gln Pro Ala Ile
            500                 505                 510

Ala Gln Phe Pro Val Val Ser Gln Gly Gly Ser Gln Gln Gln Leu Met
            515                 520                 525

Gln Asn Phe Tyr Gln Gln Gln Gln Gln Gln Gln Gln Gln Gln Gln Gln
            530                 535                 540

Gln Gln Leu Ala Thr Ala Leu His Gln Gln Leu Met Thr Gln Gln
545                 550                 555                 560

Ala Ala Leu Gln Gln Lys Pro Thr Met Ala Ala Gly Gln Gln Pro Gln
                565                 570                 575

Pro Gln Pro Ala Ala Ala Pro Gln Pro Ala Pro Ala Gln Glu Pro Ala
            580                 585                 590

Ile Gln Ala Pro Val Arg Gln Gln Pro Lys Val Gln Thr Thr Pro Pro
            595                 600                 605

Pro Ala Val Gln Gly Gln Lys Val Gly Ser Leu Thr Pro Pro Ser Ser
            610                 615                 620

Pro Lys Thr Gln Arg Ala Gly His Arg Arg Ile Leu Ser Asp Val Thr
625                 630                 635                 640

His Ser Ala Val Phe Gly Val Pro Ala Ser Lys Ser Thr Gln Leu Leu
                645                 650                 655

Gln Ala Ala Ala Ala Glu Ala Ser Leu Asn Lys Ser Lys Ser Ala Thr
            660                 665                 670

Thr Thr Pro Ser Gly Ser Pro Arg Thr Ser Gln Gln Asn Val Tyr Asn
            675                 680                 685

Pro Ser Glu Gly Ser Thr Trp Asn Pro Phe Asp Asp Asp Asn Phe Ser
            690                 695                 700

Lys Leu Thr Ala Glu Glu Leu Leu Asn Lys Asp Phe Ala Lys Leu Gly
705                 710                 715                 720

Glu Gly Lys His Pro Glu Lys Leu Gly Gly Ser Ala Glu Ser Leu Ile
                725                 730                 735

Pro Gly Phe Gln Ser Thr Gln Gly Asp Ala Phe Ala Thr Thr Ser Phe
            740                 745                 750
```

```
Ser Ala Gly Thr Ala Glu Lys Arg Lys Gly Gly Gln Thr Val Asp Ser
            755                 760                 765
Gly Leu Pro Leu Leu Ser Val Ser Asp Pro Phe Ile Pro Leu Gln Val
        770                 775                 780
Pro Asp Ala Pro Glu Lys Leu Ile Glu Gly Leu Lys Ser Pro Asp Thr
785                 790                 795                 800
Ser Leu Leu Leu Pro Asp Leu Leu Pro Met Thr Asp Pro Phe Gly Ser
                805                 810                 815
Thr Ser Asp Ala Val Ile Glu Lys Ala Asp Val Ala Val Glu Ser Leu
                820                 825                 830
Ile Pro Gly Leu Glu Pro Pro Val Pro Gln Arg Leu Pro Ser Gln Thr
            835                 840                 845
Glu Ser Val Thr Ser Asn Arg Thr Asp Ser Leu Thr Gly Glu Asp Ser
        850                 855                 860
Leu Leu Asp Cys Ser Leu Leu Ser Asn Pro Thr Thr Asp Leu Leu Glu
865                 870                 875                 880
Glu Phe Ala Pro Thr Ala Ile Ser Ala Pro Val His Lys Ala Ala Glu
                885                 890                 895
Asp Ser Asn Leu Ile Ser Gly Phe Asp Val Pro Glu Gly Ser Asp Lys
            900                 905                 910
Val Ala Glu Asp Glu Phe Asp Pro Ile Pro Val Leu Ile Thr Lys Asn
        915                 920                 925
Pro Gln Gly Gly His Ser Arg Asn Ser Ser Gly Ser Ser Glu Ser Ser
930                 935                 940
Leu Pro Asn Leu Ala Arg Ser Leu Leu Leu Val Asp Gln Leu Ile Asp
945                 950                 955                 960
Leu

<210> SEQ ID NO 3
<211> LENGTH: 823
<212> TYPE: PRT
<213> ORGANISM: Homo sapiens

<400> SEQUENCE: 3

Met Lys Lys Phe Phe Asp Ser Arg Arg Glu Gln Gly Gly Ser Gly Leu
1               5                   10                  15
Gly Ser Gly Ser Ser Gly Gly Gly Ser Thr Ser Gly Leu Gly Ser
            20                  25                  30
Gly Tyr Ile Gly Arg Val Phe Gly Ile Gly Arg Gln Gln Val Thr Val
            35                  40                  45
Asp Glu Val Leu Ala Glu Gly Gly Phe Ala Ile Val Phe Leu Val Arg
        50                  55                  60
Thr Ser Asn Gly Met Lys Cys Ala Leu Lys Arg Met Phe Val Asn Asn
65                  70                  75                  80
Glu His Asp Leu Gln Val Cys Lys Arg Glu Ile Gln Ile Met Arg Asp
                85                  90                  95
Leu Ser Gly His Lys Asn Ile Val Gly Tyr Ile Asp Ser Ser Ile Asn
            100                 105                 110
Asn Val Ser Ser Gly Asp Val Trp Glu Val Leu Ile Leu Met Asp Phe
        115                 120                 125
Cys Arg Gly Gly Gln Val Val Asn Leu Met Asn Gln Arg Leu Gln Thr
130                 135                 140
Gly Phe Thr Glu Asn Glu Val Leu Gln Ile Phe Cys Asp Thr Cys Glu
145                 150                 155                 160
```

-continued

Ala Val Ala Arg Leu His Gln Cys Lys Thr Pro Ile Ile His Arg Asp
            165                 170                 175

Leu Lys Val Glu Asn Ile Leu Leu His Asp Arg Gly His Tyr Val Leu
        180                 185                 190

Cys Asp Phe Gly Ser Ala Thr Asn Lys Phe Gln Asn Pro Gln Thr Glu
        195                 200                 205

Gly Val Asn Ala Val Glu Asp Glu Ile Lys Lys Tyr Thr Thr Leu Ser
        210                 215                 220

Tyr Arg Ala Pro Glu Met Val Asn Leu Tyr Ser Gly Lys Ile Ile Thr
225                 230                 235                 240

Thr Lys Ala Asp Ile Trp Ala Leu Gly Cys Leu Leu Tyr Lys Leu Cys
            245                 250                 255

Tyr Phe Thr Leu Pro Phe Gly Glu Ser Gln Val Ala Ile Cys Asp Gly
            260                 265                 270

Asn Phe Thr Ile Pro Asp Asn Ser Arg Tyr Ser Gln Asp Met His Cys
            275                 280                 285

Leu Ile Arg Tyr Met Leu Glu Pro Asp Pro Asp Lys Arg Pro Asp Ile
            290                 295                 300

Tyr Gln Val Ser Tyr Phe Ser Phe Lys Leu Leu Lys Lys Glu Cys Pro
305                 310                 315                 320

Ile Pro Asn Val Gln Asn Ser Pro Ile Pro Ala Lys Leu Pro Glu Pro
            325                 330                 335

Val Lys Ala Ser Glu Ala Ala Lys Lys Thr Gln Pro Lys Ala Arg
            340                 345                 350

Leu Thr Asp Pro Ile Pro Thr Thr Glu Thr Ser Ile Ala Pro Arg Gln
            355                 360                 365

Arg Pro Lys Ala Gly Gln Thr Gln Pro Asn Pro Gly Ile Leu Pro Ile
            370                 375                 380

Gln Pro Ala Leu Thr Pro Arg Lys Arg Ala Thr Val Gln Pro Pro
385                 390                 395                 400

Gln Ala Ala Gly Ser Ser Asn Gln Pro Gly Leu Leu Ala Ser Val Pro
            405                 410                 415

Gln Pro Lys Pro Gln Ala Pro Ser Gln Pro Leu Pro Gln Thr Gln
            420                 425                 430

Ala Lys Gln Pro Gln Ala Pro Pro Thr Pro Gln Gln Thr Pro Ser Thr
            435                 440                 445

Gln Ala Gln Gly Leu Pro Ala Gln Ala Gln Ala Thr Pro Gln His Gln
            450                 455                 460

Gln Gln Leu Phe Leu Lys Gln Gln Gln Gln Gln Gln Pro Pro
465                 470                 475                 480

Ala Gln Gln Pro Ala Gly Thr Phe Tyr Gln Gln Gln Ala Gln
            485                 490                 495

Thr Gln Gln Phe Gln Ala Val His Pro Ala Thr Gln Pro Ala Ile
            500                 505                 510

Ala Gln Phe Pro Val Val Ser Gln Gly Gly Ser Gln Gln Leu Met
            515                 520                 525

Gln Asn Phe Tyr Gln Gln Gln Gln Gln Gln Gln Gln Gln Gln
            530                 535                 540

Gln Gln Leu Ala Thr Ala Leu His Gln Gln Leu Met Thr Gln Gln
545                 550                 555                 560

Ala Ala Leu Gln Gln Lys Pro Thr Met Ala Ala Gly Gln Gln Pro Gln
            565                 570                 575

```
Pro Gln Pro Ala Ala Pro Gln Pro Ala Pro Ala Gln Glu Pro Ala
            580             585             590

Ile Gln Ala Pro Val Arg Gln Gln Pro Lys Val Gln Thr Pro Pro
            595             600             605

Pro Ala Val Gln Gly Gln Lys Val Gly Ser Leu Thr Pro Ser Ser
610             615             620

Pro Lys Thr Gln Arg Ala Gly His Arg Arg Ile Leu Ser Asp Val Thr
625             630             635             640

His Ser Ala Val Phe Gly Val Pro Ala Ser Lys Ser Thr Gln Leu Leu
                645             650             655

Gln Ala Ala Ala Glu Ala Ser Leu Asn Lys Ser Lys Ser Ala Thr
            660             665             670

Thr Thr Pro Ser Gly Ser Pro Arg Thr Ser Gln Gln Asn Val Tyr Asn
            675             680             685

Pro Ser Glu Gly Ser Thr Trp Asn Pro Phe Asp Asp Asp Asn Phe Ser
    690             695             700

Lys Leu Thr Ala Glu Glu Leu Leu Asn Lys Asp Phe Ala Lys Leu Gly
705             710             715             720

Glu Gly Lys His Pro Glu Lys Leu Gly Gly Ser Ala Glu Ser Leu Ile
            725             730             735

Pro Gly Phe Gln Ser Thr Gln Gly Asp Ala Phe Ala Thr Thr Ser Phe
            740             745             750

Ser Ala Gly Thr Ala Glu Lys Arg Lys Gly Gly Gln Thr Val Asp Ser
            755             760             765

Gly Leu Pro Leu Leu Ser Val Ser Asp Pro Phe Ile Pro Leu Gln Val
770             775             780

Pro Asp Ala Pro Glu Lys Leu Ile Glu Gly Leu Lys Ser Pro Asp Thr
785             790             795             800

Ser Leu Leu Leu Pro Asp Leu Pro Met Thr Asp Pro Phe Gly Ser
            805             810             815

Thr Ser Asp Ala Val Ile Glu
            820

<210> SEQ ID NO 4
<211> LENGTH: 700
<212> TYPE: PRT
<213> ORGANISM: Homo sapiens

<400> SEQUENCE: 4

Met Asp Phe Cys Arg Gly Gly Gln Val Val Asn Leu Met Asn Gln Arg
1               5                   10                  15

Leu Gln Thr Gly Phe Thr Glu Asn Glu Val Leu Gln Ile Phe Cys Asp
            20                  25                  30

Thr Cys Glu Ala Val Ala Arg Leu His Gln Cys Lys Thr Pro Ile Ile
        35                  40                  45

His Arg Asp Leu Lys Val Glu Asn Ile Leu Leu His Asp Arg Gly His
    50                  55                  60

Tyr Val Leu Cys Asp Phe Gly Ser Ala Thr Asn Lys Phe Gln Asn Pro
65                  70                  75                  80

Gln Thr Glu Gly Val Asn Ala Val Glu Asp Glu Ile Lys Lys Tyr Thr
                85                  90                  95

Thr Leu Ser Tyr Arg Ala Pro Glu Met Val Asn Leu Tyr Ser Gly Lys
            100                 105                 110
```

```
Ile Ile Thr Thr Lys Ala Asp Ile Trp Ala Leu Gly Cys Leu Leu Tyr
            115                 120                 125

Lys Leu Cys Tyr Phe Thr Leu Pro Phe Gly Glu Ser Gln Val Ala Ile
            130                 135                 140

Cys Asp Gly Asn Phe Thr Ile Pro Asp Asn Ser Arg Tyr Ser Gln Asp
145                 150                 155                 160

Met His Cys Leu Ile Arg Tyr Met Leu Glu Pro Asp Pro Asp Lys Arg
            165                 170                 175

Pro Asp Ile Tyr Gln Val Ser Tyr Phe Ser Phe Lys Leu Leu Lys Lys
            180                 185                 190

Glu Cys Pro Ile Pro Asn Val Gln Asn Ser Pro Ile Pro Ala Lys Leu
            195                 200                 205

Pro Glu Pro Val Lys Ala Ser Glu Ala Ala Lys Lys Thr Gln Pro
            210                 215                 220

Lys Ala Arg Leu Thr Asp Pro Ile Pro Thr Thr Glu Thr Ser Ile Ala
225                 230                 235                 240

Pro Arg Gln Arg Pro Lys Ala Gly Gln Thr Gln Pro Asn Pro Gly Ile
            245                 250                 255

Leu Pro Ile Gln Pro Ala Leu Thr Pro Arg Lys Arg Ala Thr Val Gln
            260                 265                 270

Pro Pro Pro Gln Ala Ala Gly Ser Ser Asn Gln Pro Gly Leu Leu Ala
            275                 280                 285

Ser Val Pro Gln Pro Lys Pro Gln Ala Pro Pro Ser Gln Pro Leu Pro
            290                 295                 300

Gln Thr Gln Ala Lys Gln Pro Gln Ala Pro Pro Thr Pro Gln Gln Thr
305                 310                 315                 320

Pro Ser Thr Gln Ala Gln Gly Leu Pro Ala Gln Ala Gln Ala Thr Pro
            325                 330                 335

Gln His Gln Gln Gln Leu Phe Leu Lys Gln Gln Gln Gln Gln Gln Gln
            340                 345                 350

Pro Pro Pro Ala Gln Gln Pro Ala Gly Thr Phe Tyr Gln Gln Gln
            355                 360                 365

Gln Ala Gln Thr Gln Gln Phe Gln Ala Val His Pro Ala Thr Gln Gln
            370                 375                 380

Pro Ala Ile Ala Gln Phe Pro Val Val Ser Gln Gly Gly Ser Gln Gln
385                 390                 395                 400

Gln Leu Met Gln Asn Phe Tyr Gln Gln Gln Gln Gln Gln Gln Gln
            405                 410                 415

Gln Gln Gln Gln Gln Leu Ala Thr Ala Leu His Gln Gln Gln Leu Met
            420                 425                 430

Thr Gln Gln Ala Ala Leu Gln Gln Lys Pro Thr Met Ala Ala Gly Gln
            435                 440                 445

Gln Pro Gln Pro Gln Pro Ala Ala Ala Pro Gln Pro Ala Pro Ala Gln
            450                 455                 460

Glu Pro Ala Ile Gln Ala Pro Val Arg Gln Gln Pro Lys Val Gln Thr
465                 470                 475                 480

Thr Pro Pro Pro Ala Val Gln Gly Gln Lys Val Gly Ser Leu Thr Pro
            485                 490                 495

Pro Ser Ser Pro Lys Thr Gln Arg Ala Gly His Arg Arg Ile Leu Ser
            500                 505                 510

Asp Val Thr His Ser Ala Val Phe Gly Val Pro Ala Ser Lys Ser Thr
            515                 520                 525
```

```
Gln Leu Leu Gln Ala Ala Ala Glu Ala Ser Leu Asn Lys Ser Lys
    530                 535                 540

Ser Ala Thr Thr Thr Pro Ser Gly Ser Pro Arg Thr Ser Gln Gln Asn
545                 550                 555                 560

Val Tyr Asn Pro Ser Glu Gly Ser Thr Trp Asn Pro Phe Asp Asp Asp
                565                 570                 575

Asn Phe Ser Lys Leu Thr Ala Glu Glu Leu Leu Asn Lys Asp Phe Ala
                580                 585                 590

Lys Leu Gly Glu Gly Lys His Pro Glu Lys Leu Gly Gly Ser Ala Glu
            595                 600                 605

Ser Leu Ile Pro Gly Phe Gln Ser Thr Gln Gly Asp Ala Phe Ala Thr
    610                 615                 620

Thr Ser Phe Ser Ala Gly Thr Ala Glu Lys Arg Lys Gly Gly Gln Thr
625                 630                 635                 640

Val Asp Ser Gly Leu Pro Leu Leu Ser Val Ser Asp Pro Phe Ile Pro
                645                 650                 655

Leu Gln Val Pro Asp Ala Pro Glu Lys Leu Ile Glu Gly Leu Lys Ser
                660                 665                 670

Pro Asp Thr Ser Leu Leu Leu Pro Asp Leu Leu Pro Met Thr Asp Pro
            675                 680                 685

Phe Gly Ser Thr Ser Asp Ala Val Ile Gly Gly Ser
    690                 695                 700

<210> SEQ ID NO 5
<211> LENGTH: 302
<212> TYPE: PRT
<213> ORGANISM: Homo sapiens

<400> SEQUENCE: 5

Met Leu Asp Cys Ser Gly Ser Arg Pro Leu Leu Met Glu Ser Glu Glu
1               5                   10                  15

Glu Asp Glu Ser Cys Arg Pro Pro Gly Lys Leu Gly Gly Ala Val
                20                  25                  30

Pro Phe Ala Pro Pro Glu Val Ser Pro Glu Gln Ala Lys Thr Val Gln
            35                  40                  45

Gly Gly Arg Lys Asn Gln Phe Gln Ala Phe Thr Gln Pro Ala Thr Asp
    50                  55                  60

Gly Leu Ser Glu Pro Asp Val Phe Ala Ile Ala Pro Phe Arg Ser Ser
65                  70                  75                  80

Arg Val Pro Asn Asp Asp Met Asp Ile Phe Ser Lys Ala Pro Phe Val
                85                  90                  95

Ser Lys Ser Ser Met Ala Pro Ser Gln Pro Glu Glu Ser Asp Val Phe
                100                 105                 110

Leu Arg Ala Pro Phe Thr Lys Lys Lys Ser Met Glu Glu Leu Thr Val
            115                 120                 125

Ile Gln Cys Thr Ser Gln Glu Leu Pro Ala Gln Thr Gly Leu Leu Ser
    130                 135                 140

Gln Thr Gly Asp Val Pro Leu Pro Ala Gly Arg Glu Arg Ala Val Tyr
145                 150                 155                 160

Thr Ser Val Gln Ala Gln Tyr Ser Thr Ala Gly Phe Val Gln Gln Ser
                165                 170                 175

Asn Leu Leu Ser His Ser Val Gln Ala Ala Asp His Leu Asp Ser Ile
                180                 185                 190

Ser Pro Arg Gly Ser Cys Leu Glu Ser Gly Gly His Ser Asn Asp Arg
            195                 200                 205
```

```
Asn Lys Gly Pro Gln Leu Gln Lys Glu Ala Val Ser Gly Pro Met Ala
            210                 215                 220

Gly Lys Pro Phe Arg Pro Gln Ser Leu Ser Lys Tyr Ser Arg His Tyr
225                 230                 235                 240

Ser Pro Glu Asp Glu Pro Ser Pro Glu Ala Gln Pro Ile Ala Ala Tyr
                245                 250                 255

Lys Ile Val Ser Gln Thr Asn Lys Gln Ser Ile Ala Gly Ser Val Ser
                260                 265                 270

Ile Thr Ser Leu Ser Ser Arg Thr Thr Glu Leu Pro Ala Ala Asp Pro
            275                 280                 285

Phe Ala Leu Ala Pro Phe Pro Ser Lys Ser Gly Lys Lys Pro
            290                 295                 300

<210> SEQ ID NO 6
<211> LENGTH: 115460
<212> TYPE: DNA
<213> ORGANISM: Homo sapiens

<400> SEQUENCE: 6
```

| | | | | | |
|---|---|---|---|---|---|
| acggggggcgg | acctcggcgc | gctcccggcc | gctcgctggc | tccggggccg | cggcggctcc       60 |
| tctgccgggt | cgcgccggac | gactggcttc | gggcggcggc | cccggcggcc | tgtggacgga      120 |
| cgggtgggcc | gaggtacagg | ccccacggcc | gccgtctccc | gcttctgccc | gcgcagagtc      180 |
| cgcgccatgg | ccgcctcgcc | gggctcgggc | agcgccaacc | cgcggaagtt | cagtgagaag      240 |
| atcgcgctgc | acacgcagag | acaggccgag | gagacgcggg | ccttcgagca | gctcatgacc      300 |
| gacctcaccc | tgtcgcgggt | gagggcccgg | gccggcgcgg | gcggggcgg | ccacggccgc       360 |
| gggcgggacc | cgcgcggcgg | gtgagaggtt | gcgggccaa | ggcgatggcg | gggccgggcg       420 |
| ggggccgcgc | ccgggaaccg | gcggctggga | ggggaccgg | agcggccgcg | gcctcggcgt       480 |
| ttccccgcct | ggcgacaccc | gctagccgtt | cgcgatcccg | ggctgaggtg | ggagggtcgc      540 |
| ccggccccgt | gtgcgggaag | atgggcaggg | gtgaagcccg | tggaggcggg | cggccgtgcg      600 |
| agggcggcct | gaggggggagg | aggacgagga | gccccgagag | gaaatcgcaa | acagctcgga     660 |
| ggccggccgg | gtggcgcggc | gcggcttctg | gtcgctccga | acatccccca | ccatcgagcc      720 |
| ctgctgttct | gccggcgtgg | aaggccgcgg | gcaccccagg | gtcccacgcg | ctcgtggggg      780 |
| gagctctgtg | cacaagtcca | tccagggccc | ggccctgggg | tggctcgggt | tgttggaacc     840 |
| acgacgggat | ccgtgtcga | gtgtgaggct | ctgctccttt | tactccttgg | aggtgcttta       900 |
| tcgggtccag | tttactttgt | tcggcccggg | atatttagtg | agaactgaca | agcgtcgctg      960 |
| gtgactggag | agggacctgg | aggaatgagt | aaggcgcgag | ccgggacaaa | cacctggaga     1020 |
| ggttaggtaa | ccgctgagtg | aggcagtgga | ggatggagag | ccaaccggag | tgtccgcgca     1080 |
| gggttgcaga | gaaggggggt | cagcaggagt | ggggctggcc | ttgaggatcc | tgaatgctga     1140 |
| ccttggagga | ccatcgggag | gatggggag | gatctgcaga | ttctggggga | ctgaggcggg      1200 |
| ggagacagtt | tgaaggagag | ctgagagcag | agttgcaaac | cagctgagtt | gcagacacat     1260 |
| tattttttgg | ccagcgcagt | gtttgggaaa | aattattgaa | tctgttgcca | gaattttaa      1320 |
| attggaagac | ttccacacaa | aatccaaatt | tccgtattat | ttatttatta | ttatttatat     1380 |
| atgttaaaaa | ttgggagacc | tggtaacact | aattctgaat | tcctacatga | cagctaccga    1440 |
| cctgctggag | ctgggtgatg | atgaaaggga | gctgagctga | gctccctttc | aaatggagta    1500 |
| agaactctag | tttgccaccg | tccactctct | gtcacagtcc | cccaagggga | gattaggtga    1560 |

```
cagttgccat ttatactcat gatggtgttt tctttcagtg aagttaagga aaaagtgaaa    1620
tatttcctgt acttacattt ctgttcacat tgagaaaaaa tatatatata gagagaaaga    1680
agctgaagat ttcaagaaaa tgttttctta taccctatca gcttcactca ttttttacct    1740
gcctggcatc cactggcatt tacatctgtg accttggtta gattcagaga tgaactcgat    1800
aagctcagag cacgttgaaa agaatgggtg ggtgaaagct gaggattagt gttgggcct     1860 gtgttgttat gtgtttttaa atacatactg tacattgttt atgtacaaat acatgcactg    1920
tatatgtctg tatacctatg gcggatccaa tctttcaccc aattcatgaa tcttctttaa    1980
aatatccctg acaggtgagg ccatgagtaa tgtacagact ctcttttaaa agcaaaaatt    2040
tttcacagat cctcactgtt tacttacttt caagtaaaaa aaaagtgttt acttacttta    2100
gagaccctgc tatagctcag ggtctcttga atttagcaag cctaatcaac tgtggcccat    2160
atgataattc agtcaccact ttattctaat tactacaaaa ttatggtgtc attttgccct    2220
tcacctggta cagggaatca tttacatatt aattctgccc gtgttttctt cttggccagt    2280
taccagtaaa gtaacactgc ttggctccac cgtgttcata aacacatctg taatgataa     2340 cactgaattt ggctactaat gtttgcttat ttaaaaatct taagggttat tttcatgaag    2400 aaaatcacaaa attagaacac ttctcataga gaactcttag attcccagca tgtctatgaa    2460
gaatgcgtct ctaaggatcc aaagatccca gttggaggag tatctgccta gttcataatt    2520
ggtaactggg tggcagatat actgactttt cattactagc ccatgacaga catgctaatt    2580
cctgactttt cattactagc ccatgacaga catgctaatc gatagggcag acattactga    2640
tctatctaga tgctctttcc cctctgagcc tgtgttggga ttcaagttct tctctacatg    2700
atcaaagcaa tccttcagag ttggccttac ttacctattc acctaggcgt tacttatcct    2760
attcacctag tgggtaggat agactagact gtagaggatt ttctctagct ttagaagtcc    2820
ggcattatca ggaagcagtg ggaaaatttt gagaagggag tactaggagg aggagttgag    2880
tggtggtacc tggaatggta aagagaggga ggaaagtggg gtcgggcgtg gtggttcacg    2940
cctgtaatcc cagcactttg ggaggctgag gcgggcagat cacgaggtca agagatcgag    3000
accatcctgg ccaacatggc gaaaccccgt ttctactaaa agtacaaaaa ttagcctggc    3060
atggtggcgt gcgcctgtag ttccagctac tcgggaggct gaggcaggag aatcgctcga    3120
acccaggagg tggaggttgc agtgagccgg gatcgcaccg ctgcactcca gcctgggcga    3180
cagagcaaga cttcatctca aaaaaaaaaa aaaaaaaaa aaaaaaaaaa aaaaaaggcc    3240
gggcgcggtg ggtcacgcct gtaatcccag cactttggaa ggccgaggcg ggcagatcac    3300
gaggtcagga gatcgagacc atcctggcta acacagtgaa accctgtctt tactaaaact    3360
acaaaaaaat tagccgggca tggtggcggg cgcctgtagt cccagctact cgggaggctg    3420
cggcaggagg gaggctgcgg caggagaatg gcgtgaaccc ggaaggcgga gcttgcagtg    3480
agccgagatc gcgccattgc actccagcct gggcgacaga gcgagactcc gcctaggaaa    3540
aaaaaaaaaa aagggaagaa agtggttgca ggtatgcctg ggaagaggct gttctgttgt    3600
tcatttatta atgtattcat ttgtcagtat ttgagtgcct actttgttgt taatgggtg     3660 tgtgtttgtg agggagaaga gtgaaaacat ggggctgtcc tttaaagatc ttactgattt    3720
gttccacaaa tttacttact gagtgagtcc ttagtgtgtg ccaggggtta ggatggacac    3780
tgggtatata gtaatgagca agcaaaaacac agtgtcccag tggattttag gatttaatga    3840
ggaagacatt catttaataa gtaaggacac atttggtgta atatcaccaa aacagaagta    3900
ggtggagctc tggacctgta tggtagggaa ttctcacctc ttccagtggc ctaaaggctc    3960
```

```
aggggagtg ggggaggcat tcgagggttt gtgtgttgag ggagggaata tgttgcaggt    4020
acagagaaca gagattcagt aaaagaggat gaggaggga tgtgagatga ggctggaggc    4080
attcataggg atcaggttgt agagacagga tttggaactt gatcttaagg gcaatgggaa    4140
gtcactgaag gggttaaact atgtgagatt tgcttttta aaagattcct ctagctccag    4200
cgtggtgggt agaagagagg aggaggagga ttttagtagg agatgtgata gtggcattta    4260
ctaagatggt ggcagtcggg aggcagagcg gtgagcagat tgatacttag gaggtggaaa    4320
gggccagatt ttgtgaatgg gtgaggaagg tgagaaagag ggagggctgg aaccatttca    4380
gggtgttctt cattaagtgg acactggcag gagcaggttt tgcggaaat gctgagtttg    4440
aggtgcctgt gaggcacata agtagagatg gtccagcagg cagctgttta gatggttttg    4500
cagctcgaga aggaaggctg agctactgag aaaaatgggg gaattttgt tatgtagcca    4560
cagaagtaga tttggctgcc taggaagaat tgatggaaca gatattgtaa actggtggct    4620
taagttctgt attttgccct ctaacatgtt tttggttttg gcccaaaatg tggttagttg    4680
gttggttggt tggttttaat tagggctaac aatgaatatt gggattttat agtaaaatct    4740
ggactttggt ttcttttgaa aaatgagata atccaacgac actcacccga catttctgga    4800
cggcaccagt tgcctggagc tgaatggtgg ctgccccatt agaaaggcca tggatgtggt    4860
cttcagttg ccacagtccc taccaccctc taaggtattc tttgcagtga tcccagactg    4920
cttcacttag attccctgct tggcagctgt aggcatttga gtttgttacc cttgtcagaa    4980
ggtgaactgt gaggccaggc gcggtggctc acgcctgtaa tcccagcact ttgggagacc    5040
aaggcaggcg gatcacctaa ggtcaggagt ttgagaccag cctgaccaac atggagaaac    5100
cccgtctcta ctaaaaatac aaaaaattag ccaggcatgg tggcgagtgc ctgtaatccc    5160
agctactcag gagactgagg caagagaatc gcttgaacct gggaggcgga ggttgcagtg    5220
agccgagatt gtgccattgc actccaacct gggcaacaag agcgaaactc cgtctcaaaa    5280
aaaaaaaaa aaaagaaag tgaaccatga ggagggccta ggagaagcca aaggaactaa    5340
ggaactacac catttgaaag ggaggtggag gagctggcca agaaggcttg aagagcaacc    5400
agaggggcag gagaaagcca ggagtactct tatgaagagg agggaatgcc gaccagctga    5460
gcctagtgct gctgacttgg tctgacacaa aagatgtgtc ctttggtcta gtcatgtgga    5520
ggtcatcaga ggaggtcatc agtaacctcg gtgagagatg ctgtattctc agggtgctgg    5580
gtgaaaggct aattgtgaga cgttgaggag tggacggggg tggggaatgg agatagggtt    5640
ggaaacttat tccagaagtt tggctgtgaa gagcaacttg tgttgaggaa ccagaggact    5700
aactcagcat atcaccctgg agtgttgatt ggacttgaat atttgcgcag actcattatt    5760
ttcatgtgaa aataaaccaa tgataagaca tagatatgtc atagattagc gagctctcag    5820
gatggaggag agagagaaga tggaaatatt aggtttgggc taaatattga ggactttcct    5880
tttgcgaggc actgtaatcc ctttcacatg ttgttatctc acatagtcct caaaatgagc    5940
ctatggtgtg tatatctgga attttcctca tttttgtgga tgagtaaact gaggcttaga    6000
gaggcatggt tgcagagctg gtaagtggta gagccagggt ttgaatctag ctatcacagt    6060
gaatgtctgt atacttagct actttaattt ccctcataag gatcttcagc tgctttact    6120
ccctgctgta aggtatcagt atcatttgtt gaaaagactt ttctttgccc attgaattgc    6180
tgtggcaatt ttgttgcaat cagttggcca tataagtgtt ggtttatttt tagactcttt    6240
tctgttccag tgatttgtat atctgtcttt ttgacaatag cacactgtct gtatattata    6300
```

```
gctttataat aaggcttaaa acctggtaat ttaagtcctc taacttagct cttttttgaaa      6360 attgctctgg ccaggtgcca tggctcatgc ctgtaatccc agcactttgg gaggctgagg      6420
cgggtagata gcttgagccc aggaattcta gaccagccta ggtaacatgg tgaaatccgt      6480
ctctaaaaaa aaaaaacgaa aattagctgg gcgtggtggc gcgtgcctgt atttgggagg      6540
tggaggttgc agtgagctgt gattgtgaca ctgcactcca gcctgggcaa cagagaccct      6600
gtctcaaaaa aaaaaaaaaa ttgctctgac tattctaggt catttgcaca tccataaatt      6660
ttagaattat cttgtcaatg tctctgaaag gacccgctgg gattttggat tgtaatcgtg      6720
ttggctattg tgagactttt ctcaaaaagg aattaatgag gcctggatct catttcctgt      6780
aggcattaaa gaaaattcca ctaagatgtg tgactgtagg ccaaaggtca ctaactcagt      6840
aagtgaggca ggtaaggaaa atgaatgag gggccaggaa tgagatgatc atggcagctg       6900
atcctgggcc atcgtgaagg gataataggg tacagtgagg acttggcaaa cacgatctaa     6960
gggggtggcc tcttctcagc ttcatccagc gatgccatgc aagaacatgg gttcagtgtt      7020
gtctgatctt tcaatcagga gaagttggaa atccatattt ttatgcagtg tcctgatttt      7080
ttcaattgaa atttaataca ctgaatgggt caacatctgg tgggtaaaca gaacactcta      7140
ggtgaaatgt ggcctatggg ctgccagtct gtgacctcgg ccttaggcta atcattcttt      7200
ggttcacatg ttcatcatct gtaaacatga aggtgttgaa gacagtctca aagttctttt      7260
tctagctcaa tgagtctaaa tttcaaagga ggaaaatgtc aaaataactc agagtttgaa     7320
gaggtagctg agatcagcaa taatgataat atcttaagtt gaccagagct ttacatttga      7380
cataccactc ttgtgtctgt gtcatttaat cctcacttta tcttgtgcag gaggcgtcag      7440
agttgtttgc ccaaccacac gggagttgca ggttacaaag tcacatcatc cgattccagg      7500
tccagtgctt tttgtttttt tagagtctcg ctctgtcgcc caggctggag tgcaatggcg      7560
ccatctcggc tcacggcaag ctccgcctcc cgggttcatg ccattctcct gcttcagcct      7620
cctgagtagt tgggactgca ggcgcccacc accatgcctg gctaattttt ttgtactttt      7680
agtagagaca gggtttcacc gtcttagcca ggatggtctc gatctcctga cctcgtgatc      7740
cgcccgcctc ggcctcccaa agttctggga tttacaggta tgagccactg ctcctggcct      7800 ttttttttgag acagagtctc actgtgtcac ccaggctgta gtacagtggc atgatcttgg      7860
ctcactgcaa cctctgcttc ctgggttcaa gcaattcttc tgcttcatcc tcccaagtag      7920
ctaggattgc aggcatgcac caccacagct ggctaatagt tagtagagac ggggtttcac      7980
cgtgttggcc aggctagccg tgttcttttt taacagtctt tgaaggcttc ggaaataggt      8040
gctttgggag ggagagcagt tatgggggat tgtgagacgg ccttcagctc agttgagggc      8100
aggtccctat ctggatttat aacttagttt ggttgaagtg tcaaggcttt tgggtaagag      8160
ttgaagcctt tgtgagaact ctctgaaggc aggaacttta gcatacattc atcttagtaa      8220
gccagtgcct ggcatactac ctgacacaca gttaagtttt tgtatcagta aatcaatgga      8280
taaattgatc cttcaaaaaa gaaatcaaag ctttaaatc aagatggctg agaattttgt       8340
ccagagaatt tcaagaatag tcagatgctt ctgataagta cttttagaat gttaagattg      8400
aaagctgaga gactttattc ctataactcc actcctagat ggaaaaaaca ccatgtcgtc      8460
ctcctcatgt ttgactctga gatttgggtt ttgattaata ggttataact gtctccctgt      8520
gcagtacatt taagaaatca aatacagcag gtataaggga agttaaagcc actgaaggat      8580
ttcgtatgcc tttaaaattt ccaaacaagt ataagtcttt atcttttgag aatacatatt      8640
gaaatatgga gtgataccat gtctgaaatt tctgtcagtg aggcactgcg ggtagtggag      8700
```

```
agggtaaaga tgaaagatga ttgtatataa gttggtaatt tttaagctag aagatggata    8760
gatgggtttt cattatactt gtctttattt cacatatact atttgaaatc tttcataata    8820
aatgtaaaaa ggaaattatc agagagcttc ataggttcaa caatgctttt ggtaaaccaa    8880
acttcacctt tttttttttt ttgagtttgt aattagtatg atcatcgagg gaaagatggg    8940
acaaaggaaa agagcatggc agaaatgggc atatgggctt tgaggctgac agccgtggct    9000
cagcctcctg ctagccacgt ggcaagtcac tgaacttccg agtctgggtc tccaggtctg    9060
taacagcagg agagtacagt ctcatttgca tggttgtggg gaggattagg gatgaagtgg    9120
gccaagtgtc cgagaacagc acctggccca tcctagggc ttagatctgg tagtgtttta     9180
ttattgttag agacagagag tgatgaaggg taaaaatctg ccccagggct ctcgtctata    9240 acccttctt ctctatatga attatagtgc caagggttat gtaaccatgg agctaattta     9300
ttattttaga aacagaactc ttaaagacca gatcagacca ctttgagatt tacaagaact    9360
gtaaccagtt tattgctttt tgaaaaatga agtaaggaag aacttacaaa gaaaagcata    9420
ttaaaatggt gggatgccat tttataccta ttgaattgac ctccttcctt accccaatta    9480 atggtaaatat ccaatatcaa tgagttttt tggtgaaact tttctcatat gtatattata    9540
aactctttgg gaaagcattt cggcagtata cgttgagagc caccaaaagg cccatatcca    9600
gagatttagt aatcacccctt tggaaggtgt tctaaggaaa taattcagaa gaactgttat   9660
atacccacta aaaattactc tgtaatagca tagaaaaggc ttatgatgag catgctaggt    9720
tgtacctatc ttatgatcac agctatgcag ttcttaccat aaatgtaaac ggaggctgga    9780
aaagagcatg aagaagggaa aacagctaat gtgttagggt tgtggatagt agcttagttt    9840
ttctttcaga aattctttta ttgttgttaa agattatgcc agtgtatcca aacatacaca    9900
ctcaaagacc ttgcaagagg acgttactat catggtatat gggacattg gaacatgggt     9960 aagctctttc cgaaaataga gtaatcaaaa cccagaaagc accggaaacc ttgagggtgt    10020
gatcacttac gtcgagaaga aattgaaaca agactttcat tcttgaaccg ttcccctaca    10080
aaatactata ctttgatgct tctttagatc tttgctgtta cctctcagcg ttcttaaatc    10140
actttgtttc caggttcaat ttcagaagct tcagcaactg cgccttacac agtaccatgg    10200
aggatcctta ccaaatgtga gccagctgcg gagcagtgcg tcagagtttc aggtacctcc    10260
agatatgtac tttcttgaag ctgaatggag tgtaaaaaat agacaaagat tatcactaaa    10320
aagatgagat cttgaaggat aagctgggcc taggtacagt tcagtcttct tttggaaagt    10380
ccattaatat tctctctcat agtttctaca gcatacgata gtgttatttc acaaatggct    10440
gaaggcagca ctggcaagta gaattataac acaagcatat gtaatttaaa atgttctagt    10500
agctacatta aagaagaaga aacacgtggg gttaatttta atatctatat ttttcaaaat    10560
gcagctttct catctataat tttaatatta cttaaataaa tgtttggctg gcatggtgg     10620 ctcacacctg taatcctagc actttgggag gccaaggctg gcagatcacc tgaggtcagg    10680
agttcgagac cagcccggtc aacatggtga aaccccatct ctactaaaaa tacaaaaatt    10740
agctaggtgt ggtggctcac agctgtagtc ccagctactt gggaagctga ggcatgagaa    10800
tcgcttgaac ccaggaggcg gagggtgcag tgagcagaga tcataccact gccctccagc    10860
ctgggcgaca gagcgagact gtctcaaaaa aaataaaaa taaaaaaata aatatttaat     10920
ccaatatatc caaatatga tcattttaac atgcaatcag cataaaaaaa ctgagaaatc     10980
tcacatactt ttctgtgtac tatgtctttg aaatctgttg tgtatttat actcaaagca     11040
```

```
tactttaatt tggaccagcc gcatttcact agtttcatgt ggctggtggc taccacatgg    11100
ctcagtgcag gtgtaagaca cagataagta gtctgtattg catttagatt actgcagtgt    11160
cctcgggtgc tttcatcgtt cacatcagtg gaaagccttg ttcaaaccaa tgtggaattg    11220
gtgtttcaga caatggtata tggcactatt gttaagacct gaattagacc tgcttagata    11280
tcccaatctg tgaaacatta ggagcctgtc attctaatta tgcaatttaa gattcggtgt    11340
taaagttgag atataaactt taagatgaag cattaattga ttgtttggat gcctgaccat    11400
tttaaaagca ctgtcttatt tctttgtggt agaaactggg ttcactttt tgatgatgtc     11460
aaataaagcc aaatgtatta tttaagttgg ggacttccat ttgagagtgc tgataggaac    11520
tccaaatata atggtgatta gaaaaagtac tacatgaaca tatttgtacc ctattgcacc    11580
ggaatcttgt cttcaatata atgcaaatgg actctttacc atattactgc ctgtattaga    11640
gatctacctt catatatcaa actacctat atattaaccc actgggttat ttagtatcca     11700
aataacatag gtctctgcct tatgcgggat ttcatacttc aggaaataca gcattgtgca    11760
agtttgctgt gtctgagatc ccaattttgt gctactttat tgtcaacttt agaggaatat    11820
agaatttact atgatgttcc cctccggttg cattggggaa tgggataaaa tgataatcct    11880
tggccttccc aggattcttt ttttcttttt tttttttga gatggagtct cactctgtcg     11940
cccaggcagg agtgcagtag tgcaatctca gctcactgca acctccatca cctgggttca    12000
agcattctcc tgcctcagcc tcctgagtag ctgggattac aggcgtgcac taccacgccc    12060
agctaatttt tatattttta gtagagatgg ggtttcacca tgttggtcaa ttggtcttga    12120
actcctgacc tcaagtaatc cacccacctt ggcctcccaa agtgctggga ttacaggcat    12180
gagccaccgt gcgtagcccc caggattctt ttcatactgt ttttgttttg ttttgttttg    12240
tttttctttg caacagtcac aaacttacac aatacttgga agtatagtcc acttaatttt    12300
tttttttttt tgagaccgag tctcattctg tcgcctaggc tggagtgcaa tagcgcgatc    12360
tcagcttact gcaacttcca gctcctgagt tcaagagatt cttctgcctc agcctcccaa    12420
gtagctggga tcataggcgt gcgtcaccac gcctggctaa ttttttgtatt tttagtagag   12480
acagtgtctc accatgttgg ccaggctggt ctcgaactcc tgacctcagg tgatccgccc    12540
atctcgtcct cccaaagtgc tgggattaca ggcatgaact actgtgccct gctgacataa    12600
cttttttttc acttgggaat aagttcctga cctgatgccc catcaccccc taatatttca    12660
ctgtgttttt cctacaagca aagacgttgt tctatataac caaaatacag ccatcaagat    12720
aagaaaatta acagtgatcc attattacaa tctgatcttc agactgcatt caccaaatgt    12780
ccccctgctg tcctctgtag caaaaggatt cagttcagaa tcacatgcag ttattgcctg    12840
cagtctcctt cagtctggaa cagcttttca gccttttatt tttgacatta attcaagtac    12900
tcttaacgtt tgtgatcctg tcacatttga agattacagg ccagtttttt tgtagatata    12960
accctcaat tggggtctgc ctaatgtatc tttgtgattt gattcagact atgcatcttt     13020
ggcaggaata acgtagaaga agtgaggctg ttatggtatc acattaggga catgattttg    13080
atgtgtcctg ttaatgatga tgttctcttt tatcaattaa ggtggtgtcc accaggcatg    13140
gtggctcaca cctgtaatcc cagcattttg ggaggctgag gcaggcagat cgcttgagct    13200
caggagtttg agccagcctg ggcaacatgg agagaccctg tctctactga aaaaaaaaaa    13260
aaaaggccag atgtggtggt gcacgcctct ggtcccagct acttgggaag ccgaagtggg    13320
aggattgagt gcttgagtcc agagagcaga gatttcagtg agctcacatg gggccacagt    13380
actccagctt gggtgacaga gccaaaccct gtctcaaaaa aaaaaaaaaa aaaaggtggc    13440
```

```
ctgtctgtca ggcttcccca tttaaagtaa ctcttttccc ctttgtaatg aataaatatt   13500
ttgcgaggag atactttatc ctgatcttca ttaaactttc aatctataca ttcatttttt   13560
atctctcggt atatggtttt atgattttct attttattca atctattata atctattatt   13620
ttatttattc attttgaag caatgaaagc acagatttat tgaaataaaa gtatgctcta    13680
cagagtaaga gtgggcttga agcgcaagct aatctattat ttttattttg atcttcacat   13740
tctccccaat taggctggtg ggagccctct tccgaactga gaaaaattct tgaaaaactg   13800
aggagagtcc cagagcacag attttttta agtaaatgtt tttgaggtat tatgtaaata    13860
caatataatt tataccttt ttaggtatac agctctttgc catataatca ccaccacaat    13920
gaagatgtag aatagttcca ttaccccaaa aggttccctt gtgtctgttt gtaagtattc   13980
tccatccccc acctccagcc tctggaaacc accatctgta gttttgactc ttccagtgtc   14040
ctattagtgg aatcaaatgt ccgtagtctt ttgagttttt ctctcactta gcatttgaga   14100
ttcatctggg tggttgcgtg tgttagtttc ctagggctgc tgtaacaaag taccacaaac   14160
ttagtgcctt aaaacaacag aaatttattt tctcatgttc tcatgttctg agtccagaag   14220
ttggaaatca gcatggtgtc agcagcacca tgaatgctct ggggaagaat ccctccttgt   14280
ctcttcctag cttccgtggt ctgcggcagt ccttaacttg tagctgcatc acttactctc   14340
tgcctctgtc atcacacgac tttcttcatt gtttgtctgt gtctgtgttt aaatcttcct   14400 ctccttttc ttataaagaa ctagtcattg gatttagggc ctaccctaat tcaatatgat    14460
ctcacctttg cttgattaca tctgcaaaga ttctgttttc aaataaagtc atattcacag   14520
gttctggggc ttaggacttg aagatatctc ttttggtggc cataatttaa cccactacat   14580
tgcattgatc agtagttcat ttcttttat tgctgagtag aattccattc tatggatgta    14640
gataatttat gcattcatca gttagttgat gggcatttgg gttgtttcca ccttttggca   14700
attatgaata aatattctat aaacattcac atacagtttt tatgtaagta gctagtagtg   14760
gaattgctag atcatacagt aagtgtatat taactttagc tttataagaa atcgccaagc   14820
tgttctccaa agtggctcta ctgtttcaca ttcttaccag cagtgcatga gagttccagc   14880
gaccctgtat ctgctctagc acttggtatt tcagagtttc aaaaaaatgg tggttaaaaa   14940
acagaacata aaatttacca tcttaaccat ttttaaagt agtttattgg tatcttctaa    15000
aaccattttt aaatgtatag ttcagtggta ttacatacat tcatattgtg caaccaatct   15060
ccagaatttt ttcatctgac aaaactgaaa ttctatgccc attcaataag aattctccat   15120
gttcccttcc caccagcctc tggcaactac tgttttttct gtctctatga ctttgactat   15180
tctaagtgcc tcatatgagg gaaatcatat actatttgtc ttttttgtga ctggcttgtg   15240
cttagtataa tgtcttcagg gttcacccgt gttatagtct gtgacatgat ttccttcctt   15300
ttcaaggctg agtaacattt cattgtatgt ggatgccaca ttttgttcca ttcatccgct   15360
aatggatact tgggttgccg ccacctcttg gctattgtga ataatgctgc tatgaacatg   15420
ggtgtgcaaa tatctcttca aggctctgct ttccattctt ttgggtacat actcagaagt   15480
aggattgctg aatcatatga caattgtggt tttaattttt ttttttttt ttgagactga    15540 atctcgctct gtcgcccagg ctggagtgta gtggcgtgat ctcagctcac tgctgcctcc   15600
gcctcccagg ttcaagcagt tctactgcct gagcctcctg agtagctggg tttacaggcg   15660
cgccccacca cacctggcta attttttgttt gttttttttt tttactttg agatggagtc    15720 tcactctttc gcccaggctg gagtgcagtg gcacgatctc ggctcactgc aacctccgcc   15780
```

```
tcctgggttc aagcaattct cctgcctcag cctcccaagt agctgggact acaggcacct    15840
gccaccacgc ccgggtaatt ttttttgtat ttttagtaga dacggggttt cactgtgtta    15900
gccaggatgg tctccatctc ctgactttgt gatccgcccg ccttggcctc ccaaagtgct    15960
gggattacag gcgtgagcca ctgcgcctgg ccttgtctag ttttaaatt gagttgttaa     16020 ttttcttaat cagttgtgag agttgtttat atattctgga taccagttct ttatcagata    16080
tgtattttgc aaatattttc tcccagtctg tggcttgttt tttcattttc tcaagtctcg    16140
aagagtagaa gttttaagtt ttgaagtcta gtttatcaat tgtgttattt tatgatttgt    16200
gcttttgtct tatctattaa taagagttct tcatctaact caagttcccg aaggtttttt    16260
ttctatgtgt ttctctatta gttttatagc tctgtctttt acacttaagt aaattatgag    16320 ttaattttt tgtgtggtac agggtttggg tttgaggctc actcattttg catagggatg     16380
ttaaattgtt ctagaaccat ttgatgaaga cttttctttc cctattgaat gccttggtac    16440
ctttgttgaa aatcaattga ccatatacat gtgggtctat ttccggactc ttctgtgtca    16500
ttggtttctt tgtctatcat tttgctaata ccatcttctg tgtcattggt ttctttgtct    16560
atcattttgc taataccaca ctgtcttgat tactgtacct ttataggaag cttggaatt     16620 aggtaatgag agtcgtcttt gttctttttt gaagctgttt tgcttatttt cattcctttg    16680
cttttccata acattttaga atcagcttgt taatgtctat aaaaacacct gctaggattt    16740
tatttttatt tttttgagac ggagtctcac tctgttgccc aggctggagt gcagtggcac    16800
gatctccact cactgcaagc tctgccccct gggttcatgc cattctcctg cctcagcttc    16860
ctgagtagct gggactacag gtgcccgcca ccacgcccag ctaattttt c tgtatttgta    16920 ttagagacgg ggtttcactg tgttagccag gatggtctcg atctcctgac ctcgtgatcc    16980
acccgcctcg gcctcccaga gtgctgggat tacaggcgtg agccacaacg cccggccaac    17040
acctgctagg attttaaaca ggattgcatt gaatctatag ataggttggg gataattgac    17100
atctttataa tatggagtct tccacgaaga agacttccat gtacagaaaa acagatttt    17160 attgaagttc agttgcttat aatcatttat atacaattct ccttttattt ttattatatt    17220
gatatatttt tgattgacaa aattgtatat atttatggta tacgatacga tattttcata    17280
aatgtatacc ttgtggaatg gctaaatcag acaaacatat gcatcctctc acatcattat    17340
catttctttt gtggtgagaa tctgctctca gcaatttgca atatatgata cattgttatt    17400
aactttagca atcatgatgt actatagata tcttgaactt gttcttcctg tctactcctt    17460
ttatgtttgt aaatcacttt ggagtttaca aaatgctttc atatctgtta ttttacttca    17520
tcctcttact acaacattgg ttggtaagtg tagtactatt ttaatatact aaagaccaat    17580
tttctatcct aatggaggat ctcaaagtgc attcttttt tctaacccaa tgagcccta     17640 tgcaaagaac gtagacttat cagatgagta aacaaaagcc aacttttcag gctgccttct    17700
gataatcttt agcaaggggc agaccatcag taaaggggta gctagggtta tagccctcat    17760
gtctctaggc agggcctggc acacatacac tgagggcaga gaggaggaag tgggcattat    17820
cttcttctct gagagcgagg gctagggctg tctcttctgc ttagtggagg gatagcatgt    17880
tccagcctgt gtaacagcta gggcacatgt tgactgaatg gcttgtcagg cagctgtaga    17940
gagagggaca aagggcttct ctctgtatag ggctttgtag gtatagttgt agcttttcgt    18000
atcctttttt tttttttttt ttttgtgaca aggtctcaag gtcacccagc tggagcgcaa    18060
tgatgtgatc ttggctcact gcaacctcca cctcctgggc tcaagggatc ctcctgtctc    18120 agcccccag ggtagcaggg agtacaggcg taagccacca cacccggcca gttttgtat    18180
```

```
ttttgtagag atagagtttc actatgttgc ccaggctggt ctcgaactcc tgagctcaag    18240
cgatccaccc gccgtggcct cccaaagtgg taggattaca ggtgtgagcc accactccca    18300
gcctcgtatc ctttatataa cctaccctag tcctttcaaa tcatatcact aaaaactaat    18360
tgtactttt acatctctga ttaactacat tttaacaaaa ttgcatcatg tcatgtgtaa    18420
ctgagggctt ttaagttcta atttagggaa caatctgatg gtcaagggaa gaaaccctta    18480
taccaaggca gtttgcaaag gcctggaggg ccaggtccag caaggtggtt ttcctggggc    18540
ccactaccaa tatgagtagt ataatgaggc ccagagttcg catagcaagt aagtaagaga    18600
accaggactt aaaaatcatg tctttgactt ccagttccat ttccatggtt ttcctttact    18660
gcatttcctt tcaagttttc ataaggttct ttaaggaaa aaaaagatt ggcaaaaga    18720
tacatcagtt aaacaaaaga aaacctaagt agcagtatta atctcaaaat accactacta    18780
accacagctg acatttattg agtatgtgct atgtgccaga cactgtgtta agctctctat    18840
gtagatggta attgtcatag cattatatga cttttatgtg ataaaacaac atagcaacaa    18900
attgcaaaaa ggaaaaactc caagaaatga gaattcgaca atagcacaat tctagatttt    18960
taattcacta cgactgagcc aatattcaaa ataaagataa taaagagtta caccattaac    19020
aaatcagaat tactgtatac caaaatttat tccctagagt ttattctcta aaaaggtaag    19080
atacctttct agatatttct agactcattt taaaagcaat acttctttt ctgattataa    19140
atgtaacact tgcttattac agaaaactgg ttacatcttt tttcaccatt tggccttttc    19200
tttcagtagt tttgcagtga ctataaatat ttttaacaa atcagcctc atatgtatgt    19260
atagttttgt attttccttc tatgtgttca atggttttca gaaacagtat ttctagtgac    19320
tacatgctat tctgtcacat ggatatgcca cagtttcact gcccccttat tgtttgggtt    19380
gttttcactc tttgttcatg gtgtgtgtgt gtgtgtgt atgtgtgtgt gtgtagtgta    19440
aattgatcac atactgggcc aaataaattc tcagtaaatt aaaaaaggag aaattgaatc    19500
tgaacataat taataaaatt gcaattaata attaaattta aatttaaaaa tccagctatt    19560
tgaaaatttt aaagcctttt taataactat tagatatact atcaggcagg ctgggtacca    19620
tggctcacgc ctgtaatcct agcactttag gaggccgagg cgggcagatt gcttgagccc    19680
aggagttgga gaaagatagt gaagagctag aagaatgcct tcactttgaa aatctgagga    19740
atgccttgga tccctcctga ggaaaatatg taaatatgta tacatgctct tattcactta    19800
ttttatttta ttcttttct ttttttttt ttttttgaga caggtctttc tctgtcaccc    19860
aggctggagt gcagaagcgt gatctcagct cactgcaact tctgcctccc aggttcaagc    19920
gattctgctg cctcagcctc ctgagtagct gagactacag gcgcctgcca ccatgcccgg    19980
ctcatttttt gtatttttag tagagacagg gtttcaccat gttggtcacg ccagtcttaa    20040
actcctgacc tcaggtgatt tgcccgccct ggcctcccaa agtgctggga ttacaggcgt    20100
gagccaccac acctggcccc attcacttct tttaaaaag tttattagt gaaaatttca    20160
aacagattac actcattttt gcttaaattt tgatcctgtg tcaagaactc ttggcctagg    20220
atgacttaca tttgtaagtt tgtattaaat atttaaaaat tggctgagtg tggtggctca    20280
cgcctgtaat cccagcactt tgggaggccg aggtgggcag atcacctgaa gtcaggagtt    20340
cgagaccaac ctgaccaaca tggagaaacc ccgtctctac taaaaataca aaattagccg    20400
ggcatggtgg tgcatgctgt aattccagct acttgggagg cttgaacccg ggaggtggaa    20460
gttgcggtgt gctgagatcg caccattgca ctccagcctg gcaacaagag tgaaactcc    20520
```

```
gtctcaaaaa aaaaaaatca tttcccttat tttcctttgc ctgttttttt ttttttgagt    20580
ctataaaatg tatttgatgg aaaattgtgg aaaatgtttt agtaacttag tacaaggtta    20640
aacaagcaga tggcactgtc atggagttat ttgaagtata tttgctgttg ctattgtccc    20700
ctttaatact caagcagcct tttagcagcc tttgaaatct catttgtcct catgcagata    20760
atccagttct gtgtgcatat ttgcatgtca gatctcgaaa cctgctttttt ttttttgttat   20820 ttcaaggtaa tataaagtag catataggta ccaccatgca taatccagaa ccccttttgct   20880 ttccatggaa gccaacctct cagggctcct gcccctcac tgaggatgca ggcctgggaa     20940
aggggatcag aaacgggttt gtagggaagg atgagctctg cctgtcctgt tgcccaggga    21000
gcactcctaa taatgccaag gagctcaatt ccaagcaggt gagaagctta cggaatgaaa    21060
caagagaggc tgattctcat taaatatttt caggttgtgt agggcagaac aatgagatga    21120
acaaagcacc gatctgtcct ctacttcctt tttctgaaag gaagaggtga agtttcttca    21180
tgccatctgg acagtgttgg ggttacataa ttagactcct cccgactgag tctccttagg    21240
taaatcacag aattctctga ctcatctaga agtgatgata atgacggtta cttgatagag    21300
ttgttcataa ggatctaatg aatgcggaat aaatgcatat ctctggaaac taaagtacta    21360
agcaaaagtc agtagtatag taatacaaat cgtgcttagg aacaattgtg aagtaggaag    21420 tttgtctttta tcactttcta cctctttttt tctgtgcttc ttactgtctc cccctcaccg    21480
ctgctgtcca atatgttagt cactagtcat ttgtggctat ttccattaat taattgtatt    21540
taattaagat taaatacaat taaaaattca gttccttggt tgcattaagc cacatttcaa    21600
gtgctcagga ggcacatgtg gctggtggcc accgaactgg acagcactgc cccctatttt    21660
gagaagtggg agagttcttg gaggaggtag gcattctaat gctgcgttct aggtcccagt    21720
ttcagcaccg gattaagtcc tcaccttccc ttaagagccc agggctttaa ggtgatcttc    21780
ccttccctgc tcgtctttat cagccaatca gatttctatg ccttggttga agtgtttctt    21840
ttagtggtaa gcaaagcacc ctgattaagt tcatatcaaa aactttgaac ctccacttaa    21900
ctgctctgag tacaagcatt tcaaaaaagg atgcccccaa aatcagatct ccgcttggta    21960
gaatttctca ctgtaaaatg tggcggttcc tctgaaaggg tgtgtggtaa ggcgcgccct    22020
tacattacat tacattacac acacgcacac acacacacgc acacacacac acacacacac    22080
acaaatgtct tctaaaggaa cagactgacc ctgtgaaggt gttgggtgtc gtggtctcct    22140
gctccgtccc tactccaaga gtggtgttaa ctacttttct ttttcactct tcattaattg    22200
attaataaat aattgaattg gcaaatgttt cccgagcgcc tgctgtggca gcaggtctgt    22260
attaggcaca ggacacatag aaacgaagaa attggcccctt ccacagaagt cagcagccca   22320
gttagtcctc gttaacacc atcaactctg tgtccagtac tgcggcccga gcagccggca     22380
tctggccact gcccctcggt gaagaaggct gctctgcctt aagccacaaa tgaccttgga    22440
atctcagaga ctattccaaa atggttctgt cttgagtcac agatcagaga gtctccacag    22500
agatctcaaa gtagcttctt gtgtcatcta atggtcttca gaaattctgt ctctgtttct    22560
gtggtcagct cccagctgct cattattcct gatcacccct catctagttc ttttgtctcc    22620
tggagtatgg gcagtgactt gtggaaactc tgcttccttt cgtactccct aggatgagct    22680
gtggtgtgat aaagatgact cgggcagcag gcaaacctgg tttgagtcct ggttctgcca    22740
ctcttttaat ctatgatttg ggcatttcct caactatctc agtctagttt tttgtatgtg    22800
aagtggggat tataatagta attatccata ggataaactg agctaagggg aggcatgagg    22860
ccttgaccaa gggggttttg gagctggatt gtgttaaggg aactggggtg taaagaaaac    22920
```

```
tgattccttc ccaagcatct aactaaattc tgatcatgtg tagtcattct tcatagtttg   22980
tggcatagtt ctttgctcag aacttaaatg tgagagggaa ttttgttccc aaggttataa   23040
tgttatattt ttttccctta gccagcccta ctcttggtac agcatgctct ctgccagccc   23100
tgagacaatc tgcttttatc caaatactgt tagatgtaat gaggcagggc agtgaccttg   23160
ggcttctgca tgagatttag aaggccacat ttataaatta ttttagcatg aattatttcc   23220
gggaaagatg ttcactgatt actaatatca tctattttat gttgtttctt attttctttt   23280
tcagagattg acattttct gaccttgtct gaattctttt taagagttcg tacctcctga    23340
actacatgca ctttgcaact ctgattttg tactgtgtct gtgtgtgatg tgctcactgg    23400
tttgcctttg attttgactt ccagcagcat gtccttctat tctgcctaag gaaatagtga   23460
gaagcacaga gagttagggg gttacttaat agttttggaa tgtgcatctg tcccgaaata   23520
ggagctgtga ccaagaatat ggttgtcgta ttttaatcc atattcgaat cattttctcc    23580 ttcctttta tctagccgta catgttgaat agaagactta tagaatgaga gagaaaagta    23640
gataactcat gaatctctaa tcatctggga taaagccttt gtttgaaatt atagaagggg   23700
cggggaaacg ttggtcccac acactgaatt aggaacatct gtacccatga aacttgagc    23760 aagagaactg gaatattgcc attttcattc tgcctcctac gtgctctcaa ttgttcatgc   23820
agtggagggg cagcaatagc atggatactt gagatcttta aaataccct ccaagtaatg    23880 ttttaaaaga ctgaatcaga ttccattaat cgaaaatttt catgccagta aagttggaag   23940
agatgggaat gtttcctgag aagtctatcc atgggataaa accaatgatc tacttgaaaa   24000
gaaatacgac aagtactaaa gtgacaacat atactttgcc ttaaaatatt atggcagaag   24060
ctttagggca gtacagaggc tgcatagtgt gatgggcaaa agggtcatac tctgaatcca   24120
aatgtggcct ctgccactt ctagctgtgt gaccttgggc aaaccactta gcatgtcttt    24180
gcctcatttt tctcacctgt aaaatgggca tagttctaat gccaatatca gagttttgtg   24240
gagaagaata aatgagttgt tatacataac acccttagaa cagtggttgg cacaaggcaa   24300
gcacattaga ggtgtttcct cttttttttt tttttgagt cagagtcttg ctctgtcacc    24360
caggctggag tgcagtggcg tgatcttggc tcactgcaac ctccctctcc tgggctcaag   24420
cagttctctg cctcagcctt ccgagcagct ggaattacag gtgtgtgcca ccaagcccag   24480 ctaattttg tattttagt agagacgggg tttcaccatg ttggccaggc tagtctcgat     24540
ctcctgacct caggtaatcc tcccgcctcg gcctcccaaa gtgctgggat tacaggcatg   24600
agccaccatg accagccaag gtatttcctc ttataattgt tcctattgct cctgcttcca   24660
ctgctgtaat tccttctgcc atcgctgaca cctctattgc cacaactaca gcgtaggctt   24720
gggcgtcagc ctggctttga gttctagcac tgctgcttac ctatttaagt ccaagtccca   24780
tttctatatt tgtaaagtag gagtgttact agtacctact tcacaggacc tggtgaggat   24840
gaaatcagat aatacgtgtg aagcgcctgg tgcagtaaat gcttatggtt ttgttgttac   24900
tgcagcagct ctcaaccagg gatcctccca caccagagtg ttgtactcca ctatgggttg   24960
ggttacaagt tatgtttctt actaaaagta ccaatggttg ggaattattt tttaaaataa   25020
ttagagttaa atcaagggta tccccaccct gacaatattg ctgttcactt ctattttgag   25080
aagtgggaga gtgcctggag gagacagccc tgcccttcta caattggcca tactctggct   25140
atatctacag ctgttgggat atgcgggtgg gggatgcaca tgtgaaaggt gagtgctttg   25200
tgtgggggca gaaaacaaat ttgagagttg ctggccttag ggtgctgtca tttctgctgc   25260
```

```
agaatgtacc actcgtgctc ttccatgtgg cagcccccct ttttagttga ttgcccagac    25320
caaagcatca ttatccccca aagcccaact gttcttatct tgcctaaaca tatatatgat    25380
ccaggaaaca tttgttctga ctattaaaat cacttttat tatattaagc agстасттgта    25440 acttgccctg aatttattca ttaataagta ttatcgagt ccctttatga gtaagatatt    25500

atctggttta tgaagaaaat gcagacacta тсagттттaag aagctcataa tcaagtatga    25560

tagactagga ggatatacaa taactatagc acaaagacgt taactctagt gttcttttc    25620

тттттттсттт tcttttatt тттатттт gagatggagt cttgctctgt cacccaggct    25680
ggagtgcagt ggcatgatct tggctaaccg caacctctgc ctcccaagtt caagtgattc    25740

tcctgctta gcatcctgag tagctgggat tataggcatg caccaccatg cccagttaat    25800

tttgtatt ttaatagaga cggggtgtca ccatgttggc aggctggtcc gaaactcctg    25860

accccaagtg atctgcctgc cttggcctcc ccaaagtgct gggattccag gtgtgagcca    25920

ccatgcctgg cctctttttc tttttagct tccattttt aacctttacg ttcaggaaaa    25980

tacattgcat ttgtttatag cttgtccctt aatctttgt tttccttat аааagтаата    26040

tgtgctcatt gtgtaaaatt tggaaaatat gtaaacatta aaaaggaaca gaaaaatga    26100 gccatttttc atcaactaga gataccatt ttaatgttaa gttatttt catgtatct    26160

tatacaggtg atatcagtct tcatatttat attatttttt тсттттсаа ссаттатата    26220

ataattattt cctatgtca ttaaaatact ttataagtat aattttaata gctaaataat    26280

atttcatcat atatgactta taatttacaa gcatttcccc aacggacatt ttagttgatt    26340

ctgatttttt taatgaataa tatggtaata aacactttta tgtatgagtc atccatattt    26400

ctgatcatag attccacaa gtagaatcct gaaaccaaag ggtagaaata tcgccaccgt    26460

tgttaataga tgtggtttca ttacttttg gcatgatat ttaccttagc aaaacttctg    26520

acactgatgg atttggatat ttattacctt aaggatagga gatcctta стттттсagат    26580

ctgacgttcc aagtgtatgt тgасстgттса agaatgactc caaagttcat gacataaagt    26640
agtttgcata tttastgaag сасаааатт aatcacacgg gcctagaggc tggtgagtga    26700

ccaaggctgc ctagcaaatg tttcattggg gстtсаttgga tctctgtgta atacgtctta    26760

tatattgact taaaactta аттттgтттga aatggacag cttttgtgaa atcaaaagg    26820 gccattaatt tatggtatac aattatgcac agaaaatcta cagccgtcag agaaatatga    26880

ctcaagaaaa tactgagagt tgatatatag atcttcatat тааааатаgaa ggtttacaac    26940 ggtctactac tttccaatga ctacttccta attgcttaat agtatgtatt gacttgtcat    27000

ttctagaaaa taatcctaat ttcattttta gtgccaacca ттggaатттат tctctttata    27060

atcaccacat ggctatatat atatata ататата ататата атстсттат    27120

aatacaatat gaaaaataaa tacattaatc aaattatcag accgagcttc tacagatgtt    27180

tgccccttac ttgctttaat tttaaaagtt ctctttggca ggaatgtctt atactctagc    27240

tagggaagaa aatgtgtaga aaacaattt aatcagtgtc tgggagtctg agaacaaact    27300

tagcaaattt agcttagaac aatcgcaagt ttagcttagc atcttcctt aacctgtac    27360

ttctaggtag gaccgcctac actgccagca cccctcaca gtctaggagc agctctctc    27420

tcccccacat tttgagctgt tcccttgag gttgcttct cgcccttgc tgacaggag    27480 gtggtggtag ctgcatttgt ctcccatctg gtccccagaa cgtttcttgc тттттgтттта    27540

cagtcttgtg acaaactagc acgccccctt cctatctcag ggcctggctt ccccagcccc    27600

caactaaggt ctcagacacg tacaaatggt gcccctcttt gaggggctcg tacatctgca    27660
```

```
catctggacc tttcacatag tgatctgtta aaggcataga atcagcctgt aatatgctga   27720
gatcaccctg gtaatatggt ggagtacaga cagagccggg tctgtctggt ttctggctct   27780 gtagccttt ccctgggtc tcctggggcc acttgaacct gactagccag cctctcaccc    27840
atctctagga cccagcctga actgaggcag agggactgag gctgcctcac actctgtaat   27900
ttggcctcaa gtcaccattg ctggccttgt gcctcagctc tgataactgg actcttgtct   27960
ggctcctgcg tgccagaatc ccatggtaac ctgcctcgtt tccctgtgcc ttgtttttat   28020
cagcctgcct cccagggatt gaaatcgtgc cctgaaacac agtgaccaat gcactttcct   28080
gatgtcaacc acccccacttg cctttctgat tggattccag agtaccttaa atttctcgtt  28140
gttctgcagt gcctgtagtc aggaaacctc tgttctggac acttttctct gtaaatgaca   28200
acttagttct tccagttact tgtgccaaaa ccttggagtc acccataact ccttgcattg    28260
tctcacatcc cacagctaag ccttcagcaa attcttggtt ctgttttaaa aatgtatcta   28320
gaatctgact accctggtcg gacccgttat cattttgtcc ctggattctt gcaagagcct   28380
cctgactggg cttctggcag aggagtcctg tcttcttca gtatattctc aacactgcca    28440
cctgactgat cctttaaaa tatgagccag attatctcac tccccacagt cctccagcgg    28500
cttcccgttt ctctcagggt aaaggcaaag tgcaaagtgc aggcagtccc tgtagggccc    28560
ccatcatctc tgctcttagc tgcttaccac acatctctcc aacacctcc tcactcactc    28620 catgccagcc acactggcct ttttctctgt tccttgaacc ttgcttagga tttctctacc   28680
aggaatgctt tttttccaga tatgtgaatg gcttacttcc tcacttccct cagctcctca   28740
ctcaaatatc acctgtcagg gaggccttgc ctctctaaaa tctaaattcc ctccaccgtc   28800
tttcctgctt gatttttctc ctcagcactt atcacgatcc agtatactat atatatatat   28860
acatatacac atttatttt ttttgagact gagtcttgct ctgtcgccca ggctggcgtg    28920
cagtggcgtg atctcggctc actgcaacct ccacctcccg ggttcaagcc attctcctgc   28980
ctcagcctcc tgagtagctg ggactacaga cgtgtgctac cacgcccggc taattttgt    29040 attttagta gagacaggat ttcaccatgt tggccaggat ggtctcgatc tcctggcctc    29100
aagtgatccg cccgccttgg cttcccaaag tgctgggatt gcaggtgtga gccaccgcgc   29160
ctgtcctact atgtattt atttatttat ctcttttata ttctgtctcc tccaagcccc    29220
ctgggagcaa gggtgctttg gttcactgct gtatttccaa agtctagagc agtacctggc   29280
cagggtatga gttccataaa tatttcttga atgaatgaat caaatagttg agtattagca   29340
ctattctgag aattttgtat gtattatctc attgaattct tacagtaacc ttatgtgatg   29400
gtacttttat gactcccatt ttacagatga gaaaactgag tcttaagagg ttaggcgact   29460
tgcccaaaag gacctgagcc accacacaag tattccacta gagcagcaag ttagaataaa   29520
cacagacttt attattatcc agatttatgt tcaagttgca gctctgtcaa ttactggttg   29580
aattaaaacc tctctaaact ttaatatcct tacttatgaa ataattattc tacctcccag   29640
gttattggaa gaattagatg agatcatggg tgcattattt tcatgtatat tttcctgatt   29700
gctggaaaag ttgaaatttt ttcatttgt ggttgtttgt ttgtttgttt gttttcgag    29760 gcaaggtctc actctgtcag tcaggctggt gtgcaatagt gtgatcttgg ctcactgcaa   29820
cctctgcttc ccgggctcaa gtgatcctcc cacctcagcc ccccaagtag ctggcaccac   29880
cggcgcatgc caccacactc ggctaatttt tgttacccgg ctcatttta tgttttggt    29940 agagatgggg ttttgccttg atggccacgt tggtctcgaa ctcctgggtg caagtgatcc   30000
```

```
atccgccttg gcctcccaaa gtgttgggat tacaggcgtg agccaccatg tctggccttt    30060
ttcatgtatt taccggccat tctggtttcc tcttctgtga atttcctgtt cataacccttt   30120 tctcagtttt ttttcttatc aaattgtagg agttcttcga atgttagaga tacatgttgt    30180
cttatatgtt ataaatagct ttcctcatac catcatttgt tgtttgatga tgttttttgg    30240
aaccttcttt tattcatcta gttagcgctc caggtttggt ggttgatcaa atacttgaga    30300
atagggattt attcattcag ctagtatttg ttgagggctg gaactctgtg ggatgtccat    30360
tcagtcagga cacctctaaa tcctgacttc cagtttacgt cactgatgat ggctctcatc    30420
cttggttcta ccagattctt gaaagagaat gtgttttctc agagccaagt agacccaaac    30480
atttcccaga ctttggccac ataatcagaa atttcaaaag agttctggaa tttgtgggct    30540
tagctccaag ttaccaggca tccgttgtct tccctgtggg cagaattcgc ttttagctta    30600
ctccaccctc ctcagctacg cagcatgatt ggggcagacg atgaatactt cagatatccc    30660
ctgtggggtt aactccagag gcagcctcag aaactagaca cataattcat atggtcaaaa    30720
cctggcaggc tcttctgaaa tcgtgtgact tcctatcagg ccaccagctc tgcagatcct    30780
caaaggtctg gctgtcagaa caatagggaa tgagagcagc gcccagatgc tgcctgctgg    30840
agctgcaggt cctgtttgag tctgaacaat aaaagtcctg gaatgaatta ccaaggctcc    30900
tgattgcacc ctgcaggttc aggtttagtt tgtggagatg tctcacataa gaactgtctt    30960
gtaagccgct tgggggttc aacaaaattg gtcaacaaaa tttaatacca tacaagccct    31020
tttcttgatc aagcaattta gtaagtctct gtcataagtc tctatgacct gccatccaat    31080
atgtcaaaat aaacaaaatt ttcatgttga tggtcacaag tgcagtccct agagtgggga    31140
tctggtgacc acttccacca ctaactagca ctggatcgta gacaagatcg ttagtctctc    31200
tgtgtctcag ctcactcatc tgcaagatgt ggctactaat agtacctaag atagagctat    31260
tgggaggatt aagttaggta atgcatgtaa atccttagaa taatgcccag cacagttgtt    31320
gttcaataca tattgcaaag ttcctagtat aaactccctg ttgcagcctt ctaatttgac    31380
ttcaatagat tgttggtacc atttgcctct ttctttgcag gtatcctacc taggcctaga    31440
gaactaagct tttgctgttc attatatgaa gcttcttaaa tgtcatacag gctagttgca    31500
tcctactaat tcttcacaga ctagataaaa atactttgc tgaagtctta atcggcctgt     31560
cctgaagtca accaggctgt atgttagtgc cttgactcag tgcagctttc aagagaggca    31620
gaaagaatac ccacagagaa ggcacatgtg ggcggtggca gtgtaggacc aggaaagaag    31680
ctaggtctct atattccctc gcattttgaa tctgtgttaa attcaatcat attagtatga    31740
agcaatcctc ttacctatct ccttaatcca gcctctgact gccagctcac aaaagaggga    31800
gaagaggcac tacatttaaa gtagtgatta tctctaacta gaattttaag tcccctacatg   31860 ttttggctgt agaaccagcc aaagttttgt tccaattccc tacaaaattt cacaatagtc    31920
aggagttaga attggtccct atgttatgaa acagctagtt tttatacttt aaacttaaaa    31980
tgaagcttta gttgtttatt attactgtgg atattttcca agagacagaa taacatctgt    32040
ggaagattct acacaggcct tgatgccaga cattgtaatt atttccctgc tcaaaggcaa    32100
tagtcagtgc ctcaaggaac tccctggcta taagcagttg gctgcctcga caacagatag    32160
ctaatgtctt agctctttc tgtctctacc gccagcctct tggggatgtg acttgagaaa     32220
gctctcccct ccccattttc tcctgtaacc tctttggagg aagtcaccag ggtaaccact    32280
ttcttttatg ctagttttct tgagtgcaag ggaaaacact tccccacaga catatgcacag   32340 aagtttaaga gtggtgagga gaagaacacg aacagttact gagtacctga gctatgcttt    32400
```

```
gtgtacctga tatcattgag ttcccacatc aaccttctga gataggcatt atcatcccca   32460
ttttactgat gcttaaacag taacatgccc aaggtcacac aagtggcaag tgacagtcag   32520
gactcaaacc caggtttatc tttctcgggc ctttgctctt attttgcaaa ttaagcaagt   32580
gtagacacac aaaaccaatt tgttttacc  taggaaacgt gttttatgct ttgtttttct   32640
cagtctggat agatgccgtt ttctagtccc ctggaaccat cgtatgccca gtttagtacc   32700
acttttgttt ggtttctcgt cttagaatat attctgctta ttcactcccc cggccacctg   32760
agaaatcttt ttactacttt tagtccaaat caaactttcc ttcccttgac tacctaggaa   32820
gtctctcctt gggtgagtct taactcgcct gaactgagag tctcaccctg gaacttggtt   32880
aagaaaggcc agagttggga ggcaacagcc tggatggaag agggggtca  gttgacactg   32940 gaggggggcaa gccagaccag ccgcaagcag gagccaaaag gtcagaaagc cagtgagaat   33000
ggggtgggcc aacaggagca gaccaggcca cacaggctgt gactcccct  tgcagtggct   33060 gctgggcact ggccatgcct gtgcttgtct ctctcagtat ctcttactct gccatcttgt   33120
cattcatgaa attgctcaag agacgctttc taccagtccg tgcctgctta gtctccgaga   33180
agttttgggg gttcatttag aattaattaa tttagaacta gcatttaaaa gttaaacggg   33240
ctgggcatga tggctcatgc ttgtgatccc agcactttgg gggactgagg cgggtggatc   33300
acttgaggtc agaagtttga gaccagcctg gcaaacattg agaaaccctg tctctactaa   33360
aaatacaaaa attagccaga tggagtggtc aatgccggta atcccagcta ctcgggaggc   33420
tgaggcagga gagtcacttg aaccgaggag gcggaagttg cagtgagtag agatcactcc   33480
actgcactct agcctgggca acagagtgag actctgtatc aaaaaataaa taaataaata   33540
aaataaaaat aaaagtttta aaacagctta taaacttgag ttaaaatata actcaagtga   33600
agcagagaga agaatattaa aggggaaaca tttaatgagg agcaaagcat agccttgacc   33660
gagcttctgc taagagcgga tggctctcac ttggcacaga catctttctg tattgcacta   33720
cttgccctgg cagaggcatc agaactgtta gaaccacaat ggactgtgca gcacttttca   33780
tgcaacactc ccccttttaag gttagccaac cgagagcaag aaaaaatagg taataagctc   33840
aacattactc agctagtaag tggctggtac aggaatcaag ttctgcttac ttagtctgaa   33900
ggttttcagc cacttcatac catttgatca acatatttgc cctttgtttt tgaatgaaat   33960
agaaaaaata atttccttct ttccttcttt ctcccgcct  tccttccttt ttttcaaaca   34020
aaattactgc catttatatt agtgtttcta ccacttctat catgaccact gctggcaaaa   34080
atgtactgaa cttttgctgt gcatcaggca atatggctaa ctaaggcttt gcatacatca   34140
tttactcttt ctagtaaccc cagagtaggt actattactg tctctattta cagggaagac   34200
tgtggaggcc aagaaggatt aaacaatttc cctgcatcac acagccaaaa atggtaaagc   34260
cagatttgaa gtccaggctc tttgattctg gagttcatgc tagtaactac cagctctccg   34320
tctggcagtg ttttgttctt ttgttgaatt actaaaacag aactattttc tctgaatgca   34380
gaagttgaaa cctgttgagg aaattcaacc agagtatttc ttgaagaaaa aagaaaccat   34440
ttcctgattt ctttatttgt taaccctatg acatcattag ggttggtagt agctgctcct   34500
ttgccttcac acacaagaaa aaagtgtgca aatagttctt aggaactact gaagctgttc   34560
agaggaccag aagctagacc ctcctctatt attttctctg ccctacgtct ggccttttta   34620
gcttgtggaa cttatcatcc ccgccatcca gtaaaggcta caaaggcccc gagactagtc   34680
cctgcagtta ctactgatgt tcttttcttg cttctcatct gctttacta  ccagttctgt   34740
```

```
cttgcccatg gtcaaaccat tatctctaaa actccacctt ctaagctacc tctgacccTt    34800
cgaatttgcc atggttagaa aaatcaggaa aataggaaac ctaaccagca aagaaacatc    34860
tgggagtgta tttgttgtca ctgtaagcaa tgacacatag attaaaacaa taagatacca    34920
taggcaggaa tggatagagt atggactcaa gagtaaggca gcttgggttc aaagcctgtc    34980
tctacccatt acaagccttg tgttcaacaa tttaaccaac cttccttcct tccttccttc    35040
cttccttcct tccttccttc cttccttcct tcctttcatg gagtttcgct cttttttgccc    35100 aggctggagt gcaatgatgc gatcttggct caccgcaacc tctgcctccc gggttcaagc    35160
gattctcctg ccacagcctc ccgagtaggt gggattacag acatgcgtga ccacgctggc    35220
taattttgta ttttttagttt ttagtagaga cggggtttct ccatgttggt caggctggtc    35280
ttgaactccc gacctcatgt gatccaccca cctcagcctc ccaaagtact gggattacag    35340
gtgtgagcca ccgtgcctgg ccaatgtaag cttttctaagt ctcggtttct taatctgtaa    35400
ggtggggata ataatagtag cacttcacag tgtcgtgagg attaaacgag ataatgtata    35460
cgaagcatct aacactgtac ctagagcata taaatgccaa taaaggctaa ttatcaaagt    35520
cataacttag cctttttacc cattaaatta ggacaaattt ttgagtgata ttcagtgttg    35580
gtgagtgggt aatgcaatgt gctcttgtat acaggcacac cttgttttat tgtggtttgc    35640
tttttctgct ttacagatac tgtgcttttt acaagttgaa ggtttgtggc aaacctgcat    35700
ggagcaagtc tattggtgcc atttttcaat ggcatgtggc tcacttcatg tctctgttgc    35760
atttcagtaa atcttgcaac atttcaaact ttttcattat tatatctgtt atggtgatct    35820
gtaatcggtc atctttggta ttactgttgt aattgttttg gggtcccgtg aacatcaccc    35880
acataagttg gtgaacttaa tcaagagaaa tgttgtgtgt cttctgactg ctccattgat    35940
cagccattcc tgtgtctctc cccctccttg ggcctccctc ttccctgaga taacaatatt    36000
gaaattaggc ctctaagtgt tcaagtgaaa gaaagagttg catgtctttc acttTaaata    36060
aaaagctgca aatgattgag gttagtgagg aaagcatgtt gaaagccaag gtaggacaaa    36120
ttcttgaagg aaattaagtg ctattctgat gaacacacaa atgataagaa agtgaaacag    36180
ccttatttgc tcataaggag aaagtttaag tggtctggat agatcaaact agccaccaca    36240
ttcccttaag ccaaaggcta atctagagca aagcctaact ctcttctgtt ctatgaagac    36300
tgagagagct gaggaagcta caaaagaaaa gtttgaagct agcagaggtt ggttcatgag    36360
gtttaaggaa agaagccatc tcacccaggc gcagtttctc atgcctgtaa tcccagcatt    36420 tgggaggct gaggtgggtg gatcgcttga ggtcaggagt ttgagaccat cctggccaat    36480
attgtgaaac cccgtctcta ctaaaaatac aaaaattagc cgggcatggt ggcgtgtgcc    36540
tgtagtcgta gctacttgga aggctgaggc aggagaattg cttgaaccca ggaggcggag    36600
gttgcagtga gccgagatca tgccactgcg ctccagcctg ggtgacagac caagactctg    36660
tctattaaaa aaaaaaaaga ggaagaagaa gccaactcca taacataaaa gtacaggatg    36720
aagcaagaat tgctgctata gaagctgcag caagttatcc agaagatctg gctgaggtca    36780
ttgctgaatg tggctgcact cagccacaga ttttctttcc tcctttcttt tttttttttt    36840
tttgagacag agtcttgctc tgtcgcccag gctggagtgc aatgacacaa tctcagctca    36900
ctgcaacatc cacctcccaa gttcaagcaa ttctcttgct tcagcctccc gagtagctgg    36960
gattataggt gcccgccacc acacctggct aattttgtg ttttttagcag agacagggtt    37020 tcactatgtt ggtcaggctg gtctcgaact cctgacctca gtaactcac ccttcttggc    37080 ctcctgaagt gctgggattg caggtgtgag ccaccgtgcc cagcctgcat tttcaacata    37140
```

```
gatgaaacag tctcttttgg aagcagatgc catctaggac tttaattcct ggcttcaaag    37200
ctccaaagga cacttcgatt ctgttgttag agactaatgc agctggtgac ttgaagtggt    37260
ttcaaaatca acgcttatta ccattcctaa aatcctaggg cccttaagaa ttatgttaaa    37320 tatacctgc ctgtgcagta tgagtggaat aacaaagcca ggatgacggt acatgtgttt     37380
gcagcatggt ttactgtaca ttttaagccc actgttgaga cctactgctc agaaaaaaaa    37440
gattcctttc aaaatattgc tgctcaattc agtgcttttt cttggttgat aaaaaacaaa    37500
caactaaaat attactcctg gctgggcttg gtggctcaca tctataatcc cagcactttg    37560
ggaggccgag gcaggtggat cacctgaggt cagcagttca agaacagcct ggccaacatg    37620
gtgaaaccct gtctccacta aaaatagaaa aaattagccg ggcatggtgg cgcatgcctg    37680
taatcccagc tactcgggaa gctgaggcag gagaattgct tgaacccggg aggcagaggt    37740
tgcagtgagc caaaattgtg ccattgtact ccagccaggg caacaagagt gaaactccgt    37800
ctcaaaaaat aaataaataa ataaataaat aaaatatcac tcctcgttga cagtgcacct    37860
aatcatccag gagctctgat ggaaatgtag aagattagtg ttttatgcc ttctaacaca     37920 acatctgttc tgcagcccat ggatcaagaa gtaatttcaa ctttcaagtc ttattattta    37980
agaaatacat ttcataaggc tatatatagc tgtcatagat agtgattccg ctgatggatc    38040
atggcacaaa gcatactgaa aaccttctgg aaagggttca ctcttttaga tgccattaag    38100
aacattcatg gttcatagga agaggtcaca accttatcaa catgagcaag agtttagatg    38160
aagttgcttc taaccctatt ggatgacttt gaggggttca agacttcagt ggaagaagta    38220
actgcagatg tgattgaaat agccagagat ctagaattag aagtggagcc tgaagatgtg    38280
actgaattgc tgcaatctca taaaacttga atggatgagg aattgcttct tgtggatgag    38340
caaagaaagt ggtttctaga gatggaatct actcctggtg aagatgttgt gaccattgtt    38400
aaaatgacaa aggattttaa aataccacat aagtttatta aatcagaagt agagttcgag    38460
aggattgact ccaattttt tttttttaaat agtctcgctc tgtcacccat gctggagtgc      38520
agtggtgcaa tctcagccta ctgcaacctc tgcctcatgg gttcaagcga ttctcctgcc    38580
tcagcctccc gagtagctag gattacaggc acatgctacc atgcctggct aattttttgta   38640 ttttagtag agatgggggtt tcatcatatt ggccaggctg gtcttgaact cctggcctta    38700
agtgttccac ctgccttggc ctcttaaagt gctgggatta cagacctatt gactccaatt    38760
ttgaaacaag ttctattgtg ggtaaaagtg ttacccagca gcatcacatg gtacagagaa    38820
atcttttgtg aaaggaagtt gatacagcca acttcgttgt tgtcatattt taagaaattt    38880
ccacagccac cccaacgttc agcaaccacc actgatcaat cagtggcctt caacatcgag    38940
gcaagaccct ctactaggaa aaagattaca actcactgaa ggctcaaatg atccttagca    39000 tttttagca ataaagtatt tttaaattaa agtgtatata tttttcatgc ataatgctat      39060
tgcacactta atagactaca gtatggtgta aacaagtata acgaaacttt ttttttttt     39120 ttaaagagac agagtttctc ccggtcaccc aggcgagagt gcagtggtgc aatcatagct    39180
cactgtagcc ttgaactcct gggctcaagc agtcttccca ttccagcctc ctgagtagct    39240
ggaactacag gcatatgcca ccatgcccag ctaataattt tcatttgaaa atttttttg     39300 tagagataga gttttcttt ttggcccagg ctggtctcaa actcctggct ttaagccgtc      39360
ttcctgcctt ggcctcccaa agtgctagga ttataggcat gagccaccat acatggcctg    39420
taaacaaaac ctttttttt tttttttct tgagatggaa ttttgctctt gttgcccagg       39480
```

```
ccgaagtgca gtggtgtgat cttgactccc tgcagcctct gcctccctgg ttcaaacgat    39540
tctcctgcca cagcctccca agtagctgag atcacaggca tgcgccacca cacctggcta    39600
attttgtatt tttagtagag atggggtttc accatgttgg ccaggctggt ctcaaactcc    39660
tgagacatat acctgttgta aattggtata cgtcttttt gcttttgtt ttagaaacag      39720 gatcttgctc tgtcacccag gctggagtgc ataggtgtga tcatagctca ctgcaacctc    39780
aaatttcaag attcaagcaa tcctcccatc ttagcttctg aagtagctgg gattgtaggt    39840
tcaccccgcc atgcctggct aatttttat ttttttgtaga gacagagtct cactatattg     39900
cctaggctga catctttca aaaacagttt tggaatatat ataaaggatg ttaagatagt     39960
aatattattt gacagattct actttgggga cactatccta agaaagtaat ttaatatctg    40020
aaaagaaaac ctgtagcctg ataatgttgt aatattattt attatagtga gtaattgatt    40080
tcagtaaaat atgatctatc agctcagtgc agtttgaaat tatgaatgta aagacttcag    40140
ctacatgaaa aaatatatta ctatgttgaa caaaatactt aaaaaggaat acaattatat    40200
ggactgatgg ttataggagt atatgaagtt ttcacacagt tgctaggaca taacttgttt    40260
gtctttagtg tctttttgac attgccaaaa gcttctgaca ctactttttt aaaaatgtgg    40320
cttaaaaaat tgtcaagtaa tgagcaaaac agagactcta cttctgtgcc ttagtctcat    40380
tgccagttgc cagcctctga tttcaggtgg gtgtgaggga tggagggaca atgagggatg    40440
aggcagggct cggagatggt ctaagaagtc acttgtatct catgtgggtt tcttctctca    40500
aattcttgag tttctcttta tagaccctca ttagaaaagt cggttatgtg ggcatcagta    40560 tgagcccta ctcttgactc caccactgtt agggacatcc tcagtgaaat ccctgacaat      40620
ttcttcagta atacatatgt tatataacac tcctttataa tgatttttt ggggaaagaa      40680 tagtaattct ttagatgcta acccagccgg ctgtaaacaa atcatggttc tttaaaaacc    40740
atggctcaca cctgtaatcc cagcactttg ggaggctgag gcaggtgaat tacctgaggt    40800
ccggataaca gtaatgcatc ctcataagag ttcaagccag taattaatga aatacaaagc    40860
caaagtcccc agaaatgaga atggtttgt gatgagagag atctggggt gtctgtggtc       40920 tgttacacac attacttgat gataaaaaca gtgatcttta cttggctta caaaaggctc      40980 gtgcttcagc agagtgcagc aaaatgttcc ctgaccaaaa cgactgtgtc tgaagggcac    41040 agctggggg aatacagcta tgaaaaaaac tacacgagga acaaaaacat tggatgaaaa      41100
tagtggttgt atttggaagg tagaattata atcctcccct tttctacgtt cctaaattgt    41160
ccataatgtg gttatatttt tttaataata aaagtccaat ttaacaaata tttattggac    41220
actgcgtgtc agacacaatg cttgatgctg gagatacaat gacccagaca ggcacagtca    41280
ctgcttggcg gaacttcagt ccagtgggag aggcagatga ttttacaagt cattgtgaca    41340
ccatgtgaca aacccacaat agaggagttc agagagtggc tggattgtgt ccgagtggtg    41400
cctaacccaa acgggttggg aggaggtccc aggaaaggct tcctggagga agaggtgact    41460
aagctgggac ctgagggcta tataactgaa gattggagtg aggagtgttc taagcaaaag    41520
aagctgcatt tggcaaagct tggaggaact gaaagtttgg tgacactgga gcatagattg    41580
agcatgagaa gggagtggtg agagatgagg ctggagcttg aagtaggaac cagatcacaa    41640
aggactttgc tttcttatta aggaatttgg attttgtcct aaggcggtgt aaagctattg    41700
gaaggatatt catttgcttg cctgcttgct cacttattta ttcttccaaa tttgttgtag    41760
aaactcaaat aatatggaag catgaaacat gaaaagtaaa agtctcccct tctctacttc    41820
acaccctccc cccagttcta atccccatgg tacctattgc taagtgtttc atctgcaccc    41880
```

```
tttctgcagt tttctgggaa gtatatgcaa gcgtgtgtgt gtatatacat attttctttc    41940
tacacaaatg gaatcatgct atactgaata actcccatct taaaagcaaa acttgactgg    42000
gtgcagtggc tcacacctgt aatcccagca ctttgggagg ccgaggcagg tggattacct    42060
gaggtcagga gttcaagacc agcctggcca acatggtgaa atcccatctc tactgaaaat    42120
acaaaaatta gctgggcatg gtggtgtgtg cctgtaatcc cagctacttg ggaggctgag    42180
gcaggagaat tgcctgagcc caagaggcgg aggttgcagt gagccaagat tgcgccatcg    42240
tactccagcg tggctgacag agcgagattc tttctcaaaa aaaaaaaaaa aaaaaaggca    42300
gaacttgata caccttaggt atctttctat gtcagtacct aaagatatat attctttcta    42360
atgacagcag cacagccatt tatgtagcta tcccatcatt tatataacca gtctcttatt    42420
gagagacaat tagattatgt ctagtttttc actattacag aggaaaactg cagggaacat    42480
tcttgttatg atatcgtgtt ggatatttac ataagggtat ttgtgagata tgttcctaga    42540
agtaaaatag ctgggtaaga aggggttgtac attttaaaatt aaggtagata ttaccgtatt    42600
attccctgtt aaggtgatat caatttctac tctcaccaac atatgagtgt ctgttctttc    42660
atatactctt ccccactgga tatatccttt ttttgatttc tatttttttga gatggagtct    42720
cactctgtca cccaggctgg agtgcagtag tgcaatcttg gcttactgta acttccacct    42780
cccgggttca gcagttctc ctgcctcagc ctcctgagta gctgggatta cagctgtgcg    42840
tcaccatacc cagctaattt ttgtattttt agtagagacg gggtttcacc atgttggcca    42900
ggctggtctt aaactcctga cctcaggtga tctgcccacc ttggcctccc aaagtgctgg    42960
gattacaggc gtgagccacc atgccccgcc aatatatcca tttttttaaaa aaactgtggt    43020
taaaaaacac ataacttaaa acttaacatc ttgatttatt tttaagttta cagttcatta    43080
gtgttaagta tattcacatt gttgtgtaaa acagatctcc agaactttt catcttgcaa    43140
agcagaaact ctgtacctat taacaactcc ccatgccacc tcccactagc tcctgaatca    43200
ccattctact ttctgtttct atgaatttaa ctattctagg tgtctcgtac aagttaaatt    43260
acacactatt tgtcttttg taccagctta tttcacttag cataatgggt agaaacaagt    43320
cacaggtgtt gcctctactc aagggcgggg attccacaaa ggcgtgaaca ccaggaggtg    43380
gacatcattg tgggatacct tggagtctgt ctaccgtaat cttccttgta tattccaaat    43440
atttttctcca tctagtagtt tttgtttggg agttttatgc tctaatttgt atgagttaaa    43500
tgtgttggtc tttctgtgac tgctgtgtta caatttctag tatgtttaga gtggccttaa    43560
tcatgccaag atttcttaaa cattcacccg tttttcatcc atattgtatt ctaatgctat    43620
tattactttg gaatttattt tgatgtgaga tttgagagag ggttcccatt tttttttttcc    43680
tctgtagcta atctattgtc tcaattcttg aataatttct tttttacata gcttgttctg    43740
tttttttactg ttttttttcc cattgatatg gctacctatt cctctgtcca tttccacatc    43800
agtatattat tgtaactttg taatatgttc tttgatttta cttttagtta tgttttttagg    43860
cagatacata tgaacataca ttcatgtggt ctaagattaa agataagcaa aaagtgcagt    43920
gaacagtatc ctctccatct ctgtcctagc cacccagttc actccccaca ggtgcaacca    43980
ctgttgtcac gtttattat tccttcagga atattttatg tatgtatcag caaatgtgaa    44040
tatatagtcc acctcatgcc acactttctt ctgaagatag ttgaccatac acatgtctgt    44100
accttgcttg aatgaagtta agtgaataaa gttaagtgaa taatacatct tggagatctt    44160
cccatgtcag ttcacaaagt acacctttat ctgtttttaaa aattagtaca cagtattctt    44220
```

```
ttatatgact ttgtcataat ttattcagct agttccctat taatgaacat ttaagtaatt    44280
tacagatttt aaaaaaatat ataaacttat tggccgggcg tggtggctca cacctgtaat    44340
cccagcactt tgggaggccg aggttggtag atcacgaggt caagagatcg agagcatcct    44400
ggtcaacatg gtgaaaccct gtctctacta aaaatacaaa aaattagctg ggtgtggtgg    44460
tgcgcacctg tagtcccagc tactcaggag gctgaggcag gaggatagct tgaacctgag    44520
aggcggaggt tgcagtgagc cgagatcgcg ccactgtact ctagcctggt gacagagcga    44580
gactctgtct caaaacaaaa caaaacaaaa aaactatgct tcaatgaaca acattatgca    44640
catacagttt catacatata caggtatagc tgcaagaaaa atgactagaa gtgaagttgc    44700
tggggcacaa gcatatgcat gtgtagtttt agtagatatt gtcagttcac cctccctaga    44760
agttgtacat tcctctctgc tgtatatgaa agtgcctgtt tgcccacatc ctccccaact    44820
cagtgttttg tcaaactgtt tgatctctgt tagtctacat agtagaaaaa ttatgtttct    44880
gtttagtttt aatttgtgca ttttttcttat gagtaacgtg tgttttttcc tgtttatgaa    44940
ccatttgtat tatgtttacc gtgaacaatc tgttcatatc ttttgccttt aattcttttg    45000
tgtggttgat cttttctta ctgattttta ggagttttta tatattagaa aaactagcca    45060
tttatctgtg atatgagatg taaatatttt ccacatttgc cacttgtcat ttgactttct    45120
ttatactgaa attttttttc taacagacat tacaattttt tcatgtatca aaagttaatg    45180
ttggctggat gcagtggctc actcctgtaa tcccagcact tgggaggct gaggtgggtg    45240 gatcacctga ggtcagcagt tcgagaccag cctggccaac tgagtgaaac ccccgtctct    45300
gctaaaaata taaaaattag atgggcgttg tggcaggtgc ctgcaattcc agctactcaa    45360
gaggctgagg cgggaaaatc gcttgaaccc gggaggcgga ggttgcagtg agccaagatt    45420
gtgccattgc actctagact gggctagaag gatgaaactc cgtctcaaaa aaagaaaag    45480 ttaatgcctt tttggttgct cccaggtttt tgttatagt tagaaagtta tcttcttttg    45540
tttttgctaa cactttatac ctttatttttc aaatataaaa tctttgatcc atcatgtgct    45600
tatgccagtg taaggtatgc agtgtgaatc tggcttattt ttttttccact ttgctagcta    45660 gttgtctcaa cactatttat gaataatcat ctttttctccg atagtttaaa tgctacttcc    45720
atcataaact aaattctcat agtttgattg gattttgaga cttcctattc tcttttatta    45780
atctgcgtgt ctattcatac accagaatca cactattttta attaatgatt atagcttcat    45840
attatatttt agaaacctgg taagattaat tcactttcat gctgcttttc ggtgattttt    45900
ctaggctatt cttgcatgtt tatttttcca gatgaacttt atttatttat ttattctctt    45960
tacaccagtg ttactgccaa ccaaatgaac tttaaaatcg gcttgttgag gtcttttaa    46020 aaaatgcttt tattattggg ttttatgcag ctaaggatat gatcagattt gtgttttagg    46080
aagattattc tgactgcagg gtagaactag gttggaggaa acaagattag agacaaaaag    46140
accaatgaca agattgttgc agtaatccag gggagaatgg atagatgagg agttgaggat    46200
agtattgggt tcaagaggtg tttagaaagt caaaatggcc aggtgcactg gcctgcatct    46260
gtagtcccag ctactcagga ggctgaggtg ggaggaccac ttgagcccag gaaattgagg    46320
ccagcctagc aacacaatg agactccatc tctaaaatat aaataaataa tacaatacaa    46380
taaataaaaa taaatagatg gtcaaaatga ccagacttgg tgatgactga gatgtgcagg    46440
gatgaggagg aagcactcaa ggatgacccc aaacttctg ggttaggccg tcgagtggcg    46500
ccattcccag cgatttgaaa cacacgagat aggggctggt ttaggaggaa gatggcaaat    46560
tcacttctaa atatattgag tttgaggtgc ctgcaggtag tcctagaaga gtgtggtcca    46620
```

```
gtgggctgtt gaatgtataa gtctgaagct ctggagagac atctgggcta gagagatgga    46680
gtgatatgac agagccctga ggaaccccag cactaaagga tggtcaggaa gttcaggagt    46740
gtgcgaagaa gactggaaag aaacactcag agaggtagga gaaaatggg acggcatgga     46800 gccccaggag ccaggagaag aatgttttca atagagcaaa ctgtcagtaa tttccagtgt    46860
tccaagaggt caggagctga aaatgcccat ttggatttag tagcgtgcaa agtctgtggt    46920
tatcttggga aatttcggtg gagcagaggg atggggctg aggtctgtgg gagttgagga     46980
agtggagttg aggcaactcc ttcatcacaa agcttggctg tgaagaggag agacaccggg    47040
acaccggggc aaggaggagg aataggatga tgcagcaagt tagcgacttt tgtgtctcct    47100
ccttccccag ctttacgtgg gagaggctgg gccatttgtt tgttttttgt tttgttttgt    47160
tttgttttgt ttttttgaga tagaatattg ccctcttgct caggctgcca tgcagtggct    47220
cacactggct ctcctcttcc cagctgtggc acatcccagc ggcagttaat cttgccactt    47280
tcaatctccc cattaccatt ataagtgctg ggattacagg caggagccac caggcccagc    47340
ctttggccca catttaaatg cagatggaaa gagctaatag aggagaggag gaagcagtct    47400
gtgatcctgt tctttgagga ccaagtaata ctgagaagga tataaggggg tggagaagtt    47460
ggccaaatca gtctggcaga gagtaagtca attatagtgt tggtatatgt tccctgacag    47520
ttttgacttt taattttgtt gagctgtcta atatttttgc ttggctattt tgagaaggag    47580
cctctaagaa attggattca ggtttagaaa tttagttgaa gattaagttt aaaaagtaag    47640
gtacagacag tgtatcagta agttaccatt tgtgtaaaaa gggaggagat atctgcactc    47700
ccatgtttat tgcagcacta tttacaatat ggaatcaacc taactgtcca tcaacagatg    47760
aatggataaa gaaacaggt tatgtataca caatggaata tcatccagcc ataaaaaaga     47820
gtgaaatcct atcatttaca gcaacactga tggaactgga ggccatttat gttaagtgaa    47880
ataagagaaa gacaaatatc gcatgttctc actcatatgt cggagctaaa aaagtagata    47940
ccacaatgac acacagttag attggtggct accagaggcc aggaaaggga gaggggatg     48000 aaggaagaaa agggatattt atttatttat ttttaaattt ttgagatgga gtctcgctct    48060
gctgcccaga ctggagtgca gtggcacgat ctgggctcac tgcaacctcc atctcccgga    48120
ttcagcagtt ctcctgtctc agcctcccga gtagctagta gcttggatta caggcgtgcg    48180
ccaccaggtc cagctaattt tttgtatttt tagtagagat gaggtttcac catgctggtc    48240
aagctggtct ggaactcctg acctcaggtg atccacctgc ctcggcctcc caaagtgctg    48300
ggattacagg catgagccac cgcacctggc caaatgtatt tattaccact gaactgtaca    48360
tttaaaaatg gtaaagatgg gctgggcaca gtggctcagc cctgtaatcc cagcactttg    48420
gaaggctgag gtgggcagat catctgaggt taggagttcg agaccagcct ggccaacata    48480
gcaaaacccc gtctctacta aaaatacaaa aattagcgag gcgtggtggc atacacctgt    48540
aatcccagct actaactact cgggaggctg agacaggaga attgctcgaa cccgggagac    48600
agagggtata gtaagctgag atcgcaacat tgcacttcag gctgggcaac agagcgagac    48660
tccatctcaa aaaaaaaaga aggtaaagat ggtaaattat aaatgcatgt atagagttat    48720
attatacaca tatgtttaat aaagagcagc agtaatatgt attcttattt gctgtacatg    48780
cataatcagt atttcaaagg actcacaaga agcaaaaaat ctggtatcga ttgtgaggtg    48840
ggaactgggc gaaggggag cgagaattga ggatgccttg tcactctcca ctgttatata    48900
gggtatttgt tgagaatgcc aatatattac ttatttaaat aacgtgatgt aaactgttta   48960
```

```
gttatcttta aaagtaatga ttacaacagg gcctgaattt tcttatttac taatgattct    49020
aagcatctgt aatctgtctg ttctgtgtct aagaagctaa atcttgctgt gtgcctgtga    49080
ggtgtggatc tttgcctgta cagttggtcc tccattatct cattatctga gggttggttt    49140
tgcatatgta gattcaacca attacagatc aaaaatatta gaaaaaaaat tgcatcctta    49200
ctaaacatgt ttttttcttt gtcattatccc ctaaacaata cagtatgaca actatttaca    49260
tagtatttgc tttgtattag gtattataaa taatttggag gtgatttata gtatatggaa    49320
ggatgtttgt aggttacata caagtactgt gcccttttat atcagggatt tgagtatgca    49380
tagattttgg tgtctgtagg gggccctgga accaatcccc ctgcgtactg agggacagct    49440
gtgctccact cttccccact ggggaccgac agccttgggg aagtggacag tcctggttct    49500
tgggtcaagg aagaggacca tggcctggaa catcctggcc ctatccacta tagcttgacc    49560
gagtgggctc taaggctggt ttatagggaa ggaaagagga aatgggtag taattattgt    49620
gtcataggca aaagcctcac actggctgtc cccttcccct gggaaaaaat tctttagcat    49680
ttctctgtaa atttcattgt gattttgagag catgtgtctg aatgattaca tggagtaaac    49740
gtatttcact ttttttttttt tttttttttt ttttgagaca gagccttgtt ctgttaccca    49800
ggctggagtg caatggcaca atcttggctc actgcaacct ctgcctcctg ggtttaagca    49860
attctcctac atcagcctcc ccagtagctg ggagcacagg cacccgccac catgcccagc    49920
taattttttgt attttcagta gagacagggt tttaccatgt tgccaggct ggtcttgaac    49980
tcctgacctc aggtgatcca cccgcctcgg cctcccaaag tgctgggatt acaggcatga    50040
gccacctgcc cagacacgta ttttacttt aatctctagt tttatattac atgctgattg    50100
cacatcccca ctcaggaaca tcagaagaaa tacaaaaaga ggaaatattt caaaactttg    50160
aaatcccaca aaaataatca cattcactaa taaatatttc tccttattta ttttttaggg    50220
taccaggtaa ggagactctc cagtttagtt aggactatgc ctaatctgag ttcccataaa    50280
tcctcaaatg aactatatat gttattcttc tggagactga ggaagctggt taatcactgt    50340
tcccttgtct gggttctcaa aggttcagca ctgaagccgg gagccaggag aggatagcat    50400
tatgaccttt actcctcagt aactcctaag gctcacagag tggttagttt ccctccccct    50460
gtctgtaggc aaaagtgggg acttgcagat aggaagaata ggcttcctta gtgtcagtcc    50520
cgctggtttt tcttcttctt ctttttttttt ttttcctga gacgagtctt gctcgctctg    50580
tcacccagac tggagtgcag tggcgtgatc ttggctcact gcacctctgc tcctgggtt    50640
caagcgattc tcctgcctta gattccgag tagttgggat tacaggcacg tgcatgacca    50700
cacccagcta atttttatat ttttagtaga gatggggttc gtcatctggc caggctggtc    50760
tcaaactcct gaccccaggt gatccacccg tctcagcctc ccaaagtgct gtgattatag    50820
gcgtgagcca ctgcacccgg cccactggtt tttctgtttg tttgacaaaa ggaatgccag    50880
accaactcag tctccaaaca agcgcccaga tccagttatg gctttaactg agattaaatg    50940
gagaatctgg tttcagggac cagttcttcc atttttggta gcttggttcg ttatggagac    51000
taaagttctt accatgatga attaaaaaaa aaatttatt tttgtatttt tctgctgttt    51060
aaaccatgat gaattttag caacctctca tctgggcaga ttctcccaag agatagtgaa    51120
tgcttaggaa cactttacag ctcagcctaa gggagaacat atcagaagca tggctggatg    51180
agaaaggagt ggcctgcctg ggaaagtact ccgttcccat cttcagaggg gtctggtggc    51240
ggctagatgc cctttggtga ggatgctgtc tggttgcatt ggctggcccg gaagatcatt    51300
ccaaactctg tggcttatga gtccagacag aacaggacaa ggacactgtg tgtgtctttt    51360
```

```
catgagctag tggccagatg aggaaaagta ccctatgctc ttttaaataa aaaacaggat    51420
gtaagttttt ttaaaaattc aatatgcttt atttagaatt accatgtgct ttatctaact    51480
aaatattcca gagcatttta ttctttccag acatgttttc tcttatactt tcctagttcc    51540
tttgtgacat cgtatgctta ttttgtcctt taaagttatc aacagtgtga aaaaagttg     51600 ttttgttggc tggctgtatg gtagaaaaca cagccttcat ctctttttt ggcatatatg     51660 tagaagttat tgagttaaaa ctgaaaaggc acctttaatt tatgacagta tcataacttt    51720
aattaaaaaa tcaaacttgt tatttggaaa tgtaaaatct tccccaaagt agaataaaga    51780 accccccatag actcatcacc agattcaata ttttttcaaca ttttgccact cttgtttcat   51840
ctgtcccctc ccctttgttt tttctctttt aattccaaat tacaatctct tctaaactca    51900
gtgaagtgtc ctaccaagtt gaatcacagc ggtggatctg gtgtgattca gaatgcagtg    51960
ggggtgaaag gagggagtcg gcaggctgac aggtgcctgt cttttacata tatttcctac    52020
ggcaggaaga ggttggtgtg ggatgaacag aggctcaggc actttgtctc ctttcctgct    52080
tggcctgaag tgcctacctg acccttgtgg cctccaaggg tgcctttggc cagttgcctt    52140
accagccact aggccggact cctgccactg ctcaagtctt agttgatcaa agccagttc     52200 ttcccttctg cagttccttt ctatcaccat aagaagcaaa tcagcttcct ctggaggaga    52260
taaatgggca aacctgattt acccagaaca tatttctcta gtcattgtct tattagcatt    52320
aaagttaaaa ggagaactac actcaacgga aggcctccct caccacccaa agatatcaca    52380
ccaggtgggg aggtggggat gggaacaggc agtttaaaac ttctacttct gtggaggctt    52440
gggtggcgct ctgtggaaag acagtaaagt gcctttagag gcttgggtct gcattcaccc    52500
tgctatgcca tccctgagaa cttgaagctg aaattcttca ttttatcgtg aaatttgta    52560 gctgtacaga aaagtaggag tagaataaga agctcccata tagccctcac cagttttta    52620 taacgatcaa cactttgcat ttaaactttt tgattatgca gcctagtagt aaaaagagtt    52680
ttatatcccc aatttgggta tgttctttgt tttttaaatt atgtacatat aacactgtat    52740
tgttaatatt aagtatacaa aaaaatagaa agctaagtgg aaacagaact tctaatgttt    52800
tccccatacc ctatgccatc ctgtaaatcc cctgggggta cacattcctc tttgagcca    52860 aatcatttag aaacatttatg taattcagca aacacgtgtt ggagcccact gtgtggctga    52920
cgctgtgcaa atgctggagg gaagatgctg ggggaggtct cactgcttac agcctgctcc    52980
atcagggtca gggaatgaac atgatccatc ttctccaggt gagaagctct gcctgagaca    53040
tagaccttat tctctgcctt ttcttgagca ggatccccca gcatgaactc tgggcgtgtt    53100
ttatgcattg tcgttatttc ttcttctttt tttttagaga tggggtctca ttatgttgcc    53160
caggctggcc tcctattctt gagctcaagc gatcctccca cctcggcctc ccaaagtgct    53220
gggattacac gtgtgagcca ccaccacacc cagccattat ttcttatttt gagaaattat    53280
tttgcctggc cctctgtgat cattttgatt ggtctgattt tgactttacc tgctaaaaac    53340
aaaacaaccc caaaactgtt ttatctctat cattttctgg agtcaccttt taacttagtt    53400
tatctgttaa ctttacttcc cttttatctt tcatttaaaa atacagacta ggaaggggca    53460
acacaagggc cacagacatg gtgataggcc aggtcctaaa tcagcaggtt gggtgctggt    53520
gccttctctg gtctgttctg ctcttcatct cttcttttca tgcctcacag caagacttat    53580
ttggtccttt ggagaagatt ggatccccag atcagctggt caaaaaaggc atagcctcca    53640
ggttaaaaac aaacaaaaaa cccatctagg tggttcaagg gctctgaaag tctaatcact    53700
```

```
tctgcgagac tggaatagac tagccccaaa gatagtgtag tgctggcagg ctgctggggg   53760
aaaagccttc caaaacccag aacagctggg agcctcacag gagttttgtg aactgaagcc   53820
cctgcctgct ggcataccta agcactgcag agggcaaagg aagagtgttg ggggctgctg   53880
tcagagaggc tggctgggtg ctggcaggtc tgacgctgga gatttgttat acattttgaa   53940
cttctcttga agtttctctt ttcttttttt tttgaatgat gttataatag ggtatttaac   54000
caagtatgac atccttttt attccgctta gtttgtaagg tagacttaaa tgatccattt   54060
aaccccaagg cagtgtgaat taatagcagc ccctttgttg tggacaggcc ttcacgactc   54120
ccccacttgt catgagaatc aaaggaggtg ctggcagtgc ctagaatgat ctccagctgg   54180
gttcccaaga gaggcacagt tgttcctttg ttatttagac ttgtccttt taaaagaggg   54240 gggctataac atcttccatt agcttcagtc tgcatataaa taaagagccc tgcaagcttc   54300
aggaacctgc cttacttcct aaacttgata aatttccact cttcaccaac gcttttttt   54360 ttttttttg agatggagtt tcttcctgt tgcccaggct ggagtgcagt ggcacgatct   54420
cagctcccta caccctccac ctcctggatt caaacaattc tcctgcctca gcctcccag   54480 tagctgggat tacaggcatg taccaccatg cttggctaat cttgtatttt tagtagacat   54540
ggggtttcac catgttggtc aggctggtct cgaactcctg acctcaggtg atcctcccgc   54600
ctcagcctcc caaagtactg ggattatagg catgagccac cgtgcccggc ccccagcaga   54660
atttttaaaa aagagttgtg gtctcattat gtcgtcagg gtggacacca acagaaattt   54720
atttagtact ggtggccaat ctgtcgcaca tttgtcaaga actaaagaag taaactaaag   54780
aagaaccaag cagcatcatg ggcaagctgg aggcccagta gagctaagtg atgagtttaa   54840
ggatgccgtt agagccaagc attaacggca gataggtag atagacacta ccctatctag   54900
tgtctctact accagctacg tttccaacca gtctcctctc ctacccaagc tctgttggaa   54960
acagatacaa acccaagtat acagaggaat taagaagggt tggggtagca ttttaattct   55020
atcagaggaa gcattatcgt caatgaatag cttttgtgact tttagctaac cgtttacata   55080
aatattaagt tagatactta ctccaaatga gactactgga gccaacgtca atttgtaggt   55140
gtgccgtttg tattgcatca tagtcaggtg tcttagcaag actgttaacc tgtaattgaa   55200
tcttaaatct tcagtggatt tagaagaatg taatacaatt tatctggaga atttcttttt   55260 cattttctt ttttgaaaca acaaggtctc gctctgtgcc ccaggctgga gtgcggtggt   55320
atgatcatag ctcactgcag cctccacctc ctgtgctcaa gggatcttcc caccctcagcc   55380 tcccaagtag ctgggactac aggtgtgtgc cactgtggct agctagtttt taaattctta   55440
gcagagacaa ggtctggcta tgctgcccag gctggtctcg aactcctggg ctcaagcagt   55500
cctcccacca tgagctccca aagtactggg attacaggca tgagccatgg tgcccagtct   55560
ggaaaattcc ttaatatttt ttttttttaac ttctgtatat atcagtacaa atctgtgtaa   55620
aatctcaaaa agaattgatt ttatgtaggc tatatagcaa aggaggcaaa gcggtgaggt   55680
aaagagaata ctgaatgagg ctcgggatcc tgagttttag ttttttaggct gctacaaact   55740 agctctgcaa tcttgagaaa aatcacttca gctctctgta ccttggtttc ccatctgtag   55800
aaggaaagag cagaattcca ctccctcttg cttttacttg tgttgctttc tctgctaagc   55860
cagcaactcc agttcccttc ctttgcctat ccccaccta ttttcaccta ctgcaagctg   55920
gaaaatgaga tgcctcagtt tgttagacct gggtggggtg tgatgcagaa ctggagggt   55980 tccttttctaa ctgctgtcct ctggggttct tatccatttt tgttatttag ggctttctt   56040 tgctttctgg ctcaccactg agatggttga aattgccaca taaatgaccc ctggctcaag   56100
```

```
ctagcacatt gtcctcatag cataaaataa tggtgacatc acattccggt gcagtcctct    56160
gtaatattga agcttcatgc aagtacccat tcccagtgtt gacgatggta ttccaggaaa    56220
atatgtgttg ctcttgcagg agttttatca cttttttctt tgatcacgag tcatcatgag    56280
gtctgtcatt gaagctacta agagttgtct tatgtagaat tgcttctgtt tgagaatatc    56340
gattaggcac ccctttgtac agatgctgag gttgtggtat tctggatcaa tacttttttca   56400 aagtattaac catttatatg cttaatcctg gttttctgca tgttttttaat atatttttta   56460 aaacttggta gaacttcttt tttttttttt ttttttttttg agatggagtc tcgctttgtc   56520
gtccaggctg gaatgcagtg gcacaatctc agctcactgc aacctctgcc ccctgggttc    56580
gagcaattct tctgccttag cctcccggta gctgggacta cggactctca ctaccatgcc    56640
cagctaattt ttgtgttttt agtagagacg gggtttctgt tggccatggc tggtcttgaa    56700
ctcctgacct catgatcacc caccttggcc tcccaaagtg ctgggattat aggtgtgagc    56760
caccgtgcct ggccctgtag aacttcttac atggaaggat gtatttggtc ataccattag    56820
catttagaaa cccatatttc acttcaaggt atttggaaat tacatttctc ctgtttttaa    56880
taactgtata aaaatacaac tataagctag gattttatttt gctacttagc tgcagaagaa    56940
aaatgtatgt cttgattgtt cacacataaa gaatatactg taccatatat gcttttgata    57000
atgataatct tcctagttga taataaacaa caactctcca attcttggac ttcagctcat    57060
ttcctaactt agcgtgggct tatgtaggaa tctgcttatg gtttaccagt caagtaagat    57120
ctggggtttc taattaacca caaacataat gatatgccaa cagtacagta catctaccca    57180
aacagttaat gcaaatgtag gtcacattga tagatcaata gtgtctaaat tagaggaagt    57240
aatttccccc ctaggtgacg aaatctagtt gcaactttttc agccattcat cccaggctgc    57300
agctttcaga tgctatgtga taggtaggtg tgcacctaca cgtaactgat atctcatcta    57360
actgagctct aggtcccttg gggaagtact ccgggagtat ggtactgtct gccgttagct    57420
ctaaacttct acctggaaat ccacaactct gcttcttttg gaagattcac acgtcctgtt    57480
tcattacaga aagagttctg ccgttagcat tagccatgtc actcccctcc ccggtctatc    57540
tagcactgga tcccagacac tgatgtggag aaccatttct gtatggaggc acagaagcct    57600
tctcttcctc atttgatgtc taggtcccat gttctgaaac agtagagtgc ttttcagatc    57660
ctgagcctaa ggccctcctt aaaacacata gagtcctatt tacaggttcg tttctttctt    57720
gcttgctttc tgtatttatt tactagagac aaggtctccc ctctgtcacc cagtctggag    57780
tgtagtggca ggatctcagt tcactgcaac ctctgcctcc caggctcaag tgatcctcct    57840
gcctcagcct cccaagtagc tgggactaca gcgtgaacc accacacctg acaaattttt    57900
gtattttttg taaagatggg gttttgccat attgccaagg ctggtctcaa acttgtgagc    57960
tcaaatgatc cacccacatc agcctcccaa agtgctggga ttacaggcct gagccactat    58020
gcctggctcc catttgcaga ttcttttgac ttacacctcc cttgttcttc aagaaaatgg    58080
ggccaggcac aatggctcat gcctgtgatc ccagcacttt gggaggccga ggggggtgga    58140
tcacttgagg ccaggagatc gagatcagcc tgggcaacat ggcaaaacca tctctactaa    58200
acataaaaat aaaaaaatta aaaaattagc caggcatggt agcacatgcc tgtaatccta    58260
gctactcaag aggctgaggc aggagaattg ctcgaacttg ggaggcagag gttacagtga    58320
gctgagatca cgccactgca ctgcagcctg ggtgacagag tgcgactctg tctcaaaaaa    58380 aaaaaaagt aagaaaaatg ggactctcta tttcattcag tctctctctg tcatcactac    58440
```

-continued

```
catattagcc agctttgctt tagtaacaat ccaaaaactc agactctcaa caaacattta    58500
tttttcactc atattacttg tccgtggtgc tggaatacct tctacgtctc tcctctgtgt    58560
atcttctcca tctgcaactg aggctgaagg agcatcccct acttaagaca tgatagtctc    58620
atggcagaag gaaagagta tgagagtttc tgtttgaaca atatgaacat cacatttgct    58680
cataagccat tggccaaagc aagtcacatg ggccagtcaa cttttttag ccattcatcc    58740
caggctgcag ctgggtgacg tcagaggtga cttggaatgg caacagatgg tgcctgagct    58800
gtaggaccgt tggggagcac cgtgggaggc tcagaatgct ggggcagtcc ctaatagtga    58860
tgctgctgct cctgaccacg aaaggactct gcaggtcagc cccacctttg acaagatgct    58920
tcccagggtt ccaccatgca gacactcatc ctcctttcca atgtccgggt atccctggga    58980
caagcagctc ttatgtatgt aacatcattt tgtcttctca acaagcctgt ggaagttatt    59040
atcatttcca cttttagat aaggaagatg aagtaacttg ttaataagtg aacatctga    59100
acttgaactg tttctttgac tccgaatcat atgtgttttt ggggttttgt tgttgtcgtc    59160
gtcgttattt ttatttttat tttttttctg agacagagtc ttactctgtc acccaggctg    59220
gagtgcagtg gcgcgatctc agctcactgc aacctccgcc tcccgggttc aagcgattct    59280
cctgcctcag cctcctgagt agctaggatt acaggcatgc accaccatgc ccagctaatt    59340
tttctatttt tagtagagat ggggtttcac cgtgttgacc aggctggtct tgaactcctg    59400
acctcatgat ccacctgcgt aggcctccca agtgctggg attacaggcg tgagccatgg    59460
cgcccagcct gttgttattt ttaagagaca gggtcttgtt ctgtcaccca ggctggagta    59520
cagtggctca atcatagttc actgtagcct gacattcctg gggtcaaggg atcctgagcc    59580
tcaacctcgg cctcctgagt agctagcact acaggtgcac atcaccacac cagctaattt    59640
aacaaaaatt tttgtagaga cagggtctca cactgtgttg tccaggctgg actcaaactc    59700
ctggcctcaa gtgaccctcc cctttggcct cccgcaatgc taggattata ggcgtgagcc    59760
actacaacca gcccaaatga tatattcttt gaatggcaac gtgcaatgtt taaaatactg    59820
gccgggtgca gttgctcacc cctgtaatcc tagtactttg ggaggccgag gcatgtggat    59880
cacttgaggt caggagttca agaccagtgt ggccaacatg gtgaaaccca gtctctacta    59940
aaaatacaaa aattggccgg gtgtcgtggc ttgtgcctgt aatcccagct actcaggaaa    60000
ctaaggcagg agaatcgctt gaacccagga ggcagaggtt gcagtgagcc aagattgcac    60060
cacactccat cctgggcaac agagagagac tccatctcaa aaaataaaaa aattaagtaa    60120
ataggctggg tgcagtggct catgcctgta atcccagtac tttgggaggc tgaggcgggc    60180
ggattgcctg aggtcaggag ttcgagacca gtctggccaa catggtgaat ccccatctct    60240
actaaaaata caaaaaatt agccgggagt ggtggcatgt tcctgtaatc ccagctactg    60300
gggaggctga ggcaggggaa ttgcttgaac caaggaagtg gaggctgcag tgagccaaga    60360
tcataccact tcactccagc ctgggtgaca cagcaaaact ccgtctcaaa aaataataa    60420
taaaataaat aaagaaaat actgtatgta ctctgcagat ataaccatgt aagaacttac    60480
atggataaaa cttgaaaagg agtagaaaaa gtgaagtgct tggccttttg agtggcacgt    60540
agtatttctt tgtcacccag gctggagtgc agtggcatga tcttggctca ctgcaacctc    60600
tgccacctga gttcaagtga ttctagtgcc accatgccta attttgtat ttttagtaga    60660
ggcagggttt tgccatgttg cccaggcaga tctcaaattc ttgacctcag acgatccacc    60720
tgcctcggcc tcccaaagtg ctgggattac aggtctgagc cactgcaccc ggcccagact    60780
tagctccttc agtttctggc ttccctaact gaacagccac tctaattcat tgatgagga    60840
```

```
agatctttga gaagtaattg agaaggttaa gccaaatata gtttggagta agatcagata   60900
ctgcaggggc agagagttga gattaggcca cagtgaagaa gagaagaaaa tatcaaatgt   60960
aagcagagat taacacccca caactgaata ccagcagtaa tacaggattt gggccagcag   61020
cagggttaat gcaaaagagg cagctgttaa atcgaaaata agagcttttg ttttgttttt   61080
tgttttagag acaaggtctt gctctgttgc tcaggctgga gtgcggtggt gtgatcatag   61140
ttcactgcag cctcgaacac ctgggttcaa gtgatcctcc tgcctcagcc tcccagtag    61200 ctaggactac aggtgggcac caccacgccc cactattttt ttttttttaa ttttttttg    61260 tagaagtgag ggcttgcagt gttacccagg ctggtcttga actcctggcc tcaagtggtc   61320
ctcccacctc atgctcccaa agtgctggga ctgcaggcat gtaccaccat gcctagctaa   61380
tttgtttgtt tgtagagcta attttctttt cttttgtaga cagggtctc cactatgttt     61440 cccaggctgg tctcaaactc ctggcctcaa gcaattctcc cacctccgcc tcccaaagtg   61500
ctgggactct agacaggagc cactgcaccc agctagaaaa tttaatagga agtctaaaag   61560
acatttcagg aactctctgc ttttgggaac gccttctaaa gacccttctc cccaccttgt   61620
ggactggcct tcaggagccc agtttggcag taattgtgca gtggctcagg catgtaatcc   61680
caacactttg ggaggccaag gtgggtagat aacttgaggt caggagttca agaccagtct   61740
ggccaaaatg gcgagacctt gtctctacaa aaaaataaaa atgtagccag catgttggca   61800
tgcactgtag tcccagctac tcaggaggct gagcctggga agtggaggtt gcattgagcc   61860
aagattgtgc cactgcactc cagcctgggc aacagagtga gaccctgtct caaaaaaaag   61920
agatcctgtg tcctcattgc atcttgccaa gaagcacctg atgtcagttt gtcccattat   61980
ttttcaggta tttcaatata ttattctcta gaatagagta ttccattgtc tgagataaat   62040
ctagcttccc tatatcatag tggctatttt tcttccagcc cagaagtttt tccttggtaa   62100
gataacttta ttttgtgagt ttatagattt ggattataaa aatagatcgg aactgttaga   62160
ctaatttggc ccagagattt tatgagtcca cttgggagaa ataggagtaa ttctcaaaac   62220
caaaatgaga aaatccatgt ttaacaaaga aaaattagtt tttagctgaa ggaagtcccc   62280
tataaaaaca ttgcgtcaca ggattccttt cacagtaagc taccaatttt atatgtgact   62340
caattgacgt aaaactctgt tttaaatgaa tagtatgtga ggtgatggat atgttaataa   62400
cttgatttca tcattttgct atgtatacat atatcaaaac atcatgttgt acagtgtaaa   62460
tatatacaat ttttctttgt cagtaacacc ttaatgctgg aggggatggg agaagaaaat   62520
ctgttttcta tatttcacaa gcacatctat tgcacaatgt atacacattg cctcattatg   62580
tgagatttat tggcccagcc taggatttgg cttttgacaa ccaaaaaggt tgcccttttgt  62640 gataccagtc tcaaaaatgt taagaacgta ccccaagcat ctctttaaaa aggattttgg   62700
atttattgac catgaatttta tctacaatct gtttctgctt tcatttgtat catttaggga   62760
ctgatgattt gtatgttttc cacttgtatt tacatagcat tccttttttc ctctttaact   62820
caggggttac acactctgaa tgtctaaaat gatgagtcag tgaaatggtt tgtgtgtaag   62880
gattcatagt aagagagtgg gtgtcccatc tacagggagc agccatgctc aacttgagcc   62940
tgagatgagt gcggctcatt gtggccaaga tattttgatt tatgggtggg tgcggtggct   63000
cacatgcctg taatcccagc actttgggag gctgaggtgg gctgatcacc tgaggtcagg   63060
agtttgagac cagcctggcc aacatggtgc aaccccgtct ctactaaaaa tacaaaaatt   63120
agctgggcgt ggtggcgcac atctgtaatc ccagctactt gggaggctga ggcaggagaa   63180
```

```
tcacttgaac ctgggaggcg gaggttgcag tgagctgaga tcacgccatt gcactccagc   63240
ctgggcaaca gagcaagact ccatctcaaa aaacaaacaa acaaaaaaaa ttctgacttt   63300
tccctagaat cctcaagtct gaattttcaa acattatgaa ttcaatcaaa aattttaaaa   63360
gacactgtgc agaacaaata ggtgcctcgt ggcttgccag tttctttctt taatatacct   63420
cttttacatt tcaaagtgtc ctttctagtt ttctgggatt tagtatatga gttcaccgtc   63480
ttctgattct cctcccccaa ttgcatgaca acttttatta ttctttcagc tttcctctta   63540
acacactaca gattatttgt cattatttta tggttattat aaagaaatag ttccatatac   63600
tactttattt accttgaccc aaggcccact aatgtataat aagtaaaact gtaaaatcgg   63660
tcctttcatc tcctgttgtt atcagttgtt cttgagggtg agtgtcaatt tcatggttgg   63720
aggccaactc ttcttccctt ctctctgcag ccgtcatttc accaagctga taatgttcgg   63780
ggaacccgcc atcacgggct ggtggagagg ccatccagga accgcttcca cccctccac    63840 cgaaggtctg gggacaagcc agggcgacaa atatcctttt ttactcttca aagggagtgt   63900
gcattctgaa atgtttgaaa agttttcagg atttatcttc cctgcaattc tcctttggcc   63960
tcagaatctt catttatctg atgaaggag gcaatacaaa taaatgagtt ggaaactaga    64020
aacatctctg cagtcaacat ttggaaacat cattgtaggt gtttatgaaa gcatcaataa   64080
agttcagttt aatgaaataa caacaaaaac aacctgtaat tcggtcccat gcagggtgt    64140 tctgagcatt ttctccagaa attggccacg ttagagttaa acctgacttt gaatcaggtt   64200
agagagcctt agtctcttta gcaaaaatgg acatagagat atgtgattta tttgtacttc   64260
ttttgatctg ctgacctgct tttgaacctt acagacaaaa tttcatatta ttttctattt   64320
gtgatgtttc aaactcagta agtgataact aaaataaacc tagaatatag gaaaatctca   64380
tgcagtgatg tacagtcaca ccaaactctg ctgttaagta gaaataaagg aaaggaaatg   64440
gtgaattcac ctgacagttt catttaatca gtcctgttta cagggcggca gtggtgggtg   64500
cagctgtgtg accagcattg tgccgaaggc tttggggaac agaactgagc tggatttttt   64560
gggagaggac acagaagtgt gccaggaggg cccgtgctct cacttcattc ttctcagtac   64620
tcgggcgcag gggtggagga aggagaagaa aggcggggtg ggtctcgctg cggagagctg   64680
aattcctggc agtgatggta gagttggctt cacaagccta gaaaccagga agtggggca    64740 gggcactcat gtttactgag cacctaccca tgccaggcgc tgtgctgggt aatttatgtg   64800
tcacttagtc ctcaaaaact cactgagtcg ttaattttt taaccctcat tttctgatga    64860
ggaaactgag tgtgtggtga agtaacccag gattcagacc aggccccgct gatggccag    64920 cctgtgctct cccctcccta tgccacctgc gaccattcgc agtgatgagg accttgtaca   64980
agggagccag gagttgtggg ggcactctag ggaaacccca acttttcttg ccttcaagct   65040
tcttgcagtt tttagtctat ttggaggcaa ggataatgac cccagggaat gttttctct    65100 cccctttctc ccgcccccag gaacacacca catttggtcc acagaaggac tgacttctga   65160
ttttgtatat tatgtggctg ttatcaagga agtaaagat gataaatgat cttgagaatc    65220
tattctggaa tgtgtgataa ctttgacatt gaatgaaaaa ggcaaaagga aatggaggca   65280
attcatcagc aaatttgtac atgtcaggat ggagtggtac atcaaaccgt tgtccaaatt   65340
gccaagaata ttcaggcaaa agacttggag tgtttctttg attgatttaa caatgtattt   65400
tttttggctg ggcatggtgg ctcacgcctg taatcccagc actttgggag gccgaggtgg   65460
gcagatcacg aggtcaggag attgagacca tcctggctaa cgtggtgaaa cccgtctct    65520 actaaaatta caaaaaatta gccaggctcg gtggtgggca cctatagtcc caggctgagg   65580
```

```
caggagaatg gtgtgaaccc gggaggtgga gcttgcggtg aaccgagatc gcgccactgc    65640
actccagcct gggcaacaga gcgagactcc gtctcaaaaa aaaaaaaaaa aaaccaatgt    65700 atatttttc agttctcagt tccctctttt tcctgtcagt gctctcattt ctatatatta    65760
gattaaacat tatgctatat atacgtgtgt gtatgtatat gtggctatct cagatacttt    65820
tgaagtacgg tctaaatgta taagcatgca tatagtttta ctaaccaaaa tagagaaggg    65880
aattgaagaa aaaagaggag aatgtttatt cacttataaa aattatttgt taagtatgtg    65940
ctagtggtca gacaccgttt tagacatttt aattcactgt aacagtaaac agcatggtcc    66000
ctgacctcaa gttgcccagg gttcagtggg agaggctact cagcaaacaa gcagccacgg    66060
caggtatggc gtctgcaggg aggcagctca ggggctgtgg gagcacgtcg gaggtgcagc    66120
ttgaactagt ctggggaaac gaagaaggca tcctggggga acatctgagg cttgaaggat    66180
aagaagtaag aggataaagt gttcattcag cagatctta cagagccccg tctctgtgcc    66240
aggcactgtt ctaagcactg ggacccagt gatgaataag ggaggcatac ttcctgcttt    66300
cttgagttca cagtcctgtg ggagatgaca gcaaacaggc aataagaaag gaaaatggtt    66360
ttagatggta atgagtgaga tttaagagag taaagcagtt gggaggtatg ttccaggcag    66420
agggaagaga atgtggtgca aagtcctacc cagaaggga gatgacttct tgtgttcagg    66480
ggaccctatc tcttatgata gggtataatc tggcactgta tggatcaact tgagagcata    66540
agcaaagcta gtcaactcct aaaggaagga gaaacaaaaa ccaagttaat atgcagagaa    66600
attaaagtta ttagacagta tgagtcagat tcactgatca tgagccatgt ctctgtggtc    66660
tcctaagctc ctaaattggg ttcctgggac tggacatcgg ttgatgcaaa gaaagttctt    66720
tagcccagtc tcttttgagg aatcaagggt ccgtgaaatg ggatgatttt atttgtgt    66780 taatctattc cacttggagg aggagggctg tgattccgtc tttgctttca cgacctgcat    66840
tctgttggtt gtgaaataat ctgcttaaaa ttgtggcctt gaacatttgt ctatgacttt    66900
ttaaatgaag tttcttcatt tgaaagtata aaacactagt ttgaatcttt gttagaacaa    66960
aaggaaaaaa tcagaattat tatagctgtt tcttggcttg ggtgttattt aagcacact    67020 ggcttagaca agggttttaa gggttcactc ctatgatagg gtgatctcaa ataaaacgaa    67080
cattgtttaa caaatactct ggcctcctct cagagtgggc agccacagca cgcagagctc    67140
tgccacagga gattccttct ggagtgggct ttgcccttgg catgggtggc cacacaagac    67200
caaggcacag ctgcagctgg gccctggcct agccccacac aggcggagga gaggcactgc    67260
cagggcttgc tcctggctgg gggcctgggc tcgggcactt ggaagagaag ctcttctgcc    67320
cttctgcaga tgtgcagtct gtagcagccc ttcttactct cactcatcaa ggttggcaga    67380
cgtgccgtgt cccaaacacc attgctaaac ttctgaacta ttaacataaa tttatagcaa    67440 ataaatatt ttctcagcct tgtggatgac acgctcagaa ggaaacacga aatgccttcc    67500
ttgaaaggaa gtcaagagtt caccagcgtg aagggtcgtg aagagatgcc taagacctac    67560
tagagttagg aatgattctc ctctctgggc tgggccttgc tttgattctt ttcatcataa    67620
tgagatgaaa atgttaggac attggtttat aggacactgt ttcttgaga tgcatggcct    67680 attacatttg agaaacacca tactctgtat cacctcttgg agcctgaccg tatatatcag    67740
ggctctgaaa agtcctgcag ttaataaact tcttatcttt aacccagaat tcaaaacttt    67800
aagtgatcac aaaatccaac tgttacctaa cacccgtctt atcttgaagg acaaggaaac    67860
attggtcttt agaattttaa ggggaaata ttctgacttc acaataccac atgcaacctg    67920
```

```
tttgcctctc atttgctgag ggaaacagga tgttcttata aatgcaagga ctcaaaaaga    67980
tgccactcat atcctccctt acagtttcac tttaagatgt cttctagtgg gacatagtta    68040
gaggtaaagg gacaaaaaga agtagaatga caataaacac atggctgagc aatcaggaag    68100
gagccaaatt gtggccagtt ttatatatta aatctgaccc tgaaacttgt cttggtaggt    68160
gggttctgtt aaccagactc cgagcccact taccccacca gctacatgga aggtctcagg    68220
cctgccccac aaactgtgtc cctggcagaa cacagagttc cagagcagga gagaaatgac    68280
tggcttccag gctgccccga caaggcagtt cctgagccct gcccaggtac actgaccgca    68340
cagggacggg aagccaagag aagggaaccc tgggcctgct cacccagccg caggtcaagc    68400
agcacaaaga aagggccagg gcgggtcttg ttttcagctt ctgtggctca gtaaccccac    68460
ccactggtaa actggccaac tgatgtcctc tcttatcaga agaagaagag ctgctcccct    68520
tcctttggtg aagagtaaga actgttccct ctaacactcc acaggttgag aggaacagca    68580
gtccctgtgt tgatggattg aggcagtaac tcgaggagga agattttcct gcacagaact    68640
gcagaggctt ggggagagag agaacacact gggatgactc tgagatccta acatgagtgt    68700
cttggtggac ggtggcctca ctaaatgaga tggactataa aagagggaac agattaaggg    68760
gacagtgatt ggttggattt ttggtagaat ttgagctgtc ttgggtactt ttggcagaga    68820
acttgagtag gcagttggaa gtatgcactt ggagttcaca aaagaactgt tgggagctgg    68880
aggtgtcgat ttatgagtta ctggactgtg ggtgacagtg gggccgaggg aaggatgcga    68940
ttggccaagg cgagcatgga ggacaggggc tctctaccag gaagacgggc actggccctg    69000
aggctcttag gaagcgcctc ctaaagctcc tgtgcccgga ggctcccgcc acccctcca    69060 cctgctcaca ctctgcctgg tgcccaggga tcctgagagc atcctttgcc tctcagagca    69120
atgcaggcag gtgtggcctg aggctgcgag gccacaggac cccagggaac atcaggacgg    69180
aaggcaaagg ggcggaaagg agtgcacaga gggataagaa aagatccatg tgagtgtggg    69240
gatttttttt tttaacttta attttttgttt ccatccattg cagccacctc ttctttgttt    69300 atcttttttca tcatccctcc tccctgcctt cctttttttaa tgtggaaatc ttccttgagc    69360
caaaggcttc actaagctta actaaggaag caatggagga ggcgctgatg tggttgttaa    69420
aagccctgtg acctgtgctg cccttccgct ggcacgctgg cacctggcag ggatgccaga    69480
aatgtttctt gagtaaatgg taaattcaag tttataaata agagtgtttc ctttgtctcg    69540
aggttgttac ttagggcatg tcagtgttgt ggagtagttt aaagccacct gaatgaagtt    69600
ttctgaagtt ttccaaagaa caaataaact tcttctagat tttccttgca ttaagtataa    69660
gtgtataaca tgagtggttc tcttgggttt tcaaatatcc actaaattag atgagagtga    69720
aaattaagag agctcagagg tcacatcttt caacttttga tgcctcaacc taattatatt    69780
aaaaatttcc aggaatttac tatattttca tgttgttaat atcaggaagg ttaaaatgct    69840
aacttacacc tcaacattga aatcaccagc gtttgatgat tacgtgacta ttacaccact    69900
gcattctaat ttgtattatc agtactatga gatcagagat actgagttta aagatggcag    69960
tgtactgaga aaaatggtaa acttctactt cctgaaatta agcgtttctg aacagagatt    70020
catcaaatct gcagaaaaga gaaaggcaga taaccgtagg ttctgaggct cggtgtttcc    70080
tccctaatgg cttttgccaac agaaatactg acaggttttg tctgtcacgg gccttactat    70140
ttatcacctt ttcctctcct acctcctact gtggtcttgc ctcatctgta cttcatgtac    70200
cttaagccta atagtgaatg ttgaagaaat gtctctcttt ggaaattatc tgttttattt    70260
tattgattta aggtcaaatt aagaaataag ataatgagac ttgtcaaaga aaacgaatac    70320
```

```
atagaagatg aaacttgcaa tcctaatgcc tctcctggca aagaagacat ttcccaccaa  70380
atcactaaga actcatgaga gcctccgttt tcctaattcc agattctgta tttatttgag  70440
ctgcccagcc caggcctgca ggataggcc ccactccatc aaggctcctg tttcctcctg   70500
agcccgagca gatggtacct tctcttatag cctccatcct tcccagaaca ctccaggtac  70560
tattttctat tttctggggg catttggcat agttcactgt ttcctgagag gcagcatagc  70620
ttagcggaga gctctcaggc tttggtgtca gtgatttgtg ggtctgaccc ctgatccacc  70680
aggcgtgcta tctgatcttg gatttctcag ctcttctaga actgagcctc agtttcttca  70740
gctataaaat ggggaaaata tctgcctctc aggattgagg ttaaataaag tgtgaactca  70800
gcacaggcct ggcacacagt aggtgcttag atatctgttt tcaaatttct gtcttaatgt  70860
gtagtttgta tcttctttat tatttccacc ttaagaaata aaagtttggg atgaaaagta  70920
ttattggtaa ctgccgaatg tatatttaat ccaatcagtg atccaggaga caaaaggaat  70980
gggcttggtt tgggtgagtg ataaggaggc aaccttccac ataggaggtg agaaagggga  71040
aatggcctta gcaaaggcag aggggcagga aaatacaggc tgtgtttgtg gaactcagaa  71100
agctggaggg aagacaagag cagaagagac cattgtcccc aaattgtgga tcaccgcaat  71160
tactaagcca gtaagttttg attttgcctt ttaggctgaa caaaatcatt gaagatttct  71220
tagcagaata atatgattaa cagtgtcttc agaaggctat tgtgtgggaa caattaacta  71280
aacgaatgaa aacagcgccc ctctgctcgg tgtgtagtgc agcatcccat ttgtgtctcc  71340
gtgcgtccag aatatgctcc aaggcatggt agacccagtg aacaacacaa gactgataag  71400
acagtgcccc caacaacact ggaaagttta ccttcttca cacatctaat gcgcctcttt   71460
tttggttata ataccagga accgccgggc gcagtggctc acacctctaa tcccagcaat   71520
ttgggaggcc gaggtgggtg gatcacctga ggtcaggagt tcaagaccag cctggccaac  71580
gtggagaaac cctgtctcta attaaaaaaa atacaaaatt agccgggtgt ggtgcgcat    71640 gcctgtaatc ccagctactc gggaggctga ggcaggagaa ttgcttgaac ctgggaggtg  71700
gaggttgcag tgagccgaga ttgcgccatt gcactccagc ctgggccaaa aaaagagtg   71760 aaactccgtc tcaaaaaata aataagtacc aggaacccac cttaacttaa aaaagaaaa   71820 tgtattggca tatgtcactg gaagcccaag ggctagatcc aagggtcat acaatgtcat   71880 tgagacctac ctctgtggta ccacttctga gatgacttca ggcataacag acaggctttc  71940
tccaaggtga agaccccag gttcagacgg cccttgggct taccagccct attggggcac  72000
tccttttttt tccactcaaa agcactctcc ttggttctgt ttgcgtcgtg agccgatccc  72060
tgagccaaac actgtttcca gggggtgagg tacctagact agaatcctgg gcctgggtcc  72120
ctcacatgtg gcacagaggg aatggcagtg ttaccaggtt tggagcaaga gtggagacag  72180
ttcctgaaaa caaaagttgc cggacaggca aaaataata aacaccccac aaaaaatcat  72240
gcaaagaaaa caccggttag aagacagcag aatagacttg tcctcaagga gggagataag  72300
agaaagcatg aaggaagagc tgtcaggtac agggataagg aaccaaaaac tcagttgttt  72360
aactctctgt gagtccacct tgttaattct gcttcatctt tccattaatt tttatttttc  72420
ctttattaaa aattctactt tgatggtagt gcttttggag ccaattattc ctcacagcct  72480
ctggatgaga gttggccaag gtaagcaaga catactttaa aagatatgat gggcatgtgt  72540
tatttttaga taatttcact ttatccactt tgaatgttgt ttagaaattt ctaatataaa  72600
gcatagaatc ctgtttttctc ttataacatt taatttcagt gggaggatca cttgagacca  72660
```

```
ggagttttga ggctgttgtg tgcgatgatg gggcctgtga atagctactg cactccagcc   72720
tgggcagcat agcaagacgc catctcttaa aaacaaacaa acaaacaaaa caacaacaac   72780
aacaacaaca acaacaaaac accttattgg ccgggcatgg tggctcatgc ctgtaatccc   72840
agcactttgg gaggctgagg cgggcagatc acaaggtcag gagattgaga ccatcctggc   72900
caacatcatg aaacccgtc tctactaaaa atacaaaaat tagctgggca tgacagcaca    72960
tgcctgtaat cccagctact tgggaggctg aagcaggaga gttgcttgaa ccagagagtc   73020
ggaggttgca gtgagctgag atcacgccac agcactccag cctggtaaca gagtgagact   73080
ccatctcaaa aaacaaaaac aaacacctaa gcatttccaa tgataggcta atatgaaagt   73140
ctaaaatgaa aagttatttta agaaatcta gatcttcata tttaaaacca aatagaaaca    73200
cttttggaat atatttacca gcagaatact cagatatggc attcttatgt ttgagactta   73260
gaaaaataag catcttggcc aggcacggtg gctcatgcct gtaatcccag cactttggga   73320
ggccaaggcg ggcagatcac aagctcagga gatcgagacc atcctcgcta acacggtgaa   73380
accccgtctc cactaaaaat acaaaaaagt agccgggcgt ggtggcaggc gcctgtagtc   73440
ccagctactc gggaggctga ggcaggagaa tggcgtgaac ccaggaggcg gagcttgcag   73500
tgagccgaga tcacgccact gcactccagc ctgggtgaca gagcgagact ccatctcaaa   73560 aaaaaagaa agaaaaataa gcatcttttc tcagagtgtc ttagtaagct gctgaaaagg    73620
acaaaagact cttaaaatgg taatttgcac agtgtatttg atttaaggtc tctttgagta   73680
tttttgtacc caatacagag ggtaacagga aatagaatta actgagaaaa agcccctgct   73740
gcatctgttg tgtgcctagt atcatttca gatcaccaag tcagatttag gacacattta    73800
aaatgtgtgt atcaaaaata tttagctctc cggattgaag tctactctcc atccattctc   73860
tgggcaaata ctgactgaga acttactgtg tataatgtag tctggatctg ggaaaggaaa   73920
taaagatggg taacagtggg tccccacctc aggtaggttt tcagctgccc tcaagaatct   73980
tgggatccag ggttgtagaa taaatacaat attttattac atcagtaaaa gtcatctcca   74040
aactgttatt tttctttat gtatccaaga aatgtcttct gcttttcaga gcaccaggac    74100
tggttagact taatattttc ataccctggg caactgtaac aattctattc ctcttcatgg   74160
ccattggtag gggaatgcaa aattttgca tccaagattg ccacggcgcc ccctacatgc    74220
acactgaact cctcatctgc ccagctagct aatcctgtgc cttatgggtt tgtagtagtt   74280
tttatactgg aaatcagaga tcacaggact ggaaggatca tggagtctta cctcattta    74340 acaatgatga gcaaaatgag cgaggtgtgg ggtattttta agtaactctt gcagagcgag   74400
gtgagtagaa gagccagttc tcaaatgcaa gtgctgaggc cctcctttgc tgtctgtgga   74460
ttgacttctt ttccttttat gttgttctgg tttttaaagg cagcagcctc cttggaaaga   74520
cgaaaagcat cctgggttca ggctgacatc tgcacttaac aggtacatgg ttgtttcct    74580 ggtaggagta gatttaaag caatttaact gtcctgatat tttttacata gcatccagtt    74640
gccagagtgt gtttatgtaa gctgtgttga tatgacatgt tcaaaacaaa acccaccatt   74700
ttttgagtgt ctacagggga aagtatagag cacacgaggt ctgggatgag actcccaggg   74760
tttgcatctt gctgtatgac cttgagtaga ttttaaact tctgattgcc tcagtttact    74820
catttgaaaa atggagataa tgctacctag atcatggggtt ggttgtgagg gttgaataag   74880
ataatacctg ggaagcatat gtgctgaata aacatcagct attatcatga tcactttggg   74940
ccagactcca ggagtaagag ttctacctca gccatttttt ttcaatcctg acaacaccct   75000
acaagaatga gtattatttt ccattctaaa aggttaagtg acttgtttaa gggccttagc   75060
```

```
taataggtga aggactagga tttgaaaaaa tgcagctgag catggtggct cacgcctata    75120
gtcccaacac tttgggaggc tgaggccaga ggatcgtgtg agtccagcag tttgaggcca    75180
gcctgggcaa gatggtgaga ccctgtctct atgaaaaaaa aaaggcgtg gtggcacgtg     75240
cctgtggttc gagctactca ggaggctgag gtggggagga tcacctaagc ccaaggaggt    75300
tgaggctgca gtgagccatg tttgcgccat tgcattccag cctgggcaag agagagacgc    75360
tgtctcaaaa taaaaagaa acccgatgaa tggtgcaaaa ttttaaatat actcaaacag     75420
aagagttata aaaggcctgt ggtgcccatc ctcagcttca ctcattatca gcattctgcc    75480
agtctctcca aacctacctc ccacctcagt cccgtgactg gctagtatag tattgtacct    75540
tgaaatgtct ccagcagttt aaggccgacg agaaccttt ttaaaaaaca taaccacaat     75600
gccgctatta cacttaacaa aattaaaaat aactccttaa tataattcaa tgcctggtcg    75660
gtatttagat tttcccagtt ggctctgcat tcgtttgata ttctcttgag tctctttgaa    75720
tctgtaaaaa gaggctggaa tctgaaccca ggtctctctg atctcagcgg ccacgctctt    75780
tctgttgcac tgtgggttct gcccttgtct gcctcttccc tcctctgaag ccacgtggct    75840
tcatagccac ctgaggctgt cactggaatg aaccacaaag aagcactgta ggctaatgaa    75900
gttgcttacc gtaaagtcct ttctatggcc gacagtttga ccttatgatg agataaatag    75960
ataatcatct cttgcaacca aagctgtgta gacattgaag ctatctggga gaatttcaga    76020
aatttgctat acattagtgg ctcccacatt ttcttttagg actactttac agccttaaaa    76080
aacatggagg cctggcgcag tggctcatgc ctgtcatccc agcattttgg gaggccaagg    76140
cgggcgaatc acctgaggtc aggagttcaa gaccagcctg gccaacatgg tgaaacaccg    76200
tctctactaa aaatacagaa attagccagg catggtagcg ggttcctgta atcccagcta    76260
cttgagaggc tgaggcgaga gagtcgcttg aacccgggag gcagaggttg cagtgaacac    76320
cactgtactg cagcctgggc gacaagagtg aaattccatc tcaaaagta acactagtaa     76380
aataaaataa aataggccag gcacagtggc tcatgcctgt aatcccagca ctttgggagg    76440
ctgaggcagg tggatcaccc gaggtcggga gttcgagacc agcctggcca acatggtgaa    76500
accccgtctc tactaaaaat acaaaagtta gctgggcatg gtgacgcacg tctataatcc    76560
cagctacacg ggaggctgag ggagaagaat tcttgaaca cgggaggcag atgttgcagt     76620
gagccgagat cacaccactg cactccagcc tgggcaacag agcgagactc tgtctcagaa    76680
aaaaataata aaataaaata aaaaaaatat tgaggccctc aaagagtatt tgtttatgtg    76740
agaatatcta ttgatattag aaattaaact gagagatttt ttaaagatac tagtgaatta    76800
aaaaaataat aagcccatta catgttaaca taaattatat ctttttgaaa agaaacacaa    76860
aaaagtatt gaaatagtg acaatgttca ccttttacaa atccctccaa ggcagctggg      76920
tggtctgtgc ctgcgctcag cggtgggggc atcacacctc acgtggccgc tggggaagcc    76980
cgccgtgctt gggagagagc gagagtgaaa aaacagagga cacttactat tcattttgag    77040
aatagtcttg atcttacctt ctccctggaa gggttttgca aaccactgct ctaagtgatc    77100
ctttacttag aaacagctac tctcaggtgg agaaaaccta gtgcagccac aggctaaact    77160
ggccacagcc agcttccgag ctgggaagaa taggaagctc ttagacgaa gccatgaatc     77220
cgaggccac cttgttgaac ttgatcgcca tgccatcagc ttcagcatat aaggctatat      77280
gagtctaagt taaatattc tggagtgtgg gcgatcctca gaggctgtta attgatataa      77340
agaacttcag gtaggtccta accccttatt tgatggttga ttataaatca gttattcttg    77400
```

```
ccttctttcc tgttggtaat attcaacaaa gactattgca ttttcactaa ggaaaacgga    77460
ttttcagcca gcctctctcc tcccctcctt aggaccaatt ctgattctgc tcttcacacg    77520
agtgctctga gtaccaagcc ccaggacccc tatggaggag ggggccagtc ggcctggcct    77580
gccccataca tgggtaagac acacaggcca ctgctgacag cagctgtgct tgctcattct    77640
gtcctaggaa ccaagggaga gagaagctga agtggtgttt gcgcttccg  gttcagtgat    77700 cttagagagg cagctcgtgg cagggaagcg tgtgtgtcca tgatgcagtc aggatggatg    77760
gagctcccag cgtcccctgc ctctgccctg cttcctccac agcacgctct ccctcttggt    77820
gtctcttggc cctcttctgg gcacccgtca tcttctaata acttcctgac tggtctcctg    77880
atttccagtc tcacatccct tcaatccagt tttatgttaa gttccccaag agtcctcttt    77940
ccccacccag gatctgaaca aactgagaaa tacaactaga agtgacagtc agagctagat    78000
atcaccttta ttactactaa gaccaggttg gaggaagtga ctgtctctgt aggttggtgg    78060
gcctgctgag actgaacccc agcatgaggc tgactccccc tgagtggctg gcagcactgg    78120
ccagtgtggt ccctgggag  gagggtcag  gcaagcctcg ggagggagg  gtggagcaga    78180 ggctgctgc  cttgagatgg gggaagagga ggtcgggctg gaactgtgca tcacctgctc    78240
agttgccccc tggccactgt gagtaagggg atggagagag gccaggagta acccggagtg    78300
gggaagaggc ccactcatgc catctcacag ctctgcttcc agagcgaacc caaacctgat    78360
catcttgctc tcccacttaa aatcctcagt gccaccctc  accttcagga gaaagagccc    78420
agatcttctt tggaatgaca tgagccccaa ggcctggctc ctgtctgcct ctctcccttt    78480
tctctctgct ccccc gcctc acacccaagg tagccatgcg aaccactttg ggttctactg    78540
gtgtttcttc ctgttcctgt ctcttcctct ctctctcact cctggccagc accctctcca    78600
tccgtaagcc tcagcttgtg tgtgtcctca tgtctgtgga gccatccttg accttccttc    78660
ctctcagctc agagttatcg tgtccttcta acatcccaga ctgctctctt agcacctgca    78720
atgcttggct gctttttat  gtgaacatgc atctcttct  ctgctcagtg tagatttctt    78780
gaaggcagca tcttaatggt cttgttctct ccagccccta gcacagtgcc cggcacagag    78840
gagcccgtac tgatggagaa gtgtgaagaa tcacacactg gctcacatgt gcacggcatt    78900
tgccaaaaca ccctctcggt gctggcacct gacctgtaca tgaagtgagg ctggtcattc    78960
agacacattt caagcctacc tttctggggt ttataatcta gaaagaacaa tggtcttgaa    79020
ttatccattc catatgcaga ttgactcttg cccagaaact ttcagggctg tgtatttgtt    79080
cttgaaacag gaataaataa atctttagcc aagaaaccag cttttctggt tttctttgct    79140
ttttggacaa tttaaagcct aaatggcctc tgttccttcc aggagaacac ttatgatcgt    79200 atttcttttgt atatagcagg gatagtactg aataataatt gttgctatat ttgttctatt    79260
ggtgcaattc agagaagact acatttgctt aaatgattgt ttgcttgtaa actatgggag    79320 cttttcagaat tggttaggga catctaccca tgcttccata catggaaata tgaaagttgg    79380
cagtgatgtt gaaattgatg ttggaattgg atatgggtgc actgctcact gcttagagga    79440
gtggggtgtg tgggaagagg gatgagttta gtttcaggat aggtagagat gggaatatgt    79500
aaacaaagcc taaaaaagc  agaggctgta atcagtgggg gtgcctgtga gcacagcagg    79560
atcctaatct ccatggaccg ggagccagct agacagacag atttttaccc tggagctcct    79620
gcatttctgc ctctgccgat ccttcattta cattaccctc tgcaaagttt acacttctct    79680
agaaagggcc aaaggcctag agaaacaagg caatcacagg taattcaagt gaggattttt    79740
tgaggcttgc atgctaagaa aaagaaagta actgaagaaa gaaattacct gagctgaagt    79800
```

```
attcattctt agcgatgtag cctctgagag aagaggtgag aaatgtcaga aggggtaagt    79860
gaggatggaa taagaaaagc aaaggaatgt aaacattggt ccaggtagac agagcaatga    79920
gaaaaacagg aagaaagaaa gaaatcctgg atcagggttc ctgcgttgac ttgagaatcg    79980
tggtggtctc tccttttcaa atcagcagtt agaaattgtt gggctacaat atctgacaac    80040
catggagggt gggctggcct ccaactcaga tgtctgaact gtgtgcctgc tcctgcagtt    80100
gccttgcaag tatagcagaa ctcagaaaca catcctaata tggatgtgtt tacatgggaa    80160
agccagtgtt taaaatatta ttcaagtctc caaggatgga aattatttct ggagaattat    80220
atttgttggt gggagctatt ttaaatagtt tcatgtattt tcctcctgtg tttcattaaa    80280
gttttcatt ttctttcctt ttggattta aaactatcaa ctggctttgc aaaaaggtat    80340
ttcttatagg accaaccaaa gaagattta acagtgatg ggaaaatata attgaagccc    80400
agaactgggt tctatgttcg aagcaataat aactcttctt tccctgggaa tctctcctag    80460
gcagaatgat gcagccacac ttttttgtta ttgttgttgc tgttgctgtg agcccatgag    80520
gagagcatct gctcacggct taactacatg agcaataaac tatgatacat tcatgagtgg    80580
agatttgtgt cacaagaaga caaagcctga tacatgttga gtaattttca taatagctat    80640
tgagttccat gacaattagg cataaatgat aagcagttgg tataaatgac agaaataaat    80700
ttttatggaa ccaaacagga ttttataat ttctctcttt ttgtttaatt attcagaatc    80760
tataaagagg gaatgttggc catttccctg gcagcatgtg caccttaatg accatttcac    80820
acttacatgc agatagggaa gcacaggact ctgtgggaca cgtgccctgt cccatagcct    80880
aggactgtct cctaacaccc ctcctgacat cgggcatgtg gaggagggac tggggtggtc    80940
tcttccttc agggaacagt ctagagctaa ggggagcaga gtgcgtaata ggtgtcttct    81000
ctgcatccag ggctgtagat gctgaatatt gccatctttg gggaccacag tactcagctc    81060
cttagcgtgg aggggcttg gcatgccttg gacctggtga cctttcacct gccaataagc    81120
tttgacctgc agagttaagg agaaggttta caatgcaaag aaccttgaaa gatgtaagcc    81180
tgttaattgc atggattggg cggggtaca gtggcaggta caagcatccc agatctgaag    81240
agggggcaaaa agagtgtcac ccagggacag gagggcccag agtggggagg ctgaaacacc    81300
agaggcctcc tttaggacaa tggttaaggg gtcttcccct tgccttccct tctacttagc    81360
aaatcaaggc tgtgtaggga gttatttag atttgccagg catgggagca cacagaagga    81420
acatggtctc ggttccctta gttagaagag accggccctc ggtggctctg aggtttcctg    81480
gaacacagtt gcagccttgg tcatcgctgt cccatccctg tgggactgat aaaattagtg    81540
tcctgtttcc agagagccag tcacaactca ttccttttc tttttaaccc tttatttgta    81600
gtgctatctt gtgggttttt aatttagcag taaaaatcca ggcttggata ttttgatgat    81660
atgttagctt ggtgccagta tatcagtcat tgccaccacc atccttctgg tcaccgcagc    81720
ccagaccctg agagttgcat ctgattactc ccattcccat gccctacgc ccattcgta    81780
gccgagtcct gttcatttta tcccagcagt atgtctcaaa tctgcctctg gttttctgtc    81840
ctcactgcca gtatcctact tggttcctgt ttgccttgga ctattgcatt ggttttctag    81900
tcggcctccc tgccttaagg cttttctcctt tcaatccacc tcctactctg ctgcaagagc    81960
agtctctgaa gcttaactct gatcatgtca cttctccaac tgaaaccttc catcccctac    82020
atcctgccaa atgaccagca gcctgcttcg gtccagccca tctcccagtc ctcccaccat    82080
gtgctgcagc cacactcttc catcttcctt ctccttctta tccttcccca accacccccc    82140
```

```
actcctcctc ctcctcctcc tcctcctcct ccgcctccac ctcctcctcc tcctccgcct    82200
cctcctccgc ctctgcctcc tcctcacact gggcatcccc ttcagcttcg cttccggttg    82260
tctaaatctt ccaggtacta cagcaaattg gttagggaca tgaacattct gaagacacac    82320
gggccagagt tctagtccca gaacttacta gcagtgtgat cttggggatg ataatagcat    82380
ctacgtcgca gagttgctgt ggggatccca tgagatcacc tgtgtaaagc gcctggcaca    82440
tagtaagtga gcagtcaggt tggctgttgg ttatcctctt cttcaccatt atccttcaat    82500
gaatggcgcc tcaggtgcca cctactccat gaagccttcc ttctgttcca gtctgaggag    82560
agcatgcact aatggggctg tcacatgggg tatctgccag ccactcaggc agtttcacat    82620
ggtagccctc agttgagtcc tcatgtttca gggacaggtc aggcttaata attaaacctc    82680
gagtgactgg tgtcttgatg atgaagagat gcttcagcac gccataccag attgctatat    82740
aaaacctagt ttttagtttt taacaggata gtcactttt agtaatcaga atgaagttcc     82800
ctgccctttc ttaatatgag ggtctcagga aagccaaaat aggaatccgc aactcctgtc    82860
cttttgacgt tgctggttgt agagccacag cttccacagc ttttctctct ctgcacctca    82920
gtgttcacct gttcacactg cctgtctttt gatgggttaa atggctgata agtaagaatg    82980
ggccaaggac cttctgcaat agagtctcct gagacgacaa ttaaaaatgt aggctgggcg    83040
tggtggctca cacctgtaat cccagcactt gggaggctg aggcagacag attacctgag     83100
gtcaggaggt taagaccagc ctggccatca tggtgaaacc ccgtctctac caaaaaatag    83160
aaaaattagc cgggcctggt ggcacgcgcc tgtaatccca actactgggg aggctgaggc    83220
ccaggaggtg gaggttgcag tgagccaagg tcacgccacc gcactccagc ctgggcaaca    83280
aagtgagact ctgtctcggg aaaaaaaaaa aaaaaaaaa aaatgtaga ttccttggcc      83340 gactctcaca ccttctgaat caaaatcttt gagggttggg cccaagaatc tgcattttag    83400
caggctcacc caagggctct ttatgtgctg taaaataaag ctttcagtca cttacttaga    83460
gtctggttct gtgggcctga agaaattct gtctttgtgt gtctgcttca tttatcgacc     83520
tcttcgtatt cctgggcact cttcctgttg cccctgggct ctgttaaaat gttatatctt    83580
ctacctgtgt tatagaatgt gctaccgtgt taccctgatc tgtcttctca cctacactgt    83640
atcacccggc cccacctagc acttaatgca gaaacttatt aaatatgggt tgagtgaatg    83700
gttattagac atttcattca aattgtatag actaatcagg ttaacctata ggttaaccttt   83760 agccaaaaac tcatctaaaa tgtaagtaag ctatacttaa aggcttagaa ctttataata    83820
atgtatcctg attctgtact gaaaacttat ttggtatatt tgattgctct taagggaatg    83880
ctaagatatt acattcttgg cacggttctt tagttttagc ttagagcaat aggaaatact    83940
atgctttgtc atctgcagta taatttatgg attaaaaata cttcattcag ccagaattta    84000
ttccaagtca aagtttaaa actttgtgaa tagctatctc atgtacccctt taaattaact    84060 tagactccag ataaatcttc ttcttaaaat aacttcactg cataagaaat atatataata    84120
tcctacagca tgaaacttcg gatttgttcc tgtagacacc catggtaagt atcaaacagt    84180
gatgtaggct ttttgagtta cctgctctta accccatgat gaagcatttg aagagaatt     84240 tccatctata cttctttact ttgtggtttg aatagagatt ctcaggcttt gtaaaaattg    84300
ttctcctctc aggacagtga cagtaagaaa atttcagaca gacaatttta aggaaaaga     84360 aaaaggaacc aaatttagtt tcaaattagc tataccctatt tttagtataa atgataaagc   84420
accttaaatg aaaatcagtg tatcaaaagt gccttagaat tttcaaaatt ctatttcaaa    84480
tcataaagag ttactgattc ataaattcat gaaaatgaaa gtaccacata aagtgttttt    84540
```

-continued

```
cttttttttct ttttcctttc ccgctaggtt tctgtgatgg tgagaataat ggacatgggg  84600
aaggtatgaa ctgattttac ctacctatat tggagtggga tgctgattag tggacataac  84660
ctttcaatac ctttactaat aaatattcat gttttcagga ctcccccaaa tgctgacaac  84720
tgctgattgg cttactttc agagagcctc tagaaaatta aggctagcca tgttcaggc   84780
caggagaaag gaaatatgtg gttgcattac aaaggttcct ttttatctag gtccccacag  84840
tcacaaggtt gagcaaggaa ccaaaaattg taatcacatg aaaatatgaa tgaattggcc  84900
tggcacagtg gctcatgcct gtaatcccag cactttggga ggctgaggta ggtggatcac  84960
ttgaagtcag gagttcgaga ccagcctgac caacatggtg aaaccccgtc tctactaaaa  85020
atacaaaaat tagccgggcg tggtggcacg tgcctgtggt cccagatact caggaggctg  85080
aggcaggaga atcgcttgaa cacgggaggc ggaggttaca gtgagttgag attgtgccac  85140
tgcactccag tctggcgacc gagcgagact ccgtctaaaa ataaataaat aaataaataa  85200
ataaattaat taattgatca cttaaacaat tagttattcc agtagtctac ccatttagaa  85260
cgtcttcgtt gacagataac aatgccagga aaatgcaaat tggttatgaa atgaaaatgc  85320
aaaccttaca taagatactg agtttcgtaa agccaattaa acattgttg gagatctatg   85380
gaaatgacac tcaaagccat tgacaaatga gggtcagaca cagttcattt atttactcag  85440
taccagggac tgttttcttt tctctaaatc tttataatct ggaatttaat ttttataatc  85500
taaaaataaa caactaaatt aggtttatat gtcacagagg tgagaccta gggggacat   85560
gatgaatgag gagcatcttg caagacgcac agctctctgt catcatcctg cagctccttt  85620
tctgggcaag cccttttagg ccatgaataa aatcacaaaa aggtaaaaca tcaataaaca  85680
tctaatccac tagaacagaa attaataaat ggcttcaagg ttgactgcat tccttcagtg  85740
cttcgaagaa ttcccaacaa atcttggata tgaaagggga ctaaaaacaa tgaactctaa  85800
gaaaacagtc cccattaagg cactggagtc tgccccaacc atgttcttat aaccaacctc  85860
ttgtgagaag tagccttgag ctgtgtgtga tgacaccta ctcagtcctt caaacttttc   85920
ccagcatttg acagtaccct tcagggcaat tttatttat ttttatttat ttttattttt   85980
atttttttt tggagacgga gtctcgctct gtcgccaggc tggagtgcag tggtgtgacc  86040
tcggctcact gcaaacctcc gcctcctggg ttcaagcgat tctcctgcct cagcctcccg  86100
agtagctggg actacaggca cccaccacca cacccagcta atttttttt ttgtattttt    86160
agtagagatg gaattttgcc gcattgtcca ggctggtctc aatgattatc attatattaa  86220
tgattaagtc aggtaacatt tgaagaaaag agaatcaaca aggatgttga caaaatacgc  86280
tcttcaaaag agagtgatgt aaatatcagg attaagagag acacctggga acactgacaa  86340
agcatggcct ggtttagcag aaatgactgc tgccctggtg gtactggaca ggttgcctga  86400
agagcattgt atcctcccct taccgtgctg tcaaataagt tagaccgcta cccatactta  86460
attcattcta gaagtccaca actgcattta tatcatcagt tttattaaat acaagataaa  86520
cttattttag agtttttgtt tcaaagtctt ttctcaaaat ttactaggaa agtttgggcc  86580
ctgtgtcatg tgacttcttt ctggggtcca ttattcttgg gtaccggcc atcttgtgtg   86640
gggctaagac aggatagtca tgacagtcac actggagctt ctgtggccac tggaactcaa  86700
cagcattcct ggttctgagt agtcactggt gtccctaact tggaatcccc ttcctgacat  86760
cagatcactt aactcctgag ggctggccct tgttttctgg tctctttctg agaataaaaa  86820
gtatttactt gttctgtgac ccagcattct tgttttacct ggcacgactg agagagttaa  86880
```

|  |  |
|---|---|
| agcagaaagc cctggaatgg tccctttata caggttgttt catagcatta aagagccaac | 86940 |
| agccgtcccg gcagctgccc agcctcagat cctcttggtt gttggttcct ctttgtcccc | 87000 |
| catttccatc ccacaaccaa ggagcttcac tgccaccatg tcttccagct aatactcctc | 87060 |
| ttctcaatac tttccccatt tcatcgttgt tgcaggttct ctcctcatcc ctcttcttcc | 87120 |
| attctctcct ttgccaagcc tgcagagccc ccctgccctg gcctcaattg tctacatttt | 87180 |
| acttcctacc atcccctga ctcagcctac actccagttg aaaagagttg ctccactctt | 87240 |
| accttcccct ctcttggaat tcccttctcc tgtgtctcta aagggctccc cccagtgccc | 87300 |
| agctccaaag ccctcctggc ctcttcctct tctgcacttc atctctcagc agcatcatac | 87360 |
| cctcggctct ctcgggcttc cactcgtttt ttccttcagt gatcgttatt tatgtgttgc | 87420 |
| ccttatccac tgactagatt acacattcgt gaaaggttga atccatgtct tactcatttc | 87480 |
| tgcaactccc acagtagtgc ccaaagtggc ttccctagta gacagtccat aaatgagtca | 87540 |
| tttttgtgtg ttaaataagt caaacatttt atttgttaaa tcagttttta caaagataat | 87600 |
| ttgttcagcc aaaggtaggt aggatggatg ctttctcttt ttgttgttgt ctttgttttt | 87660 |
| ttgggacagg gtcttgttct gttgcccagc ctggagtgca gtggcaccgt catgactcag | 87720 |
| tgcagcctca gcctctcagg ctcaaggaga cctcccacct cagcctccca agtagttggg | 87780 |
| actacaggtg tgagccgcca cacccagcta attttttaaat ttttttgtaga dacggggggtc | 87840 |
| tcactatgtt gcccaggctt gtctcaaact cctgggctca agcgatcctc ctgcctcagc | 87900 |
| cccataaagt gctaggatta taggcgtgag ccaccgtgcc cggcctggat tcctgccttc | 87960 |
| tcatgcaatg actgtgctgc ttttttttttc cctttagtag catctttccc tggcccattg | 88020 |
| aaagaagaga atctgttaaa tgttccgaag ccactgccaa acaactgtg ggagaccaag | 88080 |
| gaggtgggtg aacagtactc agctatgttt gttgtcactg aatgtttgta cttagaggtc | 88140 |
| attgaaaaat cctgcagagg tgaaagcaag aggaactggg ggaaaaggag aagatttgtc | 88200 |
| tgagaacaga gataagaata tacaagggaa ggacgtttca agtaaaaatt atcgcgcttg | 88260 |
| tgtcaatgaa ttagcacatt gatctcttgg cttactaatt ttcatatgaa ttgacttatt | 88320 |
| taaaaaaaaa aaaaaaaccc tgctaagtcc tccatatctt attttgttttg ctaaaagctc | 88380 |
| tgaaacctgg ttgtaagtca taggcagatt tttctgtttt tttagccagc actttatacc | 88440 |
| agtctccagc ttctgtccag aattactggt ataccagata gctctttta actcaagggc | 88500 |
| atttgacctg agtcctccaa gagtcagtag acaagtcatc tgttttacta tgatttccat | 88560 |
| gcgcctttga gaatttgtat ctaaaattgt gctagctgac ctccacctcg gctctctaaa | 88620 |
| cctcacccac tgtggaagaa agggaggtc ccacggtact tgccttggcc tttcttccca | 88680 |
| gagggaagct gtgttgactt tgaaagaaaa cagttaatct gttccagccc ttaaggatgc | 88740 |
| tctattgcaa ttgtttgtat tgcctgtgta cttaactatc cccacctgtt taggatccct | 88800 |
| ttggcccagt tccattttct tctgccaagt ctaccagagt caccattagc attagttgtc | 88860 |
| ttaaaaggct ttttgtaaaa gcaagatgta tttgatgttt aatcatttgg gaagtaaaaa | 88920 |
| agagatatga tttaaaattt acatatttaa acacaggaga agcaaccaca ctgtctttg | 88980 |
| gctgtgagag gcacatgtgg ttgtggaggc ttttatcaga ggataactat gtcttctcca | 89040 |
| ccaaagaggg cagtggtgtg ccctcctccc tgagtaccag ggactggtct ctggaaagag | 89100 |
| atgttcatct cccttggttc ttgtggattt gtaatactca ttcctgtccg tctggagctt | 89160 |
| atattctagt tgaaatagct tagttcttc tgacattcat ttcttttttc accctgcttt | 89220 |
| tttcttttat ttatttcatt tcctctcaag ccaattggaa aagaaatgtt tatttaaaag | 89280 |

```
ctctatgtcg tccagaccca gtggctcatg cctgtaatcc cagcactttg ggaggccgag   89340
gcgggtggat cacctgaggt cgggagtttg agaccagcct ggccaacatg gtgaaacccc   89400
gtctctacta aaatacaaaa aattagccga gtgtggtggt gcatgcctgt gatcccagct   89460
actcgggagg ctgaggcagg agaatcgctt gaacccagga gcggaggtt gctgtgagct    89520 gagatgtgcc actgccactc cagcctggat gacaagagtg aaactccgta aaaagctcta   89580
tgtgtaaaac attggtcttt taatgttaat ccagaaggta aattgataag gcatcaaatt   89640
aggaaaatgt attaatatta tgcctcccctt aggcctggaa gtttgagttt aaaaaagtca   89700
tgccaaaacc taaaaggctg ctgtgtgagg actctgtcga cacgcaagct ctcacttgcg    89760
cccactagag cctcaaggtc cttacgaaga cacttttcaa aaacttgaat ttggctttac   89820
agcgagtaag cccagctttc attgtctctt ctcagattca gtccctgtca ggacgccctc    89880
gatcctgtga tgttggaggt ggcaagtaag taatattctt tctgttcgtg tttcagggac    89940
tatcctgaag gttttccca aaagtctcgc tgctttgtta cagaactctc agaaacgtaa     90000
cttgctatgc ataaattgaa agtcaactgc attttcataa aaacagccac tctctttgta   90060
tactcatatt tcatctgttt aaactaatta aattacatga ctataataac aaacaaaact   90120
tacataagta tgtttgagaa tcacacaact gactcttggt aaatacacaa ctctccgggt   90180
agaagcagtg tcagaagcag aaacgtgcag gaatcgagag gagcctacca gccccgagct   90240
gtggcaggct gtgggcatcg gtgacatcct ggccagggga aaagggaagc atcagttcac    90300
ctggcagctt aatggcacag aagttaatta agagagtttc tgtgaatgta cttaatgtca    90360
ctgaactgta cacacagaaa tggttaaaat ggtaaatttt atggtatatt tattttacaa    90420
caatttaaaa acataaatgg aagataaata tattttccat ttgcaataca aaaaagtttc   90480
tatgaaacca ttaatttgtt agtggattta atagtatgca acttcactcc ctaaaaggtt   90540
tgagacaact tacaaaaata tagtacaagc aaatgaaaaa ggaagttcat gaggaagttg   90600
agtctaagag agaacgagga gatgagagag ataatgaggc ccttgcctta acagaaactg   90660
ccttgggagg gccggctggt gtgctgcgtg ggacggtaca gacagctgct ggggaggttc    90720
acagagagga ccccttggaa ctcgatgggc tgtgtcctga gagagcccca aggaggcttc    90780
ctggggctgt ttatcatagt gtccgtgaga gcagtcccac cacttggaac tgaagccaat    90840
tcagaaacag caaggctgca gggccaaaat aatgtggttt ggaaatggga ttcttgcatg   90900
atctgactta gtacatacaa tcaccagtgg gtcagtgggt gaactaaatc cacttcaagc   90960
agtcattgaa tgtgatttcc cccaacagag cttcctgtga gtatctcaca gcagcgcagt   91020
caaggcactc tctactgagt acctggagct cagacattct ttctggcagg ttaaacgtaa   91080
actcaggtga tttgctgagc tgcgccacgg gttgatgttt gcttcagaaa gtgggcaagc   91140
ctgccaggac gcatgcccaa caaaagacag gccgccgaga ggtgcaggac attcccatgg   91200
aaggggcaag ctttcctca agggagtctc cctcaaccta gtctggttca ggggcttcct     91260
ggtaaaatgg aaatttggaa acaaaaacaa aaacaaaaac aaacatttc ctcaagaatc     91320 aattttggct taaccatcag ataaccttca ggctctgaaa gcctaacatt atagaattgg    91380
gctgcagtac tttagccctc aagaggtttt tgttgttgtt gtttagttag tttgttgta    91440 tttatttatt tatttgagat ggagtatcgc tctgtcgctc aggctggagt gcagtggcat    91500
gctcttggct cacagcaacc tctgcctccc aggttcaagc gattctccta cctcagcctc    91560
ccaagtagct ggaattacag acgtgcacca ccatacctgg ctaatttttt tatttataga    91620
```

```
aaagataggg tttcaccata ttggccaggc tggtcttgaa ctcctgacct caggtgatcc   91680
acccactttg gcctcccaaa gtgctaggat tacaggcatg agccaccatg cccagcctgt   91740
tttgttttta aagatagata gggccttgct atgttggcca ggttggtctt gaactcctag   91800
tctcaagtga tcctcccaaa gcactgggat tacaggtgtg agccaccatg cctggccaac   91860
ctggagagtt ttaaagcagg tgtttcttag gtagagaaag ttgctttctt gctcttactt   91920
tacagataga attccattca gtgacttcta gtcatgcaga tatttattga ccccctaatt   91980
cttggcactg ggttaaacaa tgaacaaaac agatcaagtt cctgctttcg aggagctaat   92040
aatctagtag agcaagatgg gcagaaacaa ataagcaaag cacagcaaaa gtcatgtgtg   92100
ggtaaatgca ctgaaggaga cgcaactgtg gcaggtggac aggcagccac cagcgggcgt   92160
tgaggaaacc tttctgatag tgtgaagcga cgcagagagg gctccaggca gcaggaacag   92220
caagtgcaaa gaccccaagg caggagtggg cctggagttc aaggaggctt gtattgcttg   92280
gatctgacgc agagaagatg ggagtcgtta gagggtcttg aaccgggggg cgcattactt   92340
tccttagatc agtggtgact ccgttaggta gtaactatat ttggaaagga accacctgta   92400
tttctcccag ctgcagagga attgtgtgaa cgttactaat gacctgtttc acagtggtca   92460
cattttttcc atccttgctc tgtgctgttg gacgcttctc cctgccgcgc ccctgctctc   92520
tctgccttca ctcccacctg atcacccatg gatctttctt ctcagtcaga aagcccatct   92580
gctgtcacgt tgagggctct gaggtctcaa ttttattttt ctagtccttg atctttaacc   92640
ctataaacag ttccatactt ccagccatct aagacaaaat tcaggctggg cgcagtggct   92700
catgcctgta atcgcagcac tttgggaggc tgaggcaggc cgatcacttg aggtcaggag   92760
ttcaagacca gcctggccaa catggcgaaa ccctgtctct actaaaaata caaaaatttg   92820
ctgggtatgg tagtacatgc ctgtaatccc agctactcgg gaggctgagg caggagaatt   92880
gtttgaaccc gggaggcaga ggttgcagtg agccaagatc gcaccactgc actccagcct   92940
gggcgacaga gcaagactct gtctcaaaaa acacaaaaat aaaataaaaa gacaaaattt   93000
atattcagtt tttctacaac caaaatgagc cttcttcctc accctccggt tggacacctc   93060
tcctgctgcc tcatttcttt ccaaaactcc acagttcgcc cagtcctact tttaccaaga   93120
aaagtgaggc gaggctggca ggagtgagtg ctcagctctc ttctgccact gattccccg    93180 tcaccaccct tctctggtcc tagggacacc gaggtccctc ctagtcaggc cggccacttt   93240
accactccct ggccctcctc ccgctggatt tgtggaggcc tttctctgct agttaactgt   93300
ccctcatctc cagaattctc cgccatgctt tctgaaagca tatttactct caggtgttcc   93360
ttcctgctta cccatcatca gcccaccatg ccctggctgc cacctctgct gttcagtgga   93420
accttgagaa tgtcggttgc ctcctgtacg taactgagag agaaatatcc ctgctgcatg   93480
tcttcctagt gagcagaaac tcaaagccaa aatagaattc gtgatctcat ccatacccct   93540
gccctcattc ccaatctgct cacatcttca gtgtccctg tctcagtgag gggctccacc    93600
agtccccagg ctaaaggccc cagagttgtt cttgagtcct acttccctgt ctctagagtc   93660
tagcctgcct ctccctccct gcgctcgtgg cctcctgctg gagcgttcag cagagtcata   93720
gcggcctctc cacctccagg cctgctccgt gcacccaag acccctccc caagtctgtt     93780 agccacgctg tcctaagaaa agctgatacc tctccccac cacactgccc accccgcgtc    93840
cagccttcca ctggcgtcgt gtcagcctct catcagtccc agcctcgggt gctctctacc   93900
tgcttttcca cttccatctc ccaccactaa ccagccctcc taaactcaac ctcccgtggt   93960
ctgaatcctc acagttctga gggcacacca tgtggtctca cacctccctg cttttgcgca   94020
```

```
tgctgtgagc tttgcctgaa atcttttttcc tgactagatc acctgagttc tttagccttt  94080
aaactaagct cagatgtcct ccaaggaagc ctccccaggt cagctgggct tccctccaca  94140
tggcctccct ccaggctcta tcactgcact actgaattgt attatgttgc cggttatgct  94200
ccttatggct cagtctcttg aagccctgat gccagtgggc ggccctgggg aggtgctctg  94260
ctgatgtgtg caggagggaa tgaagtgtcc tcaggattcg tgacttccct ctgctcctgg  94320
ctggtggcac cttctcccgc attctcctcc gcgtcaccct cactgctctt ttcctatatc  94380
accccctggac cactgcaggt ggtccttcta attggttctc cctgcctctc cttctgcctg  94440
ctgaggccat cctccacact ggaaccacag tgacatttct gaaacgccat tctccagctt  94500
aacctggcct ccctctttcc acagtccctg atccagactc ctgagaacag cacattctct  94560
cccgcctgcc tctccctccc catgtgccac cctccctcct caccctctgc cctgacacct  94620
gacacctcag ccatgcccag ctactcttaa ttccacgcac acactgtgtc acatccatgg  94680
caaacccgtc ccctccacag cccatcctga catggacaac tcctgctttt ttgctcccgg  94740
tgtcacttat atgcactggt tacacacacc ccttctcaaa cccagcatag cgcgcttcct  94800
gccacgttgc agttacttgc tttcccaggc tgtctctcct gcccatctgt gaattccaaa  94860
acaaggtcct ctcagacctg gctagcaggc ccctccctgg ggccccgccc ttgagagggc  94920
ttcattccca aagggaacgt accaccagtg tatacgcact aggcctgggg ggtggctaga  94980
gagtcagcag ggtgtggaca gagtttggct gcataggctg ggatagctat gtgcgtactg  95040
cagtacagaa cagaactagg gggaagagaa ggggacgtgg actgagggcc aggctgtctc  95100
cctgtgcatt ctggcacaga actccaagaa gtctgagaat tctacatgta aatctggctt  95160
cacaggctat tatgaaggta taatatgtca ggatagacac atagaacaaa gttcatgtaa  95220
gggtttgttc atttgattta aacttttaa aaatggaaac agatggtatg cgggccttct  95280
tttatactct tgctccaggc ctgtacattt caggagtagg cctgacccg gcggacacac  95340
tcgccctgct tgttcatcat ggtgccgcca acatgcggcc cgctgcctgg cacacagtgc  95400
ctagcccata gattgtgatg aatgaatggc aacatctctt tgtcacttta aagtttatga  95460
agactgtaat tttaaaaata tatcttggaa ggtatattgg aaggtagcta gttactcaga  95520
gatactttt ctggtagcaa agataactta aaaatctagc aaaaagaact acataaatag  95580
cagtgcctca cattttatag agtggttat aattttcaga atacttttgc atccataatc  95640
taatctggtc ttgattattc tagaccctaa tctagtattc ctgtaatgtg gcacaggta  95700
gtgggtgagg atatgtgttt cggagaggtt aagccgagca ccagtgttct cagaatcaga  95760
gaggccgcac caggacctcg gtcttttgta gccactgctc ttatttgaca aggaaaaggt  95820
ttcagccatg tttggtttcc caacagccaa atacattgta gaaagtcatt cttaatcttt  95880
cttttttcag tgcttttcca cataatggtc aaaacctagg cctctcaccc ttcttgggga  95940
ccttgaacac tggagggtca ttgccagatc taaccaacct ccactactcg acaccccctgc  96000
cagcctccct ggacaccacc gaccaccact ttggcagtat gagtgtgggg aatagtgtga  96060
acaacatccc agctgctatg acccacctgg gtataagaag ctcctctggt gagtatctcc  96120
tgcttagcag tgacctggtg gcttaatcat aggtggtccc cacccatgtg gcctgttcag  96180
tgaatcattg aatgagaatg actgcatccc agttagagat gataatgtac cttcttgtat  96240
ctcctgaccc tgcggacatt tttcttggat gtttctgttt ctcctgggtt gatgaatttg  96300
gggcagctct gctgaacctc attccttatc atcctcactc gctgctctat ccagggactt  96360
```

| | | | | | |
|---|---|---|---|---|---|
| ggggaataag | atatgggagc | caagaaataa | gcatccactc | cgtgttggct | gaacagtatt | 96420 |
| agtggctgtc | atcaacatat | gataaatttat | aatttaggcc | atctctctgg | attcctttca | 96480 |
| ttttccatta | gatttctaaa | ggcaatattc | tgcattttag | aaaatttaca | gtggatatga | 96540 |
| tgaaaatatt | tatacttaat | atctgtgtgt | gaagtagaaa | tcccccacag | ttccagttaa | 96600 |
| agatgtagca | ttagctatat | aaagatgcta | cccataatgg | gacttgggtg | ttactctctg | 96660 |
| ggtttgattg | tccacagctc | agaccccata | ttgaaattat | gactacattt | gtttgaagcc | 96720 |
| tgacactttt | ttttttttt | ttttgagatg | gggtcttact | ctgtcaccta | ggctagagtg | 96780 |
| cagtggcacg | atctcagctc | gctgcaacct | ctgcttccca | ggttcaagca | attcttctgc | 96840 |
| ctcagcctcc | agggtagctg | ggattacagg | catgtgccac | gatgccgagc | taatcgtttt | 96900 |
| tgtatttta | gtagacag | ggtttcacca | tgttggccag | gctggtctcg | aactcctgac | 96960 |
| ctcaagtgat | ccacccgcct | tggcctccca | aagtgctggg | attacaggcg | tgagccacca | 97020 |
| ctgacatacc | cttgtcaatg | tctagggcag | gtgataatcc | tcttactccc | agtggtgcag | 97080 |
| tacagcccct | ggccgtaaca | gtcctaccca | gaattgtgtt | gtggagcatt | tcatttggaa | 97140 |
| gggatgctca | gtgatggtct | ccaggtgaaa | gcagtgtttg | ctgcctttca | ctctgagact | 97200 |
| catccatgca | aatcagaact | caccacccaa | atgagagtgg | tccccttcag | gggggtcac | 97260 |
| ctggaagttt | ttctaatgat | tgcagtgatg | ctgcctggtg | caacacaatc | ttaggtttga | 97320 |
| agaattgatt | tcagagaaca | cctttatttt | tgttttttgg | gtcattttag | tatccttaat | 97380 |
| agtagcaggt | ttttcatcga | ctgagtctca | gttttgatat | ttatacattt | gcttcatagg | 97440 |
| agaaatttga | tatttgcttc | acaggagaaa | ctctcgaaac | ctttatgccc | agattcagag | 97500 |
| tctgggcaat | tcacctttg | ggtgaatcct | caatgtatga | agatatctag | ggtcccagaa | 97560 |
| gtaaagcagc | atcagcacat | agctcctttg | ggtctcaggg | aagctggcat | tttccagtac | 97620 |
| agcctttgac | actttgcttc | aagctgaaga | tcttatgttt | agtcactggt | tgtcttctca | 97680 |
| aaaaagcact | attttatcca | gaacatgtca | gaaccaatgt | cagtttctgt | attttctttt | 97740 |
| tttttttct | ttttgagaca | gactcttgct | gtgtcgccca | ggctggagtg | cagtggcgcc | 97800 |
| atctcggctc | actgcaagct | ctgcctccta | ggttcacgcc | attctcctgc | ctcagcctcc | 97860 |
| ccagtagctg | ggactacagg | cacctgccac | cacgcccggc | taattttttt | agtagagacg | 97920 |
| gggtttcacc | ttgttagcca | ggatggtctt | gatctcctga | cctcatgatc | cacccgcctc | 97980 |
| ggcctcccaa | agtgccggga | ttacaggcgt | gagccacgcc | cagccggcaa | aattattttt | 98040 |
| aagaatttta | ggctgggtgc | ggtggctcac | tcctgtaatc | ccggcacttt | gggaggccga | 98100 |
| ggcgagtgga | tcacgaggtc | aggagatcga | gaccatcctg | gctaacacgg | tgaaacccca | 98160 |
| tctctactaa | aattacaaaa | aattaaccag | gcgtggcggc | acatgcctgt | agtcccagct | 98220 |
| acttgggagg | ctgaggcagg | agaatggcgt | gaacccggga | gacggagctt | gcagtgagct | 98280 |
| gagatcatgt | cactgcactc | cagcctgggt | gacagagcga | gactctgtct | caaaaaaaat | 98340 |
| aataataata | atagtgataa | taataatttt | gccagctgct | ggattttgt | catttcttcc | 98400 |
| ttttcgtaac | ttttatcaaa | cacttaaatt | ttttgtcaac | acgaaacaac | acatagttct | 98460 |
| gcttacccca | cctgctggta | caagaaagat | gggctgaagg | ttaaaacgta | ggtattgcca | 98520 |
| gttgagatac | acacagcagc | agcagccgaa | taattgattc | actgggcgaa | cctgctccat | 98580 |
| gccaggccct | gtgccaggtg | ctgaggatcc | agcagggcat | aggacaggat | ccccagtttc | 98640 |
| tgggagctca | tgccctagca | gcctatgctg | caaagatctc | tctcccaaat | ttccttgctc | 98700 |
| atgatcaaat | tcacccctgt | cccccaaata | aagcaccagc | aaaaacttcc | ttttccctga | 98760 |

```
gttggtatag actgtgatga acaatttcct gggaaccaga aaatcaaaga gggaccctgg   98820
ggtgggagat acagggaagt gtcccttcct gtgactccct agtgtgctaa gggtaattaa   98880
agaccaccaa gacagctccc caagggccat gactcgccgt ggaaggatgt tctccaaagg   98940
tagcagggga tgcaggcagt gtgcttggga cagagacctt ccggggctct aaacagaatt   99000
tgttgtacag ccctagggtc cttttccctgg gtctgggccg agcacctgga atatttgcct   99060
ctgttacccc ggtttaccta gttttgctca cctaggggtt gttgacgtga tctccctcct   99120
catgggaaaa catcgttgtc atctttgtgg ccccatctct gttagtgcag gggcatcttt   99180
tccttgccat tggtgcatcg gatgcagtcc ctgtaggaga gctgtccagg agctccttta   99240
cctacagaat catcatcgca tgtgacagta gacagttttc tttcattttt ggaatacaaa   99300
agatttggtc tgaaattata agtaacttgt gaatttgttg tcttccaggt ctccagagtt   99360
ctcggagtaa cccctccatc caagccacgc tcaataagac tgtgctttcc tcttccttaa   99420
ataaccaccc acagacatct gttcccaacg catctgctct tcacccttcg ctccgtctgt   99480
tttcccttag caacccatct cttttccacca caaacctgag cggcccgtct cggcgtcggc   99540
agcctcccgt cagccctctc acgctttctc ctggccctga agcacatcaa ggtttcagca   99600
gacagctgtc ttcaaccagc ccactggccc catatcctac ctcccaggta aacacacaca   99660
gacagaccaa ccactacagt gaaacagact gcaagatata ggaagtgcat tcctcctctt   99720
tactattttg ggttacactc attattacac caagcaccca tgaggtctca agtgcagtct   99780
gttcgctctt atatgtgaaa tcagagcaga agtgtcaata atgcagaatg aattcatgat   99840
tttcttttct tttttttgaga aagggtctca ctctgttgcc caggctggag tgcagtggca   99900
caatcgcggc tcactgcagc ctcacctccc gggctcaagc gatcttctca ccttagtctt   99960
cggagtagct gggaccacag gcatgcacca ccatacctga ctaattttttt gattttttg    100020 tagagacaag ttctcgatat gttgcccaag ctggtctcaa atgcctggac tcaagccatc  100080
ctcccagcgt ggcctcccaa agtgctggga ttacaggcat gagccactgc acccagccta  100140
attaatgatt ttttattata ataatagcag atttgctgtg ttgattactc tttaagcaaa  100200
tgttgaacaa tctgtagtca ctaactcaca aacttggggt tgagaggaac ggtaggatat  100260
agagaatgcc atccaggtaa gtctaaggca actgagggaa accaggttag gatttcaaag  100320
ttggcatgga aaatcagtca ttgactctct aagtacatta agccataggg gaaagccaaa  100380
gaaaacattt aataccttcc tgaagctttg ataatgaatt agacctcttc cctaattgtc  100440
tacagatttg agaaacaata cttttattgt tcatgaaatg ctaagtatgt tgaggattat  100500
atctcttata aggatgaaaa gaagtctgtt gagaaagagg cacatttaaa agtcacccac  100560
ccatacaaaa aatggaaaaa ttagctgggt gtggtggcac acgcctgtag tcccagctac  100620
tccagagcgg aggtgggagg ctcacttgag cccaggaggt cgaggctgca gtgagccaag  100680
atagcctcac tgcactgtag cctggcaaca gagtgagacc ctgtctcaaa agaaaagaaa  100740
agcccattat agaaacacag gggttgaaac atcctataaa ttctaaactc agaggtggtt  100800
ctccttatac cataatcatc gaggaatgtg ttttcaacct tttgtcacat cctctgtcta  100860
ttacagcatc atttttttt ttttttttt ttttttttt tttgagacgg agtctcgctc  100920
tgtcgcccag gtcggactgc ggactgcagt ggcgcaatct cggctcactg caagctccgc  100980
ttcccgggtt cacgccattc tcctgcctca gcctcccgag tagctgggac tacaggcgcc  101040
cgccaccgtg cccggctaat tttttgtatt tttagtagag acggggtttc accttgttag  101100
```

```
ccaggatggt ctcgatctcc tgacctcatg atccacccgc ctcggcctcc caaagtgctg   101160
ggattacagg cgtgagccac cgcgcccggc ctattacagc atcattaact actcaccacc   101220
tcgccataaa ttaatgattt agaaggaaga gttgacagaa cacaacggag agttagagga   101280
tcttgttatt ggtcactctt taccaattac tagccgtggc gtgttgatcg tatgagtgat   101340
ctcttttggg cgagggtgag aggacatttc ataatttta agtctcactc tgtcgcccaa   101400
gctggagcac aatggcacga tcgcggctcc cttgccttga attcctgggc ccaagtgatc   101460
ctcctgcctc agctgggatt cttcaagtaa atgtgactac aggcccatgt caccacaccc   101520
agctaatttt tttaattttt ttgtagaaac agggtctccc tgggctgggt gtgtgcctca   101580
cacctgtaat ccagcacttt gggagtccaa ggcagacgga tcacttgagg gtaggagttt   101640
gagtccagcc tggttaacat gacgaaaccc catctctact aaaaatacaa aaattaaccg   101700
ggcatggtgg cacacgcctg taatcccacc tactcaggat gctgcgacgt gagaattgct   101760
tgcaccctgg aggtggaagt ttgcagtgag ccaggattgc accactgcac tccagcctgg   101820
gtgacagagt tactctgtct caaaaaaaaa aaaaaattag aattaaaaaa agaaaagaaa   101880
gaaataggt  ctccctatgt tttccaggct ggtcttaaac tcctgagctc aagtgatcct   101940
cgcacctcag cctcccaaag ggctggaatt agccagtgtg ccttgtgcca ggcatgagcc   102000
actgtgccct gccataattt ttattttttt ttagagacag cgtttcactc tgtcacccag   102060
gctcgagtgc agtggcgcga tcacagctca ctgcagcctt gaactcctg  agctcaggtg   102120
atcctcccac cttaacctcc caagcacata ggactacagg tgtataccat cacacccgac   102180
taatttttgt atttttttt  ttttgtagag atggggtttc accatattgc ccaggctagt   102240
ccataattat tgttttcgtg gttcttatgt tattgaatta cctttaattt tattttgcaa   102300
gattatttta taagatctaa aagtattctt gcttttagc  tacatttaa  ggagactgta   102360
tggccagagt gtcccctttc agatgtgttt ttaatttgtt taatatttag atttttttta   102420
aatgaatgtt gctggacaca gttgttctga ctgtaatccc agctactcag gaggcagaga   102480
ctggaggatt gcttaaggcc cggagttcaa gaccagcctt ggcaacatag tgacacccta   102540
tctatctctt aaaaaaagga aattttaaaa agtgaatgtt attcatgcac atagtttaaa   102600
aagtaaaata gttctaaagg gcttgttata gaaaacagc  tgtctttccc tctcgttagg   102660
catattcctc actgcctaga gatggctgtc aaccatttta actaatctct ttggtataac   102720
catgttatta ttattttgag acagagtctt gctctgtcac ccaggctggg gtgtagtggt   102780
gcgatctcaa ctcactgaaa cctccacctc ccaggttcaa gcgattttcc tgcctcagct   102840
tcctaagtag ctgggactac aggcatgtgc cacgacgcct ggctacttt  tgtatttta    102900
gtagatacag ggttttacca tgttagccag gctggtttcg aactcctgac ctcaggcagt   102960
ctgcccgcct cggcgtccca aagtgctgga ttacaggcat gagccacctc acccagccta   103020
accatgttgt tttatgcttt ttttgttcta cattttggt  gttaggcatt atctaatgac   103080
atcctaccaa tgaagattag aatttaattc tctttccact ctcccacaga ctccaccaca   103140
cacatatgtg cgcacatgtg cacacacaat ttcctaccca ccctcctcat ttattataat   103200
tttggttaga gcaatactca atatttagtg ttttatagt  tacaatgtag tcagagttga   103260
catatagtat actatgaaac aagaaaatga gaatttttt  tcctcttggg agttaataaa   103320
tgtctgactt ttttttattag cctggttatc tatatgtatc tatgtgtatg actaattcag   103380
tccccaactc ttggagttgg gcagatctcc tctcgacaca ttcaaaacta aattctctag   103440
tagctctata gcaaagagtg cctgtgactt tgtatgactt aaaatgtctt tatttgatct   103500
```

```
gccatttaat tattatttgg ctgaatatag aattctaaat ttgaaataat tttcccttgg 103560
catctattgc ctattcattt gtaagttgca ttgagaaatc cagtgccatt cggactctta 103620
acactttgca tggaatcccc ctgctccacc ccaggcttgt gagatctttt tgtcccagt  103680
gttctgaaac ttcaagatga tgtggcttgg cgtgagtctg catatttggt gggttccttc 103740
aatctggaaa ctcacagcct tcatttctgg gaaatgttct ttatttcttc aatgatttct 103800
tcccttcagt tttctctgtt ctttctctct ggaactctac gaatgttgac tatcctggac 103860
ttttcctcta ttatccttat cttctctctc tcctcttttg cttctctgtg gttgcttcct 103920
tgtttgtttg ttttgctttg ctttctggaa gattgtctca gctttatctt ccaacacttc 103980
tgttgagttt tccatttctg ctctcatttt taaattgcta tgagttcttt tttgttctct 104040
gagtgttctt ttttaatagc atcatactta ttccacagat gcaatatcat cttttatctc 104100
tcaggttttt agtggtcttt tttttcgaa tttatcttta ttttctataa tagaattttc  104160
ctaaattgca taaagtaga gaacataata caataagtcc tcctataccc atcatttacc  104220
ctcaacaatt aatttttttt ttttgagaca gggtcttgct ctgttgccca ggctggagtg 104280
cagtggtgtg atctcggctc attgtaacct ccgccatcca ggttcaaacc attctcctgg 104340
cctcagcctc ccgaatagct gggactacag gtgcacacca ccacacctgg ctaattttg  104400
taatttttag tagagacggg atttcaccat gttggccagg ctggtttcaa actcctgacc 104460
tcaggtgatc cacccacctc agcctcccaa agtctgagat tacaggcgtg agccagcacg 104520
ccagccttgt tatcttgttt catccatacc ctgcttttaa aaattgcaga tatttaata  104580
tgtatctcta atagataagg attttcttag tagcctaaat attgtcatgc tgattttggt 104640
ttttcacaac tacttcttcc tgcacacatc tttccaagat tgtgtgtgtc tgctctggcc 104700
tctgactttc acggcagatg gtttcctcag ggcctggtga tcctcagtgc tctgctcatg 104760
tttaagaaca ggacactgag gggctgtctc cttgcggctc tacactagag cggagtatga 104820
gactgaggcg aagggagtca tggcaggaca agcgtgtaga aagttttttc cactctctga 104880
ctgagtattg gttggaagga gcgctgctaa aactgtaacc aaaggaggca ttttgcttcc 104940
agaaaaatct caaggaaaag tattgcaagc aacagtagtc actgttggat cgggttctaa 105000
aggtaaggct ggagagattc aaccagttag cgtgaaagtt ggagataaag ttcttctccc 105060
agaatatgga ggcaccaaag tagttctaga tgacaaggat tatttcctat ttagagatgg 105120
tgacattctt ggaaagtaca tagactgaaa taagtcacta ctgaaatggc atcagtgtga 105180
agctgcccat tccactgaag ttctgaaatc tttcatcatg taaataattt ccatatttct 105240
tataataaac taatgataac taatgacatc cagtgtctcc aaaattgttt ccttgtactg 105300
atataaacat ttccaaataa aaatatgtaa atgagaaaaa aaaaggaca ctgagaagct  105360
ggctggcagc tctgtgtatg tgggcaggcc tgctgagtgt ggtcttcatt gtagaatgat 105420
ctagcttggt catttccttg ggaaactcct ggtgtcataa gttttacatt cttctctggc 105480
caggcgtggt ggctcacacc tgtaatctca gcactttggg aggccgaggc gggtggatca 105540
cctgaggtca ggagttcgag accagcctgg ccaacatggt gaaacccgt ctctactaaa  105600
aatacaaaaa ttagccaggc gtgttagcat gctcctgtaa tctcagctac tcgggagact 105660
gaggcaggag aattgcttga acccaggagg tggaggttgc agtgagccaa ggtcatgcca 105720
ctgcactcca gctgggtgac agagcaaga ctctgtctcc agaaaaactc tgtctccaga  105780
aaaaaagatt ttctctcttc aggccttgtc aggttcccta aaggacactc ttccaatgtc 105840
```

```
gcacctcggc atatcaggat tccggcatcc tgtgagccgg gttgggaaag aaaggtggag   105900
atcttaagat tcgatcgtga aatttcttct aaagaataaa ataccctagga atccaactta   105960 taagggatgt gaaggacctc ttcaaggaga actacaaacc actgctcaat gaaataaaag   106020
aggatacaaa caaatggaag aacattccat gctcatgggt aggaagaatc aatattgtga   106080
aaatggccat actgcccaag gtaatttata gattcaatgc catccccatc aagctaccaa   106140
tgactttctt cacagaattg gaaaaaacta ctttaaagtt catatggaac cgaaaaagag   106200
cccacattgc caagtcaatc ctaagccaaa agaacaaagc tggaggcatc atgctacctg   106260
acttcaaact atactacaag gctacagtaa ccaaaacagc atggtactgg taccaaaaca   106320
gagatataga ccaatggaac agaacagagc cctcagatat aatgccacat atctacaacc   106380
atctgatctt tgacaaacct gacaaaaaca agaaatgggg aaaggattcc ctatttaata   106440
aatggtgctg ggaaaactgg ctagccatac gtagaaagct gaaactggat cccttcctta   106500
caccttatac aaaaattaat tcaagatgga ttaaagactt aaatgttaga cctaaaacca   106560
taaaaaccct agaagaaaac ctaggcaata ccattcagga cataggcatg ggcaaggact   106620
tcatgtctaa acaccaaaaa gcaatggcaa caaaagccaa aattaacaaa tgggatctaa   106680
ttaaactaaa gagcttctgc acagcaaaag aaactaccat cagagtgaac aggcaaacta   106740
cagaatggga gaaattttt gcaatctact catctgacaa agggctaata tccagaatct   106800
acaaagaact caaatttaca agaaaaaaac aaacaacccc atcaaaaagt gggcgaagga   106860
tatgaacaga cactcttcaa aagaagacat ttatgcagct aaaagacaca tgaaaaaatg   106920
ctcatcatca ctggccatca gagaaatgca aatcaaaacc acaatgaggt accatctcac   106980
accagttaga atggcaatca ttaaaaagtc aggaaacaac aggtgctgga gaggatgtgg   107040
agaaatagga acacttttac actgttggtg ggactgtaaa ctagttcaac cattgtggaa   107100
gtcagtgtgg cgattcctta gggatcttga actagaaata ccatttgacc cagccatccc   107160
attactgggt atatacccaa aggattataa atcatgctgc tataaaaaca catgcacaca   107220 tatgttatt gcagcactat tcacaatagc aaagacttgg aaccaagcca gatgtccaac   107280
aacgatagac tggattaaga aaatgtggca catatacacc atggaatact atgcagccat   107340
aaaaaatgat gagttcatgt cctttgtagg gacatggatg aagctggaaa ccatcattct   107400
cagcaaactg tcgcaaggac aaaaaaccaa acaccacata ttctcactca taggtgggaa   107460
ttgaacaatg agaacacatg gacacaggaa ggggaacatc acacaccggg gcctgttgtg   107520
ggatgcgggg aaggggggagg gatagcattg ggagatatac ctaacgtaaa tgacgagtta   107580
atgggtgtag cacaccaaca tggcacgtgt atacatatgt aacaaacctg catgttgtgc   107640
acatgtaccc tagaacttaa aaaaataaaa tattaaagaa aaagaaattt cttctaaacc   107700
ctgtgttttc agtaaagtgc ctcaccttct aatatccaga gacccttagt tttattatct   107760
cgaaagtaga accttccagt ctcctggcag gtggcaggat ggtgggggcc agtgcgcaga   107820
agcacactca aggcaagggc tctgcaggtc caactgcccc ttacacaaac tgtgaccaga   107880
atctcctggt tttagcttca ccgcctgctc cctgctgtcc ccagtcccag agccctgtgg   107940
ggactgagtg ctgtcagtga gattgcctcc tggttttttcc tcactgccag cctagcatcg   108000
ggttttctca gctctgctaa gccagctgcc accgggccat ctgctgctca ttttccagct   108060
tttgttgcca ttttcttctc tcccgttatc tttgtcctcg tgttgtttgt tatcatttag   108120
tgttctgtgc tgttgtttag tgtttttat taatgcttat tgcttgttaa tgttgtagtg   108180 tcttgttttta acaggatttg gggatgacag agctaagggc cttttttcaat tttccacttt   108240
```

```
taaccagaag acacggctat aaaacaaaac aaaacatgat tttcacggag aaaactgaaa    108300
ggaaattggt taaattggct gttttcttgt ttagttcttt taagacaata gaacttgtca    108360
ttgaatggaa catgctttgt ggggaagtaa aatttgagat atactttgaa ggatgagaaa    108420
cgggcttctc acagcattgc acagaacacc gcggtgagga aaatctcagg cttcctctca    108480
ctctgacatt tcctaatcct aaaggactta acgccagaaa cgcagaagct cattagtggc    108540
tttgtgtgtt tgttttgcag atggtgtcct cagaccgaag ccaactttcc tttctgccca    108600
cagaagctca agcccaggtg tcgccgccac ccccttaccc tgcacccag gagctcaccc     108660 agccctcct gcagcagccc cgcgccctg aggccctgc ccagcagccc caggcagcct      108720
cctcactgcc acagtcagac tttcagcttc tcccggccca ggtgagttct ggcaggagcg    108780
ttggtgcaga gggaatgctt gttttgctct gagttccaag ctaaatgatc atctccttat    108840
tccctgaagg gctcatcttt gaccaacttc ttcccagatg tgggttttga ccagcagtcc    108900
atgaggccag gccctgcctt tcctcaacag gtgggtgatc gccctgcct tctcctccct     108960 tggtgcataa actgtaccat ttaggttgtt cattctgtag aattcagaac tgagcagacc    109020
agacatgcca ctttcctggt tctggttgtg ttctgtggct agaagagcct ttcatcttct    109080
ttggccctaa aatgctttct ctggctgcct tatttagtat caggcttcag cagaggaact    109140
attggaacaa tcggcaggag acttttgatg acactctcgt tgtagaactg taaaatcatg    109200
aacactggaa gggacacagc acctgcctcc tcagcgccct catgttgaaa ctgaggcata    109260
gggagagtgg cgcctgctcc caccgcagag tcagaaggtg gcgccgcatt tggcctgcac    109320
ccaggctggt gcacccagca cagcgtgggg cctcctgggg agagctcagt cctggggagt    109380
gaggggagtg cgttccgtaa ggtattttca actcggccac tttcttttac agtttagttt    109440
tttcctaaca ttgactattt ttaatattct agattttata gtattcaata gtattcaata    109500
agtatggact gggccctccg atggattaag gagtggaaga agggttgaac aggttccaga    109560 acttttttt ttttttttt ttgagacaga atcttaatct gtcgcctagg ctggagtgca     109620
gtggcgtgat ctcggcttac tgcaacctcc acctcctggg ttcaagtgat tctcatgtct    109680
cagactcctg agtaattggg gttacaggca tgtaccccta cacctggcta attttatat    109740 ttttagtaga gatggggttt cactttgttg accaggctaa tcttgaactc cggacctcaa    109800
gtgatccacc cgccttggcc tcccaaagtg ctgggattac aggtgcgagc cactgtgccc    109860
agccaagaac ttaataaaat agctgggcat agtggctcac gcctgtaatc ccagcagttt    109920
gggaggccga ggcgggcgga tcatgaggtc aggagatcga gaccatcctg gctaacacgg    109980
tgaaaccttg tctctactaa aaaatacaaa aaaattagct gggcgtggtg gcaggcacct    110040
gtagtcccag ctactcggga ggctgaggca ggagaatggc gtgaagccgg gaggcggagc    110100
ttgcagtgag ctgagatcgc accactgcac ttcagtctgg acaacaaagc aagactctgt    110160
ctcaaaataa gtaaataaaa taataataat aaaataaatt aagatagctg tttcctaagc    110220
aggccacaga tgaagctttg tggcaagaac caatcctcct tgcctccctg tttcccaaag    110280
agccatttta gtctaggtgg gaatcaccgt ctccctgaaa aatgatagac acttcttttg    110340
agactttttt taaaatggct tagaaaatta atttcaggaa aggaacctaa aattggcact    110400
ggttataacc agtcctcata gaggctttct cataggaggg agcttgcctg agtttcctcc    110460
ttctgagtgt gaaaaggaaa gccttcccct ttctcagttt tctagaaacc agggaagagg    110520
ccaggtgcag tggctcacac ccataatccc agcactttgg gaggccaagg ccagtggctt    110580
```

```
acttgaactc aggagtttga gaccagcctg ggtaaaatac agcaagaccc tgtctctaaa    110640
aaaaatacaa aaattagcca ggcatggtgg catgtggtcc cagctatttg ggaggctaag    110700
gtggacggat tgcttgagcc tgggagctgg aggtttcagt gagccgagat ggcgccattg    110760
cactccagcc tgggcaacag agaccctatc tttaaaaaaa aaagaagaa agaaaccaag     110820
gaagaagagt ccatacttcc ttggttatag acagagcctt tgaagggttc ccacagaagg    110880
cagtttgcaa aggccttggt gaggctgagg acagatgtct gaggggccac agaaccatg     110940
agcattggtg tctcttggga tggtgtagtg ggctggggaa aagtcaccac gctgtggacc    111000
tcagggaccc ctcctccacc ccagcgtctg cctgcctgac aagaatattg tgcatgcatt    111060
accataagag caaagcactc tgggatcctg gaaagaaggg aatatggatt agtttgcaag    111120
tcaggttttg ctctgggagc acattgcaat actcacttcc tccttggaaa cagaggtgtg    111180
gccttcctca catgaccttc gatgcttcca ggtgcctctg gtgcaacaag gttcccgaga    111240
actgcaggac tcttttcatt tgagaccaag cccgtattcc aactgcggga gtctcccgaa    111300
caccatcctg ccaggtgagc gagctatccc tcagcttctt tactgctttt atgttgttgt    111360
gtgttcagga accttcataa gagagtttaa acaacataat attatataaa gcaaaaagtt    111420
aacgttccct gggtcgactt gacttttga gatgcaggtg tccagcctca gagaccgtga     111480
cacagggcgg tgggcctggt agtcaaagcc ttttctgaaa gatttcatct ggcccagtgc    111540
ggtggctcac gcctgtaatc ccagcacttt gggaggccga ggtgggcgga tcatcaggtc    111600
aggagatcga gaccattctg gctaacacag cgaaacccg tctctactaa aaaatacaaa     111660
aaaaattagc tgggcatggc ggcgggcgcc tgtggtctca gctactcggg aggctgagc     111720
agaatggcac caacccagga ggtggagctt gcagtgagcc gagattgtgc cactgtactc    111780
cagcctgggc aacagtctcc aaaaaaaaaa aaagatttca tcttaggtga ctgatgactg    111840
ttcaaaagga aaaacctgc aaaaattggg agttgtgcaa ctgactgaca agaatgtaga     111900
ttccagggca agaactgtgg gcctgggggt ggtcaggatg tgtgggatag cagtttaggg    111960
gactgtcatc agctgggttt gcttagtagc ctggagcctt cgcgcctcct aaccgcactg    112020
ttttcccctc tggccactcc tttcagaaga ctccagcacc agcctgttca aagacctcaa    112080
cagtgcgctg gcaggcctgc ctgaggtcag cctgaacgtg gacactccat ttccactgga    112140
agaggagctc cagattgaac ccctgagcct ggacggactc aacatgttaa gtgactccag    112200
catgggcctg ctggacccct ctgttgaaga gacgtttcga gctgacagac tgtgaacaga    112260
aggcagtgga acagaagaat gttttctgc aacagccaaa atagaatgga atagaatgaa     112320
gccagctgat accacgggct tcgttatct tgacatagaa ggaagcaatg ccacggctcc     112380
agggtttcag atgagatccc atctcagaca ctgtggcttc ctccagatca cacagctttg    112440
tactgcctct cccgcctgtg gccaaagtcg tgttgcagca ggcaggctgc ttggagcttc    112500
ccatgaactg gaaagctcac ctccactgca tcttttact ggccatccag tcagccgatg     112560
tgtaagagta ggaaatactg tgtcactgga ggcctccgta gcattgtgta gtgtgctcag    112620
aaccactgat ctccgtccgc accgaaggcg ggcccggagt gggaggctcg gcctggggcg    112680
gcggcaccgg agagggcacc tcgatgcctg ctctgacctg acccagaggg cgaggccctc    112740
cagcggggga cattcccagg ctgagtggac cccacggctc tctcccacgc ctggattacg    112800
acatgaagtt tttaccacaa gcccgagggc aggcttgagt taggcagact gaaggctaat    112860
tttcattttc tcccagctgg tttctgctgc ttcagaaaag tacaccttt ccttatggac     112920
cagaggaaga ggaagaccat tttatcagtc actgaaaaga gtccctggc actgatgagc     112980
```

```
ctgaagagaa ctgtgctcct cctcgggggc tggggaagga agacagggac tgcaggtgtc   113040
tcatactcag tggcctccag acaaactcca gacaagcaca gacctcccca ctaagagcag   113100
ccagagggag ctggtgaggc cctaacccca cccaccgagc aactgagctt ccccatccct   113160
ccccagagct gtgtctctgt gggctgggag tctaatgtca ccccctaga ccgtaagctc   113220 cttgagggca gggacagtgc cttatcattg ttgaacccgt agcacctaac acgtgcgtgg   113280
cagcacagtc gtgtgctgga gtgagtgctg cagaaccgtg cgtgcagcgc atgatgaatg   113340
agtgcgtccg ccatgccgta aggcaggctc acctgtagct atccccttcc ctgccagatc   113400
ttctcagagc tttagctttt ctagcactcg tgcctatggt gaagcatgca cttaatatg    113460 cttttaacac taggtgacca aatcacagtg aagccgggca ctgcattctc cttgggctgt   113520
gctccacgcg ggtgggtggg agctgtcttc tgagtacatc cggaagggct gagcaggtga   113580
gtgccctgag catcctggct gggccccacc caggaagatc ttccttctca gatccacgtt   113640
tggctctaaa ttgcttcaag tagagattca ttctttgagg ttgaaaaaat agtttatagt   113700
aaaacgaagg cctaattcat ggaagcatca ttagtcatca ataccttctc ataaaataga   113760
tgggccagat ttccaccacc gcctgcctcc tctaacttgg gtgatgccag taggtttgaa   113820
gggggcagag cactgcaggg ggagggggg gtctaggctg tgagaggaca gggtggagag    113880
gaggagaacc ctgaaggaga gacggaagat gccaggacct ttgcttggac agccattgcc   113940
cttccaggag accctggagt gtactgaggg ttgctggact gttccaccca gaggagcaag   114000
gctgtacaat gagggtctga atctggcaca cctgtccctt atgtaaaagg agtcgtggtc   114060
acaagaccct gggctggtta gcctctcccg acctcattcc atttctatct tctgaccttg   114120
cctctcatct ttaaaataac cctcatgggg tgcccctcca ccttcctctg gaatccaagt   114180
attcctgttt cacatttgcc ccaaatcttt gctgtgaat tgggaaatca aaccagagtc    114240
ctcctcgcct gatttccagc tcaggaaggg cctgctggcc tgccctgttc ccagttacac   114300
tttcagatcc ctttgtgctc aagatctcag agggggtggc tttttgttaa agagccttca   114360
gtcgcaatgc tacccagcac cccatgtgcc aaaagaaacc agctcctgtg tcaaagggct   114420
tccaaacctg atctcactct caacaggcga tggtgctgat gtttcaagaa ttgtgttttt   114480
ataaaacaga ggtctcagca tagtcactct tcacatagtg ccttaccat gggtatcgtc     114540 atatccgggt cccagttcag tttgtctgca cagcagccac cctgcctggc aacagagacc   114600
ccaagaccta cacagtgaac cctactgccc caaaggcgtt ctccaggtga cttgtgaaaa   114660
cagacctccg gggaagtgat ttattggggg tgtacactgg gggcaatatg gtttagcact   114720
gaattcaatt tgtccttagg tctatgagtg agtccgatct tttcttgtga aaggttttgg   114780
gcatcgtaca acccactctg cctagaaggt gtggaggact caccacgggc agggtcgccc   114840
tggcccacag cacgtgagcc tgcactcact gcggcctttg taacaaaacc agttgtggtc   114900
ctcagcattt gaagcagctg catacttcag agtaaactat ttttcattat ttagttttgt   114960
cacaagaaat cgaccattgt actactctca cttacagcag ttaaacagca tagaactaaa   115020
aacctgtctg catttccatt ttttcttct gtatggttgt gggttttagg acatagggg     115080 ttaggagaag gggtttcttg atcatgtcat gaattctcct ttgtcctgtt tctcctgttt   115140
catttctcct ccgcctgctg tatattacct gagctggtgt tgtatcttca agtccatatg   115200
cgtatttgca gaccttttcct gttcccactc ttgttggctc ttctgattta tgcacagatg   115260
gttcccagca tgtgtccagt gcttcatgga tgggaccatc ccagcaacta atcagacttc   115320
```

```
ctgccagtgt cctaacccccc agggcaccct gttcaaccat atttaaaaat tggaatttgt   115380
ataaagttgc ttccaagttt tataatgcat cattttacat cttttgtaat taaaagcatc   115440
acaatgaggt tgtctctgca                                                115460
```

```
<210> SEQ ID NO 7
<211> LENGTH: 619
<212> TYPE: PRT
<213> ORGANISM: Homo sapiens

<400> SEQUENCE: 7
```

| Met | Ala | Ala | Ser | Pro | Gly | Ser | Gly | Ser | Ala | Asn | Pro | Arg | Lys | Phe | Ser |
|---|---|---|---|---|---|---|---|---|---|---|---|---|---|---|---|
| 1 | | | | 5 | | | | | 10 | | | | | 15 | |

| Glu | Lys | Ile | Ala | Leu | His | Thr | Gln | Arg | Gln | Ala | Glu | Glu | Thr | Arg | Ala |
|---|---|---|---|---|---|---|---|---|---|---|---|---|---|---|---|
| | | | 20 | | | | | 25 | | | | | 30 | | |

| Phe | Glu | Gln | Leu | Met | Thr | Asp | Leu | Thr | Leu | Ser | Arg | Val | Gln | Phe | Gln |
|---|---|---|---|---|---|---|---|---|---|---|---|---|---|---|---|
| | | 35 | | | | | 40 | | | | | 45 | | | |

| Lys | Leu | Gln | Gln | Leu | Arg | Leu | Thr | Gln | Tyr | His | Gly | Gly | Ser | Leu | Pro |
|---|---|---|---|---|---|---|---|---|---|---|---|---|---|---|---|
| | 50 | | | | | 55 | | | | | 60 | | | | |

| Asn | Val | Ser | Gln | Leu | Arg | Ser | Ser | Ala | Ser | Glu | Phe | Gln | Pro | Ser | Phe |
|---|---|---|---|---|---|---|---|---|---|---|---|---|---|---|---|
| 65 | | | | | 70 | | | | | 75 | | | | | 80 |

| His | Gln | Ala | Asp | Asn | Val | Arg | Gly | Thr | Arg | His | His | Gly | Leu | Val | Glu |
|---|---|---|---|---|---|---|---|---|---|---|---|---|---|---|---|
| | | | | 85 | | | | | 90 | | | | | 95 | |

| Arg | Pro | Ser | Arg | Asn | Arg | Phe | His | Pro | Leu | His | Arg | Ser | Gly | Asp |
|---|---|---|---|---|---|---|---|---|---|---|---|---|---|---|
| | | | 100 | | | | | 105 | | | | | 110 | |

| Lys | Pro | Gly | Arg | Gln | Phe | Asp | Gly | Ser | Ala | Phe | Gly | Ala | Asn | Tyr | Ser |
|---|---|---|---|---|---|---|---|---|---|---|---|---|---|---|---|
| | | 115 | | | | | 120 | | | | | 125 | | | |

| Ser | Gln | Pro | Leu | Asp | Glu | Ser | Trp | Pro | Arg | Gln | Gln | Pro | Pro | Trp | Lys |
|---|---|---|---|---|---|---|---|---|---|---|---|---|---|---|---|
| | 130 | | | | | 135 | | | | | 140 | | | | |

| Asp | Glu | Lys | His | Pro | Gly | Phe | Arg | Leu | Thr | Ser | Ala | Leu | Asn | Arg | Thr |
|---|---|---|---|---|---|---|---|---|---|---|---|---|---|---|---|
| 145 | | | | | 150 | | | | | 155 | | | | | 160 |

| Asn | Ser | Asp | Ser | Ala | Leu | His | Thr | Ser | Ala | Leu | Ser | Thr | Lys | Pro | Gln |
|---|---|---|---|---|---|---|---|---|---|---|---|---|---|---|---|
| | | | | 165 | | | | | 170 | | | | | 175 | |

| Asp | Pro | Tyr | Gly | Gly | Gly | Gly | Gln | Ser | Ala | Trp | Pro | Ala | Pro | Tyr | Met |
|---|---|---|---|---|---|---|---|---|---|---|---|---|---|---|---|
| | | | 180 | | | | | 185 | | | | | 190 | | |

| Gly | Phe | Cys | Asp | Gly | Glu | Asn | Asn | Gly | His | Gly | Glu | Val | Ala | Ser | Phe |
|---|---|---|---|---|---|---|---|---|---|---|---|---|---|---|---|
| | | 195 | | | | | 200 | | | | | 205 | | | |

| Pro | Gly | Pro | Leu | Lys | Glu | Glu | Asn | Leu | Leu | Asn | Val | Pro | Lys | Pro | Leu |
|---|---|---|---|---|---|---|---|---|---|---|---|---|---|---|---|
| | 210 | | | | | 215 | | | | | 220 | | | | |

| Pro | Lys | Gln | Leu | Trp | Glu | Thr | Lys | Glu | Ile | Gln | Ser | Leu | Ser | Gly | Arg |
|---|---|---|---|---|---|---|---|---|---|---|---|---|---|---|---|
| 225 | | | | | 230 | | | | | 235 | | | | | 240 |

| Pro | Arg | Ser | Cys | Asp | Val | Gly | Gly | Asn | Ala | Phe | Pro | His | Asn | Gly |
|---|---|---|---|---|---|---|---|---|---|---|---|---|---|---|
| | | | | 245 | | | | | 250 | | | | | 255 |

| Gln | Asn | Leu | Gly | Leu | Ser | Pro | Phe | Leu | Gly | Thr | Leu | Asn | Thr | Gly | Gly |
|---|---|---|---|---|---|---|---|---|---|---|---|---|---|---|---|
| | | | 260 | | | | | 265 | | | | | 270 | | |

| Ser | Leu | Pro | Asp | Leu | Thr | Asn | Leu | His | Tyr | Ser | Thr | Pro | Leu | Pro | Ala |
|---|---|---|---|---|---|---|---|---|---|---|---|---|---|---|---|
| | | 275 | | | | | 280 | | | | | 285 | | | |

| Ser | Leu | Asp | Thr | Thr | Asp | His | His | Phe | Gly | Ser | Met | Ser | Val | Gly | Asn |
|---|---|---|---|---|---|---|---|---|---|---|---|---|---|---|---|
| | 290 | | | | | 295 | | | | | 300 | | | | |

| Ser | Val | Asn | Asn | Ile | Pro | Ala | Ala | Met | Thr | His | Leu | Gly | Ile | Arg | Ser |
|---|---|---|---|---|---|---|---|---|---|---|---|---|---|---|---|
| 305 | | | | | 310 | | | | | 315 | | | | | 320 |

| Ser | Ser | Gly | Leu | Gln | Ser | Ser | Arg | Ser | Asn | Pro | Ser | Ile | Gln | Ala | Thr |
|---|---|---|---|---|---|---|---|---|---|---|---|---|---|---|---|
| | | | | 325 | | | | | 330 | | | | | 335 | |

| Leu | Asn | Lys | Thr | Val | Leu | Ser | Ser | Ser | Leu | Asn | Asn | His | Pro | Gln | Thr |
|---|---|---|---|---|---|---|---|---|---|---|---|---|---|---|---|
| | | | 340 | | | | | 345 | | | | | 350 | | |

```
Ser Val Pro Asn Ala Ser Ala Leu His Pro Ser Leu Arg Leu Phe Ser
        355                 360                 365

Leu Ser Asn Pro Ser Leu Ser Thr Thr Asn Leu Ser Gly Pro Ser Arg
        370                 375                 380

Arg Arg Gln Pro Pro Val Ser Pro Leu Thr Leu Ser Pro Gly Pro Glu
385                     390                 395                 400

Ala His Gln Gly Phe Ser Arg Gln Leu Ser Ser Thr Ser Pro Leu Ala
                    405                 410                 415

Pro Tyr Pro Thr Ser Gln Met Val Ser Ser Asp Arg Ser Gln Leu Ser
                420                 425                 430

Phe Leu Pro Thr Glu Ala Gln Ala Gln Val Ser Pro Pro Pro Pro Tyr
            435                 440                 445

Pro Ala Pro Gln Glu Leu Thr Gln Pro Leu Leu Gln Gln Pro Arg Ala
        450                 455                 460

Pro Glu Ala Pro Ala Gln Gln Pro Gln Ala Ala Ser Ser Leu Pro Gln
465                 470                 475                 480

Ser Asp Phe Gln Leu Leu Pro Ala Gln Gly Ser Ser Leu Thr Asn Phe
                    485                 490                 495

Phe Pro Asp Val Gly Phe Asp Gln Gln Ser Met Arg Pro Gly Pro Ala
                500                 505                 510

Phe Pro Gln Gln Val Pro Leu Val Gln Gln Gly Ser Arg Glu Leu Gln
            515                 520                 525

Asp Ser Phe His Leu Arg Pro Ser Pro Tyr Ser Asn Cys Gly Ser Leu
        530                 535                 540

Pro Asn Thr Ile Leu Pro Glu Asp Ser Ser Thr Ser Leu Phe Lys Asp
545                 550                 555                 560

Leu Asn Ser Ala Leu Ala Gly Leu Pro Glu Val Ser Leu Asn Val Asp
                    565                 570                 575

Thr Pro Phe Pro Leu Glu Glu Glu Leu Gln Ile Glu Pro Leu Ser Leu
                580                 585                 590

Asp Gly Leu Asn Met Leu Ser Asp Ser Ser Met Gly Leu Leu Asp Pro
            595                 600                 605

Ser Val Glu Glu Thr Phe Arg Ala Asp Arg Leu
        610                 615

<210> SEQ ID NO 8
<211> LENGTH: 586
<212> TYPE: PRT
<213> ORGANISM: Homo sapiens

<400> SEQUENCE: 8

Met Ala Ala Ser Pro Gly Ser Gly Ser Ala Asn Pro Arg Lys Phe Ser
1               5                   10                  15

Glu Lys Ile Ala Leu His Thr Gln Arg Gln Ala Glu Glu Thr Arg Ala
            20                  25                  30

Phe Glu Gln Leu Met Thr Asp Leu Thr Leu Ser Arg Pro Ser Phe His
        35                  40                  45

Gln Ala Asp Asn Val Arg Gly Thr Arg His His Gly Leu Val Glu Arg
    50                  55                  60

Pro Ser Arg Asn Arg Phe His Pro Leu His Arg Ser Gly Asp Lys
65                  70                  75                  80

Pro Gly Arg Gln Phe Asp Gly Ser Ala Phe Gly Ala Asn Tyr Ser Ser
                85                  90                  95
```

-continued

```
Gln Pro Leu Asp Glu Ser Trp Pro Arg Gln Pro Trp Lys Asp
            100                 105             110

Glu Lys His Pro Gly Phe Arg Leu Thr Ser Ala Leu Asn Arg Thr Asn
            115                 120                 125

Ser Asp Ser Ala Leu His Thr Ser Ala Leu Ser Thr Lys Pro Gln Asp
130                 135                 140

Pro Tyr Gly Gly Gly Gln Ser Ala Trp Pro Ala Pro Tyr Met Gly
145                 150                 155                 160

Phe Cys Asp Gly Glu Asn Asn Gly His Gly Glu Val Ala Ser Phe Pro
                165                 170                 175

Gly Pro Leu Lys Glu Glu Asn Leu Leu Asn Val Pro Lys Pro Leu Pro
            180                 185                 190

Lys Gln Leu Trp Glu Thr Lys Glu Ile Gln Ser Leu Ser Gly Arg Pro
            195                 200                 205

Arg Ser Cys Asp Val Gly Gly Gly Asn Ala Phe Pro His Asn Gly Gln
210                 215                 220

Asn Leu Gly Leu Ser Pro Phe Leu Gly Thr Leu Asn Thr Gly Gly Ser
225                 230                 235                 240

Leu Pro Asp Leu Thr Asn Leu His Tyr Ser Thr Pro Leu Pro Ala Ser
                245                 250                 255

Leu Asp Thr Thr Asp His His Phe Gly Ser Met Ser Val Gly Asn Ser
                260                 265                 270

Val Asn Asn Ile Pro Ala Ala Met Thr His Leu Gly Ile Arg Ser Ser
            275                 280                 285

Ser Gly Leu Gln Ser Ser Arg Ser Asn Pro Ser Ile Gln Ala Thr Leu
            290                 295                 300

Asn Lys Thr Val Leu Ser Ser Ser Leu Asn Asn His Pro Gln Thr Ser
305                 310                 315                 320

Val Pro Asn Ala Ser Ala Leu His Pro Ser Leu Arg Leu Phe Ser Leu
                325                 330                 335

Ser Asn Pro Ser Leu Ser Thr Thr Asn Leu Ser Gly Pro Ser Arg Arg
            340                 345                 350

Arg Gln Pro Pro Val Ser Pro Leu Thr Leu Ser Pro Gly Pro Glu Ala
            355                 360                 365

His Gln Gly Phe Ser Arg Gln Leu Ser Ser Thr Ser Pro Leu Ala Pro
            370                 375                 380

Tyr Pro Thr Ser Gln Met Val Ser Ser Asp Arg Ser Gln Leu Ser Phe
385                 390                 395                 400

Leu Pro Thr Glu Ala Gln Ala Gln Val Ser Pro Pro Pro Tyr Pro
                405                 410                 415

Ala Pro Gln Glu Leu Thr Gln Pro Leu Leu Gln Gln Pro Arg Ala Pro
            420                 425                 430

Glu Ala Pro Ala Gln Gln Pro Gln Ala Ala Ser Ser Leu Pro Gln Ser
            435                 440                 445

Asp Phe Gln Leu Leu Pro Ala Gln Gly Ser Ser Leu Thr Asn Phe Phe
            450                 455                 460

Pro Asp Val Gly Phe Asp Gln Gln Ser Met Arg Pro Gly Pro Ala Phe
465                 470                 475                 480

Pro Gln Gln Val Pro Leu Val Gln Gly Ser Arg Glu Leu Gln Asp
                485                 490                 495

Ser Phe His Leu Arg Pro Ser Tyr Ser Asn Cys Gly Ser Leu Pro
            500                 505                 510
```

```
Asn Thr Ile Leu Pro Glu Asp Ser Thr Ser Leu Phe Lys Asp Leu
            515                 520                 525

Asn Ser Ala Leu Ala Gly Leu Pro Glu Val Ser Leu Asn Val Asp Thr
530                 535                 540

Pro Phe Pro Leu Glu Glu Leu Gln Ile Glu Pro Leu Ser Leu Asp
545                 550                 555                 560

Gly Leu Asn Met Leu Ser Asp Ser Ser Met Gly Leu Leu Asp Pro Ser
            565                 570                 575

Val Glu Glu Thr Phe Arg Ala Asp Arg Leu
            580                 585

<210> SEQ ID NO 9
<211> LENGTH: 428
<212> TYPE: PRT
<213> ORGANISM: Homo sapiens

<400> SEQUENCE: 9

Met Gly Phe Cys Asp Gly Glu Asn Asn Gly His Gly Glu Val Ala Ser
1               5                   10                  15

Phe Pro Gly Pro Leu Lys Glu Glu Asn Leu Leu Asn Val Pro Lys Pro
            20                  25                  30

Leu Pro Lys Gln Leu Trp Glu Thr Lys Glu Ile Gln Ser Leu Ser Gly
        35                  40                  45

Arg Pro Arg Ser Cys Asp Val Gly Gly Gly Asn Ala Phe Pro His Asn
50                  55                  60

Gly Gln Asn Leu Gly Leu Ser Pro Phe Leu Gly Thr Leu Asn Thr Gly
65                  70                  75                  80

Gly Ser Leu Pro Asp Leu Thr Asn Leu His Tyr Ser Thr Pro Leu Pro
                85                  90                  95

Ala Ser Leu Asp Thr Thr Asp His His Phe Gly Ser Met Ser Val Gly
            100                 105                 110

Asn Ser Val Asn Asn Ile Pro Ala Ala Met Thr His Leu Gly Ile Arg
        115                 120                 125

Ser Ser Ser Gly Leu Gln Ser Ser Arg Ser Asn Pro Ser Ile Gln Ala
130                 135                 140

Thr Leu Asn Lys Thr Val Leu Ser Ser Ser Leu Asn Asn His Pro Gln
145                 150                 155                 160

Thr Ser Val Pro Asn Ala Ser Ala Leu His Pro Ser Leu Arg Leu Phe
                165                 170                 175

Ser Leu Ser Asn Pro Ser Leu Ser Thr Thr Asn Leu Ser Gly Pro Ser
            180                 185                 190

Arg Arg Arg Gln Pro Pro Val Ser Pro Leu Thr Leu Ser Pro Gly Pro
        195                 200                 205

Glu Ala His Gln Gly Phe Ser Arg Gln Leu Ser Ser Thr Ser Pro Leu
210                 215                 220

Ala Pro Tyr Pro Thr Ser Gln Met Val Ser Ser Asp Arg Ser Gln Leu
225                 230                 235                 240

Ser Phe Leu Pro Thr Glu Ala Gln Ala Gln Val Ser Pro Pro Pro
                245                 250                 255

Tyr Pro Ala Pro Gln Glu Leu Thr Gln Pro Leu Leu Gln Gln Pro Arg
            260                 265                 270

Ala Pro Glu Ala Pro Ala Gln Gln Pro Gln Ala Ala Ser Ser Leu Pro
        275                 280                 285

Gln Ser Asp Phe Gln Leu Leu Pro Ala Gln Gly Ser Ser Leu Thr Asn
290                 295                 300
```

```
Phe Phe Pro Asp Val Gly Phe Asp Gln Gln Ser Met Arg Pro Gly Pro
305                 310                 315                 320

Ala Phe Pro Gln Gln Val Pro Leu Val Gln Gln Gly Ser Arg Glu Leu
                325                 330                 335

Gln Asp Ser Phe His Leu Arg Pro Ser Pro Tyr Ser Asn Cys Gly Ser
            340                 345                 350

Leu Pro Asn Thr Ile Leu Pro Glu Asp Ser Ser Thr Ser Leu Phe Lys
        355                 360                 365

Asp Leu Asn Ser Ala Leu Ala Gly Leu Pro Glu Val Ser Leu Asn Val
    370                 375                 380

Asp Thr Pro Phe Pro Leu Glu Glu Glu Leu Gln Ile Glu Pro Leu Ser
385                 390                 395                 400

Leu Asp Gly Leu Asn Met Leu Ser Asp Ser Ser Met Gly Leu Leu Asp
                405                 410                 415

Pro Ser Val Glu Glu Thr Phe Arg Ala Asp Arg Leu
                420                 425
```